(12) United States Patent
Martinborough et al.

(10) Patent No.: US 7,767,680 B2
(45) Date of Patent: Aug. 3, 2010

(54) ION CHANNEL MODULATORS AND METHODS OF USE

(75) Inventors: Esther Martinborough, San Diego, CA (US); Nicole Zimmermann, San Diego, CA (US); Robert B. Perni, Marlborough, MA (US); Michael Arnost, North Andover, MA (US); Upul K. Bandarage, Lexington, MA (US); Francois Maltais, Tewksbury, MA (US); Guy Bemis, Arlington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 279 days.

(21) Appl. No.: 11/266,142

(22) Filed: Nov. 3, 2005

(65) Prior Publication Data

US 2006/0160817 A1 Jul. 20, 2006

Related U.S. Application Data

(60) Provisional application No. 60/624,718, filed on Nov. 3, 2004, provisional application No. 60/624,716, filed on Nov. 3, 2004, provisional application No. 60/624,800, filed on Nov. 3, 2004.

(51) Int. Cl.
*A61K 31/497* (2006.01)
*A61K 31/505* (2006.01)
*C07D 403/00* (2006.01)
*C07D 239/02* (2006.01)

(52) U.S. Cl. .................. 514/252.14; 514/275; 544/295; 544/329

(58) Field of Classification Search ........................ None
See application file for complete search history.

(56) References Cited

U.S. PATENT DOCUMENTS

| 5,475,132 A | 12/1995 | Pepin et al. |
| 5,530,000 A | 6/1996 | Sanfilippo et al. |
| 6,274,588 B1 | 8/2001 | Boes et al. |
| 2002/0128277 A1 | 9/2002 | Dworetzky et al. |
| 2002/0156087 A1 | 10/2002 | Nuss et al. |
| 2002/0183335 A1 | 12/2002 | Hewawasam et al. |
| 2004/0009991 A1 | 1/2004 | Ohno et al. |
| 2005/0004151 A1 | 1/2005 | Yang et al. |
| 2005/0038243 A1 | 2/2005 | Singh et al. |
| 2005/0202973 A1 | 9/2005 | Schaetzer et al. |

FOREIGN PATENT DOCUMENTS

| BR | 8904477 | 4/1990 |
| WO | WO 9639400 | 12/1996 |
| WO | WO 0250066 | 6/2002 |
| WO | WO 03030909 | 4/2003 |
| WO | WO 03091214 | 11/2003 |
| WO | WO 03091215 | 11/2003 |
| WO | WO 2004005283 | 1/2004 |
| WO | WO 2004032933 | 4/2004 |
| WO | WO 2005/075458 | 8/2005 |

OTHER PUBLICATIONS

Dorwald F. A. Side Reactions in Organic Synthesis, 2005, Wiley: VCH, Weinheim p. IX of Preface.*
International Search Report and Written Opinion of the International Searching Authority for International Application No. PCT/US2005/039881, filed Nov. 3, 2005.
Black, Joel A., et al. "Sensory neuron-specific sodium channel SNS is abnormally expressed in the brains of mice with experimental allergic encephalomyelitis and humans with multiple sclerosis"; *Proc Natl Acad Sci U S A*, 97(21): 11598-602, (2000).
Graboyes, Harold, et al.; "Pteridines. X. Some pyrimidopyrimidine"; *Journal of Medicinal Chemistry*,11 (3), (1986).
Strichartz, Gary R., et al. "Therapeutic concentrations of local anaesthetics unveil the potential role of sodium channels in neuropathic pain"; *Novartis Found Symp*, 241:189-201, (2002).

* cited by examiner

*Primary Examiner*—James O Wilson
*Assistant Examiner*—Jeffrey H Murray
(74) *Attorney, Agent, or Firm*—Honigman Miller Schwartz and Cohn LLP; Jonathan P. O'Brien; Heidi M. Berven

(57) ABSTRACT

In general, the invention relates to novel 4-phenylpyrimidine compounds useful as ion channel modulators. It has now been found that compounds of this invention, and pharmaceutically acceptable compositions thereof, are useful as inhibitors of voltage-gated sodium channels and/or calcium channels.

23 Claims, No Drawings

ION CHANNEL MODULATORS AND METHODS OF USE

CLAIM OF PRIORITY

This application claims priority to U.S. Provisional Patent Application Nos. 60/624,718; 60/624,716; and 60/624,800, all of which were filed on Nov. 3, 2004. The entire contents of the aforementioned applications are incorporated in their entirety.

TECHNICAL FIELD OF THE INVENTION

The present invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such, they play key roles in a variety of disease states such as epilepsy (See, Moulard, B. and D. Bertrand (2002) "Epilepsy and sodium channel blockers" *Expert Opin. Ther. Patents* 12(1): 85-91)), pain (See, Waxman, S. G., S. Dib-Hajj, et al. (1999) "Sodium channels and pain" *Proc Natl Acad Sci U S A* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci U S A* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 235-42), irritable bowel (See, Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)-null mice" *J Neurosci* 22(19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" *J Neurosci* 21(21): 8690-6), as well as an array of psychiatry dysfunctions such as anxiety and depression (See, Hurley, S. C. (2002) "Lamotrigine update and its use in mood disorders" *Ann Pharmacother* 36(5): 860-73).

Voltage gated Na channels comprise a gene family consisting of 9 different subtypes (NaV1.1-NaV1.9). As shown in Table A, these subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259(1): 213-6).

TABLE A (Abbreviations: CNS = central nervous system, PNS = peripheral nervous sytem, DRG = dorsal root ganglion, TG = Trigeminal ganglion):

| Na isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrythmia, long QT |
| NaV1.6 | CNS widespread, most abuntant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" *Pain* 87(1): 7-17.), bupivacaine, phenytoin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8.), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" *Annu Rev Physiol* 63: 871-94.). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$ induced hyperalgesia (See, Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" *Nat Neurosci* 2(6): 541-8.). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62.). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13.). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

In neuropathic pain states, there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See, Dib-Hajj, S. D., J. Fjell, et al. (1999) "Plasticity of sodium channel expression in DRG neurons in the chronic constriction injury model of neuropathic pain." *Pain* 83(3): 591-600.) The timecourse of the increase in NaV1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See, Cummins, T. R., F. Aglieco, et al. (2001) "Nav1.3 sodium channels: rapid repriming and slow closed-state inactivation display quantitative differences after expression in a mammalian cell line and in spinal sensory neurons" *J Neurosci* 21(16): 5952-61.). NaV1.3 is expressed in the central and peripheral systems of man. NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v)1.9 (NaN) in nociceptive primary afferent neurons." *J Neurosci* 22(17): 7425-33.). It has a slow rate of inactivation and left-shifted voltage dependence for activation (See, Dib-Hajj, S., J. A. Black, et al. (2002) "NaN/Nav1.9: a sodium channel with unique properties" *Trends Neurosci* 25(5): 253-9.). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma—evidence from immunocytochemistry" *Acta Neurochir* (*Wien*) 144(8): 803-10; discussion 810.). NaV1.6 and NaV1.7 are also expressed in dorsal root ganglion neurons and contribute to the small TTX sensitive component seen in these cells. NaV1.7 in particular may therefore be a potential pain target in addition to its role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" *Embo J* 14(6): 1084-90).

NaV1.1 (See, Sugawara, T., E. Mazaki-Miyazaki, et al. (2001) "Nav1.1 mutations cause febrile seizures associated with afebrile partial seizures." *Neurology* 57(4): 703-5.) and NaV1.2 (See, Sugawara, T., Y. Tsurubuchi, et al. (2001) "A missense mutation of the Na+ channel alpha II subunit gene Na(v)1.2 in a patient with febrile and afebrile seizures causes channel dysfunction" *Proc Natl Acad Sci U S A* 98(11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" *Novartis Found Symp* 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J Clin Invest* 99(7): 1714-20).

Several Na channel blockers are currently used or being tested in the clinic to treat epilepsy (See, Moulard, B. and D. Bertrand (2002) "Epilepsy and sodium channel blockers" *Expert Opin. Ther. Patents* 12(1): 85-91.); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant Na+ currents and inflammatory hyperalgesia." *Proc Natl Acad Sci U S A* 96(14): 7645-9), and neuropathic pain (See, Strichartz, G. R., Z. Zhou, et al. (2002) "Therapeutic concentrations of local anaesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See, An, R. H., R. Bangalore, et al. (1996) "Lidocaine block of LQT-3 mutant human Na+ channels" *Circ Res* 79(1): 103-8, and Wang, D. W., K. Yazawa, et al. (1997) "Pharmacological targeting of long QT mutant sodium channels" *J Clin Invest* 99(7): 1714-20); for neuroprotection (See, Taylor, C. P. and L. S. Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain." *Novartis Found Symp* 241: 189-201).

Various animal models with clinical significance have been developed for the study of sodium channel modulators for numerous different pain indications. E.g., malignant chronic pain, see, Kohase, H., et al., Acta Anaesthesiol Scand. 2004; 48(3):382-3; femur cancer pain (see, Kohase, H., et al., Acta Anaesthesiol Scand. 2004; 48(3):382-3); non-malignant chronic bone pain (see, Ciocon, J. O. et al., J Am Geriatr Soc. 1994; 42(6):593-6); rheumatoid arthritis (see, Calvino, B. et al., Behav Brain Res. 1987; 24(1):11-29); osteoarthritis (see, Guzman, R. E., et al., Toxicol Pathol. 2003; 31(6):619-24); spinal stenosis (see, Takenobu, Y. et al., J Neurosci Methods. 2001; 104(2):191-8); neuropathic low back pain (see, Hines, R., et al., Pain Med. 2002; 3(4):361-5; Massie, J. B., et al., J Neurosci Methods. 2004; 137(2):283-9); myofascial pain syndrome (see, Dalpiaz & Dodds, J Pain Palliat Care Pharmacother. 2002; 16(1):99-104; Sluka K A et al., Muscle Nerve. 2001; 24(1):37-46); fibromyalgia (see, Bennet & Tai, Int J Clin Pharmacol Res. 1995;15(3):115-9); temporomandibular joint pain (see, Ime H, Ren K, Brain Res Mol Brain Res. 1999; 67(1):87-97); chronic visceral pain, including abdominal (see, Al-Chaer, E. D., et al., Gastroenterology. 2000; 119(5): 1276-85); pelvic/perineal pain, (see, Wesselmann et al., Neurosci Lett. 1998; 246(2):73-6); pancreatic (see, Vera-Portocarrero, L. B., et al., Anesthesiology. 2003; 98(2):474-84); IBS pain (see, Verne, G. N., et al., Pain. 2003; 105(1-2):223-30; La J H et al., World Gastroenterol. 2003; 9(12):2791-5); chronic headache pain (see, Willimas & Stark, Cephalalgia. 2003; 23(10):963-71); migraine (see, Yamamura, H., et al., J Neurophysiol. 1999; 81(2):479-93); tension headache, including cluster headaches (see, Costa, A., et al., Cephalalgia. 2000; 20(2):85-91); chronic neuropathic pain, including post-herpetic neuralgia (see, Attal, N., et al., Neurology. 2004; 62(2):218-25; Kim & Chung 1992, Pain 50:355); diabetic neuropathy (see, Beidoun A et al., Clin J Pain. 2004; 20(3):174-8; Courteix, C., et al., Pain. 1993; 53(1):81-8); HIV-associated neuropathy (see, Portegies & Rosenberg, Ned Tijdschr Geneeskd. 2001; 145(15):731-5; Joseph E K et al., Pain. 2004; 107(1-2):147-58); Oh, S. B., et al., J Neurosci. 2001; 21(14):5027-35); trigeminal neuralgia (see, Sato, J., et al., Oral Surg Oral Med Oral Pathol Oral Radiol Endod. 2004; 97(1):18-22; Imamura Y et al., Exp Brain Res. 1997; 116(1):97-103); Charcot-Marie Tooth neuropathy (see, Sereda, M., et al., Neuron. 1996; 16(5):1049-60); hereditary sensory neuropathies (see, Lee, M. J., et al., Hum Mol Genet. 2003; 12(15):1917-25); peripheral nerve injury (see, Attal, N., et al., Neurology. 2004; 62(2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46(1):15-22; Devor & Raber, Behav Neural Biol. 1983; 37(2):276-83); ectopic proximal and distal discharges (see, Liu, X. et al., Brain Res. 2001; 900(1):119-27); radiculopathy (see, Devers & Galer, (see, Clin J Pain. 2000; 16(3):205-8; Hayashi N et al., Spine. 1998; 23(8):877-85); chemotherapy induced neuropathic pain (see, Aley, K. O., et al., Neuroscience. 1996; 73(1):259-65); radiotherapy-induced neuropathic pain; post-mastectomy pain (see, Devers & Galer, Clin J Pain. 2000; 16(3):205-8); central pain (Cahana, A., et al., Anesth Analg. 2004; 98(6):1581-4), spinal cord injury pain (see, Hains, B. C., et al., Exp Neurol. 2000; 164(2):426-37); post-stroke pain; thalamic pain (see, LaBuda, C. J., et al., Neurosci Lett. 2000; 290(1):79-83); complex regional pain syndrome (see, Wallace, M. S., et al., Anesthesiology. 2000; 92(1):75-83; Xantos D et al., J Pain. 2004; 5(3 Suppl 2):S1); phanton pain (see, Weber, W. E., Ned Tijdschr Geneeskd. 2001; 145(17):813-7; Levitt & Heyback, Pain. 1981; 10(1): 67-73); intractable pain (see, Yokoyama, M., et al., Can J Anaesth. 2002; 49(8):810-3); acute pain, acute post-operative pain (see, Koppert, W., et al., Anesth Analg. 2004; 98(4): 1050-5; Brennan, T. J., et al., Pain. 1996; 64(3):493-501); acute musculoskeletal pain; joint pain (see, Gotoh, S., et al., Ann Rheum Dis. 1993; 52(11):817-22); mechanical low back pain (see, Kehl, L. J., et al., Pain. 2000; 85(3):333-43); neck pain; tendonitis; injury/exercise pain (see, Sesay, M., et al., Can J Anaesth. 2002; 49(2):137-43); acute visceral pain, including abdominal pain; pyelonephritis; appendicitis; cholecystitis; intestinal obstruction; hernias; etc (see, Giambemardino, M. A., et al., Pain. 1995; 61(3):459-69); chest pain, including cardiac Pain (see, Vergona, R. A., et al., Life Sci. 1984; 35(18):1877-84); pelvic pain, renal colic pain, acute obstetric pain, including labor pain (see, Segal, S., et al., Anesth Analg. 1998; 87(4):864-9); cesarean section pain; acute inflammatory, bum and trauma pain; acute intermittent pain, including endometriosis (see, Cason, A. M., et al.,Horm Behav. 2003; 44(2):123-31); acute herpes zoster pain; sickle cell anemia; acute pancreatitis (see, Toma, H; Gastroenterology. 2000; 119(5):1373-81); breakthrough pain; orofacial pain, including sinusitis pain, dental pain (see, Nusstein, J., et al., J Endod. 1998; 24(7):487-91; Chidiac, J. J., et al., Eur J Pain. 2002; 6(l):55-67); multiple sclerosis (MS) pain (see, Sakurai & Kanazawa, J Neurol Sci. 1999; 162(2):162-8); pain in depression (see, Greene B, Curr Med Res Opin. 2003; 19(4):272-7); leprosy pain; behcet's disease pain; adiposis dolorosa (see, Devillers & Oranje, Clin Exp Dermatol. 1999; 24(3):240-1); phlebitic pain; Guillain-Barre pain; painful legs and moving toes; Haglund syndrome; erythromelalgia pain (see, Legroux-Crespel, E., et al., Ann Dermatol Venereol. 2003; 130(4):429-33); Fabry's disease pain (see, Germain, D. P., J Soc Biol. 2002;196(2):183-90); Bladder and urogenital disease, including urinary incontinence (see, Berggren, T., et al., J Urol. 1993; 150(5 Pt 1):1540-3); hyperactivity bladder (see, Chuang, Y. C., et al., Urology. 2003; 61(3): 664-70); painful bladder syndrome (see, Yoshimura, N., et al., J Neurosci. 2001; 21(21):8690-6); interstitial cyctitis (IC) (see, Giannakopoulos& Campilomatos, Arch Ital Urol Nefrol Androl. 1992; 64(4):337-9; Boucher, M., et al., J Urol. 2000; 164(1):203-8); and prostatitis (see, Mayersak, J. S., Int Surg. 1998; 83(4):347-9; Keith, I. M., et al., J Urol. 2001; 166(1): 323-8).

Voltage-gated calcium channels are membrane-spanning, multi-subunit proteins that open in response to membrane depolarization, allowing Ca entry from the extracellular milieu. Calcium channels were initially classified based on the time and voltage-dependence of channel opening and on the sensitivity to pharmacological block. The categories were low-voltage activated (primarily T-type) and high-voltage activated (L,N,P,Q or R-type). This classification scheme was replaced by a nomenclature based upon the molecular subunit composition, as summarized in Table B (Hockerman G H, Peterson B Z, Johnson B D, Catterall W A. 1997. *Annu Rev Pharmacol Toxicol* 37: 361-96; Striessnig J. 1999. *Cell Physiol Biochem* 9: 242-69). There are four primary subunit types that make up calcium channels—$\alpha_1$, $\alpha_2\delta$, $\beta$ and $\gamma$See, e.g., De Waard et al. Structural and functional diversity of voltage-activated calcium channels. In Ion Channels, (ed. T. Narahashi) 41-87, (Plenum Press, New York, 1996)). The $\alpha_1$ subunit is the primary determinant of the pharmacological properties and contains the channel pore and voltage sensor (Hockerman et al., 1997; Striessnig, 1999). Ten isoforms of the etl subunit are known, as indicated in Table I below. The $\alpha_2\delta$ subunit consists of two disulfide linked subunits, $\alpha_2$, which is primarily extracellular, and a transmembrane $\delta$ subunit. Four isoforms of $\alpha_2\delta$ are known, $\alpha_2\delta$-1, $\alpha_2\delta$-2, $\alpha_2\delta$-3 and $\alpha_2\delta$-4. The $\beta$ subunit is a non-glycosylated cytoplasmic protein that binds to the a, subunit. Four isoforms are known, termed $\beta_1$ to $\beta_4$. The ysubunit is a transmembrane protein that has been biochemically isolated as a component of $Ca_v1$ and $Ca_v2$ channels. At least 8 isoforms are known ($\gamma_1$ to $\gamma_8$) [Kang M G, Campbell K P. 2003. *J Biol Chem* 278: 21315-8]. The nomenclature for voltage-gated calcium channels is based upon the content of the $\alpha_1$ subunit, as indicated in Table B. Each type of $\alpha_1$, subunit can associate with a variety of $\beta$, $\alpha_2\delta$ or $\gamma$ subunits, so that each $Ca_v$ type corresponds to many different combinations of subunits.

TABLE B

| Cav Nomenclature | $\alpha_1$ subunit | Pharmacological name |
| --- | --- | --- |
| $Ca_v1.1$ | $\alpha_{1S}$ | L-type |
| $Ca_v1.2$ | $\alpha_{1C}$ | L-type |
| $Ca_v1.3$ | $\alpha_{1D}$ | L-type |
| $Ca_v1.4$ | $\alpha_{1F}$ | |
| $Ca_v2.1$ | $\alpha_{1A}$ | P- or Q-type |
| $Ca_v2.2$ | $\alpha_{1B}$ | N-type |
| $Ca_v2.3$ | $\alpha_{1E}$ | R-type |
| $Ca_v3.1$ | $\alpha_{1G}$ | T-type |
| $Ca_v3.2$ | $\alpha_{1H}$ | T-type |
| $Ca_v3.3$ | $\alpha_{1I}$ | T-type |

$Ca_v2$ currents are found almost exclusively in the central and peripheral nervous system and in neuroendocrine cells and constitute the predominant forms of presynaptic voltage-gated calcium current. Presynaptic action potentials cause channel opening, and neurotransmitter release is steeply dependent upon the subsequent calcium entry. Thus, $Ca_v2$ channels play a central role in mediating neurotransmitter release.

$Ca_v2.1$ and $Ca_v2.2$ contain high affinity binding sites for the peptide toxins ω-conotoxin-MVIIC and ω-conotoxin-GVIA, respectively, and these peptides have been used to determine the distribution and function of each channel type. $Ca_v2.2$ is highly expressed at the presynaptic nerve terminals of neurons from the dorsal root ganglion and neurons of lamina I and II of the dorsal horn (Westenbroek R E, Hoskins L, Catterall W A. 1998. *J Neurosci* 18: 6319-30; Cizkova D, Marsala J, Lukacova N, Marsala M, Jergova S, et al. 2002. *Exp Brain Res* 147: 456-63). $Ca_v2.2$ channels are also found in presynaptic terminals between second and third order interneurons in the spinal cord. Both sites of neurotransmission are very important in relaying pain information to the brain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain, on the other hand, may last for much longer periods of time and its intensity is more graded. Inflammation may occur for many reasons including tissue damage, autoimmune response, and pathogen invasion. Inflammatory pain is mediated by an "inflammatory soup" that consists of substance P, histamines, acid, prostaglandin, bradykinin, CGRP, cytokines, ATP, and neurotransmitter release. The third class of pain is neuropathic and involves nerve damage that results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX2 inhibitors, opioids, tricyclic antidepressants, and anticonvulsants. Neuropathic pain has been particularly difficult to treat as it does not respond well to opiods until high doses are reached. Gabapentin is currently the favored therapeutic for the treatment of neuropathic pain although it works in only 60% of patients where it shows modest efficacy. The drug is however very safe and side effects are generally tolerable although sedation is an issue at higher doses.

Validation of Cav2.2 as a target for the treatment of neuropathic pain is provided by studies with ziconotide (also known as ω-conotoxin-MVIIA), a selective peptide blocker of this channel (Bowersox S S, Gadbois T, Singh T, Pettus M, Wang Y X, Luther R R. 1996. *J Pharmacol Exp Ther* 279: 1243-9; Jain K K. 2000. *Exp. Opin. Invest. Drugs* 9: 2403-10; Vanegas H, Schaible H. 2000. *Pain* 85: 9-18). In man, intrathecal infusion of Ziconotide is effective for the treatment of intractable pain, cancer pain, opioid resistant pain, and neuropathic pain. The toxin has an 85% success rate for the treatment of pain in humans with a greater potency than morphine. An orally available antagonist of $Ca_v2.2$ should have similar efficacy without the need for intrathecal infusion. $Ca_v2.1$ and $Ca_v2.3$ are also in neurons of nociceptive pathways and antagonists of these channels could be used to treat pain.

Antagonists of $Ca_v2.1$, $Ca_v2.2$ or $Ca_v2.3$ should also be useful for treating other pathologies of the central nervous system that apparently involve excessive calcium entry. Cerebral ischaemia and stroke are associated with excessive calcium entry due to depolarization of neurons. The $Ca_v2.2$ antagonist ziconotide is effective in reducing infarct size in a focal ischemia model using laboratory animals, suggesting that Ca$_v$2.2 antagonists could be used for the treatment of stroke. Likewise, reducing excessive calcium influx into neurons may be useful for the treatment of epilepsy, traumatic brain injury, Alzheimer's disease, multi-infarct dementia and other classes of dementia, amyotrophic lateral sclerosis, amnesia, or neuronal damage caused by poison or other toxic substances.

Ca$_v$2.2 also mediates release of neurotransmitters from neurons of the sympathetic nervous system and antagonists could be used to treat cardiovascular diseases such as hypertension, cardiac arrhythmia, angina pectoris, myocardial infarction, and congestive heart failure.

Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel and Ca channel antagonists, preferably those with higher potency and fewer side effects. Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel and Ca channel antagonists, preferably those with higher potency and fewer side effects.

SUMMARY OF THE INVENTION

In general, the invention relates to compounds useful as ion channel modulators. It has now been found that compounds of this invention, and pharmaceutically acceptable compositions thereof, are useful as inhibitors of voltage-gated sodium channels. These compounds have the general formula I:

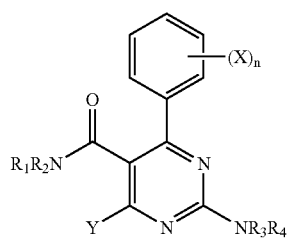

or a pharmaceutically acceptable salt thereof, wherein R$_1$, R$_2$, R$_3$, R$_4$, X, Y and n are described generally below.

In another aspect, compounds of this invention, and pharmaceutically acceptable compositions thereof, are useful as inhibitors of voltage-gated sodium channels and/or calcium channels. These compounds have the general formula Ia:

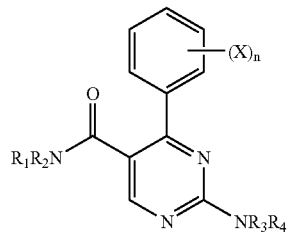

or a pharmaceutically acceptable salt thereof, wherein R$_1$, R$_2$, R$_3$, R$_4$, X, and n are described generally below.

The present invention also includes methods for treating or lessening the severity of a disease, condition, or disorder where activation or hyperactivity of calcium and/or sodium ion channels is implicated in the disease state. Methods for treating or lessening the severity of a pain condition are also disclosed. In one aspect, the method comprises the step of administering to the patient an effective amount of a pharmaceutical composition comprising at least one compound of the present invention.

The compounds of the present invention are useful for treating or lessening the severity of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

I. DEFINITIONS

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "modulating" as used herein means increasing or decreasing, e.g. activity, by a measurable amount. Compounds that modulate ion channel activity, such as calcium ion channel activity and/or sodium ion channel activity, by increasing the activity of the ion channel, e.g., a calcium ion channel and/or a sodium ion channel, are called agonists. Compounds that modulate ion channel activity, such as calcium ion channel activity and/or sodium ion channel activity, by decreasing the activity of the ion channel, e.g., calcium ion channel and/or sodium ion channel, are called antagonists. An agonist interacts with an ion channel, such as calcium ion channel, to increase the ability of the receptor to transduce an intracellular signal in response to endogenous ligand binding. An antagonist interacts with an ion channel and competes with the endogenous ligand(s) or substrate(s) for binding site(s) on the receptor to decrease the ability of the receptor to transduce an intracellular signal in response to endogenous ligand binding.

The phrase "treating or reducing the severity of an ion channel mediated disease" refers both to treatments for diseases that are directly caused by ion channel activities and alleviation of symptoms of diseases not directly caused by ion channel activities. Examples of diseases whose symptoms may be affected by ion channel activities include, but are not limited to, acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be optionally substituted with one or more substituents such as halo, cycloalkyl, heterocycloalkyl, aryl, heteroaryl, alkoxy, aroyl, heteroaroyl, alkoxycarbonyl, alkoxycarbonylamino, alkylcarbonyloxy, nitro, cyano, amino, acyl, sulfonyl, sulfinyl, sulfanyl, sulfoxy, urea, thiourea, sulfamoyl, sulfamide, oxo, carbamoyl, cycloalkyloxy, heterocycloalkyloxy, aryloxy, heteroaryloxy, aralkyloxy, heteroarylalkoxy, or hydroxyl.

As used herein, an "alkenyl" group refers to an aliphatic carbon group that contains 2-10 (e.g., 2, 3, 4, 5, 6, 7, 8, 9 or 10) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group may be optionally substituted with one or more substituents such as halo, cycloalkyl, heterocycloalkyl, aryl, heteroaryl, alkoxy, aroyl, heteroaroyl, alkoxycarbonyl, alkylcarbonyloxy, nitro, cyano, amino, acyl, sulfonyl, sulfinyl, sulfanyl, sulfoxy, urea, thiourea, sulfamoyl, sulfamide, oxo, carbamoyl, cycloalkyloxy, heterocycloalkyloxy, aryloxy, heteroaryloxy, aralkyloxy, heteroarylalkoxy, or hydroxyl.

As used herein, an "alkynyl" group refers to an aliphatic carbon group that contains 2-8 (e.g., 2-6 or 2-4) carbon atoms and at least one triple bond. Like an alkyl group, an alkynyl group can be straight or branched. An alkynyl group may be optionally substituted with one or more substituents such as halo, cycloalkyl, heterocycloalkyl, aryl, heteroaryl, alkoxy, aroyl, heteroaroyl, alkoxycarbonyl, alkylcarbonyloxy, nitro, cyano, amino, acyl, sulfonyl, sulfinyl, sulfanyl, sulfoxy, urea, thiourea, sulfamoyl, sulfamide, oxo, carbamoyl, cycloalkyloxy, heterocycloalkyloxy, aryloxy, heteroaryloxy, aralkyloxy, heteroarylalkoxy, or hydroxyl.

As used herein, an "amino" group refers to —NR$^X$R$^Y$ wherein each of R$^X$ and R$^Y$ is independently hydrogen, alkyl, cycloalkyl, sulfonyl, (cycloalkyl)alkyl, aryl, aralkyl, heterocycloalkyl, (heterocycloalkyl)alkyl, heteroaryl, or heteroaralkyl each of which are defined herein and are optionally substituted. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); tricyclic (e.g., fluorenyl, tetrahydrofluorenyl, anthracenyl, or tetrahydroanthracenyl); or a benzofused group having 3 rings. For example, a benzofused group includes phenyl fused with two or more C$_{4-8}$ carbocyclic moieties. An aryl is optionally substituted with one or more substituents including aliphatic (e.g., alkyl, alkenyl, or alkynyl); cycloalkyl; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; amino; aminoalkyl; nitro; —C(O)OH; carbonyl (e.g., alkoxycarbonyl, alkylcarbonyl, aminocarbonyl, (alkylamino)alkylaminocarbonyl, arylaminocarbonyl, heteroarylaminocarbonyl, ; or sulfonylcarbonyl); aralkylcarbonyloxy; sulfonyl (e.g., alkylsulfonyl or aminosulfonyl); sulfinyl (e.g., alkylsulfinyl); sulfanyl (e.g., alkylsulfanyl); cyano; halo; hydroxyl; acyl; mercapto; sulfoxy, urea, thiourea, sulfamoyl, sulfamide, oxo, or carbamoyl. Alternatively, an aryl may be unsubstituted.

Examples of substituted aryls include haloaryl, alkoxycarbonylaryl, alkylaminoalkylaminocarbonylaryl, p, m-dihaloaryl, p-amino-p-alkoxycarbonylaryl, m-amino-m-cyanoaryl, aminoaryl, alkylcarbonylaminoaryl, cyanoalkylaryl, alkoxyaryl, aminosulfonylaryl, alkylsulfonylaryl, aminoaryl, p-halo-m-aminoaryl, cyanoaryl, hydroxyalkylaryl, alkoxyalkylaryl, hydroxyaryl, carboxyalkylaryl, dialkylaminoalkylaryl, m-heterocycloaliphatic-o-alkylaryl, heteroarylaminocarbonylaryl, nitroalkylaryl, alkylsulfonylaminoalkylaryl, heterocycloaliphaticcarbonylaryl, alkylsulfonylalkylaryl, cyanoalkylaryl, heterocycloaliphaticcarbonylaryl, alkylcarbonylaminoaryl, hydroxyalkylaryl, alkylcarbonylaryl, aminocarbonylaryl, alkylsulfonylaminoaryl, dialkylaminoaryl, alkylaryl, and trihaloalkylaryl.

As used herein, an "araliphatic" group refers to an aliphatic group (e.g., a C$_{1-4}$ alkyl group, a C$_{1-4}$ alkenyl group, or a C$_{1-4}$ alkynyl group) that is substituted with an aryl group. Both "aliphatic" and "aryl" have been defined above.

As used herein, an "aralkyl" group refers to an alkyl group (e.g., a C$_{1-4}$ alkyl group) that is substituted with an aryl group. Both "alkyl" and "aryl" are defined herein. An example of an aralkyl group is benzyl.

As used herein, a "bicyclic ring system" includes 7-12 (e.g., 9, 10, or 11) membered structures that form two rings, wherein the two rings have at least one atom in common (e.g., 2 atoms in common). Bicyclic ring structures include bicycloaliphatics (e.g., bicycloalkyl or bicycloalkenyl), bicycloheteroaliphatics (e.g., bicycloheteroalkyl or bicycloheteroalkenyl), bicyclic aryls, and bicyclic heteroaryls.

The term "cycloaliphatic" means a saturated or partially unsaturated monocyclic, bicyclic, or tricyclic hydrocarbon ring that has a single point of attachment to the rest of the molecule. Cycloaliphatic rings are 3-8 membered monocyclic rings (e.g., 3-6 membered rings). Cycloaliphatic rings also include 8-12 membered bicyclic hydrocarbon rings, (e.g., 10 membered bicyclic hydrocarbon rings). A cycloaliphatic group encompasses a "cycloalkyl" group and a "cycloalkenyl" group.

As used herein, a "cycloalkyl" group refers to a saturated carbocyclic mono-, bi-, or tri-, or multicyclic (fused or bridged) ring of 3-10 (e.g., 5-10) carbon atoms. Without limitation, examples of monocyclic cycloalkyl groups include cyclopropyl, cyclobutyl, cyclopentyl, cyclohexyl, cycloheptyl, or the like. Without limitation, examples of bicyclic cycloalkyl groups include octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, bicyclo[2.2.1]heptanyl, bicyclo[3.1.1]heptanyl, or the like. Without limitation, multicyclic groups include adamantyl, cubyl, norbornyl, or the like. Cycloalkyl rings can be optionally substituted at any chemically viable ring position.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, and bicyclo[3.3.1]nonenyl. Cycloalkenyl ring structures can be optionally substituted at any chemically viable position on the ring or rings.

A cycloalkyl or cycloalkenyl group can be optionally substituted with one or more substituents such as aliphatic (e.g., alkyl, alkenyl, or alkynyl), cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxyl, acyl, mercapto, sulfonyl (e.g., alkylsulfonyl or arylsulfonyl), sulfinyl (e.g., alkylsulfinyl), sulfanyl (e.g., alkylsulfanyl), sulfoxy, urea, thiourea, sulfamoyl, sulfamide, oxo, carbamoyl, or the like.

Without limitation, examples of substituted cycloaliphatics include alkylcycloalkyl (e.g., propylcyclohexyl), alkylbicyclo[3.1.1]heptyl, alkylcycloalkenyl, or the like.

As used herein, the term "heterocycloaliphatic" and "heterocyclic" encompasses a heterocycloalkyl group and a heterocycloalkenyl group.

As used herein, a "heterocycloalkyl" group refers to a 3-10 membered mono or bicyclic (fused or bridged) (e.g., 5 to 10 membered mono or bicyclic) saturated ring structure, in which one or more of the ring atoms is a heteroatom (e.g., N, O, S, or combinations thereof). Examples of a heterocycloalkyl group include optionally substituted piperidinyl, piperazinyl, tetrahydropyranyl, tetrahydrofuranyl, 1,4-dioxolanyl, 1,4-dithianyl, 1,3-dioxolanyl, oxazolidyl, isoxazolidyl, morpholinyl, thiomorpholinyl, octahydro-benzofuranyl, octahydro-chromenyl, octahydro-thiochromenyl, octahydro-indolyl, octahydro-pyrindinyl, decahydro-quinolinyl, octahydro-benzo[b]thiophenyl, 2-oxa-bicyclo[2.2.2] octyl, 1-aza-bicyclo[2.2.2]octyl, 3-aza-bicyclo[3.2.1]octanyl, 2,6-dioxa-tricyclo[3.3.1.0$^{3,7}$]nonyl, tropane. A monocyclic heterocycloalkyl group may be fused with a phenyl moiety such as tetrahydroisoquinoline. Heterocycloalkyl ring structures can be optionally substituted at any chemically viable position on the ring or rings.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Examples of heterocycloalkenyls include 2-pyrrolyl, 3-pyrrolyl, 2-imidazolyl, or 2-pyrazolyl.

Monocyclic heterocycloaliphatics are numbered according to standard chemical nomenclature. For instance:

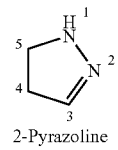

2-Pyrazoline

Heterocycloalkenyl ring structures can be optionally substituted at any chemically viable position on the ring or rings.

A heterocycloalkyl or heterocycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl (such as a benzimidazolidinyl), (heterocycloalkyl)alkyl, aryl, heteroaryl, alkoxy (two alkoxy groups on the same atom or adjacent atoms may form a ring together with the atom(s) to which they are bound), cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxyl, acyl, mercapto, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, or carbamoyl.

Without limitation, examples of substituted heterocycloaliphatics include alkoxycarbonylheterocycloalkyl (e.g., ethoxycarbonyltropane), alkoxycarbonylheterocycloalkyl (e.g., ethoxycarbonylpiperidyl), or the like.

A "heteroaryl" group, as used herein, refers to a monocyclic, bicyclic, or tricyclic ring structure having 4 to 15 ring atoms wherein one or more of the ring atoms is a heteroatom (e.g., N, O, S, or combinations thereof) and wherein one or more rings of the bicyclic or tricyclic ring structure is aromatic. A heteroaryl group includes a benzofused ring system having 2 to 3 rings. For example, a benzofused group includes benzo fused with one or two $C_{4-8}$ heterocyclic moieties (e.g., indolizyl, indolyl, isoindolyl, 3H-indolyl, indolinyl, benzo[b] furyl, benzo[b]thiophenyl, quinolinyl, or isoquinolinyl). Some examples of heteroaryl are azetidinyl, pyridinyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo [1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pyranyl, pyridinyl, pyridazinyl, pyrimidyl, pyrazolyl, pyrazyl, or 1,3,5-triazyl. Monocyclic heteroaryls are numbered according to standard chemical nomenclature. For instance:

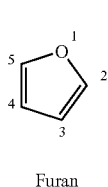 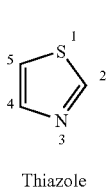 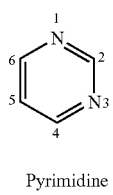

Furan　　　Thiazole　　　Pyrimidine

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature. For instance:

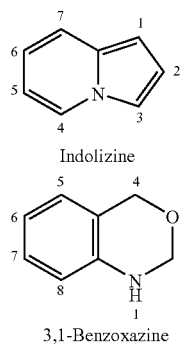 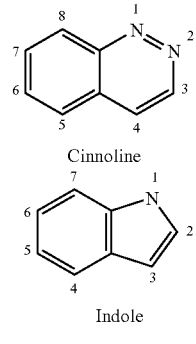

Indolizine　　　　　Cinnoline

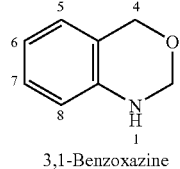

3,1-Benzoxazine　　　　Indole

Quinoxaline

A heteroaryl is optionally substituted with one or more substituents such as aliphatic including alkyls (e.g., alkoxyalkyl, carboxyalkyl, hydroxyalkyl, oxoalkyl, aralkyl, (alkylsulfonylamino)alkyl, (sulfonylamino)alkyl, cyanoalkyl, aminoalkyl, oxoalkyl, alkoxycarbonylalkyl, (cycloalkyl)alkyl heterocycloalkyl, (heterocycloalkyl)alkyl aralkyl, and haloalkyl such as trifluoromethyl), alkenyl, alkynyl; cycloaliphatic including cycloalkyl (e.g., cyclopropyl, cyclobutyl, cyclopentyl, and cyclohexyl); heterocycloaliphatic including heterocycloalkyl (e.g., thiomorpholinyl, piperazinyl, 1,3,5-trithianyl, morpholinyl, pyrrolyl, 1,3-dioxolanyl, pyrazolidyl, or piperidinyl); aryl, heteroaryl (e.g., quinolyl, indolyl, 3H-indolyl, isoindolyl, benzo[b]-4H-pyranyl, cinnolyl, quinoxylyl, benzimidazyl, benzo-1,2,5-thiadiazolyl, benzo-1,2,5-oxadiazolyl, or benzthiophenyl); alkoxy; cycloalkyloxy; heterocycloalkyloxy; aryloxy; heteroaryloxy; aralkyloxy; heteroaralkyloxy; aroyl; heteroaroyl; amino (e.g., carbonylamino, alkylcarbonylamino, alkylsulfonylamino, arylcarbonylamino, cycloalkylcarbonylamino, arylcarbonylamino, heteroarylcarbonylamino, (heterocycloalkyl)carbonylamino, (cycloalkyl)alkylcarbonylamino, sulfanylamino, and (heterocycloalkyl)alkylcarbonylamino); nitro; carboxy; carbonyl (e.g., alkylcarbonyl, alkoxycarbonyl, aminocarbonyl, arylaminocarbonyl, thiazoleaminocarbonyl, thiomorpholinecarbonyl, aminoalkylaminocarbonyl); alkylcarbonyloxy; cyano; halo; hydroxyl; acyl; mercapto; sulfonyl (e.g., aminosulfonyl, alkylsulfonyl, morpholinesulfonyl, or arylsulfonyl); sulfinyl (e.g., alkylsulfinyl); sulfanyl (e.g., alkylsulfanyl); sulfoxy; urea; thiourea; sulfamoyl; sulfamide; oxo; or carbamoyl.

A "heteroaraliphatic" group, as used herein, refers to an aliphatic group (e.g., $C_{1-4}$ alkyl group, $C_{1-4}$ alkenyl group, or $C_{1-4}$ alkynyl group) that is substituted with a heteroaryl group. Both "aliphatic" and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic moiety" includes cycloalkyl, heterocycloalkyl, cycloalkenyl, heterocycloalkenyl, aryl, or heteroaryl, each of which has been defined previously.

As used herein, "cyclic group" includes mono-, bi-, and tri-cyclic structures including cycloaliphatic, heterocycloaliphatic, aryl, or heteroaryl, each of which has been previously defined.

As used herein, an "acyl" group refers to a formyl group or alkyl-C(=O)— (also referred to as "alkylcarbonyl") where "alkyl" has been defined previously. Acetyl and pivaloyl are examples of acyl groups.

As used herein, a "carbonyl" group, when used alone or as part of another structure refers to the structure —C(O)—.

As used herein, a "carbamoyl" group refers to a group having the structure —O—CO—$NR^XR^Y$ or —$NR^X$—CO—O—$R^Z$ wherein $R^X$ and $R^Y$ have been defined above and $R^Z$ can be alkyl, aryl, aralkyl, heterocycloalkyl, heteroaryl, or heteroaralkyl.

As used herein, a "carboxy" and a "sulfo" group refer to —C(O)OH or —C(O)$OR^X$ and —$SO_3H$ or —$SO_3R^X$, respectively.

As used herein, an "alkoxy" group refers to an alkyl-O— group where "alkyl" has been defined previously. Moreover an alkoxy group includes structures comprising two alkoxy groups on the same atom or adjacent atoms that form a ring together with the atom(s) to which they are bound.

As used herein, a "sulfoxy" group refers to —O—SO—$R^X$ or —SO—O—$R^X$, where $R^X$ has been defined above.

As used herein, a "mercapto" group refers to —SH.

As used herein, a "sulfonyl" group refers to —$S(O)_2$—.

As used herein a "sulfinyl" group refers to —S(O)—.

As used herein a "sulfanyl" group refers to —S—.

As used herein, a "halogen" or "halo" group refers to fluorine, chlorine, bromine or iodine.

As used herein, a "haloaliphatic" group refers to an aliphatic group substituted with 1-3 halogen. For instance, the term haloalkyl includes the group —$CF_3$.

As used herein, a "sulfamoyl" group refers to the structure —$S(O)_2$—$NR^XR^Y$ or —$NR^X$—$S(O)_2$—$R^Z$ wherein $R^X$, $R^Y$, and $R^Z$ have been defined above.

As used herein, a "sulfamide" group refers to the structure —$NR^X$—$S(O)_2$—$NR^YR^Z$ wherein $R^X$, $R^Y$, and $R^Z$ have been defined above.

As used herein, a "carbonylamino" group used alone or in connection with another group refers to an amido group such as $R^X$—C(O)—$NR^X$. For instance an alkylcarbonylamino includes alkyl-C(O)—$NR^X$—, wherein Rx has been defined above.

As used herein, a "aminocarbonyl" group used alone or in connection with another group refers to an amido group such as $N(R^X)_2$—C(O)—.

As used herein, an "alkoxycarbonyl" used alone or in connection with another group refers to a carbonyl group such as alkyl-O—C(O)—.

As used herein, an "alkoxyalkyl" refers to an alkyl group such as alkyl-O-alkyl-, wherein alkyl has been defined above.

As used herein, an "aminocarbonyl" refers to an amido group such as —NR$^X$—C(O)—, wherein R$^X$ has been defined above.

As used herein, an "aminosulfonyl" refers to the structure —N(R$^X$)$_2$—S(O)$_2$—, wherein R$^X$ has been defined above.

As used herein, an "oxo" refers to =O.

As used herein, an "aminoalkyl" refers to the structure N(R$^X$)$_2$-alkyl-.

As used herein, a "cyanoalkyl" refers to the structure (CN)-alkyl-.

As used herein, an "alkylsulfonyl" group refers to the structure alkyl-S(O)$_2$—.

As used herein, a "sulfonylamino" group refers to the structure R$^X$—S(O)$_2$—N(R$^X$)$_2$—, wherein R$^X$ has been defined above.

As used herein, a "guanidinyl" group refers to the structure NH$_2$C(NH)NH—.

As used herein, an "aliphatic chain" refers to a branched or straight aliphatic group. A straight aliphatic chain has the structure —[CH$_2$]$_p$—, where p is 1-6. A branched aliphatic chain is a straight aliphatic chain that is substituted with one or more aliphatic groups. A branched aliphatic chain has the structure —[CHW]$_p$— where W is hydrogen or an aliphatic group; however, W shall be an aliphatic group in at least one instance.

As used herein, a "urea" group refers to the structure —NR$^X$—CO—NR$^Y$R$^Z$ and a "thiourea" group refers to the structure —NR$^X$—CS—NR$^Y$R$^Z$. R$^X$, Ry, and R$^Z$ have been defined above.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group may have a substituent at each substitutable position of the group, and when more than one position in any given structure may be substituted with more than one substituent selected from a specified group, the substituent may be either the same or different at every position. A ring substituent, such as a heterocycloalkyl, may be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

II. Compounds

A. Generic Compounds

The present invention provides a method of modulating a sodium ion channel comprising the step of contacting said ion channel with a compound of formula I:

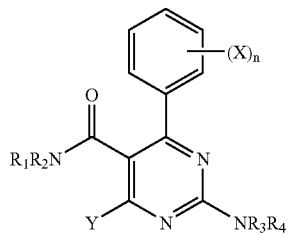

I or a pharmaceutically acceptable salt thereof.

Each X is defined by -Z$^A$R$_6$, wherein each Z$^A$ is independently a bond or an optionally substituted branched or straight C$_{1-6}$ aliphatic chain wherein up to two carbon units of Z$^A$ are optionally and independently replaced by —CO—, —CS—, —COCO—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$NR$^A$CO—, —NR$^A$CO—, —S—, —SO—, —SO$_2$—, —NR$^A$—, —SO$_2$NR$^A$—, —NR$^A$SO$_2$—, or —NR$^A$SO$_2$NR$^A$—.

Each R$_6$ is independently R$^A$, halo, —OH, —NH$_2$, —NO$_2$, —CN, —CF$_3$, or —OCF$_3$.

Each R$^A$ is independently hydrogen, an optionally substituted C$_{1-8}$ aliphatic group; a 3-8 membered optionally substituted fully saturated, partially unsaturated, or fully unsaturated monocyclic ring having 0-3 heteroatoms independently selected from nitrogen, oxygen, or sulfur; an 8-12 membered optionally substituted fully saturated, partially unsaturated, or fully unsaturated bicyclic ring system having 0-5 heteroatoms independently selected from nitrogen, oxygen, or sulfur; or two occurrences of R$^A$ are taken together with the atom(s) to which they are attached to form an optionally substituted 3-12 membered fully saturated, partially unsaturated, or fully unsaturated monocyclic or bicyclic ring having 0-4 heteroatoms independently selected from nitrogen, oxygen, or sulfur.

Each n is 1-4.

Each $R_1$ and $R_2$ is defined by —$Z^B R_7$, wherein each $Z^B$ is independently a bond or an optionally substituted straight or branched $C_{1-6}$ aliphatic chain wherein up to two carbon units of $Z^B$ are optionally and independently replaced by —CO—, —CS—, —COCO—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$NR$^B$CO—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—.

Each $R_7$ is independently $R^B$, halo, —OH, —NHC(NH)NH$_2$, —NH$_2$, —NO$_2$, —CN, —CF$_3$, or —OCF$_3$.

Each $R^B$ is independently hydrogen, an optionally substituted $C_{1-8}$ aliphatic group, an optionally substituted 3-8 membered fully saturated, partially unsaturated, or fully unsaturated monocyclic ring having 0-3 heteroatoms independently selected from nitrogen, oxygen, or sulfur; an optionally substituted 8-12 membered fully saturated, partially unsaturated, or fully unsaturated bicyclic ring system having 0-5 heteroatoms independently selected from nitrogen, oxygen, or sulfur; or two occurrences of $R^B$ are taken together with the atom(s) to which they are attached to form an optionally substituted 3-12 membered fully saturated, partially unsaturated, or fully unsaturated monocyclic or bicyclic ring having 1-4 heteroatoms independently selected from nitrogen, oxygen, or sulfur.

Each $R_3$ and $R_4$ is defined by —$Z^C R_8$, wherein each $Z^C$ is independently a bond or an optionally substituted straight or branched $C_{1-6}$ aliphatic chain wherein up to two carbon units of $Z^C$ are optionally and independently replaced by —CO—, —CS—, —COCO—, —CONR$^C$—, —CONR$^C$NR$^C$—, —CO$_2$—, —OCO—, —NR$^C$O$_2$—, —O—, —NR$^C$CONR$^C$—, —OCONR$^C$—, —NR$^C$NR$^C$—, —NR$^C$NR$^C$CO—, —NR$^C$CO—, —S—, —SO—, —SO$_2$—, —NR$^C$—, —SO$_2$NR$^C$—, —NR$^C$SO$_2$—, or —NR$^C$SO$_2$NR$^C$—

Each $R_8$ is independently $R^C$, halo, —OH, —NH$_2$, —NO$_2$, —CN, —CF$_3$, or —OCF$_3$.

Each $R^C$ is independently hydrogen, or an optionally substituted $C_{1-8}$ aliphatic group, an optionally substituted 3-8 membered fully saturated, partially unsaturated, or fully unsaturated monocyclic ring having 0-3 heteroatoms independently selected from nitrogen, oxygen, or sulfur; an optionally substituted 8-12 membered fully saturated, partially unsaturated, or fully unsaturated bicyclic ring system having 0-5 heteroatoms independently selected from nitrogen, oxygen, or sulfur; or two occurrences of $R^C$ are taken together with the atom(s) to which they are attached to form an optionally substituted 3-12 membered saturated, partially unsaturated, or fully unsaturated monocyclic or bicyclic ring having 1-4 heteroatoms independently selected from nitrogen, oxygen, or sulfur.

Each Y is hydrogen or unsubstituted $C_{1-3}$ alkyl.

B. Specific Embodiments

1. Substituents $R_1$ and $R_2$

Each $R_1$ and $R_2$ are defined by —$Z^B R_7$, wherein each $Z^B$ is independently a bond, or an optionally substituted straight or branched $C_{1-6}$ aliphatic chain wherein up to two carbon units of $Z^B$ are optionally and independently replaced by —CO—, —CS—, —COCO—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$NR$^B$CO—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—.

Each $R_7$ is independently $R^B$, halo, —OH, —NHC(NH)NH$_2$, —NH$_2$, —NO$_2$, —CN, —CF$_3$, or —OCF$_3$.

Each $R^B$ is independently hydrogen, an optionally substituted $C_{1-8}$ aliphatic group, an optionally substituted 3-8 membered fully saturated, partially unsaturated, or fully unsaturated monocyclic ring having 0-3 heteroatoms independently selected from nitrogen, oxygen, or sulfur; an optionally substituted 8-12 membered fully saturated, partially unsaturated, or fully unsaturated bicyclic ring system having 0-5 heteroatoms independently selected from nitrogen, oxygen, or sulfur; or two occurrences of $R^B$ are taken together with the atom(s) to which they are attached to form an optionally substituted 3-12 membered fully saturated, partially unsaturated, or fully unsaturated monocyclic or bicyclic ring having 1-4 heteroatoms independently selected from nitrogen, oxygen, or sulfur, each of which is optionally substituted with 1 to 3 substituents.

In several embodiments, $R_1$ and $R_2$ are independently hydrogen; or $C_{1-8}$ aliphatic, aralphatic, heteroaralkyl, alkoxyalkyl, heterocycloaliphatic, guanidinylalkyl, aryloxyalkyl, $C_{1-6}$ cycloaliphatic; or $R_1$ and $R_2$ together with the nitrogen atom to which they are attached form an optionally substituted 5-8 membered fully saturated, partially unsaturated, or fully unsaturated heterocyclic ring.

In several other embodiments, one of $R_1$ and $R_2$ is an optionally substituted araliphatic or arylcycloaliphatic. Several examples of $R_1$ or $R_2$ include —$C_{1-3}$ aliphatic-aryl that is optionally substituted. In another set of examples, $R_1$ or $R_2$ is optionally substituted arylcycloalkyl (e.g., -cyclopropyl-aryl, -cyclobutyl-aryl, -cyclopentyl-aryl, or the like). In still other examples, $R_1$ or $R_2$ is optionally substituted monocyclic or bicyclic aralkyl. Several more examples of $R_1$ or $R_2$ include optionally substituted —$C_{1-3}$ aliphatic-phenyl (e.g., phenylmethyl, phenylethyl, phenylpropyl). In other examples, $R_1$ or $R_2$ is optionally substituted bicyclic —$C_{1-3}$ aliphatic-aryl (e.g., —$C_{1-3}$ aliphatic-naphthyl or —$C_{1-3}$ aliphatic-indenyl). In other examples, $R_1$ or $R_2$ is a naphthylmethyl, naphthylethyl, naphthylpropyl, indenylmethyl, indenylethyl, or indenylpropyl, each of which is optionally substituted. In other examples, $R_1$ or $R_2$ is an unsubstituted naphthylmethyl, naphthylethyl, naphthylpropyl, indenylmethyl, indenylethyl, or indenylpropyl. In several embodiments, $R_1$ or $R_2$ is a substituted aralkyl or arylcycloalkyl. For example, $R_1$ or $R_2$ is an aralkyl that is substituted at any chemically feasible position along the aliphatic chain, or on the aryl group. In several embodiments, $R_1$ or $R_2$ is substituted with 1-3 of halo, hydroxy, cyano, nitro, aliphatic, haloaliphatic, alkylamino, cycloaliphatic, heterocycloaliphatic, (heterocycloaliphatic)alkyl, aminocarbonyl, aryl, heteroaryl, or combinations thereof, each of which is optionally substituted. In one embodiment, $R_1$ or $R_2$ is an unsubstituted aralkyl. In one example, $R_1$ or $R_2$ is an unsubstituted phenylmethyl, unsubstituted phenylethyl, or an unsubstituted phenylpropyl.

In several other embodiments, $R_1$ or $R_2$ is a $C_{1-8}$ aliphatic that is optionally substituted with 1-3 substituents. In several embodiments, $R_1$ or $R_2$ are optionally substituted straight (e.g., ethyl, propyl, sec-butyl, or the like) or branched (e.g., isopropyl, isobutyl, sec-propyl, sec-butyl, or the like) aliphatic. For example, $R_1$ or $R_2$ is methyl, ethyl, propyl, butyl, pentyl, hexyl, heptyl, or octyl, each substituted with 1-3 substituents (e.g., 1-2 substituents). In other examples, $R_1$ or $R_2$ is an isopropyl that is optionally substituted with 1-2 substituents, or $R_1$ or $R_2$ is an unsubstituted isopropyl. In more examples, $R_1$ or $R_2$ is a sec-propyl that is substituted with 1-2 substituents. In several embodiments, $R_1$ or $R_2$ is substituted with 1-3 halo, cyano, hydroxy, or optionally substituted aryl, aryloxy, alkylamino, heteroaryl, cycloaliphatic, heterocycloaliphatic, or combinations thereof. In another embodiment, $R_1$ or $R_2$ is substituted with alkoxyalkyl. In other embodiments, $R_1$ or $R_2$ is unsubstituted methyl or sec-propyl.

In other embodiments, $R_1$ or $R_2$ is an optionally substituted monocyclic or bicyclic cycloaliphatic. For example, $R_1$ or $R_2$ is an optionally substituted monocyclic $C_{3-8}$ cycloaliphatic. In other examples, $R_1$ or $R_2$ is fully saturated or partially unsaturated. In other examples, $R_1$ or $R_2$ is a cyclopropyl, cyclobutyl, cyclopentyl, cyclohexyl, cycloheptyl, or cyclooctyl, each of which is optionally substituted with 1-2 substituents. For example, In some embodiments, $R_1$ or $R_2$ is unsubstituted cyclopropyl, cyclobutyl, cyclopentyl, or cyclohexyl. In other embodiments, $R_1$ or $R_2$ is substituted cyclopropyl. For example, $R_1$ or $R_2$ is substituted with 1-3 of halo, hydroxy, aliphatic, aryl, heteroaryl, or combinations thereof. In other embodiments, $R_1$ or $R_2$ is an optionally substituted bicyclic cycloaliphatic. In other examples, $R_1$ or $R_2$ is an optionally substituted bridged bicyclic cycloaliphatic. In other embodiments, $R_1$ or $R_2$ is optionally substituted bicyclo[2.1.1]hexyl, bicyclo[3.1.1]heptyl, or bicyclo[2.2.1]heptyl. In more examples $R_1$ or $R_2$ is unsubstituted bicyclo[2.1.1]hexyl, or bicyclo[2.2.1]heptyl substituted with 1-3 methyl groups. In another example, $R_1$ or $R_2$ is 2,6,6-trimethylbicyclo[3.1.1]heptyl.

In some embodiments, $R_1$ or $R_2$ is an optionally substituted aryl. For example, $R_1$ or $R_2$ is an optionally substituted 6-10 membered monocyclic or bicyclic aryl. In other examples, $R_1$ or $R_2$ is an optionally substituted phenyl, indenyl, dihydroindenyl or naphthyl. In other embodiments, $R_1$ or $R_2$ is substituted with 1-2 halo, hydroxy, cyano, or optionally substituted aliphatic, alkoxy, aryl, or heteroaryl; or combinations thereof. In other embodiments, $R_1$ or $R_2$ is unsubstituted phenyl, indenyl, dihydroindenyl or naphthyl.

In some embodiments, $R_1$ or $R_2$ is an optionally substituted monocyclic or bicyclic heterocycloaliphatic including 1-3 heteroatoms selected from N, O, and S. In one group of examples, $R_1$ or $R_2$ is fully saturated or partially unsaturated. In one group of examples, $R_1$ or $R_2$ is an optionally substituted fully saturated monocyclic heterocycloaliphatic. In another group of examples, $R_1$ or $R_2$ is morpholinyl, pyrroldinyl, thiomorpholinyl, tetrahydro-2H-pyranyl, or tetrahydrothiophenyl, each of which is optionally substituted. For example, $R_1$ or $R_2$ is morpholinyl, pyrroldinyl, thiomorpholinyl, tetrahydro-2H-pyranyl, or tetrahydrothiophenyl, each of which is optionally substituted with 1-3 substituents selected from halo, hydroxyl, aliphatic, or aryl. In another group of examples, $R_1$ or $R_2$ is unsubstituted morpholinyl, thiomorpholinyl, tetrahydro-2H-pyranyl, or tetrahydrothiophenyl. In another group of examples, $R_1$ or $R_2$ is an unsubstituted tropane.

In some embodiments, $R_1$ or $R_2$ is an optionally substituted heteroaraliphatic. In some embodiments, $R_1$ or $R_2$ includes a straight or branched aliphatic chain. For example, $R_1$ or $R_2$ includes a straight $C_{1-4}$ aliphatic chain. In another example, $R_1$ or $R_2$ is optionally substituted —$C_{1-3}$ aliphatic-heteraryl. As noted above, $R_1$ or $R_2$ can be substituted at any chemically feasible position on the aliphatic chain or on the heteroaryl group. In other embodiments, $R_1$ or $R_2$ includes a 6-10 membered monocyclic or bicyclic heteroaryl group attached to the core structure with a $C_{1-3}$ aliphatic chain. For example, $R_1$ or $R_2$ is an optionally substituted 2,3-dihydrobenzofurylalkyl, indolinylalkyl, 2,3-dihydrobenzo[b][1,4]dioxinylalkyl, benzo[d][1,3]dioxolylalkyl, pyridinylalkyl, isoindolinylalkyl, or quinolinylalkyl. In other examples, $R_1$ or $R_2$ is an unsubstituted heteroaralkyl.

In some embodiments, $R_1$ or $R_2$ is an optionally substituted heteroaryl. For example, $R_1$ or $R_2$ is 2,3-dihydrobenzo[b][1,4]dioxinyl, or benzo[d][1,3]dioxolyl, each of which is optionally substituted. In several examples, $R_1$ or $R_2$ is unsubstituted 2,3-dihydrobenzo[b][1,4]dioxinyl, or benzo[d][1,3]dioxolyl.

In several other embodiments, $R_1$, $R_2$, and the nitrogen atom to which they are attached form an optionally substituted 4-12 membered monocyclic or bicyclic fully saturated or partially unsaturated ring having 1-3 heteroatoms. In several examples, $R_1$ and $R_2$ form a morpholinyl, piperadinyl, piperazinyl, pyrrolyl, 2-pyrrolinyl, 3-pyrrolinyl, pyrrolidinyl, imidazolidinyl, pyrazolyl, pyrazolidinyl, thiomorpholinyl, or 3,4-dihydro-benzo[b][1,4]oxazine, each of which is optionally substituted with 1-3 substituents independently selected from halo, alkylcarbonyl, $C_{1-4}$ alkyl, ethyl, alkoxy, and heterocycloalkyl. In another embodiment, $R_1$, $R_2$, and the nitrogen atom to which they are attached form a partially saturated heterocyclic ring that is optionally substituted with 1-2 substituents. For example, $R_1$, $R_2$, and the nitrogen atom to which they are attached form a substituted 1,2,3,6-tetrahydropyridinyl. In other examples, $R_1$, $R_2$, and the nitrogen atom to which they are attached form a piperidinyl, or tetrahydropyridinyl substituted with 1-2 substituents selected from alkyl, alkylcarbonyl, alkoxy, haloaryl, alkoxyaryl, or aryl. In other examples, $R_1$, $R_2$, and the nitrogen atom to which they are attached form an unsubstituted fully saturated or partially unsaturated heterocycloaliphatic.

In some embodiments, $R_1$ and $R_2$ together with the nitrogen atom to which they are attached form an optionally substituted 5-10 membered monocyclic or bicyclic ring that is partially unsaturated, or fully unsaturated, and has 1-3 heteroatoms selected from N, O, and S. In several embodiments, $R_1$ and $R_2$ together with the nitrogen atom to which they are attached form an optionally substituted monocyclic or bicyclic heteroaryl. In several examples, the heteroaryl formed from $R_1$, $R_2$, and the nitrogen atom to which they are attached is substituted with 1-3 of halo, cyano, hydroxyl, alkoxy, aliphatic, aryl, or cycloaliphatic. For example, $R_1$, $R_2$, and the nitrogen atom to which they are attached are optionally substituted indolinyl, 1,2,3,4-tetrahydroquinolinyl, or 3,4-dihydro-2H-benzo[b][1,4]oxazinyl. In other examples, the heteroaryl formed from $R_1$, $R_2$, and the nitrogen atom to which they are attached is substituted with 1-2 aliphatic groups. In other examples, the heteroaryl formed from $R_1$, $R_2$, and the nitrogen atom to which they are attached is substituted with 1-2 methyl groups.

In some embodiments, $R_1$ or $R_2$ is hydrogen.

In some embodiments, $R_1$ or $R_2$ is an optionally substituted guanidinylalkyl having 1-2 substituents. In other embodiments, $R_1$ or $R_2$ is an unsubstituted guanidinylalkyl.

In several embodiments, $R_1$ and $R_2$ are each independently selected from: hydrogen, methyl, ethyl,

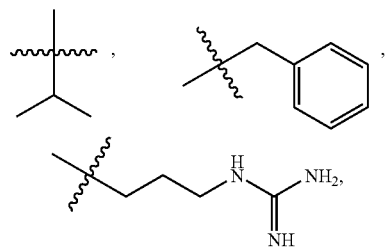

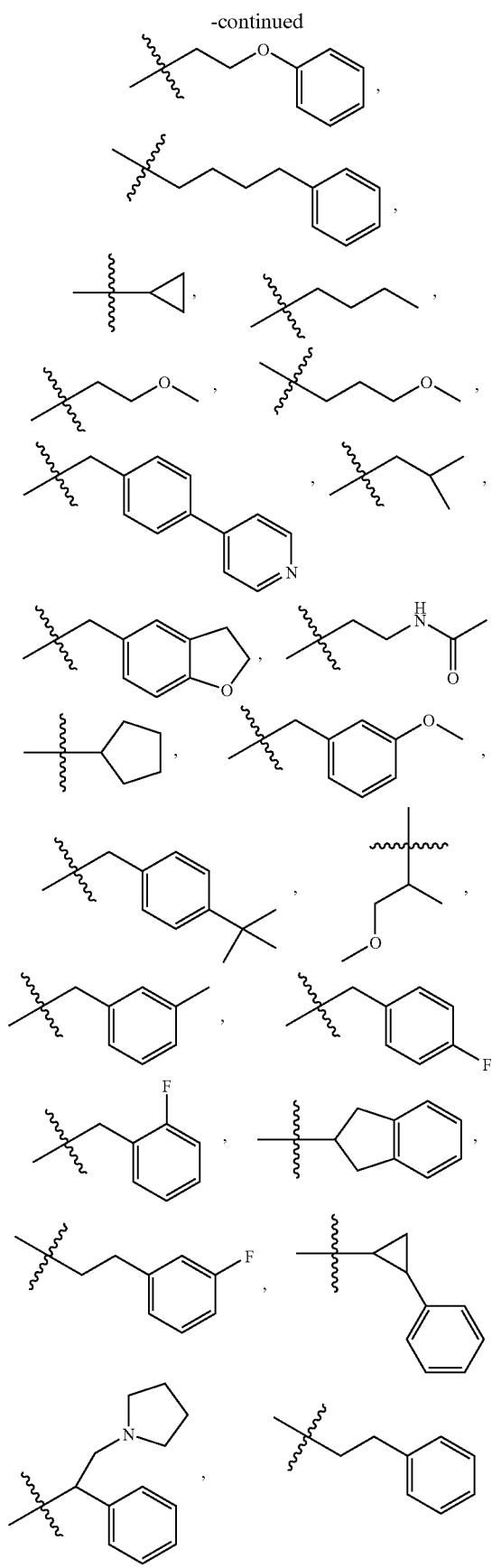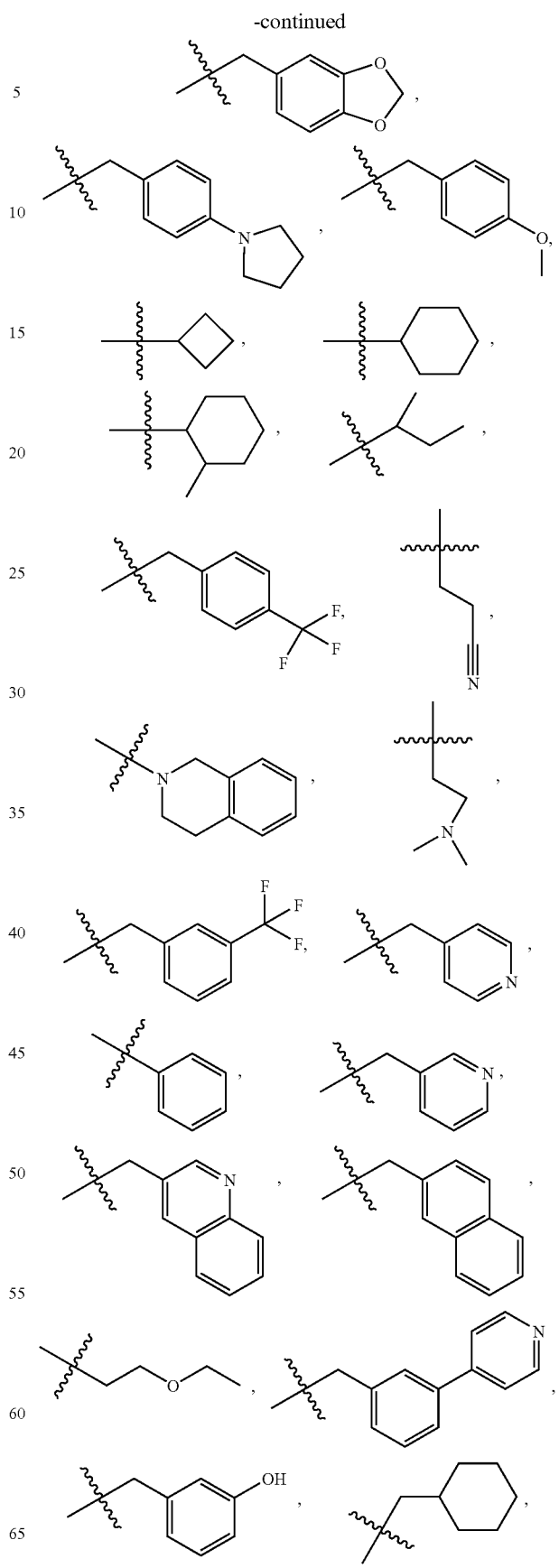

-continued

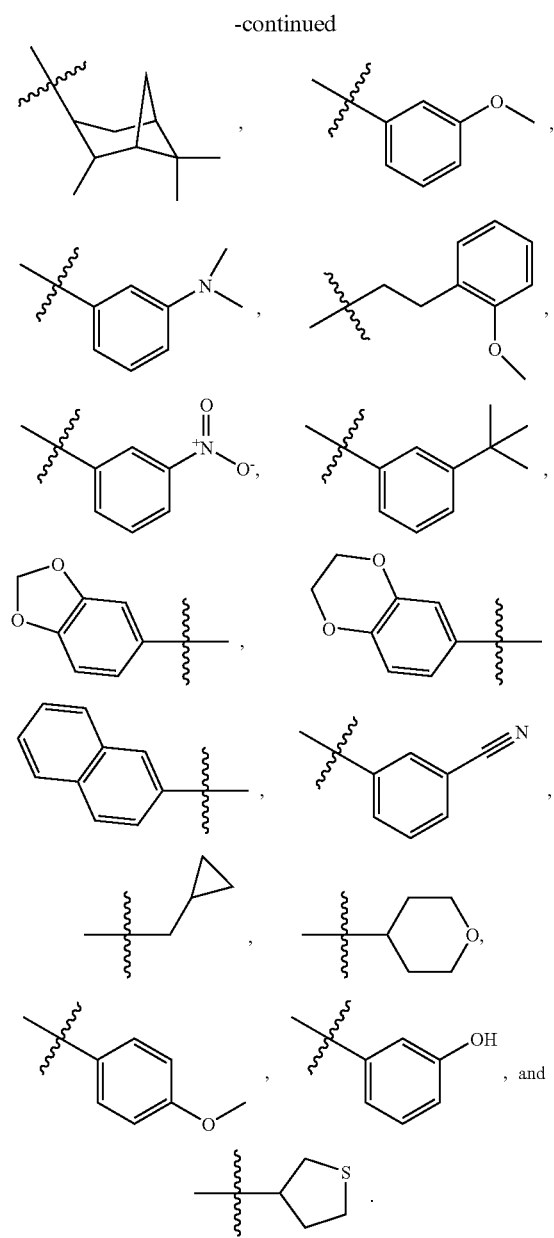

In several embodiments, $R_1$, $R_2$ and the nitrogen atom to which they are attached form a heterocycloaliphatic or a heterocycloaliphatic fused with phenyl selected from:

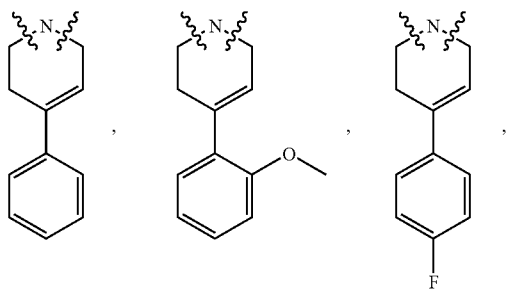

-continued

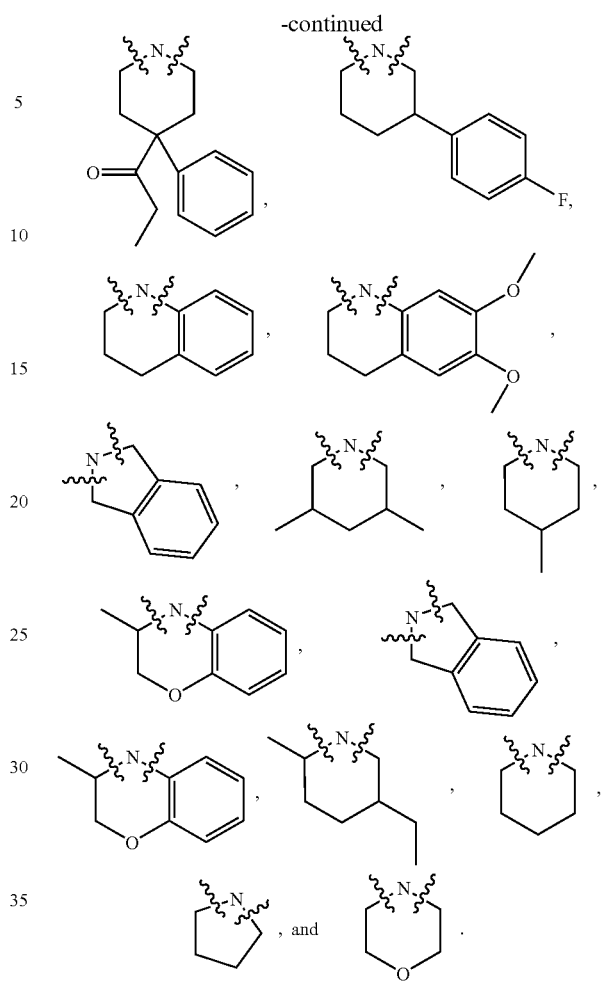

2. Substituents $R_3$ and $R_4$

Each $R_3$ and $R_4$ are defined by $-Z^C R_8$, wherein each $Z^C$ is independently a bond or an optionally substituted straight or branched $C_{1-6}$ aliphatic chain wherein up to two carbon units of $Z^C$ are optionally and independently replaced by $-CO-$, $-CS-$, $-COCO-$, $-CONR^C-$, $-CONR^C NR^C-$, $-CO_2-$, $-OCO-$, $-NR^C CO_2-$, z—O—, $-NR^C CO-NR^C-$, $-OCONR^C-$, $-NR^C NR^C$, $-NR^C NR^C CO-$, $-NR^C CO-$, $-S-$, $-SO-$, $-SO_2-$, $-NR^C-$, $-SO_2 NR^C-$, $-NR^C SO_2-$, or $-NR^C SO_2 NR^C-$ Each $R_8$ is independently $R^C$, halo, $-OH$, $-NH_2$, $-NO_2$, $-CN$, $-CF_3$, or $-OCF_3$.

Each $R^C$ is independently hydrogen, an optionally substituted $C_{1-8}$ aliphatic group; an optionally substituted 3-8 membered fully saturated, partially unsaturated, or fully unsaturated monocyclic ring having 0-3 heteroatoms independently selected from nitrogen, oxygen, or sulfur; an optionally substituted 8-12 membered fully saturated, partially unsaturated, or fully unsaturated bicyclic ring system having 0-5 heteroatoms independently selected from nitrogen, oxygen, or sulfur; or two occurrences of $R^C$ are taken together with the atom(s) to which they are attached to form an optionally substituted 3-12 membered saturated, partially unsaturated, or fully unsaturated monocyclic or bicyclic ring having 1-4 heteroatoms independently selected from nitrogen, oxygen, or sulfur, each of which is optionally substituted with 1 to 3 substituents.

In several embodiments, $R_3$, $R_4$ and the nitrogen atom to which they are attached form an optionally substituted 4-8 membered saturated or partially unsaturated monocyclic or bicyclic heterocycloaliphatic. In several embodiments, the heterocycloaliphatic formed from the $R_3$, $R_4$ and the nitrogen atom to which they are attached is substituted with 1-3 substituents.

In several embodiments, $R_3$, $R_4$ and the nitrogen atom to which they are attached form an optionally substituted monocyclic heterocycloaliphatic with 1-3 heteroatoms selected from N, O, and S. In another example $R_3$, $R_4$ and the nitrogen atom to which they are attached form a fully saturated optionally substituted heterocycloaliphatic (e.g., heterocycloalkyl). In yet another example, $R_3$, $R_4$, and the nitrogen atom to which they are attached form an optionally substituted morpholinyl, thiomorpholinyl, piperadinyl, piperazinyl, pyrrolidinyl, tetrahydrofuranyl, or imidazolinyl. In several embodiments the fully saturated heterocycloaliphatic formed by $R_3$, $R_4$, and the nitrogen atom to which they are attached is substituted with 1-3 substituents selected from halo, cyano, hydroxy, or optionally substituted $C_{1-5}$ aliphatic, heterocycloaliphatic, alkoxy, alkoxycarbonyl, alkylaminocarbonyl, or aralkyl. In several embodiments, the heterocycloaliphatic formed from $R_3$, $R_4$, and the nitrogen atom to which they are attached is a piperadinyl that is substituted with aliphatic, cycloaliphatic, alkoxy, alkoxycarbonyl, heterocycloaliphatic, cycloaliphatic, heteroaralkyl or aralkyl; or it is an unsubstituted piperadinyl. For example, the piperadinyl formed from $R_3$, $R_4$ and the nitrogen atom to which they are attached is substituted with methyl, pyrrolidinyl, cyclopentyl, phenylmethyl, or pryridinylmethyl. In some embodiments, $R_3$, $R_4$, and the nitrogen atom to which they are attached form unsubstituted morpholinyl, thiomorpholinyl, piperadinyl, piperazinyl, pyrrolidinyl, or tetrahydrofuranyl. In some embodiments, $R_3$, $R_4$, and the nitrogen atom to which they are attached form an alkyl substituted piperazinyl or morpholinyl. For example, $R_3$, $R_4$, and the nitrogen atom to which they are attached form a piperazinyl or morpholinyl that is optionally substituted with 1-2 alkyl groups. In other examples, $R_3$, $R_4$, and the nitrogen atom to which they are attached form a piperazinyl or a morpholinyl, each of which is substituted with 1-2 alkyl groups.

In several embodiments, $R_3$, $R_4$, and the nitrogen atom to which they are attached form an optionally substituted fully saturated or partially unsaturated bicyclic heterocycloaliphatic. For example, the bicyclic heterocycloaliphatic formed from $R_3$, $R_4$, and the nitrogen atom to which they are attached has 1-3 heteroatoms selected from N, O, and S. In other embodiments, the heterocycloaliphatic formed by $R_3$, $R_4$, and the nitrogen atom to which they are attached is substituted with 1-3 substituents. In other embodiments, $R_3$, $R_4$, and the nitrogen atom to which they are attached form an optionally substituted decahydroquinaolinyl, tropane, or octahydroindolyl. In several embodiments, $R_3$, $R_4$, and the nitrogen atom to which they are attached form an unsubstituted decahydroquinaolinyl. In several other embodiments, $R_3$, $R_4$, and the nitrogen atom to which they are attached form a decahydroquinolinyl that is optionally substituted with 1-2 methyl groups.

In several embodiments, $R_3$, $R_4$, and the nitrogen atom to which they are attached form an optionally substituted 6-10 membered heteroaryl. For example, the heteroaryl formed by $R_3$, $R_4$, and the nitrogen atom to which they are attached is substituted with 1-3 substituents. The optionally substituted heteroaryl formed by $R_3$, $R_4$, and the nitrogen atom to which they are attached is a monocyclic or bicyclic ring system. In several embodiments, $R_3$, $R_4$, and the nitrogen atom to which they are attached form optionally substituted 1,2,3,4-tetrahydroquinolinyl, or octahydroisoindolyl. In another embodiment, $R_3$, $R_4$, and the nitrogen atom to which they are attached form unsubstituted 1,2,3,4-tetrahydroquinolinyl, or octahydroisoindolyl.

In several embodiments, one of $R_3$ or $R_4$ is an optionally substituted 6-10 membered monocyclic or bicyclic aryl. In another example, $R_3$ or $R_4$ is substituted with 1-3 substituents. In some embodiments, $R_3$ or $R_4$ is an optionally substituted monocyclic aryl. For example $R_3$ or $R_4$ is a monocyclic aryl substituted with 1-3 of halo, cyano, hydroxy, methyl, alkoxy, alkoxycarbonyl, $C_{1-6}$ aliphatic, aminocarbonyl, or combinations thereof. In other examples, $R_3$ or $R_4$ is a phenyl. In several embodiments, $R_3$ or $R_4$ is an optionally substituted bicyclic aryl. In several embodiments, $R_3$ or $R_4$ is an optionally substituted naphthyl or indenyl. In several embodiments, $R_3$ or $R_4$ is substituted with 1-3 substituents. For example, $R_3$ or $R_4$ is substituted with 1-3 substituents selected from halo, cyano, hydroxy, alkoxy, alkoxycarbonyl, alkylaminocarbonyl, $C_{1-4}$ aliphatic, aryl or heteroaryl. In other examples, $R_3$ or $R_4$ is an unsubstituted naphthyl or indenyl.

In several embodiments $R_3$ or $R_4$ is an optionally substituted straight or branched $C_{1-8}$ aliphatic. For example, $R_3$ or $R_4$ is optionally substituted straight (e.g., methyl, ethyl, propyl, butyl, or the like) or branched (e.g., isopropyl, isobutyl, sec-propyl, sec-butyl or the like) aliphatic. For example, $R_3$ or $R_4$ is methyl, ethyl, propyl, butyl, pentyl, hexyl, heptyl, or octyl, each substituted with 1-3 substituents (e.g., 1-2 substituents). In other examples, $R_3$ or $R_4$ is an isopropyl or sec-propyl that is optionally substituted with 1-3 substituents (e.g., 1-2 substituents), or $R_3$ or $R_4$ is an unsubstituted sec-propyl or isopropyl. In several embodiments, $R_3$ or $R_4$ is unsubstituted methyl, ethyl, propyl, butyl, pentyl, or hexyl. In other embodiments, $R_3$ or $R_4$ is a —C(O)OH substituted aliphatic (e.g., alkyl-C(O)OH). For example, $R_3$ or $R_4$ is a methyl, ethyl, or propyl, each of which is substituted with —C(O)OH. In several embodiments, $R_3$ or $R_4$ is substituted with 1-2 substituents including halo, cyano, hydroxy, or optionally substituted cycloaliphatic, heterocycloaliphatic, aryl, alkoxy, haloalkylaryl, bicycloaliphatic, aryloxy, haloaryl, alkylamino, heteroaryl, cycloaliphatic, heterocycloaliphaticpropyl, isopropyl, or combinations thereof. In other embodiment, $R_3$ or $R_4$ is methyl, ethyl, or propyl that is substituted with a monocyclic optionally substituted aryl. For example, $R_3$ or $R_4$ is methyl, ethyl, or propyl that is substituted with alkoxyphenyl, cycloaliphaticphenyl, haloalkylphenyl, cyanophenyl, halophenyl, or hydroxyphenyl. In other embodiments, $R_3$ or $R_4$ is methyl, ethyl, or propyl that is substituted with a bicyclic aryl. For example $R_3$ or $R_4$ is methyl, ethyl, or propyl that is substituted with unsubstituted naphthyl or indenyl. In other embodiments, $R_3$ or $R_4$ is substituted with two substituents independently selected from halo, cyano, hydroxyl, aliphatic, aryl, heteroaryl, cycloaliphatic, heterocycloaliphatic, or alkoxy. In some embodiments, $R_3$ or $R_4$ is methyl substituted with aliphatic and aryl. In several embodiments, $R_3$ or $R_4$ includes an optionally substituted partially unsaturated aliphatic (e.g., alkenyl or alkynyl). In several examples, $R_3$ or $R_4$ includes optionally substituted ethenyl, propenyl, or butenyl. In other embodiments, $R_3$ or $R_4$ includes unsubstituted propenyl.

In several embodiments, $R_3$ or $R_4$ is an optionally substituted heteroaryl. For example $R_3$ or $R_4$ is an optionally substituted 6-10 membered monocyclic or bicyclic heteroaryl. In some examples, $R_3$ or $R_4$ is a monocyclic heteroaryl optionally substituted with 1-3 substituents. In other examples, $R_3$ or $R_4$ is a substituted pyridinyl, pyrimidinyl, pyridazinyl, or pyrazinyl. In other examples $R_3$ or $R_4$ is an unsubstituted pyridinyl, pyrimidinyl, pyridazinyl, or pyrazinyl. In several embodiments, $R_3$ or $R_4$ is an optionally substituted bicyclic heteraryl. For example, $R_3$ or $R_4$ is a bicyclic heteroaryl substituted with 1-3 substituents. In other examples, $R_3$ or $R_4$ is an optionally substituted isoindolinyl. In some embodiments, $R_3$ or $R_4$ is unsubstituted isoindolinyl.

In several embodiments, $R_3$ or $R_4$ is an optionally substituted monocyclic or bicyclic cycloaliphatic. In some embodiments, $R_3$ or $R_4$ is a monocyclic cycloaliphatic optionally substituted with 1-3 substituents including hydroxy, alkoxy, alkylamino, alkyl carbonyl, aliphatic, halo, or combinations thereof. In other embodiments, $R_3$ or $R_4$ is optionally substituted cyclopropyl, cyclobutyl, cyclopentyl, cyclohexyl, or cycloheptyl. For example, $R_3$ or $R_4$ is unsubstituted cyclopropyl, cyclobutyl, cyclopentyl, cyclohexyl, or cycloheptyl. In other embodiments, $R_3$ or $R_4$ is optionally substituted bicycloaliphatic. In several examples, $R_3$ or $R_4$ is bicycloaliphatic or bridged bicycloaliphatic optionally substituted with 1-3 substituents selected from hydroxy, alkoxy, alkylamino, alkyl carbonyl, aliphatic, and halo. In other examples, $R_3$ or $R_4$ is optionally substituted bicyclo[2.1.1]hexyl, bicyclo[3.1.1]heptyl, or bicyclo[2.2.1]heptyl. In other examples $R_3$ or $R_4$ is unsubstituted bicyclo[2.1.1]hexyl, or bicyclo[2.2.1]heptyl.

In several embodiments, $R_3$ or $R_4$ is hydrogen.

In several embodiments, each $R_3$, $R_4$, is independently selected from: hydrogen, methyl, ethyl,

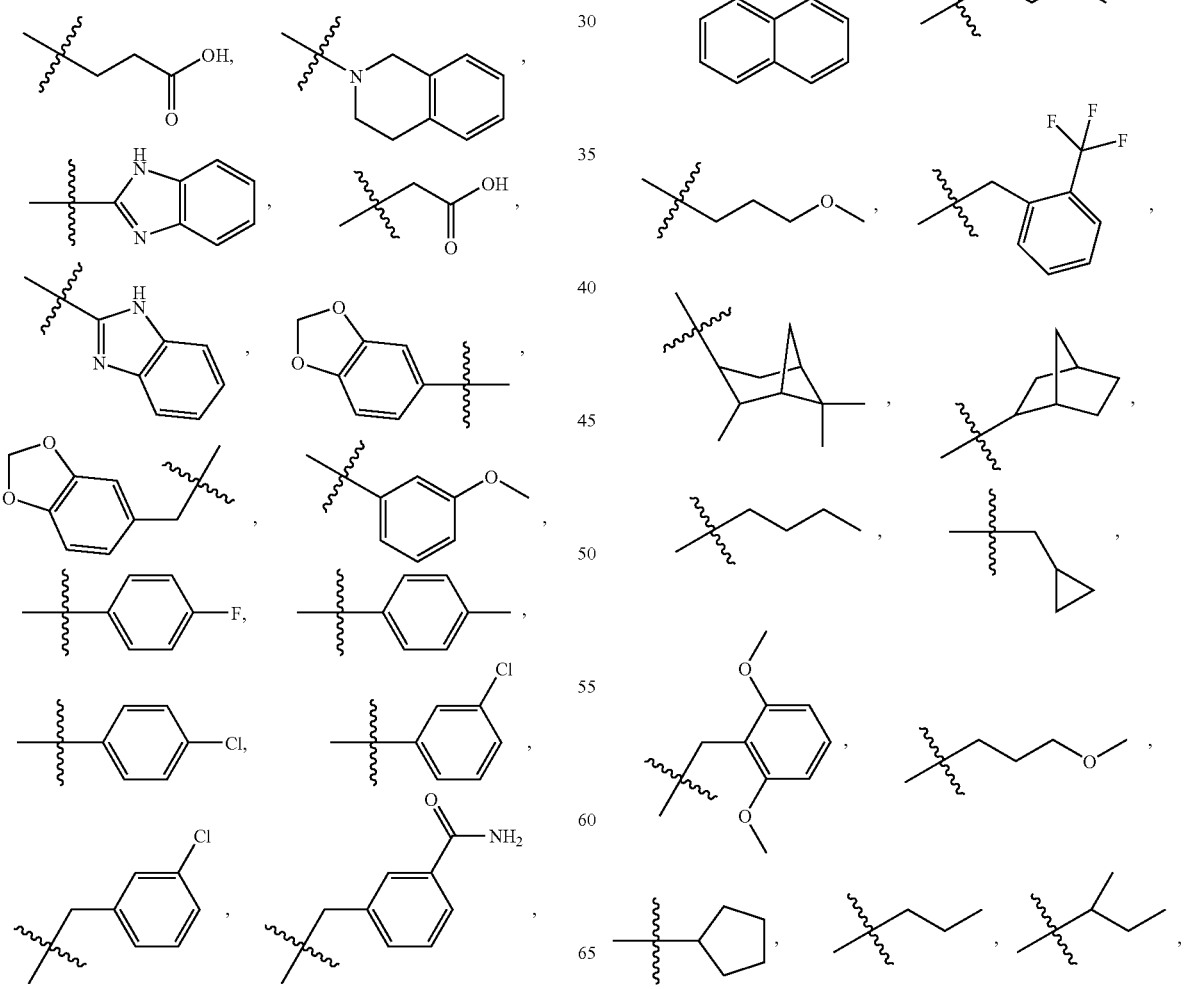

-continued

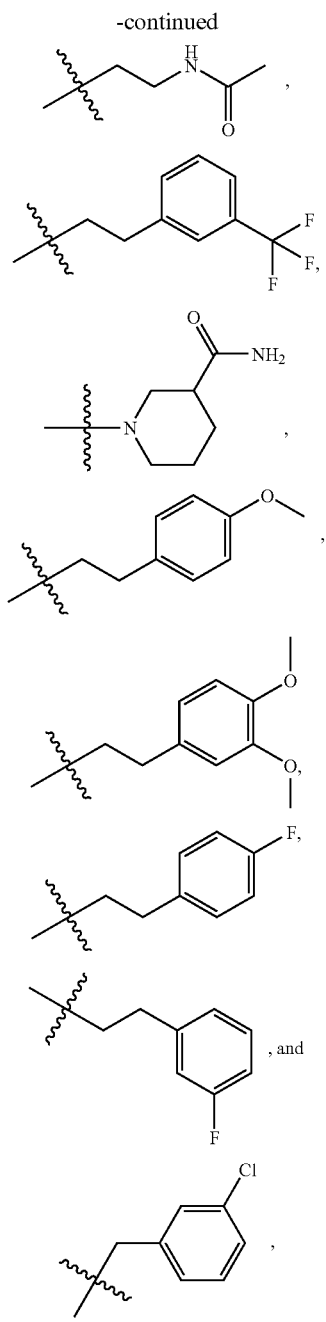

In several embodiments, $R_3$, $R_4$, and the nitrogen atom to which they are attached is one selected from:

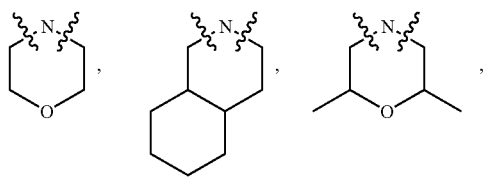

-continued

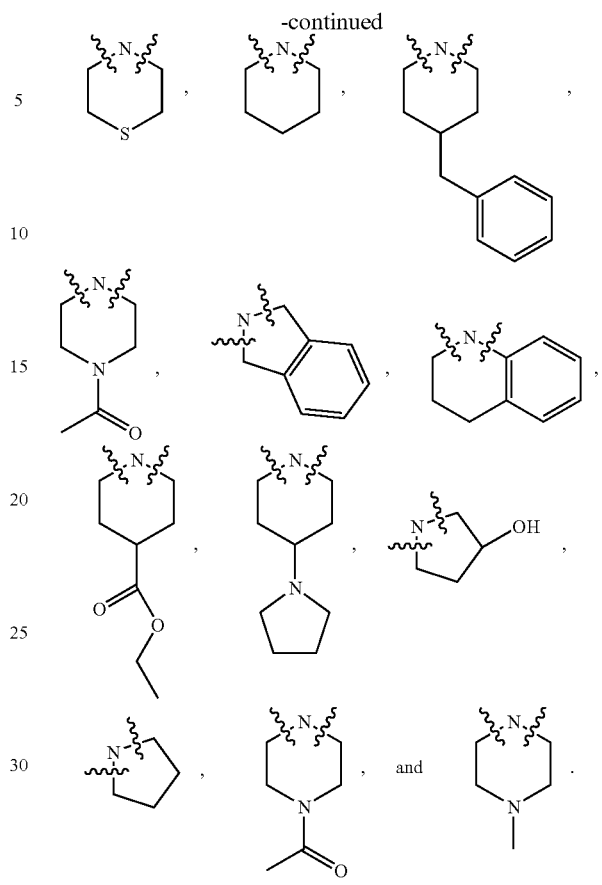

3. Substituent X

Each X is defined by —$Z^A R^6$, wherein $Z^A$ is independently a bond or an optionally substituted branched or straight $C_{1-6}$ aliphatic chain wherein up to two carbon units of $Z^A$ are optionally and independently replaced by —CO—, —CS—, —COCO—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$, —NR$^A$NR$^A$CO—, —NR$^A$CO—, —S—, —SO—, —SO$_2$—, —NR$^A$—, —SO$_2$NR$^A$—, —NR$^A$SO$_2$—, or —NR$^A$SO$_2$NR$^A$—.

Each $R_6$ is independently $R^A$, halo, —OH, —NH$_2$, —NO$_2$, —CN, —CF$_3$, or —OCF$_3$.

Each $R^A$ is independently hydrogen, an optionally substituted $C_{1-8}$ aliphatic group; a 3-8-membered optionally substituted fully saturated, partially unsaturated, or fully unsaturated monocyclic ring having 0-3 heteroatoms independently selected from nitrogen, oxygen, or sulfur; an 8-12 membered optionally substituted fully saturated, partially unsaturated, or fully unsaturated bicyclic ring system having 0-5 heteroatoms independently selected from nitrogen, oxygen, or sulfur; or two occurrences of $R^A$ are taken together with the atom(s) to which they are attached to form an optionally substituted 3-12 membered fully saturated, partially unsaturated, or fully unsaturated monocyclic or bicyclic ring having 0-4 heteroatoms independently selected from nitrogen, oxygen, or sulfur.

In several embodiments, X is a $C_{1-6}$ aliphatic that is optionally substituted and branched or straight. For example, X is an optionally substituted branched or straight $C_{1-6}$ aliphatic that is fully saturated or partially unsaturated. In other examples, X is fully saturated (e.g., alkyl). In some embodiments, X is methyl, ethyl, propyl, butyl, pentyl, or hexyl, each of which is optionally substituted with 1-3 substituents. In other embodiments, X is an optionally substituted branched aliphatic. For example, X is an isopropyl, isobutyl, isopentane, sec-butyl, or sec-propyl, each of which is optionally substituted with 1-2 substituents. In several examples, X is an unsubstituted $C_{1-6}$ aliphatic. For example, X is unsubstituted methyl, ethyl, propyl, butyl, pentyl, or hexyl. In other embodiments, X is substituted with 1-3 substituents independently selected from alkylcarbonyl, alkoxy, —C(O)OH, aryl, heteroaryl, cycloaliphatic, heterocycloaliphatic, and alkylamino. In several embodiments, X is optionally substituted $C_{1-6}$ aliphatic that is partially unsaturated. For example, X is an optionally substituted $C_{1-6}$ aliphatic that has at least 1 C—C double bond, or at least 1 C—C triple bond. In other examples, X is optionally substituted ethenyl, propenyl, but-1-enyl, or but-2-enyl. In some embodiments, X is substituted with 1-3 substituents independently selected from alkylcarbonyl, alkoxy, —C(O)OH, aryl, heteroaryl, cycloaliphatic, heterocycloaliphatic, and alkylamino. In other embodiments, X is ethenyl substituted with —C(O)OH (e.g., acrylic acid).

In several embodiments, X is an optionally substituted $C_{1-6}$ alkoxy. The alkyl group of the alkoxy can be optionally substituted with 1-3 substituents. For example, X is methoxy, ethoxy, propoxy, butoxy, pentoxy, or hexoxy, each of which is optionally substituted. In other examples, X is prop-2-oxy, but-2-oxy, pent-2-oxy, or pent-3-oxy, each of which is optionally substituted. In several embodiments, X is unsubstituted prop-2-oxy, but-2-oxy, pent-2-oxy, or pent-3-oxy. In other examples, X is substituted with a $C_{1-3}$ aliphatic group. For example, X is ethoxy, propoxy, butoxy, pentoxy, or hexoxy, each of which is substituted with methyl or ethyl.

In several embodiments, X is an optionally substituted ring system that that is fully saturated, partially unsaturated, or fully unsaturated and attaches to the core phenyl with an oxy (—O—) group. In several examples, X is selected from optionally substituted aryloxy, heteroaryloxy, cycloaliphaticoxy, or heterocycloaliphaticoxy. In several embodiments, X is an unsubstituted aryloxy, heteroaryloxy, cycloaliphaticoxy, or heterocycloaliphaticoxy. For example, X is an unsubstituted phenoxy. In other embodiments, X is a phenoxy that is substituted with 1-3 substituents selected from halo, —CF$_3$, alkoxy, alkylcarbonyl, and cyano.

In several embodiments, X is an optionally substituted amino. For example X is substituted with 1-3 substituents selected from aliphatic, alkoxy, alkylsulfonyl, alkylcarbonyl, aryl, heteroaryl, cycloaliphatic, and heterocycloaliphatic. In several examples, X is alkylcarbonylamino.

In several embodiments, X is a halo (e.g., F, Cl, Br, or I).

In several embodiments, each X is independently selected from: halo,

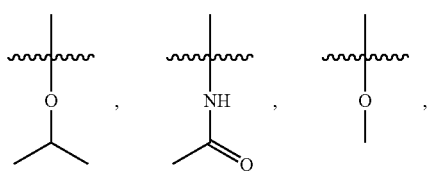

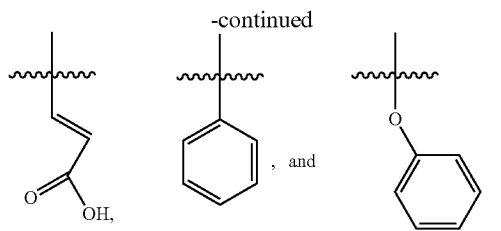

4. Substituents Y and n

Each Y is hydrogen, or optionally substituted methyl.

Each n is 1-4.

In several embodiments, Y is methyl.

In several embodiments, n is 1 or 2.

5. Exemplary Compound Families

Another aspect of the present invention includes compounds of formula Ia:

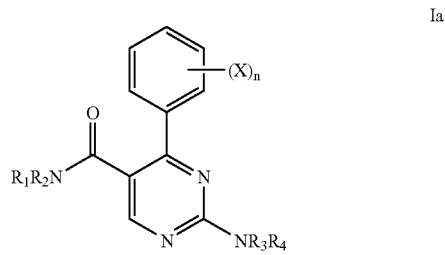

or a pharmaceutically acceptable salt thereof, where $R_1$, $R_2$, $R_3$, $R_4$, X and n are defined above.

In several embodiments of formula Ia, when $R_1$ is alkyl, $R_2$ is not 3,5-bis-trifluoromethyl-phenyl-alkyl; when $R_1$ and $R_2$ together form pyrrolidinyl, morpholinyl, or piperidinyl, each optionally substituted with —CH$_3$ or —CH$_2$CH$_3$, then X is not m-methyl, o-halo, p-aryl, orp-cyano; when $R_1$ or $R_2$ are aliphatic or alkoxyalkyl, then X is not m-methyl, o-halo, p-aryl, or p-cyano; and when $R_1$ is phenylmethyl optionally substituted with 1-2 —CH$_3$ groups or cycloaliphatic, and $R_2$ is one selected from unsubstituted methyl, ethyl, and isopropyl, then (1) $R_3$ together with $R_4$ form pyrrolidinyl, morpholinyl, piperidinyl optionally substituted with aliphatic, aminocarbonyl, or alkylcarbonyl, or one of $R_3$ or $R_4$ is phenylmethyl, methylfuranyl, or methoxypropyl, and (2) X is not m-methyl, p-aryl, o-halo or p-cyano.

In other embodiments of formula Ia, $R_3$ or $R_4$ is heterocycloaliphatic, bicycloaryl, bicycloheteroaliphatic, bicycloheteroaryl, heterocycloalkenyl, cycloaliphatic, alkenyl, 5-membered heterocycloaliphatic, heteroaralkyl, or bicycloaralkyl, each of which is optionally substituted; or one of $R_3$ and $R_4$ is hydrogen, $R_3$ or $R_4$ is alkyl substituted with cycloaliphatic, heteroaryl, heterocycloaliphatic, cyano, alkoxycarbonyl, —C(O)OH, guanidinylalkyl, bicycloaryl, halo, or alkoxy, or $R_3$ together with $R_4$ form a ring system selected from thiomorpholinyl, bicycloheteroaryl, bicyclic heterocycloaliphatic, 5-membered heterocycloaliphatic, and 6-membered heterocycloalkenyl, provided that when $R_1$ and $R_2$ together form pyrrolidinyl, morpholinyl, piperidinyl, each optionally substituted with —CH$_3$ or —CH$_2$CH$_3$, then X is not one selected from m-methyl, o-halo, p-aryl, and p-cyano; when $R_1$ and $R_2$ are aliphatic or alkoxyalkyl, then X is not one selected from m-methyl, o-halo, p-aryl, and p-cyano; and (1) when $R_1$ is phenylmethyl optionally substituted with 1-2 —$CH_3$ groups or cycloaliphatic, and $R_2$ is one selected from unsubstituted methyl, ethyl, and isopropyl, then $R_3$ together with $R_4$ must form pyrrolidinyl, morpholinyl, piperidinyl optionally substituted with aliphatic, aminocarbonyl, or alkylcarbonyl; or one of $R_3$ and $R_4$ is phenylmethyl, methylfuranyl, or methoxypropyl, and (2) X is not o-halo or p-cyano.

Another aspect of the present invention includes compounds of formula II:

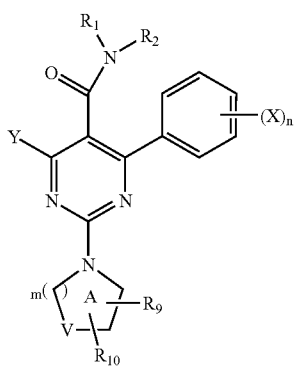

or a pharmaceutically acceptable salt thereof, wherein $R_1$, $R_2$, X, n, and Y are defined above.

Each V is one selected from —CH—, —$CH_2$—, —N—, —O—, and —S—.

Each m is 1 or 2.

Each $R_9$ and $R_{10}$ are defined by —$Z^D R_{14}$, wherein each $Z^D$ is independently a bond or an optionally substituted straight or branched $C_{1-6}$ aliphatic chain wherein up to two carbon units of $Z^D$ are optionally and independently replaced by —CO—, —CS—, —COCO—, —$CONR^D$—, —$CONR^D$-$NR^D$—, —$CO_2$—, —OCO—, —$NR^D CO_2$—, —O—, —$NR^D CONR^D$—, —$OCONR^D$—, —$NR^D NR^D$—, —$NR^D N$-$R^D CO$—, —$NR^D CO$—, —S—, —SO—, —$SO_2$—, —$NR^D$—, —$SO_2 NR^D$—, —$NR^D SO_2$—, or —$NR^D SO_2 NR^D$—.

Each $R_{14}$ is independently $R^D$, halo, —OH, —$NH_2$, —$NO_2$, —CN, —$CF_3$, or —$OCF_3$.

Each $R^D$ is independently hydrogen, or an optionally substituted $C_{1-8}$ aliphatic group, an optionally substituted 3-8 membered saturated, partially unsaturated, or fully unsaturated monocyclic ring having 0-3 heteroatoms independently selected from nitrogen, oxygen, or sulfur, or an optionally substituted 8-12 membered saturated, partially unsaturated, or fully unsaturated bicyclic ring system having 0-5 heteroatoms independently selected from nitrogen, oxygen, or sulfur; or two occurrences of $R^D$ are taken together with the atom(s) to which they are attached form an optionally substituted 3-12 membered saturated, partially unsaturated, or fully unsaturated monocyclic or bicyclic ring having 1-4 heteroatoms independently selected from nitrogen, oxygen, or sulfur, each of which is optionally substituted with 1 to 3 substituents.

In several embodiments of formula II, when $R_1$ or $R_2$ is 3,5-bis-trifluoromethylphenylmethyl, ring A together with $R_9$ and $R_{10}$ is not piperazinyl, optionally substituted piperidinyl, morpholinyl, or imidazolyl; when $R_1$ and $R_2$ together form pyrrolidinyl, morpholinyl, piperidinyl, each optionally substituted with —$CH_3$ or —$CH_2 CH_3$, then X is not m-methyl, o-halo, p-aryl, and p-cyano; when $R_1$ and $R_2$ are aliphatic or alkoxyalkyl, then X is not from m-methyl, o-halo, p-aryl, and p-cyano; and when $R_1$ is phenylmethyl optionally substituted with 1-2 —$CH_3$ groups or cycloaliphatic, and $R_2$ is one selected from unsubstituted methyl, ethyl, and isopropyl, then (1) ring B must form pyrrolidinyl, morpholinyl, piperidinyl optionally substituted with aliphatic, or aminocarbonyl, or alkylcarbonyl, and (2) X is not o-halo, p-aryl, m-alkyl, or p-cyano.

Each $R_9$ and $R_{10}$ is hydrogen, halo, hydroxy, cyano, or $C_{1-6}$ aliphatic, alkoxy, alkoxycarbonyl, alkoxycabonylamino, aryl, heteroaryl, aralkyl, heteroaralkyl, cycloaliphatic, or heterocycloaliphatic, each of which is optionally substituted with 1-3 substituients; or $R_9$ and $R_{10}$ together with the atom(s) to which they are attached form a 5-6 membered ring that is optionally substituted with 1-3 substituents.

In several embodiments, $R_9$ or $R_{10}$ is an optionally substituted $C_{1-6}$ aliphatic. For example, $R_9$ or $R_{10}$ is an optionally substituted straight or branched $C_{1-6}$ aliphatic. For example, $R_9$ or $R_{10}$ is optionally substituted straight (e.g., methyl, ethyl, propyl, butyl, or the like) or branched (e.g., isopropyl, isobutyl, sec-propyl, sec-butyl or the like) aliphatic. For example, $R_9$ or $R_{10}$ is methyl, ethyl, propyl, butyl, pentyl, hexyl, heptyl, or octyl, each substituted with 1-3 substituents. In other examples, $R_9$ or $R_{10}$ is an isopropyl or sec-propyl that is optionally substituted with 1-2 substituents, or $R_9$ or $R_{10}$ is an unsubstituted sec-propyl or isopropyl. In several embodiments, $R_9$ or $R_{10}$ is unsubstituted methyl, ethyl, propyl, butyl, pentyl, or hexyl. In other embodiments, $R_9$ or $R_{10}$ is a —C(O)OH substituted aliphatic (e.g., hydroxycarbonylalkyl). For example, $R_9$ or $R_{10}$ is a methyl, ethyl, or propyl, each of which is substituted with —C(O)OH. In several embodiments, $R_9$ or $R_{10}$ is substituted with halo, cyano, hydroxy, or optionally substituted cycloaliphatic, heterocycloaliphatic, aryl, alkoxy, haloalkylaryl, bicycloaliphatic, aryloxy, haloaryl, alkylamino, heteroaryl, cycloaliphatic, or heterocycloaliphatic. In other embodiment, $R_9$ or $R_{10}$ is methyl, ethyl, or propyl that is substituted with a monocyclic optionally substituted aryl. For example, $R_9$ or $R_{10}$ is methyl, ethyl, or propyl that is substituted with alkoxyphenyl, cycloaliphaticphenyl, haloalkylphenyl, cyanophenyl, halophenyl, or hydroxyphenyl. In other embodiments, $R_9$ or $R_{10}$ is methyl, ethyl, or propyl that is substituted with a bicyclic aryl. For example $R_9$ or $R_{10}$ is methyl, ethyl, or propyl that is substituted with unsubstituted naphthyl or indenyl. In other embodiments, $R_9$ or $R_{10}$ is di-substituted with two substituents independently selected from halo, cyano, hydroxyl, aliphatic, aryl, heteroaryl, cycloaliphatic, heterocycloaliphatic, or alkoxy. In some embodiments, $R_9$ or $R_{10}$ is methyl substituted with aliphatic and aryl. In several embodiments, $R_9$ or $R_{10}$ includes an optionally substituted partially unsaturated aliphatic (e.g., alkenyl or alkynyl). In several examples, $R_9$ or $R_{10}$ includes optionally substituted ethenyl, propenyl, or butenyl. In other embodiments, $R_9$ or $R_{10}$ includes unsubstituted methyl or propenyl. —In several embodiments, $R_9$, $R_{10}$, and the atom(s) to which they are attached form a 5-6 membered ring that is optionally substituted with 1-3 substituents. For example, $R_9$ and $R_{10}$ are attached to different carbon atoms and together with the carbon atoms form an optionally substituted 5-6 membered ring that is fused to ring A of formula II. In some embodiments, $R_9$, $R_{10}$, and the carbon atoms to which they are attached form an optionally substituted fully saturated, partially unsaturated, or fully unsaturated ring that is optionally substituted. In some embodiments, $R_9$, $R_{10}$, and the carbon atoms to which they are attached form a fully saturated 5-6 membered ring that is optionally substituted. For example, $R_9$, $R_{10}$, and the carbon atoms to which they are attached form a 5-6 membered cycloalkyl or heterocycloalkyl that is optionally substituted. In some embodiments, $R_9$, $R_{10}$, and the carbon atoms to which they are attached form an optionally substituted cyclohexyl or cyclopentyl ring that is fused to ring A. For example, $R_9$, $R_{10}$, and the carbon atoms to which they are attached form an unsubstituted cyclohexyl that is fused to ring A to create an unsubstituted decahydroquinolinyl or octahydroindolyl. In another embodiment, $R_9$, $R_{10}$, and the carbon atoms to which they are attached form an unsubstituted cyclopentyl that is fused to ring A to create an unsubstituted octahydrocyclopenta[b]pyridinyl or octahydrocyclopenta[b]pyrrolyl. In other embodiments, $R_9$, $R_{10}$, and the carbon atoms to which they are attached form a cycloalkyl ring that is fused to ring A and substituted with halo, aliphatic, alkoxy, cycloaliphatic, heterocycloaliphatic, aryl or heteroaryl. In some embodiments, $R_9$, $R_{10}$, and the carbon atoms to which they are attached form an optionally substituted aryl ring that is fused to ring A. For example, $R_9$, $R_{10}$, and the carbon atoms to which they are attached form an optionally substituted phenyl that is fused to ring A to form a substituted or unsubstituted 1,2,3,4-tetrahydroquinolinyl or indolinyl.

In several embodiments, $R_9$ or $R_{10}$ is an optionally substituted alkoxy. For example, the aliphatic chain of the alkoxy can be straight or branched and substituted at any chemically feasible position. In some embodiments, $R_9$ or $R_{10}$ is an optionally substituted methoxy, ethoxy, propoxy, butoxy, pentoxy, or hexoxy. In other embodiments, $R_9$ or $R_{10}$ is unsubstituted.

In several embodiments, $R_9$ or $R_{10}$ is an optionally substituted alkoxy carbonyl. For example, the aliphatic chain of the alkoxy can be straight or branched and substituted at any chemically feasible position. In some embodiments, $R_9$ or $R_{10}$ is an optionally substituted methoxycarbonyl, ethoxycarbonyl, propoxycarbonyl, butoxycarbonyl, pentoxycarbonyl, or hexoxycarbonyl.

In several embodiments, $R_9$ or $R_{10}$ is an optionally substituted monocyclic or bicyclic cycloaliphatic. In some embodiments, $R_9$ or $R_{10}$ is a monocyclic cycloaliphatic optionally substituted with 1-3 substituents selected from hydroxy, alkoxy, alkylamino, alkyl carbonyl, aliphatic, and halo. In other embodiments, $R_9$ or $R_{10}$ is optionally substituted cyclopropyl, cyclobutyl, cyclopentyl, cyclohexyl, or cycloheptyl. For example, $R_9$ or $R_{10}$ is unsubstituted cyclopropyl, cyclobutyl, cyclopentyl, cyclohexyl, or cycloheptyl. In other embodiments, $R_9$ or $R_{10}$ is optionally substituted bicycloaliphatic. In several examples, $R_9$ or $R_{10}$ is bicycloaliphatic optionally substituted with 1-3 substituents selected from hydroxy, alkoxy, alkylamino, alkyl carbonyl, aliphatic, and halo. In other examples, $R_9$ or $R_{10}$ is optionally substituted bicyclo[1.1.1]pentane, bicyclo[2.1.1]hexane, or bicyclo[2.2.1]heptane. In other examples, $R_9$ or $R_{10}$ is unsubstituted bicyclo[2.1.1]hexyl, or bicyclo[2.2.1]heptyl.

In several embodiments, $R_9$ or $R_{10}$ is an optionally substituted monocyclic or bicyclic heterocycloaliphatic including 1-3 heteroatoms selected from N, O, and S. In one group of examples, $R_9$ or $R_{10}$ is fully saturated or partially unsaturated. In one group of examples, $R_9$ or $R_{10}$ is an optionally substituted fully saturated monocyclic heterocycloaliphatic. In another group of examples, $R_9$ or $R_{10}$ is morpholinyl, pyrroldinyl, thiomorpholinyl, tetrahydro-2H-pyranyl, or tetrahydrothiophenyl, each optionally substituted with 1-3 substituents. In another group of examples, $R_9$ or $R_{10}$ is unsubstituted morpholinyl, pyrrolidinyl, thiomorpholinyl, tetrahydro-2H-pyranyl, or tetrahydrothiophenyl. In another group of examples, $R_9$ or $R_{10}$ is an unsubstituted tropane.

In several examples of compounds of formula II, when $R_9$ and $R_{10}$ are hydrogen, neither $R_1$ nor $R_2$ are H, —$CH_3$, or —$CH_3C_6H_5$.

Another aspect of the present invention includes compounds of formula III:

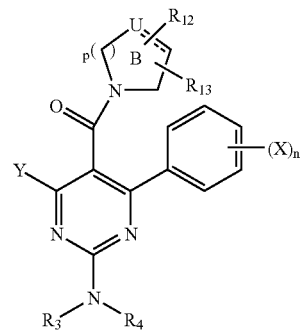

III or a pharmaceutically acceptable salt thereof, wherein $R_3$, $R_4$, X, Y, and n are defined above; and Each U is one selected from —CH—, —$CH_2$—, —N—, —O—, and —S—.

Each p is 1 or 2.

Each $R_{12}$ and $R_{13}$ are defined by —$Z^E R_{15}$, wherein each $Z^E$ is independently a bond or an optionally substituted straight or branched $C_{1-6}$ aliphatic chain wherein up to two carbon units of $Z^C$ are optionally and independently replaced by —CO—, —CS—, —COCO—, —$CONR^E$—, —$CONR^E NR^E$—, —$CO_2$—, —OCO—, —$NR^E CO_2$—, —O—, —$NR^E CONR^E$—, —$OCONR^E$—, —$NR^E NR^E$—, —$NR^E N-R^E CO$—, —$NR^E CO$—, —S—, —SO—, —$SO_2$—, —$NR^E$—, —$SO_2 NR^E$—, —$NR^E SO_2$—, or —$NR^E SO_2 NR^E$—.

Each $R_{15}$ is independently $R^E$, halo, —OH, —$NH_2$, —$NO_2$, —CN, —$CF_3$, or —$OCF_3$.

Each $R^E$ is independently hydrogen, an optionally substituted $C_{1-8}$ aliphatic group, an optionally substituted 3-8 membered fully saturated, partially unsaturated, or fully unsaturated monocyclic ring having 0-3 heteroatoms independently selected from nitrogen, oxygen, or sulfur; an optionally substituted 8-12 membered fully saturated, partially unsaturated, or fully unsaturated bicyclic ring system having 0-5 heteroatoms independently selected from nitrogen, oxygen, or sulfur; or two occurrences of $R^E$ are taken together with the atom(s) to which they are attached to form an optionally substituted 3-12 membered fully saturated, partially unsaturated, or fully unsaturated monocyclic or bicyclic ring having 1-4 heteroatoms independently selected from nitrogen, oxygen, or sulfur, each of which is optionally substituted with 1 to 3 substituents.

In some embodiments of formula III, when ring B is pyrrolidinyl, morpholinyl, piperidinyl, and $R_{12}$ or $R_{13}$ is —$CH_3$ or —$CH_2CH_3$, then X is not m-methyl, o-halo,p-aryl, or p-cyano.

Each $R_{12}$ and $R_{13}$ is hydrogen, halo, hydroxy, cyano, or $C_{1-6}$ aliphatic, alkoxy, alkoxycarbonyl, alkoxycabonylamino, aryl, heteroaryl, aralkyl, heteroaralkyl, cycloaliphatic, or heterocycloaliphatic, each of which is optionally substituted with 1-3 substituents; or $R_{12}$ and $R_{13}$ together with the atom(s) to which they are attached form a 5-6 membered ring that is optionally substituted with 1-3 substituents.

In several embodiments, $R_{12}$, $R_{13}$, and the atom(s) to which they are attached form a 5-6 membered ring that is optionally substituted with 1-3 substituents. For example, $R_{12}$ and $R_{13}$ are attached to different carbon atoms and together with the carbon atoms form an optionally substituted 5-6 membered ring that is fused to ring B of formula III. In some embodiments, $R_{12}$, $R_{13}$, and the carbon atoms to which they are attached form an optionally substituted fully saturated, partially unsaturated, or fully unsaturated ring that is optionally substituted. In some embodiments, $R_{12}$, $R_{13}$, and the carbon atoms to which they are attached form a fully saturated 5-6 membered ring that is optionally substituted. For example, $R_{12}$, $R_{13}$, and the carbon atoms to which they are attached form a 5-6 membered cycloalkyl or heterocycloalkyl that is optionally substituted. In some embodiments, $R_{12}$, $R_{13}$, and the carbon atoms to which they are attached form an optionally substituted cyclohexyl or cyclopentyl ring that is fused to ring B. For example, $R_{12}$, $R_{13}$, and the carbon atoms to which they are attached form an unsubstituted cyclohexyl that is fused to ring B to create an unsubstituted decahydroquinolinyl or octahydroindolyl. In another embodiment, $R_{12}$, $R_{13}$, and the carbon atoms to which they are attached form an unsubstituted cyclopentyl that is fused to ring B to create an unsubstituted octahydrocyclopenta[b]pyridinyl or octahydrocyclopenta[b]pyrrolyl. In other embodiments, $R_{12}$, $R_{13}$, and the carbon atoms to which they are attached form a cycloalkyl ring that is fused to ring B and is substituted with halo, aliphatic, alkoxy, cycloaliphatic, heterocycloaliphatic, aryl or heteroaryl. In some embodiments, $R_{12}$, $R_{13}$, and the carbon atoms to which they are attached form an optionally substituted aryl ring that is fused to ring B. For example, $R_{12}$, $R_{13}$, and the carbon atoms to which they are attached form an optionally substituted phenyl that is fused to ring B to form a substituted or unsubstituted 1,2,3,4-tetrahydroquinolinyl or indolinyl. In other examples, $R_{12}$, $R_{13}$, and the carbon atoms to which they are attached form a mono- or di-substituted phenyl. In some embodiments, $R_{12}$, $R_{13}$, and the carbon atoms to which they are attached form a phenyl that is substituted with alkoxy (e.g., methoxy), aliphatic, alkylcarbonyl, or alkoxycarbonyl. In several examples, $R_{12}$, $R_{13}$, and the carbon atoms to which they are attached form a phenyl substituted with 1-2 methoxy groups that is fused to ring B.

In several embodiments, $R_{12}$ or $R_{13}$ is optionally substituted aryl. For example, $R_{12}$ or $R_{13}$ is aryl substituted with 1-2 substituents. In other examples, $R_{12}$ or $R_{13}$ is aryl substituted with aliphatic, halo, hydroxy, cyano, aryl, alkoxy, alkylcarbonyl, or alkoxycarbonyl. In several examples, $R_{12}$ or $R_{13}$ is unsubstituted.

In several examples, $R_{12}$ or $R_{13}$ is an optionally substituted alkoxy. For example, $R_{12}$ or $R_{13}$ is optionally substituted $C_{1-6}$-alkoxy. In several examples, $R_{12}$ or $R_{13}$ is optionally substituted methoxy, ethoxy, propoxy, butoxy, pentoxy, or hexoxy. In several other examples, $R_{12}$ or $R_{13}$ is substituted with aliphatic, aryl, heteroaryl, cycloaliphatic, or heterocycloaliphatic. In several embodiments, $R_{12}$ or $R_{13}$ is unsubstituted methoxy, ethoxy, propoxy, butoxy, pentoxy, or hexoxy.

In several embodiments, $R_{12}$ or $R_{13}$ is optionally substituted alkylcarbonyl. For example, $R_{12}$ or $R_{13}$ is optionally substituted $C_{1-6}$-alkyl-carbonyl. Other examples include methylcarbonyl, ethylcarbonyl, propylcarbonyl, butylcarbonyl, pentylcarbonyl, or hexylcarbonyl, each of which is optionally substituted with 1-2 substituents. In several embodiments, $R_{12}$ or $R_{13}$ is substituted with aliphatic, amino, hydroxyl, aryl, or heteroaryl. In several embodiments, $R_{12}$ or $R_{13}$ is unsubstituted methylcarbonyl, ethylcarbonyl, propylcarbonyl, butylcarbonyl, pentylcarbonyl, or hexylcarbonyl.

In several embodiments, $R_{12}$ or $R_{13}$ is an optionally substituted $C_{1-6}$ aliphatic. For example, $R_{12}$ or $R_{13}$ is an optionally substituted straight or branched $C_{1-6}$ aliphatic. For example, $R_{12}$ or $R_{13}$ is optionally substituted straight (e.g., methyl, ethyl, propyl, butyl, or the like) or branched (e.g., isopropyl, isobutyl, sec-propyl, sec-butyl or the like) aliphatic. For example, $R_{12}$ or $R_{13}$ is methyl, ethyl, propyl, butyl, pentyl, hexyl, heptyl, or octyl, each substituted with 1-3 substituents. In other examples, $R_{12}$ or $R_{13}$ is an isopropyl or sec-propyl that is optionally substituted with 1-2 substituents, or $R_{12}$ or $R_{13}$ is an unsubstituted sec-propyl or isopropyl. In several embodiments, $R_{12}$ or $R_{13}$ is unsubstituted methyl, ethyl, propyl, butyl, pentyl, or hexyl. In other embodiments, $R_{12}$ or $R_{13}$ is a —C(O)OH substituted aliphatic (e.g., alkyl-C(O)OH). For example, $R_{12}$ or $R_{13}$ is a methyl, ethyl, or propyl, each of which is substituted with —C(O)OH. In several embodiments, $R_{12}$ or $R_{13}$ is substituted with halo, cyano, hydroxy, or optionally substituted cycloaliphatic, heterocycloaliphatic, aryl, alkoxy, haloalkylaryl, bicycloaliphatic, aryloxy, haloaryl, alkylamino, heteroaryl, cycloaliphatic, or heterocycloaliphatic. In other embodiment, $R_{12}$ or $R_{13}$ is methyl, ethyl, or propyl that is substituted with a monocyclic optionally substituted aryl. For example, $R_{12}$ or $R_{13}$ is methyl, ethyl, or propyl that is substituted with alkoxyphenyl, cycloaliphaticphenyl, haloalkylphenyl, cyanophenyl, halophenyl, or hydroxyphenyl. In other embodiments, $R_{12}$ or $R_{13}$ is methyl, ethyl, or propyl that is substituted with a bicyclic aryl. For example $R_{12}$ or $R_{13}$ is methyl, ethyl, or propyl that is substituted with unsubstituted naphthyl or indenyl. In other embodiments, $R_{12}$ or $R_{13}$ is di-substituted with two substituents independently selected from halo, cyano, hydroxyl, aliphatic, aryl, heteroaryl, cycloaliphatic, heterocycloaliphatic, or alkoxy. In some embodiments, $R_{12}$ or $R_{13}$ is methyl substituted with aliphatic and aryl. In several embodiments, $R_{12}$ or $R_{13}$ includes an optionally substituted partially unsaturated aliphatic (e.g., alkenyl or alkynyl). In several examples, $R_{12}$ or $R_{13}$ includes optionally substituted ethenyl, propenyl, or butenyl. In other embodiments, $R_{12}$ or $R_{13}$ includes unsubstituted methyl or propenyl.

In several examples of compounds of formulae Ia, II, or III:

When R is alkyl, $R_2$ is not 3,5-bis-trifluoromethyl-phenyl-alkyl.

When $R_1$ and $R_2$ together form pyrrolidinyl, morpholinyl, or piperidinyl, each optionally substituted with —$CH_3$ or —$CH_2CH_3$, then X is not m-methyl, o-halo, p-aryl, or p-cyano.

When each $R_1$ or $R_2$ is aliphatic or alkoxyalkyl, then X is not m-methyl, o-halo, p-aryl, and p-cyano.

When $R_1$ is phenylmethyl optionally substituted with 1-2 —$CH_3$ groups or cycloaliphatic, and $R_2$ is unsubstituted methyl, ethyl, or isopropyl, then $R_3$ together with $R_4$ must form pyrrolidinyl, morpholinyl, piperidinyl optionally substituted with aliphatic, aminocarbonyl, or alkylcarbonyl, or each $R_3$ or $R_4$ is phenylmethyl, methylfuranyl, or methoxypropyl, and X is not m-methyl, p-aryl, o-halo or p-cyano.

6. Examples of Compounds

Exemplary compounds of the present invention include, but are not limited to, those illustrated in Table 1 below.

TABLE 1
Examples of compounds of the present invention
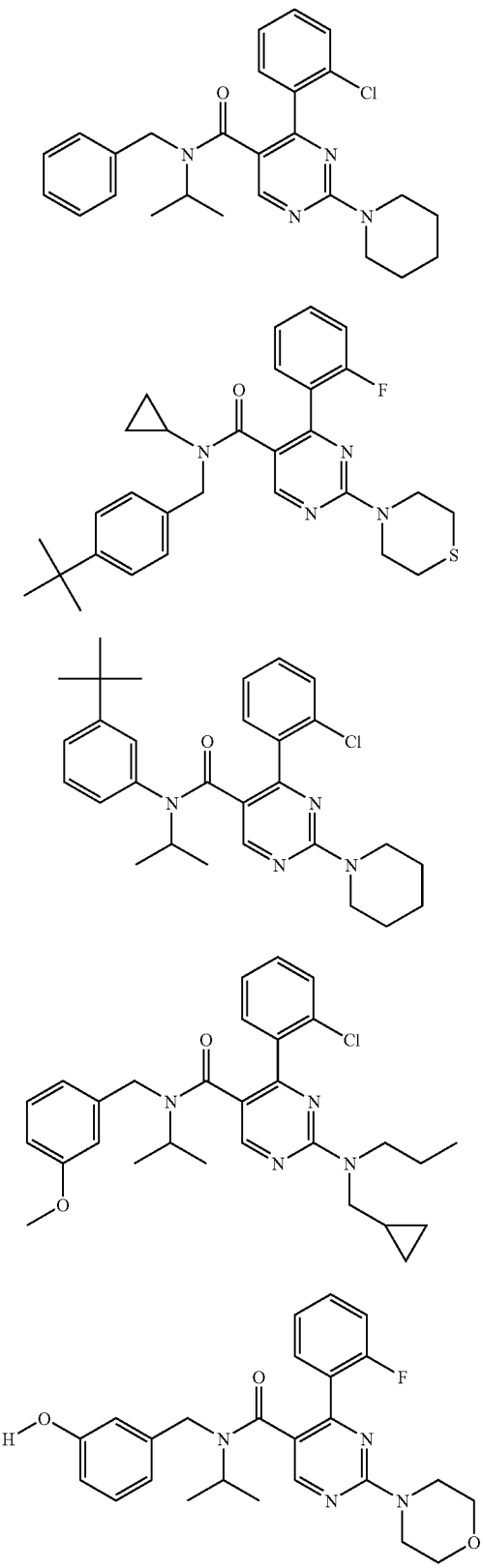
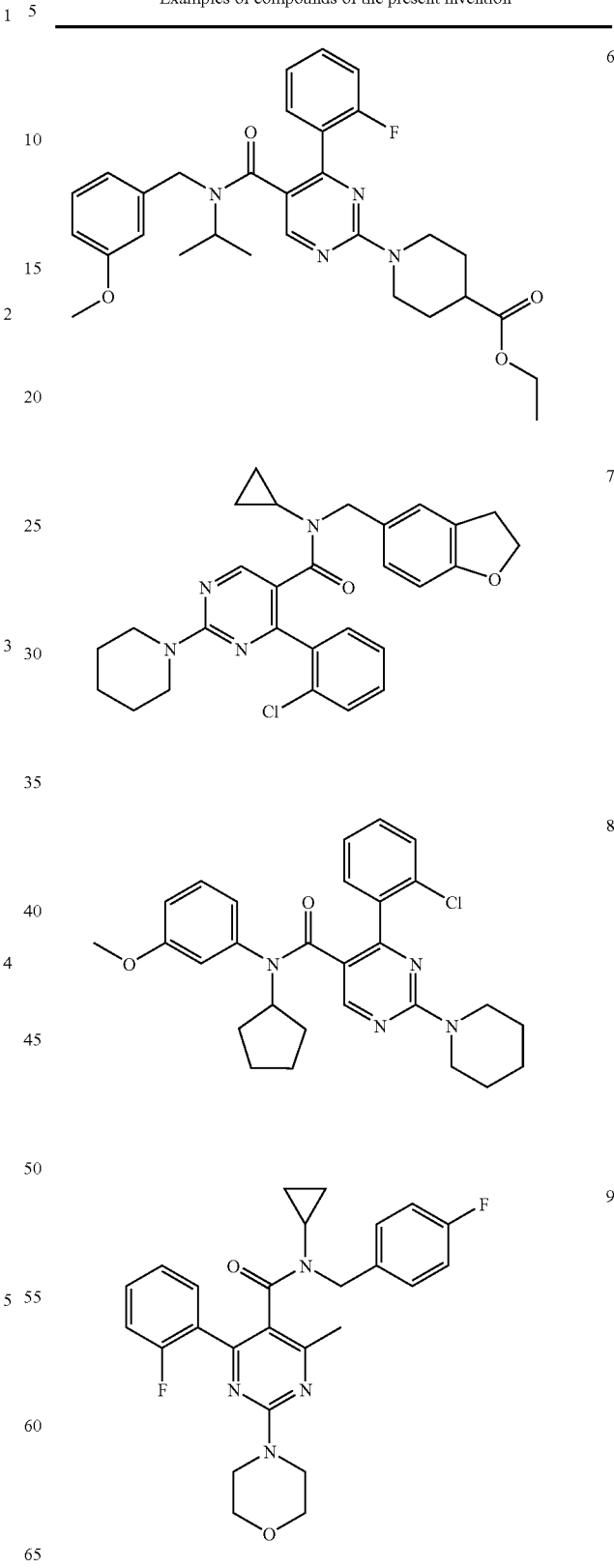

TABLE 1-continued
Examples of compounds of the present invention
10
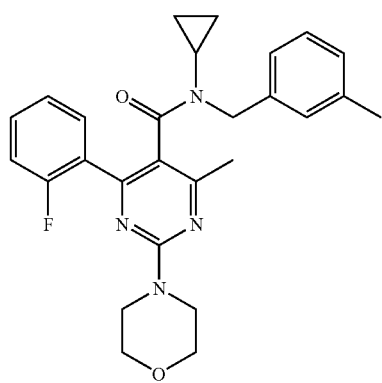
11
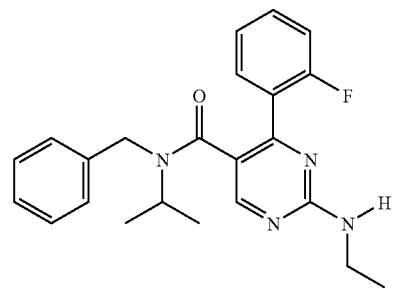
12
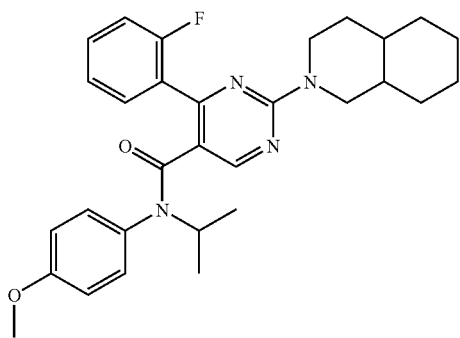
13
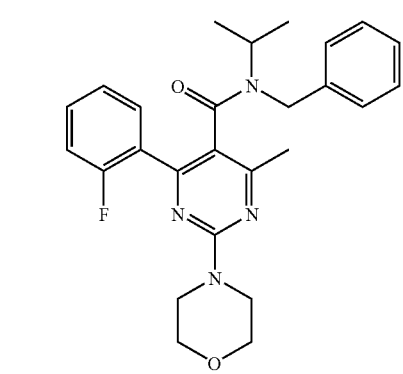
TABLE 1-continued
Examples of compounds of the present invention
14
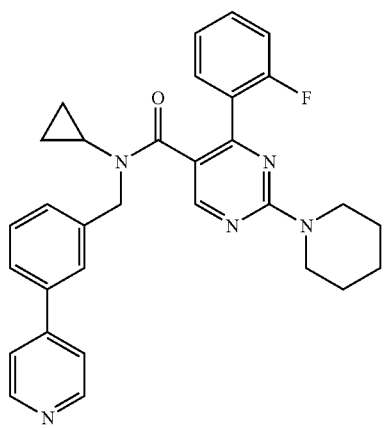
15
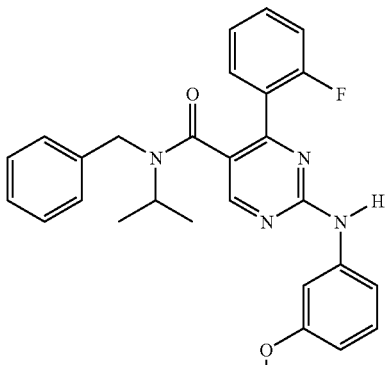
16
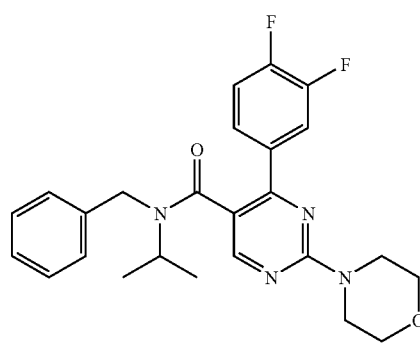
17
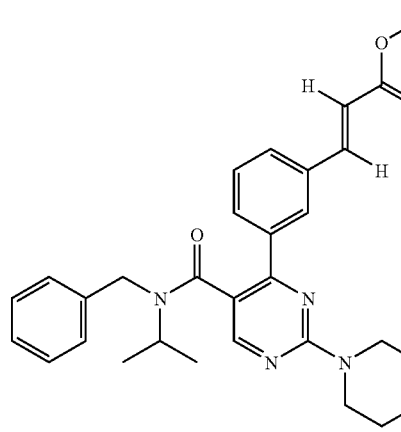

TABLE 1-continued
Examples of compounds of the present invention
18
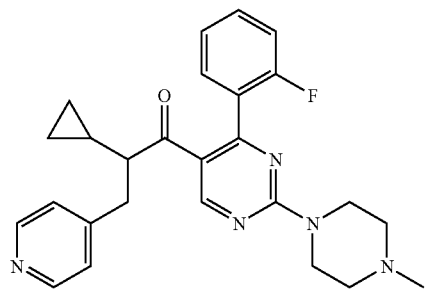
19
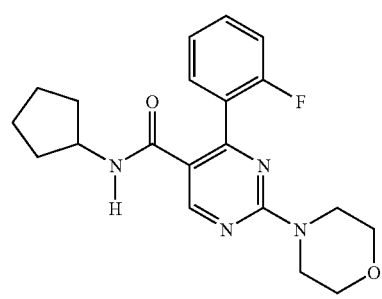
20
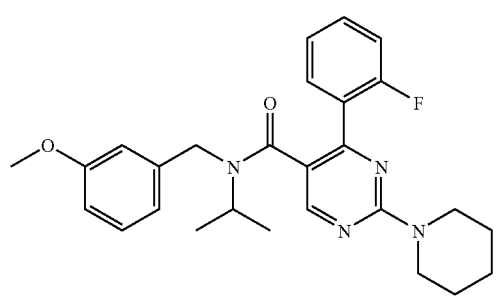
21
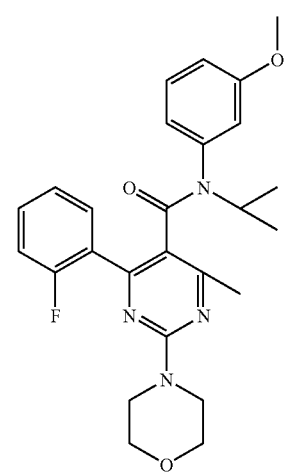
TABLE 1-continued
Examples of compounds of the present invention
22
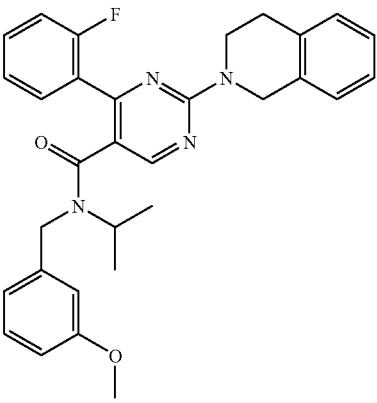
23
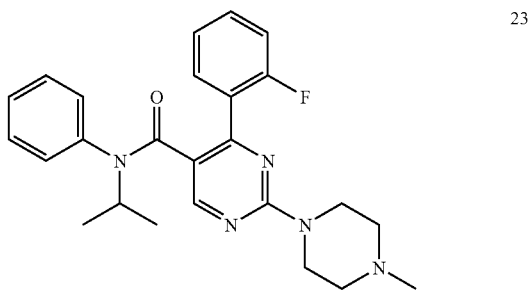
24
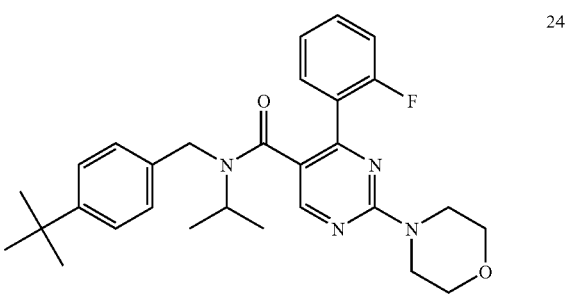
25
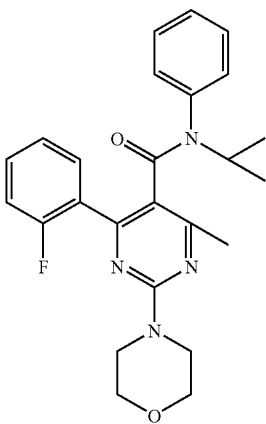

TABLE 1-continued
Examples of compounds of the present invention
26 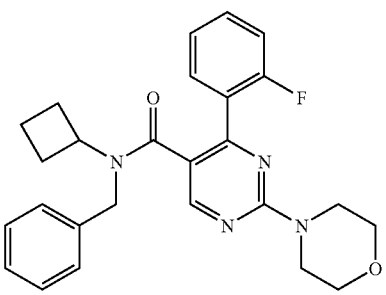
27 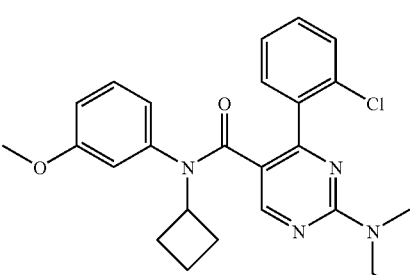
28 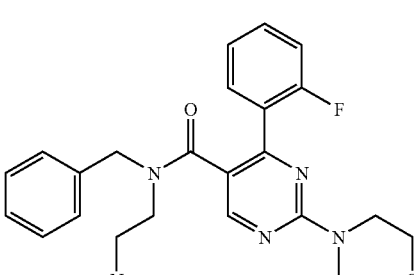
29 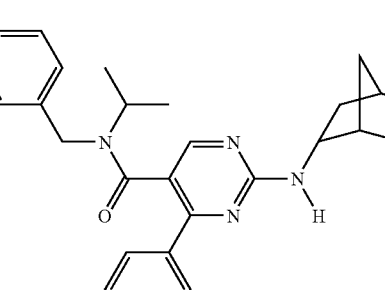
30 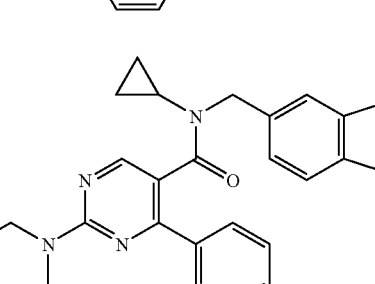
TABLE 1-continued
Examples of compounds of the present invention
31 
32 
33 
34 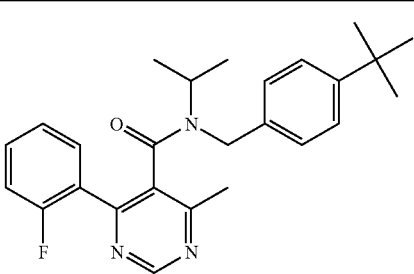

TABLE 1-continued
Examples of compounds of the present invention
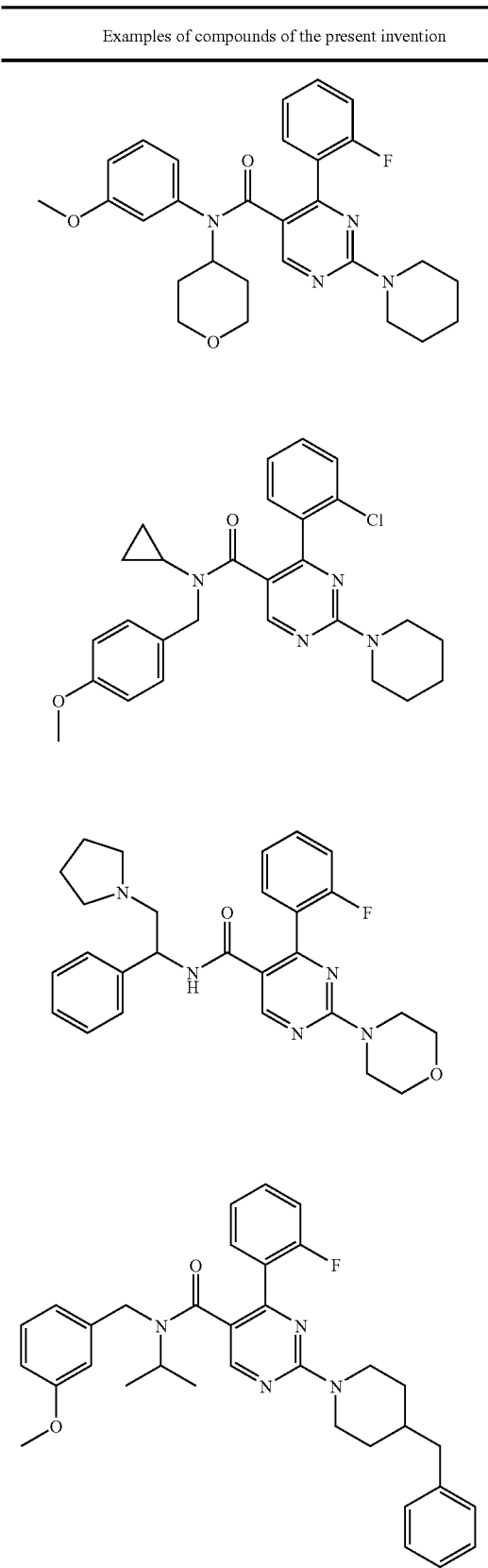
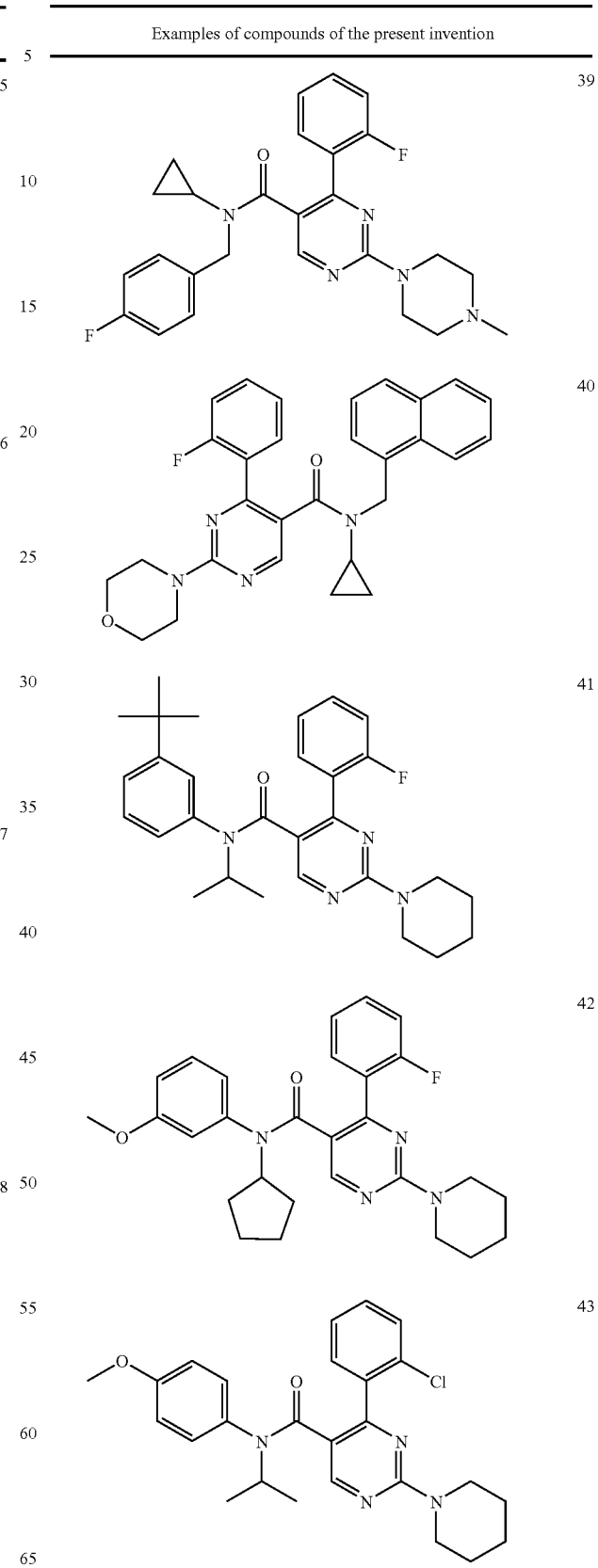

TABLE 1-continued
Examples of compounds of the present invention
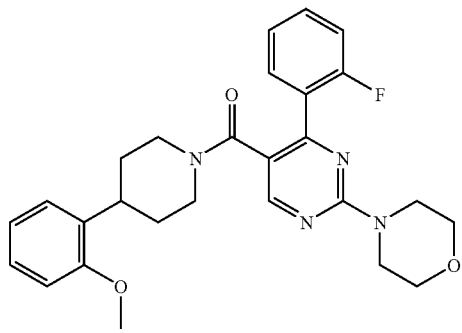
44
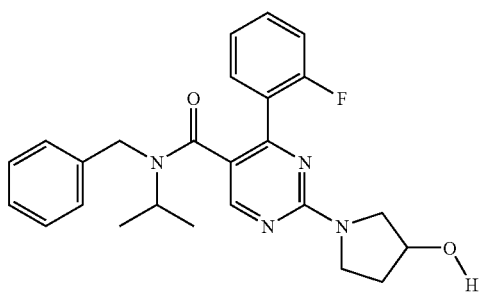
45
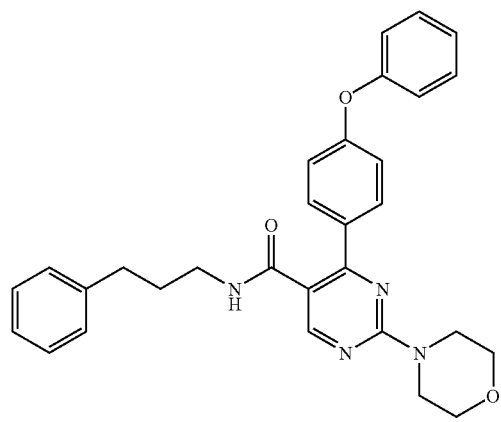
46
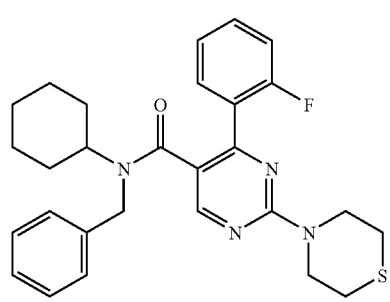
47
TABLE 1-continued
Examples of compounds of the present invention
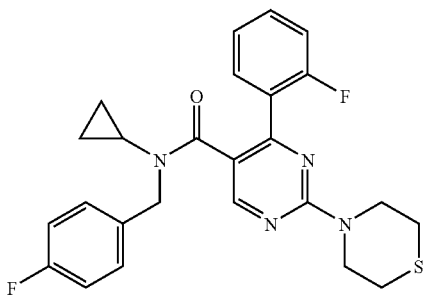
48
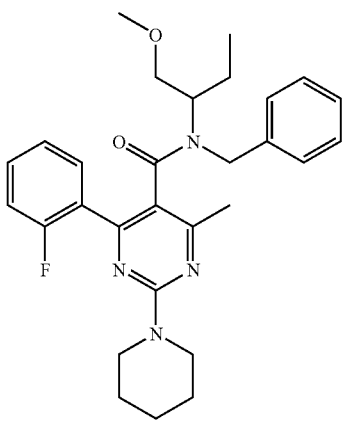
49
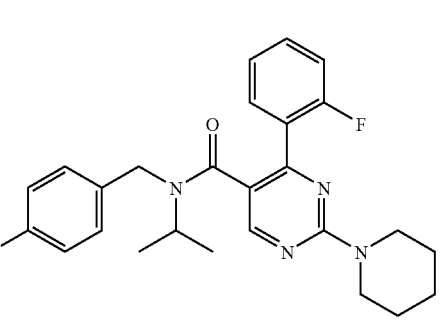
50
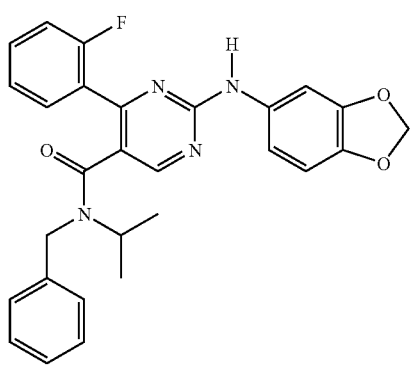
51

TABLE 1-continued
Examples of compounds of the present invention
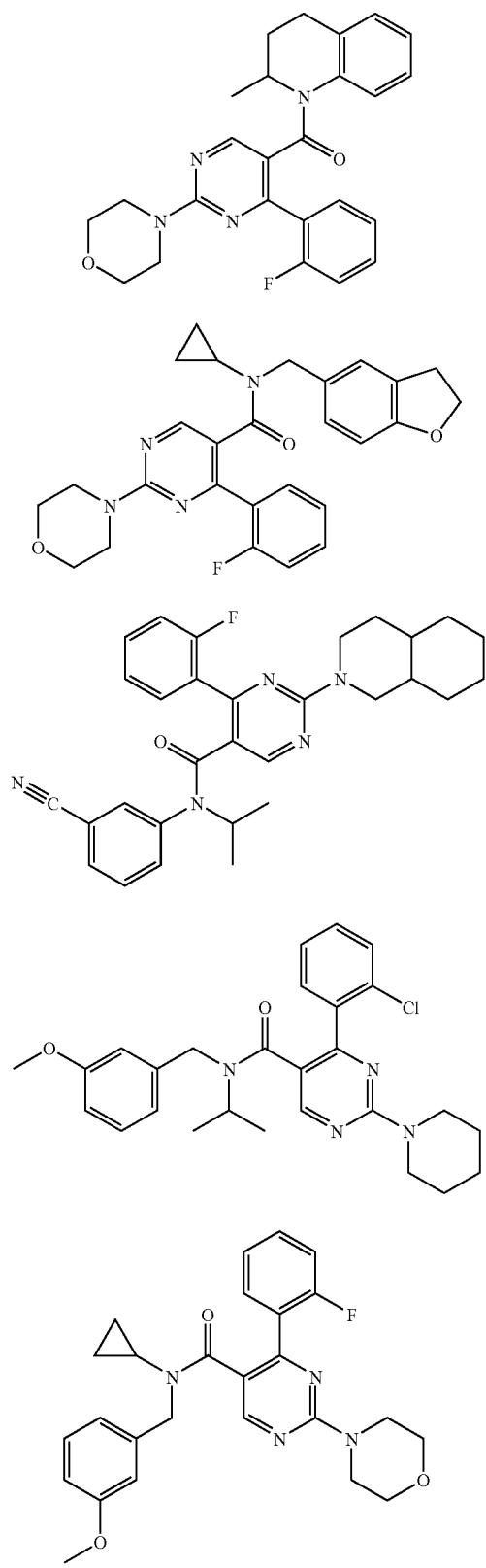
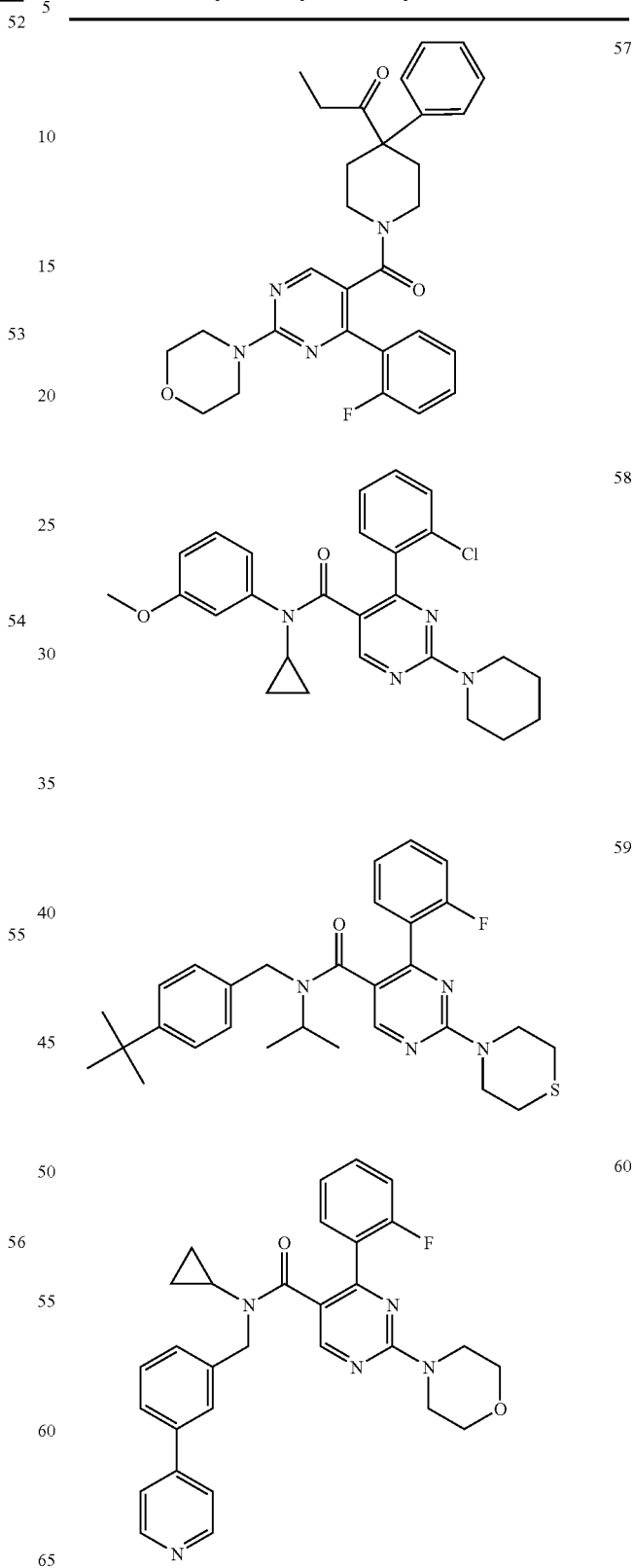

TABLE 1-continued
Examples of compounds of the present invention
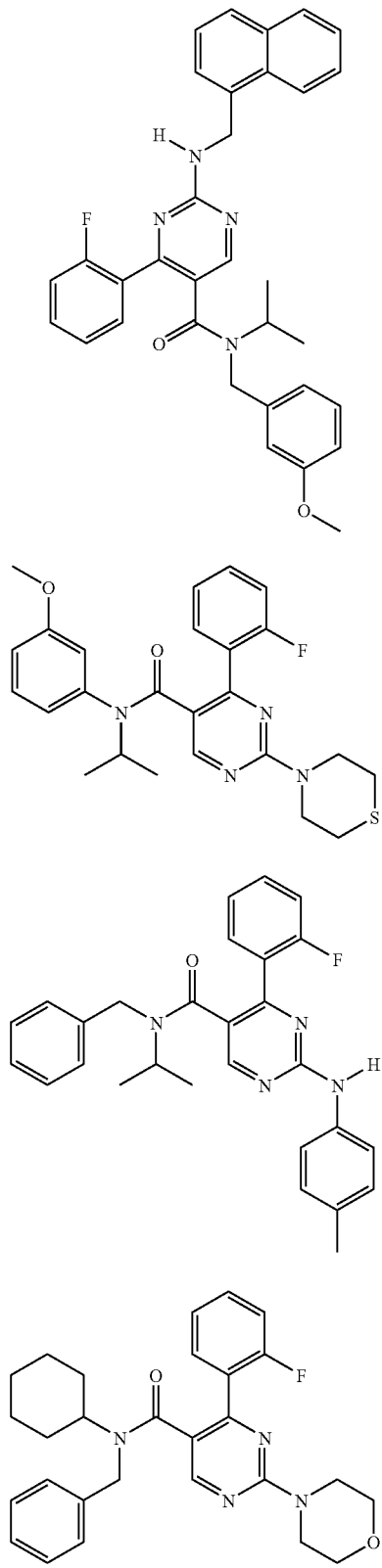
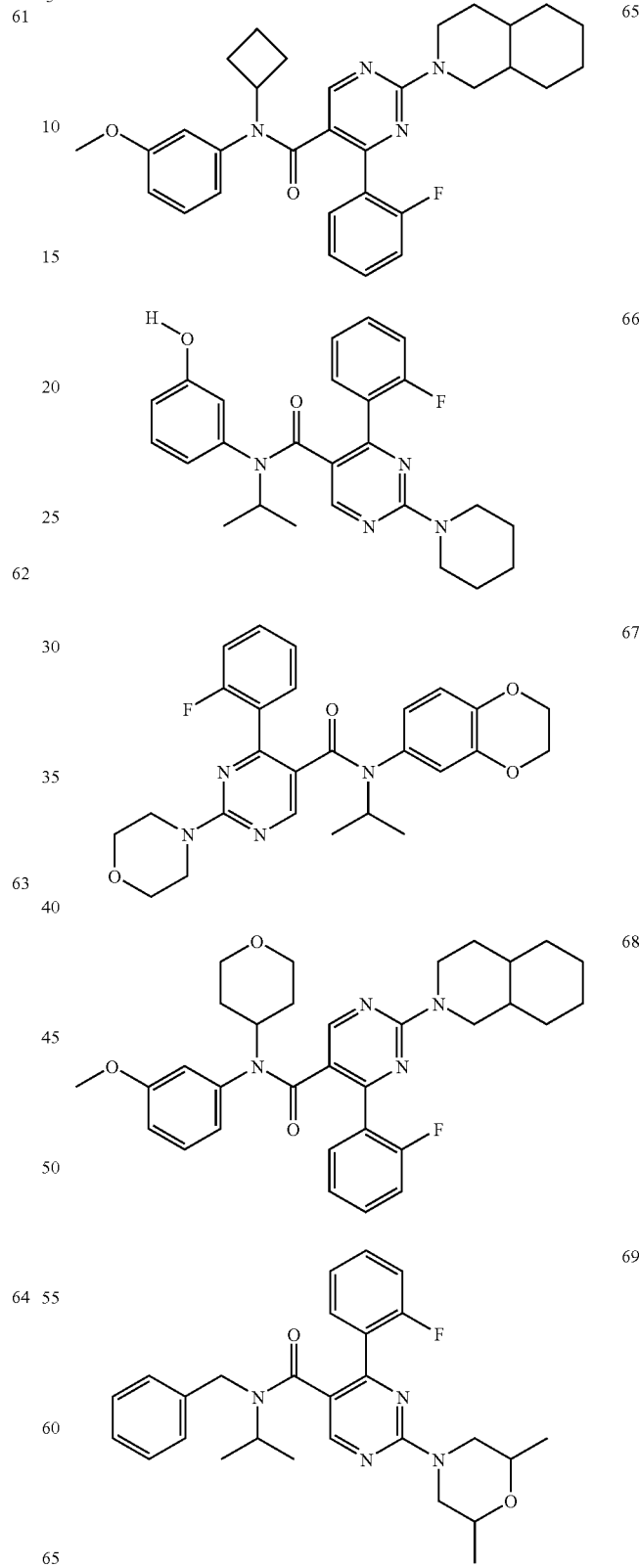

TABLE 1-continued
Examples of compounds of the present invention
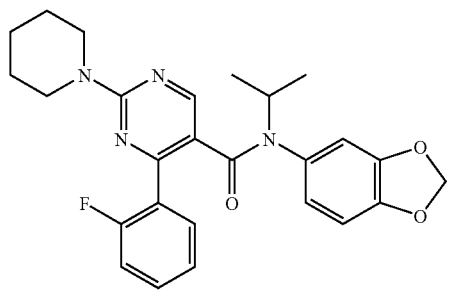
70
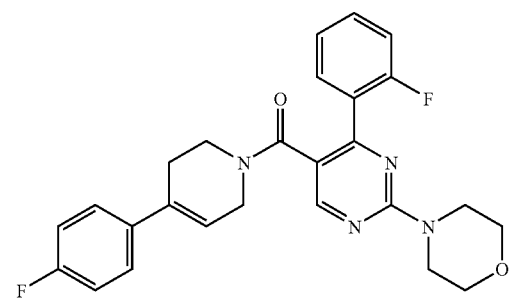
71
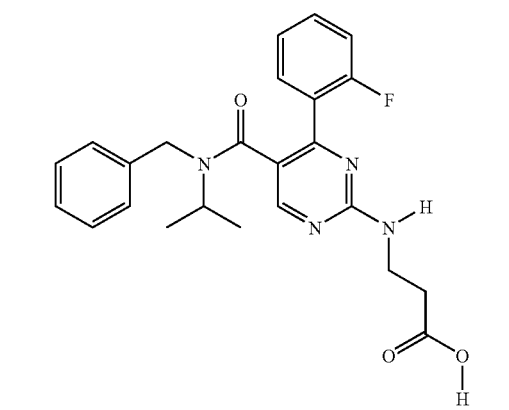
72
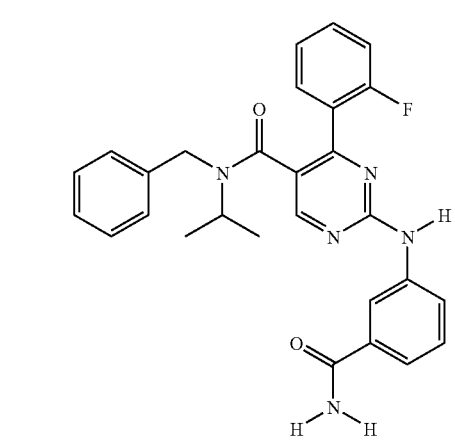
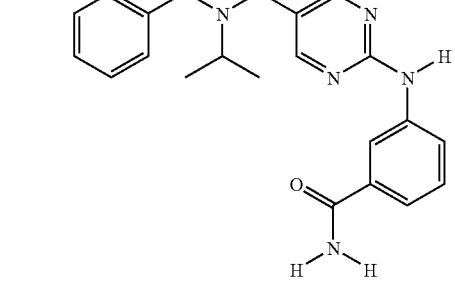
73
TABLE 1-continued
Examples of compounds of the present invention
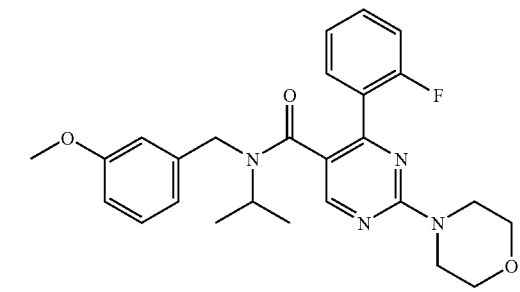
74
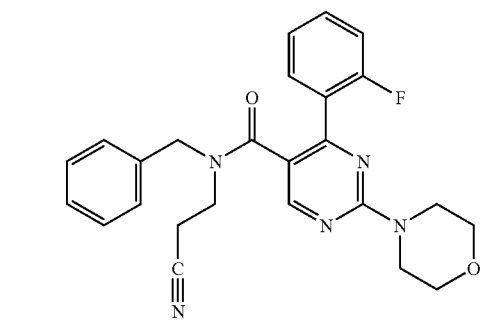
75
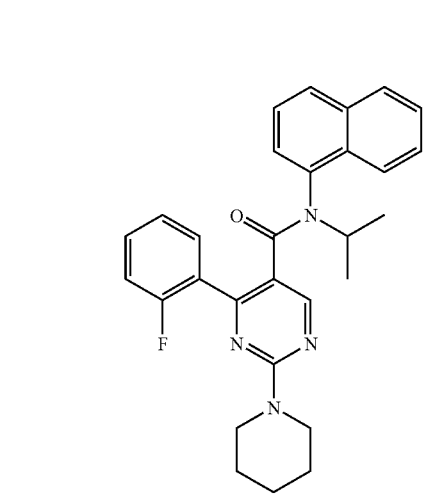
76
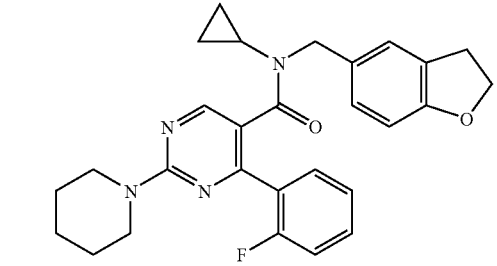
77

TABLE 1-continued
Examples of compounds of the present invention
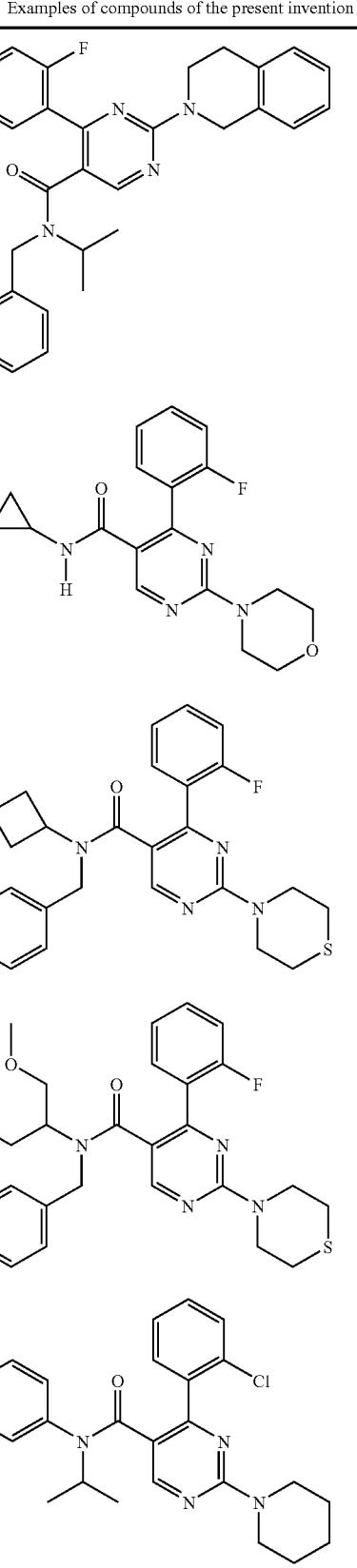
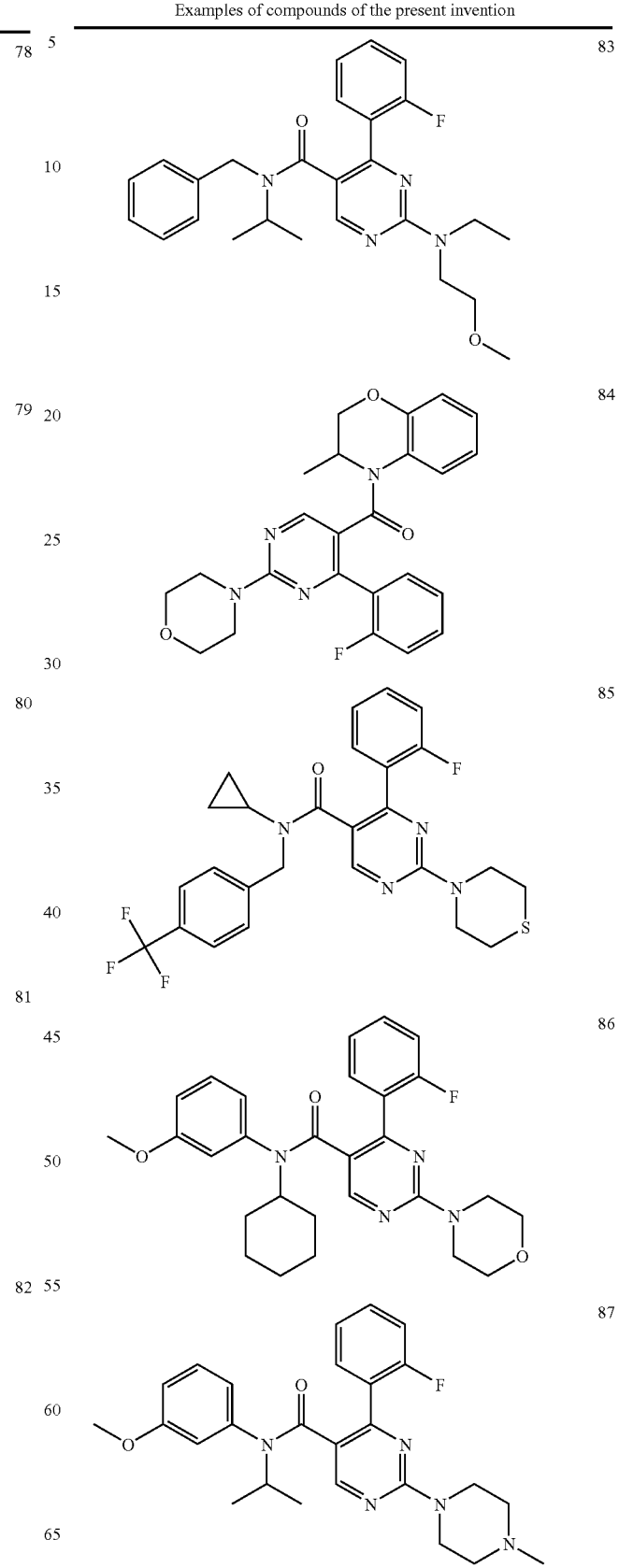

TABLE 1-continued

Examples of compounds of the present invention

TABLE 1-continued

Examples of compounds of the present invention

TABLE 1-continued
Examples of compounds of the present invention
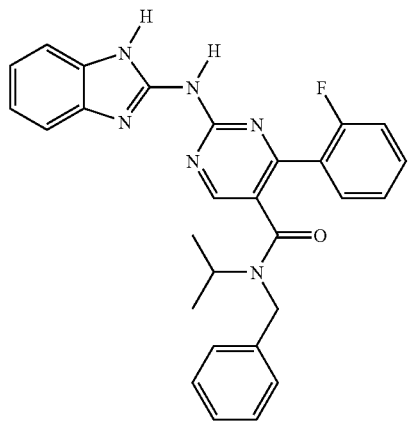
106
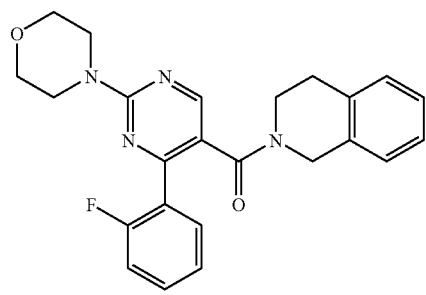
107
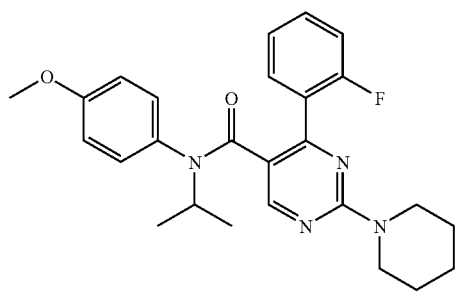
108
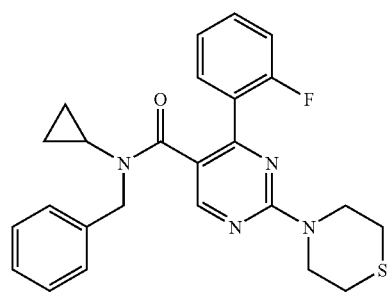
109
TABLE 1-continued
Examples of compounds of the present invention
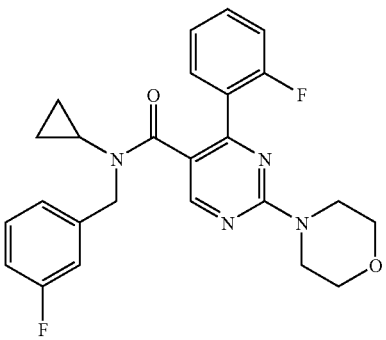
110
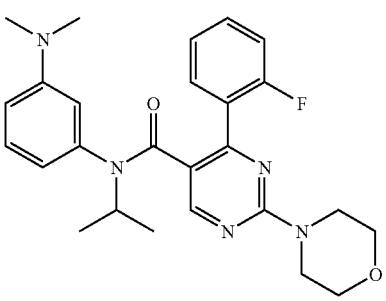
111
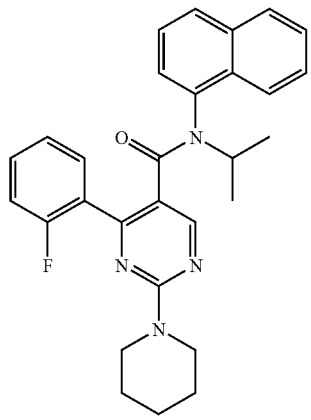
112
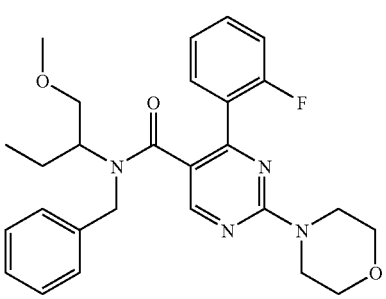
113

TABLE 1-continued
Examples of compounds of the present invention
| | |
|---|---|
| 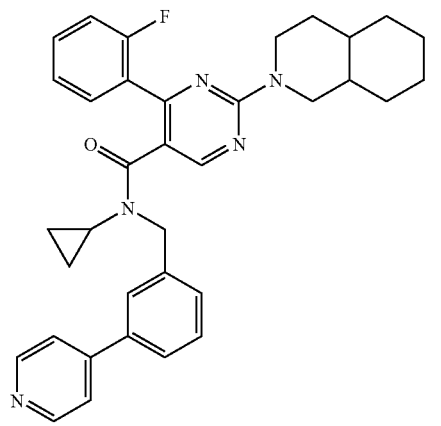 114 | 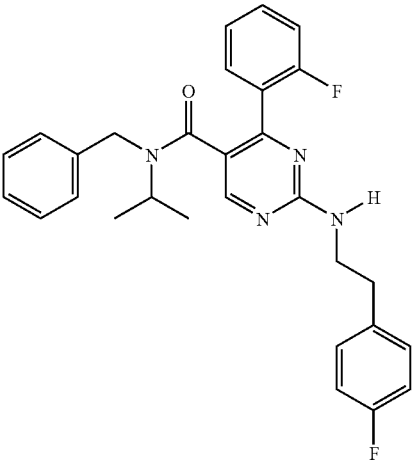 118 |
| 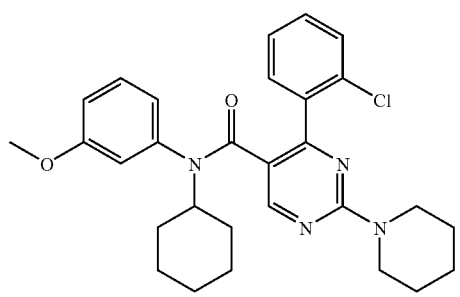 115 | 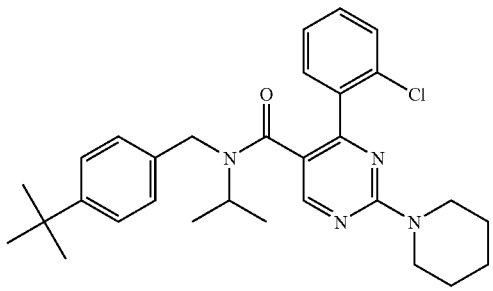 119 |
| 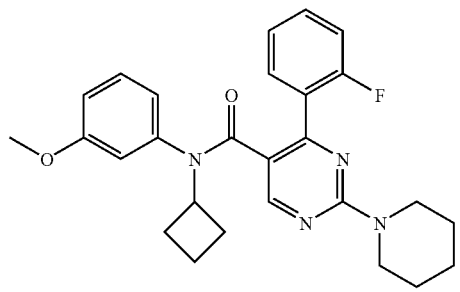 116 | 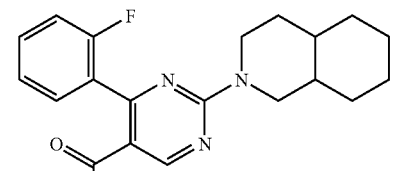 120 |
| 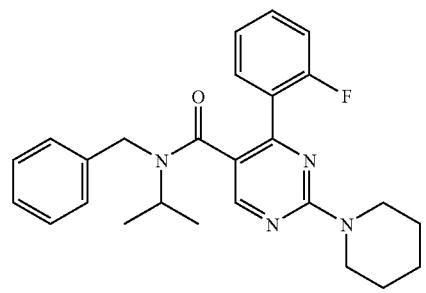 117 | 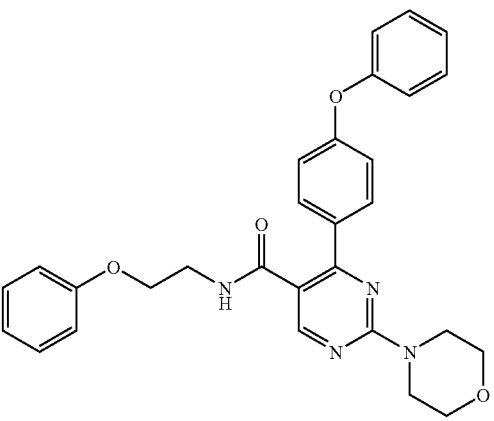 121 |

TABLE 1-continued
Examples of compounds of the present invention
122 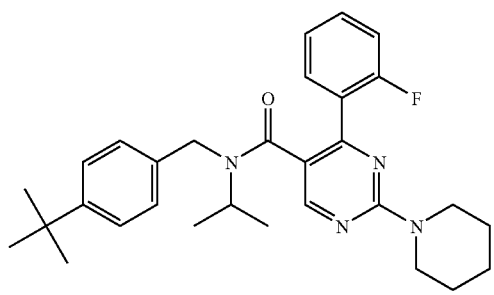
123 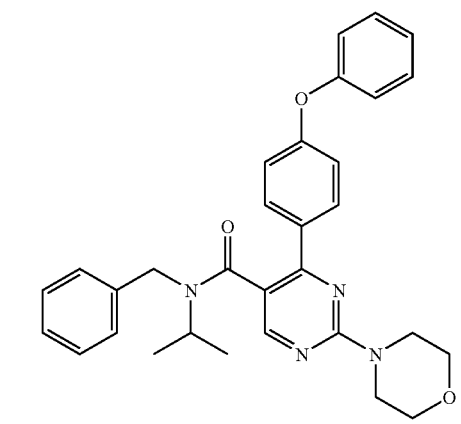
124 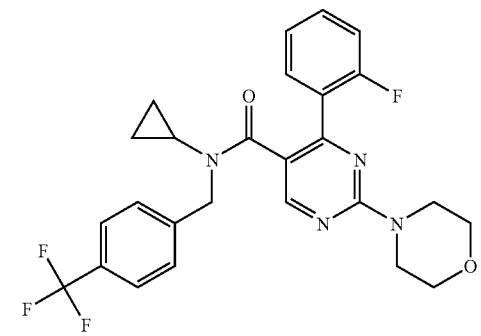
125 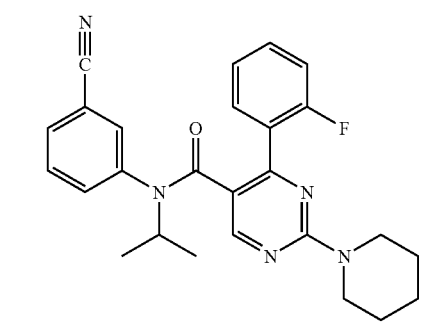
TABLE 1-continued
Examples of compounds of the present invention
126 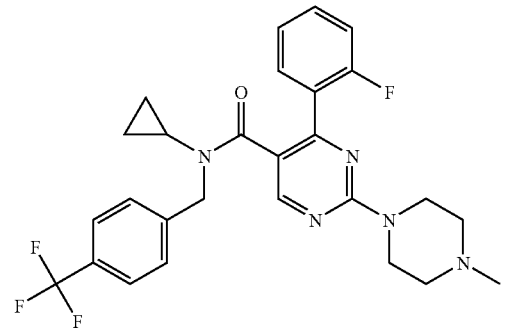
127 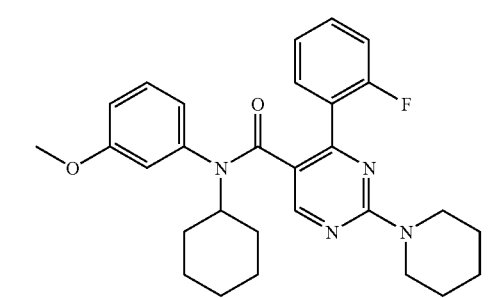
128 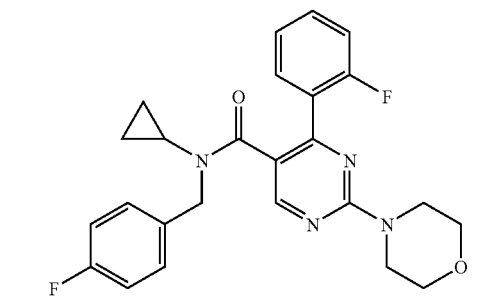
129 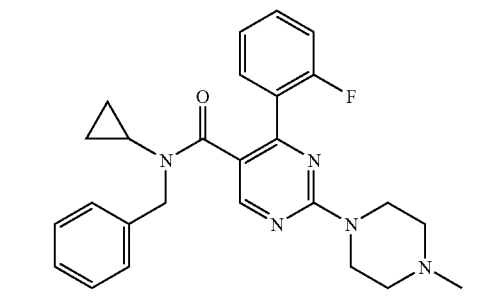
130 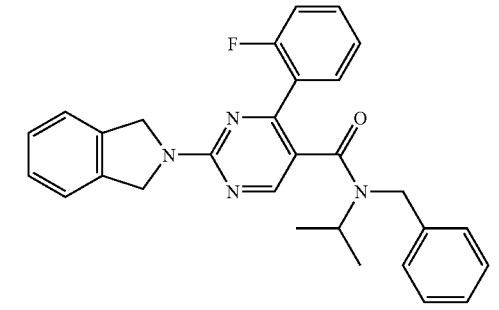

TABLE 1-continued
Examples of compounds of the present invention
131 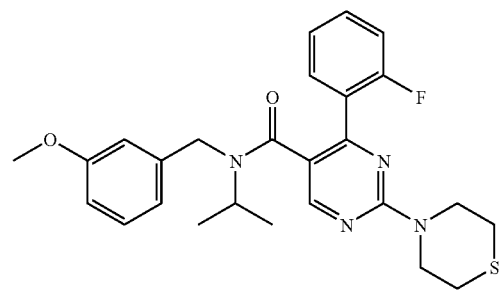
132 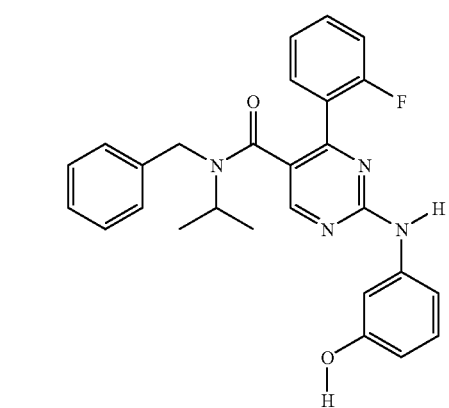
133 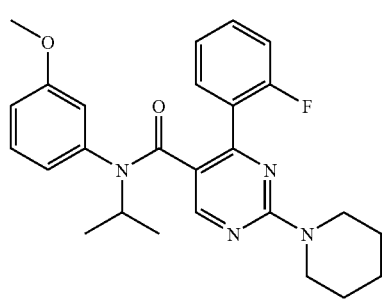
134 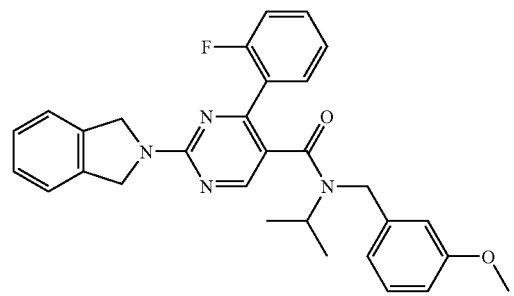
TABLE 1-continued
Examples of compounds of the present invention
135 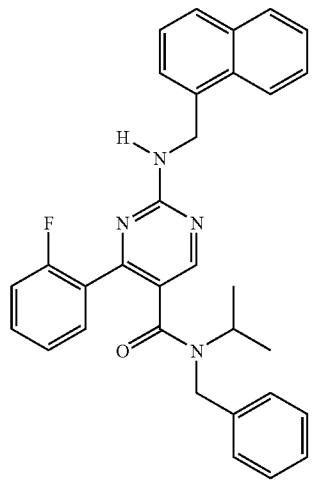
136 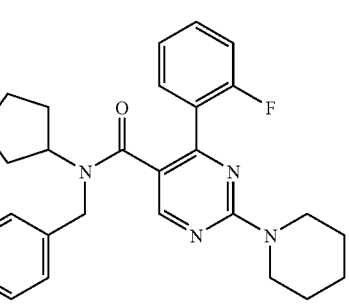
137 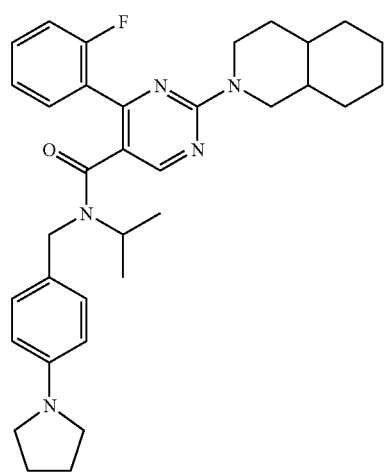
138 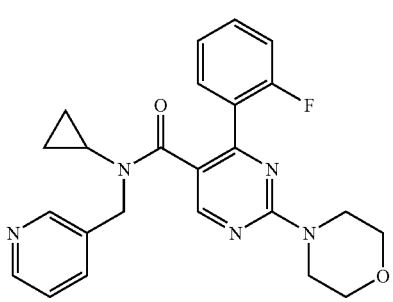

TABLE 1-continued
Examples of compounds of the present invention
| | |
|---|---|
| 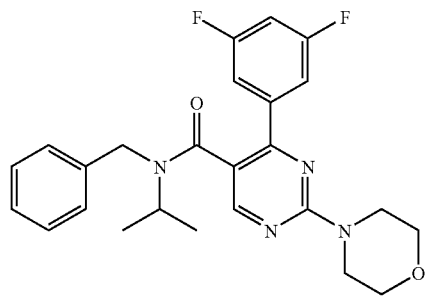 | 139 |
| 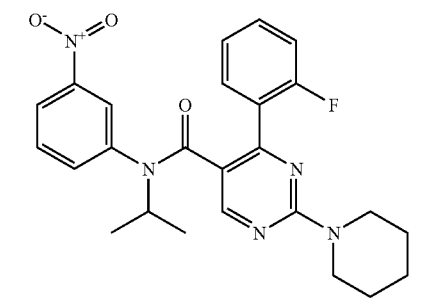 | 140 |
| 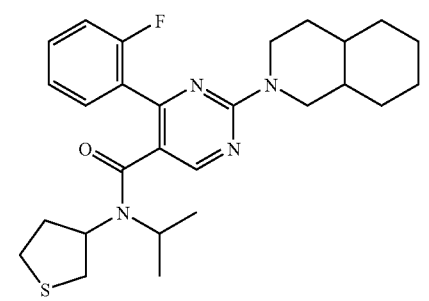 | 141 |
| 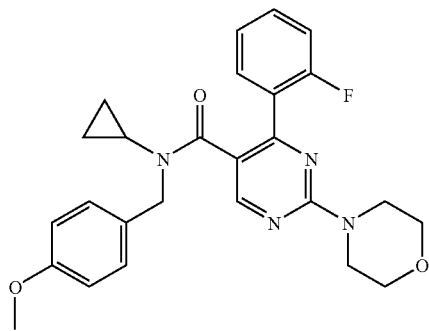 | 142 |
| 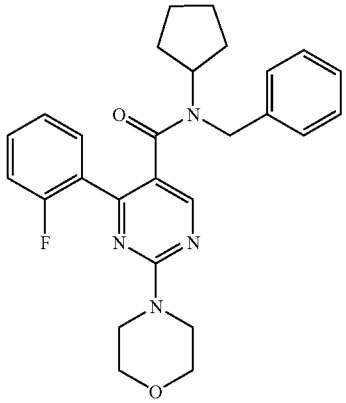 | 143 |
| 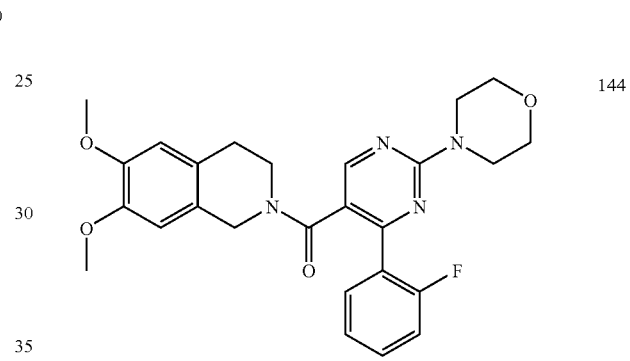 | 144 |
| 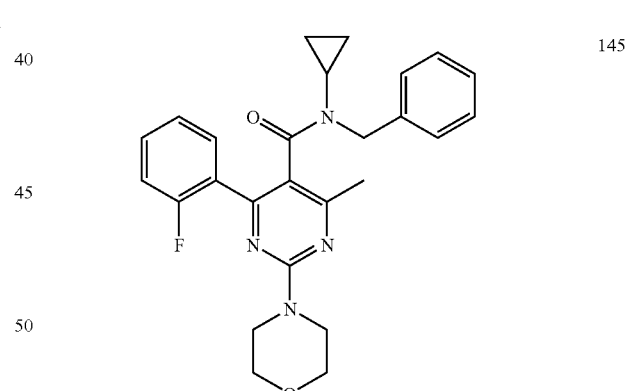 | 145 |
| 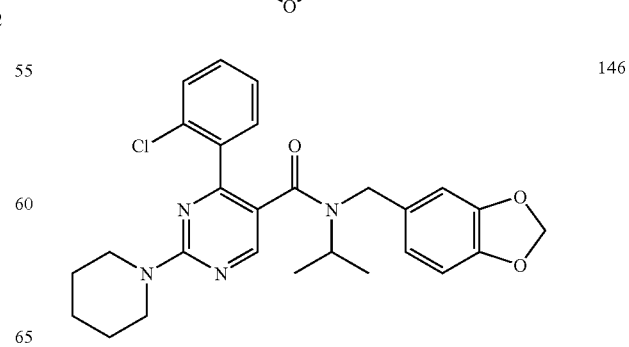 | 146 |

TABLE 1-continued
Examples of compounds of the present invention
147
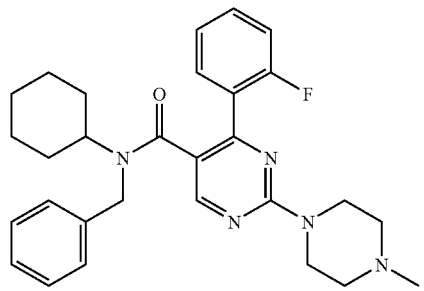
148
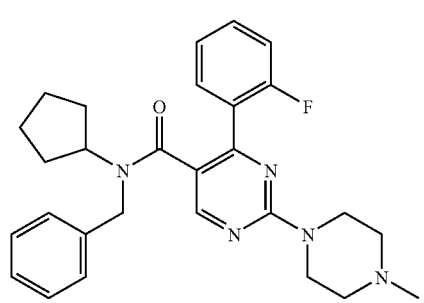
149
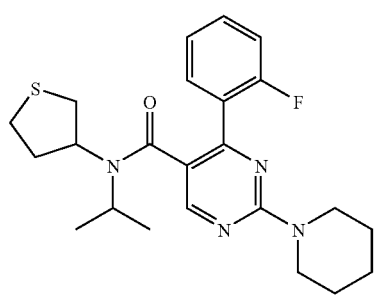
150
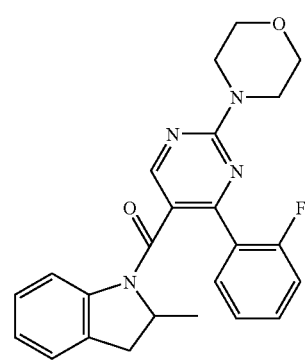
TABLE 1-continued
Examples of compounds of the present invention
151
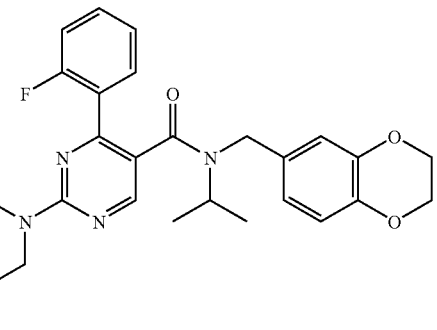
152
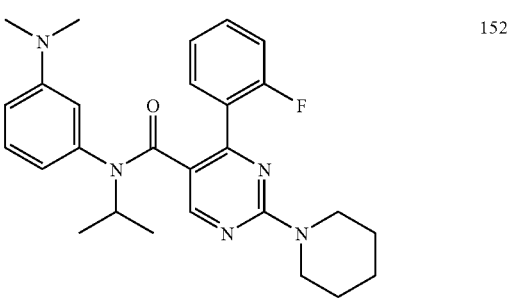
153
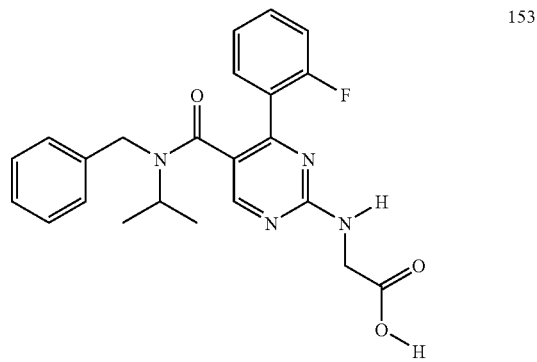
154
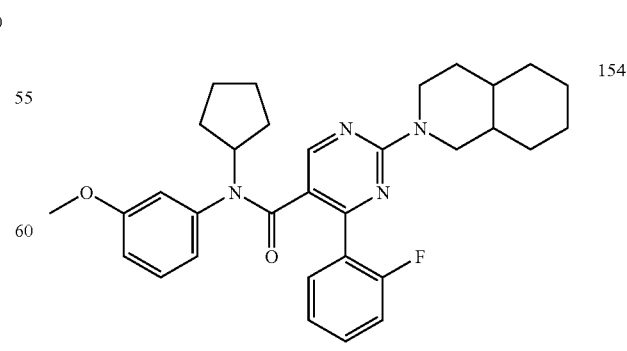

TABLE 1-continued
Examples of compounds of the present invention
155
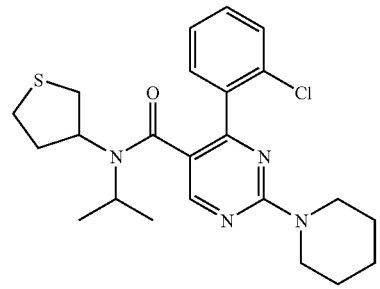
156
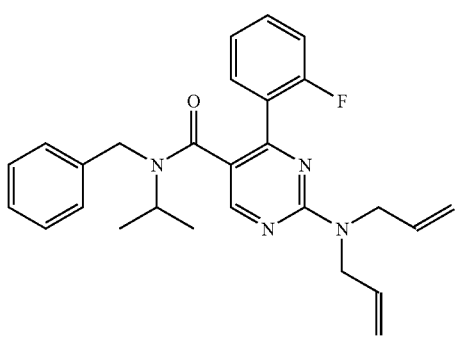
157
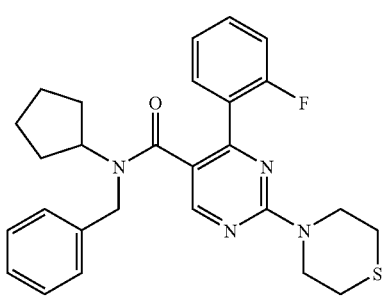
158
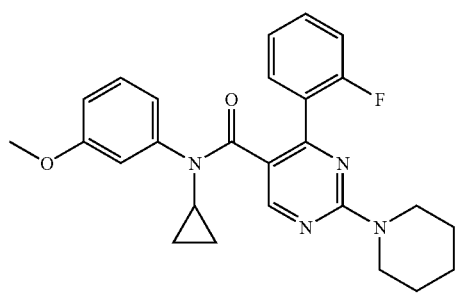
159
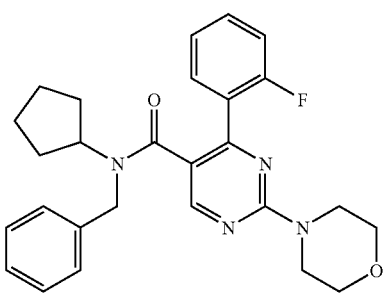
TABLE 1-continued
Examples of compounds of the present invention
160
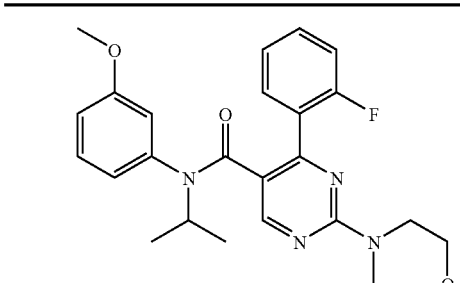
161
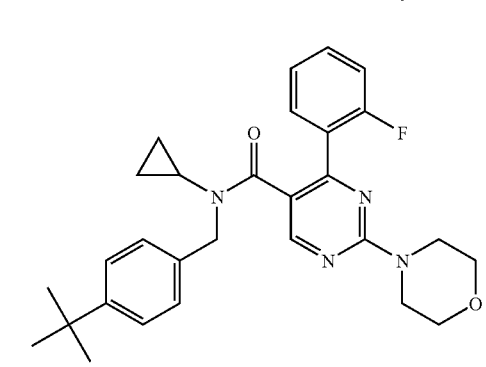
162
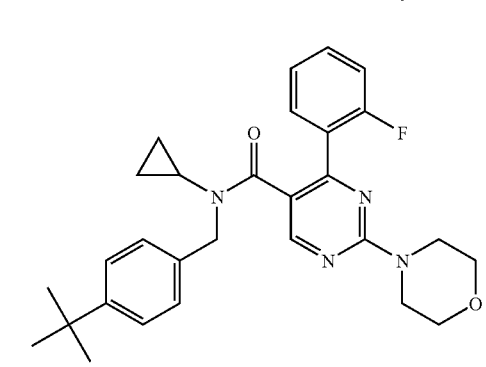
163
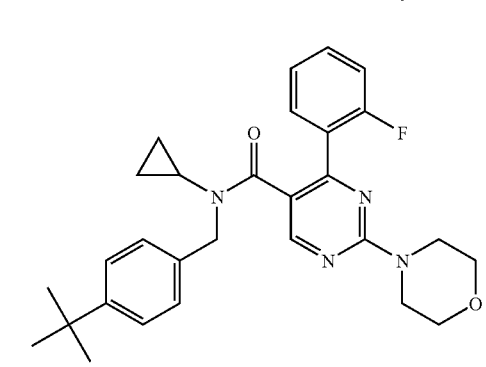

TABLE 1-continued
Examples of compounds of the present invention
164
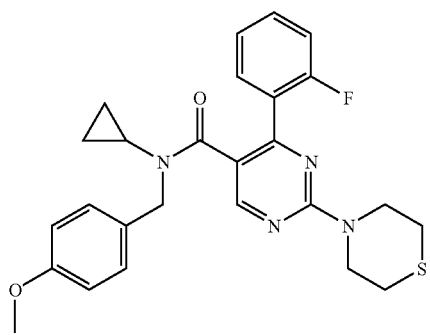
165
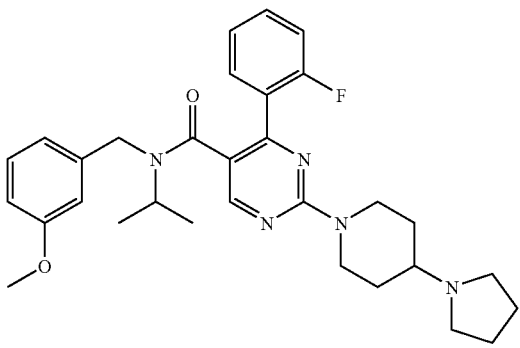
166
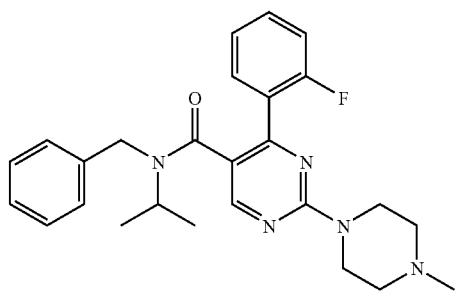
167
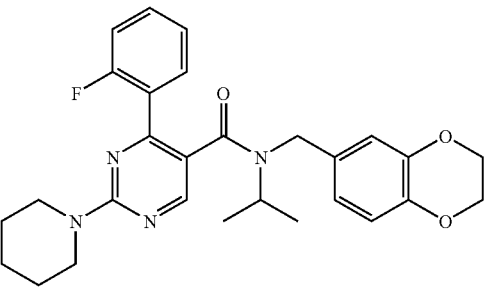
TABLE 1-continued
Examples of compounds of the present invention
168
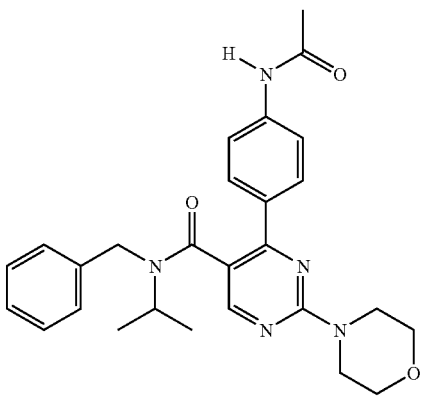
169
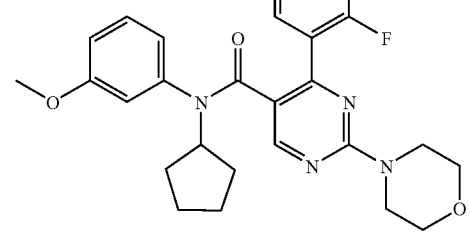
170
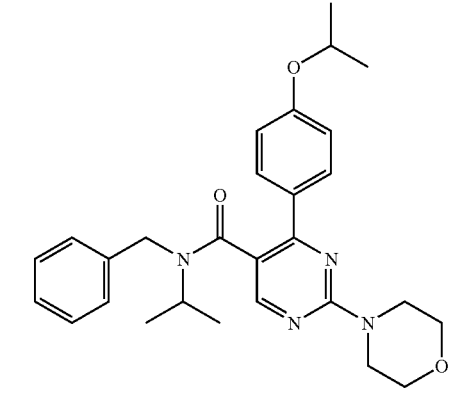
171
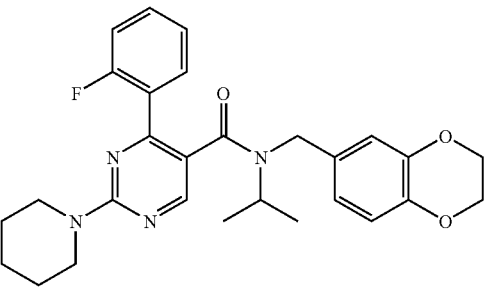

TABLE 1-continued
Examples of compounds of the present invention
172
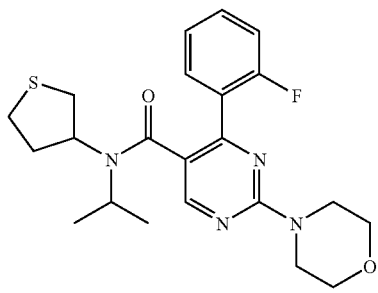
173
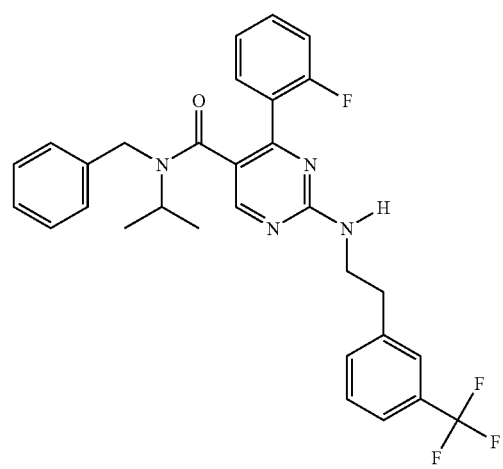
174
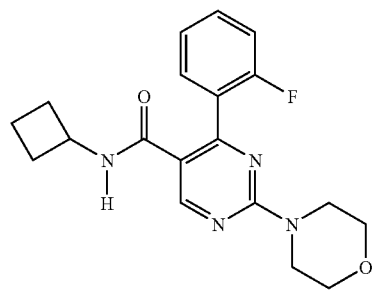
175
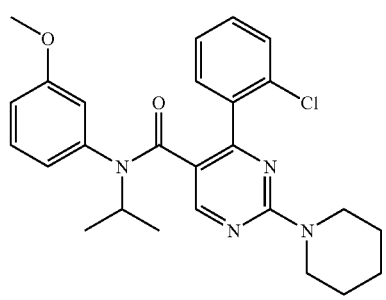
TABLE 1-continued
Examples of compounds of the present invention
176
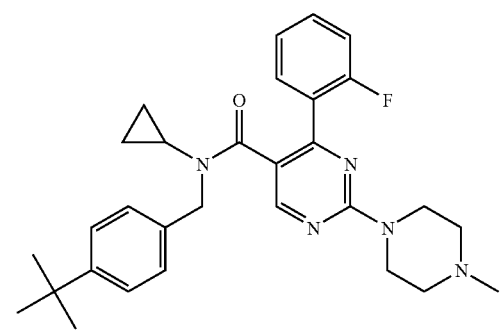
177
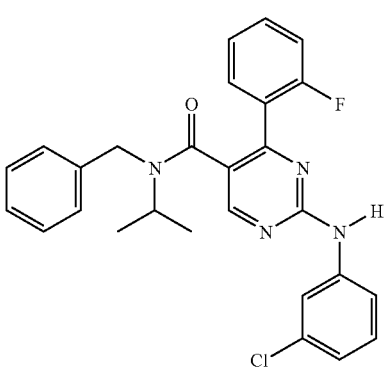
178
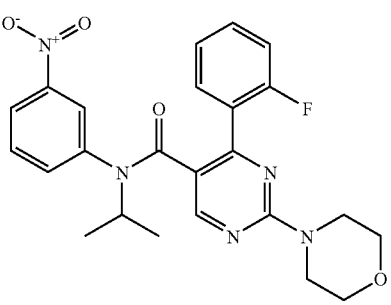
179
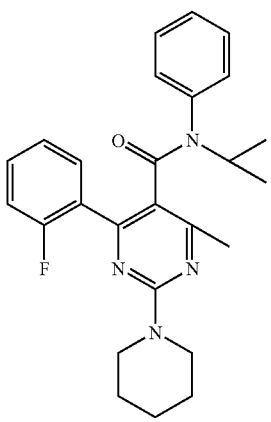

TABLE 1-continued
Examples of compounds of the present invention
180
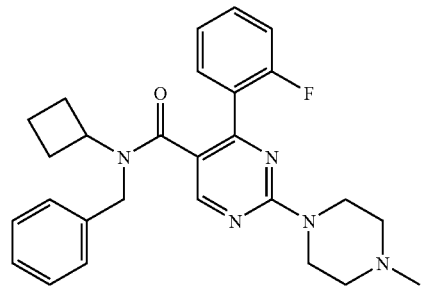
181
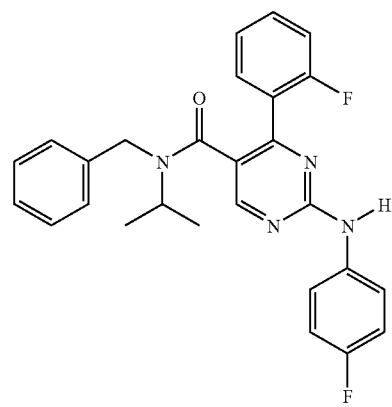
182
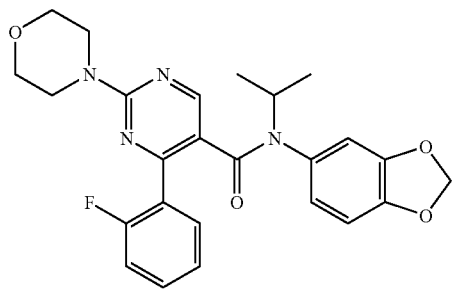
183
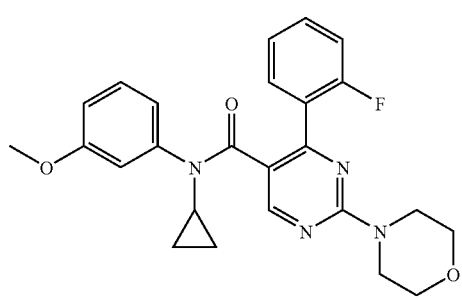
TABLE 1-continued
Examples of compounds of the present invention
184
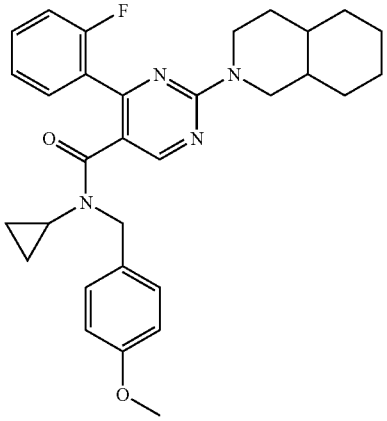
185
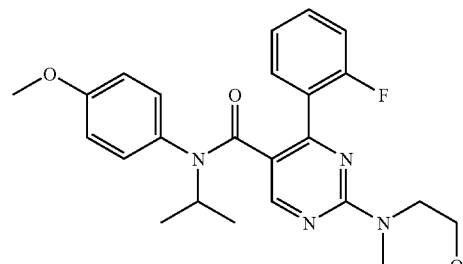
186
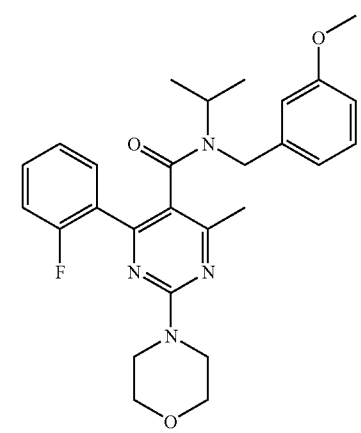
187
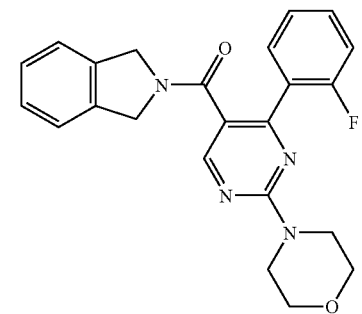

TABLE 1-continued
Examples of compounds of the present invention
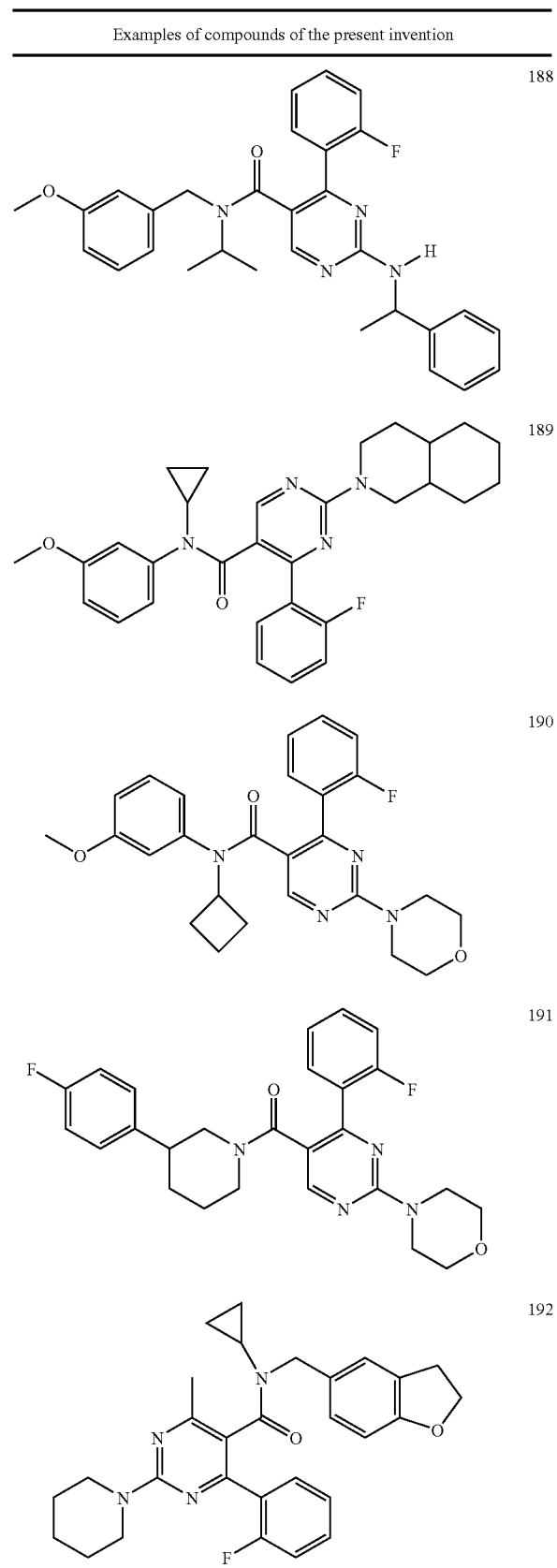
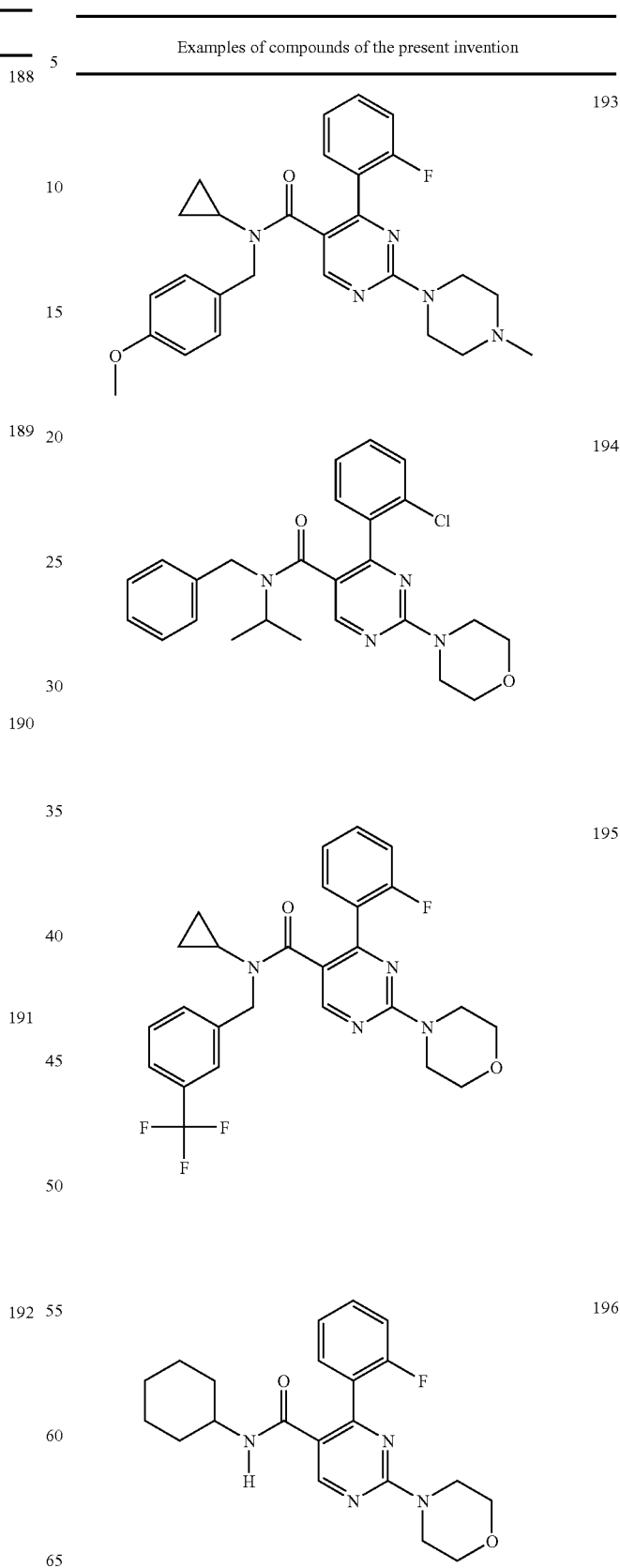

TABLE 1-continued
Examples of compounds of the present invention
197
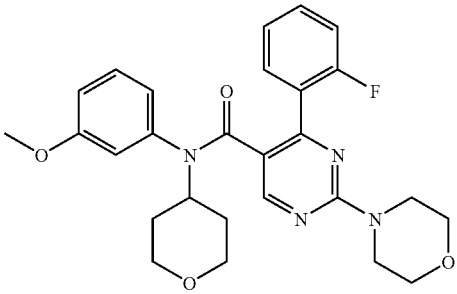
198
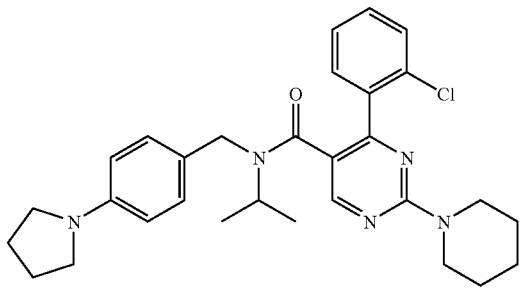
199
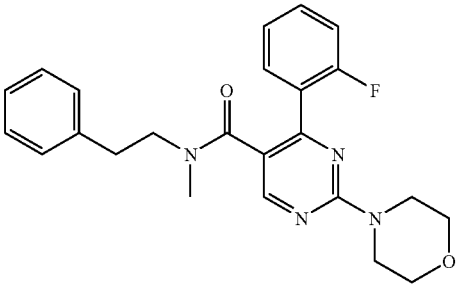
200
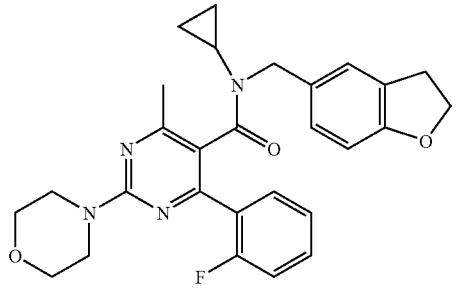
201
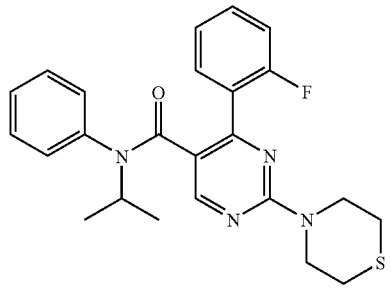
TABLE 1-continued
Examples of compounds of the present invention
202
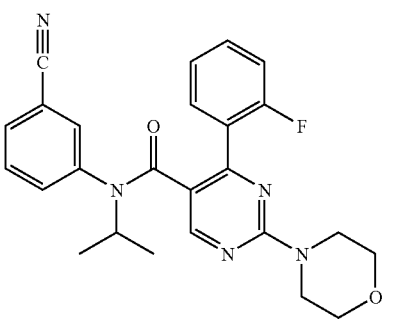
203
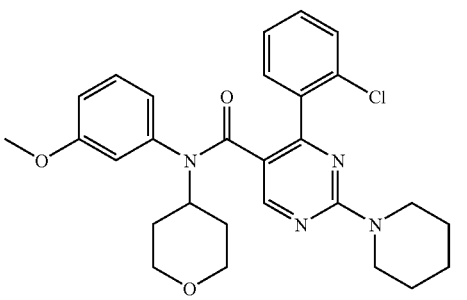
204
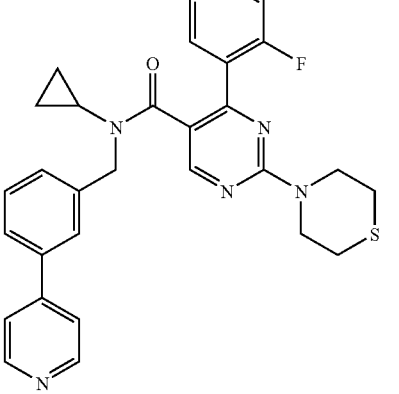
205
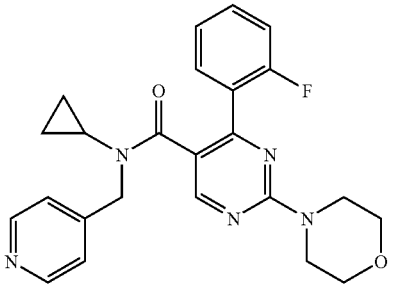

TABLE 1-continued
Examples of compounds of the present invention
| | |
|---|---|
| 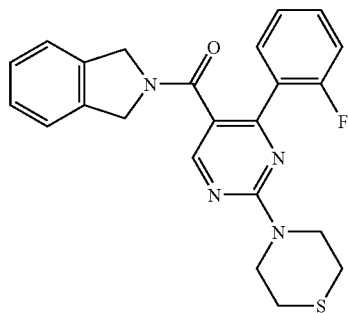 206 | 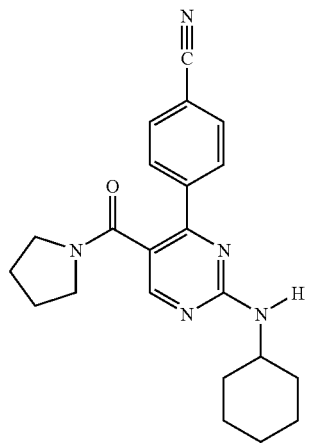 210 |
| 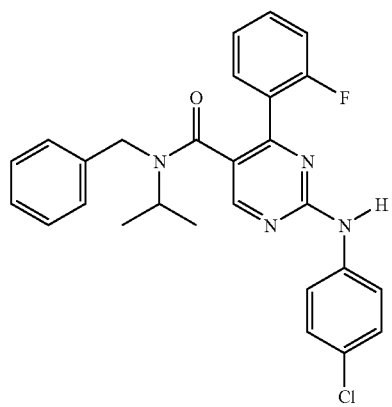 207 | 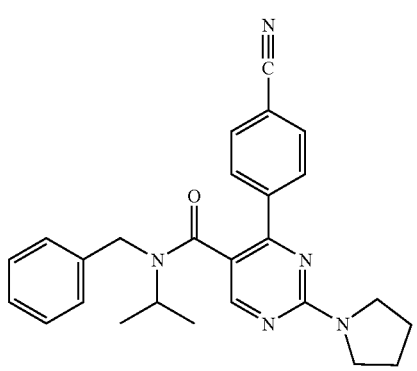 211 |
| 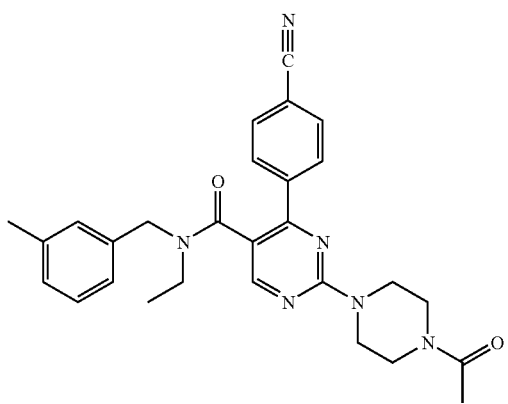 208 | 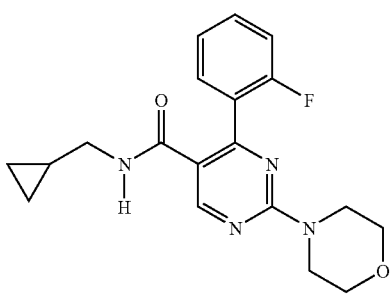 212 |
| 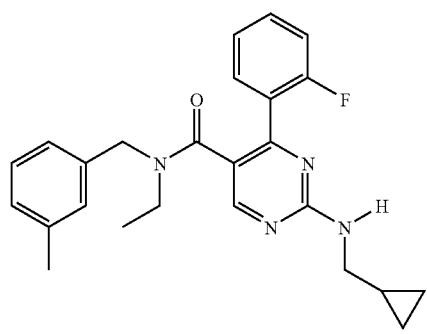 209 | 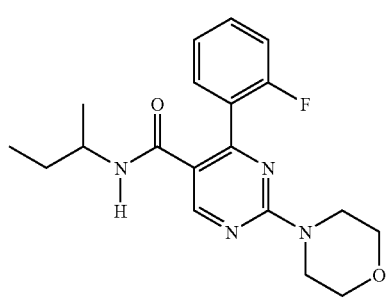 213 |

TABLE 1-continued
Examples of compounds of the present invention
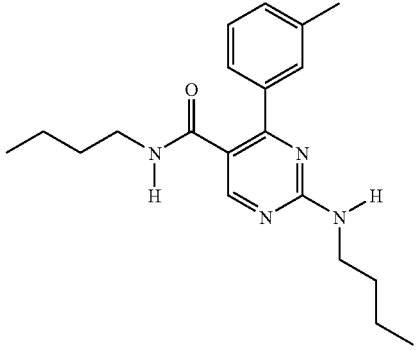 214
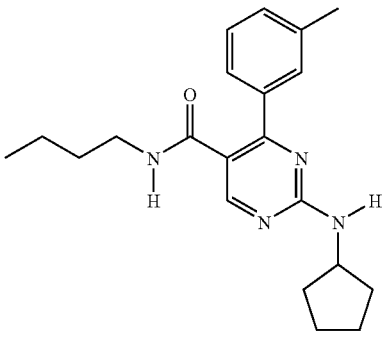 215
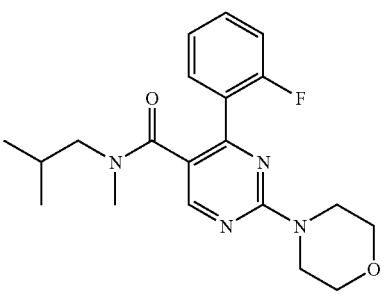 216
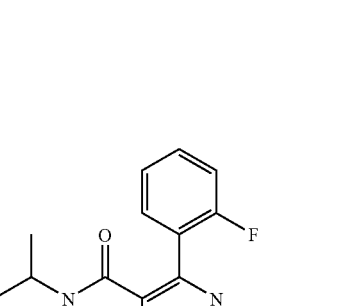 217
TABLE 1-continued
Examples of compounds of the present invention
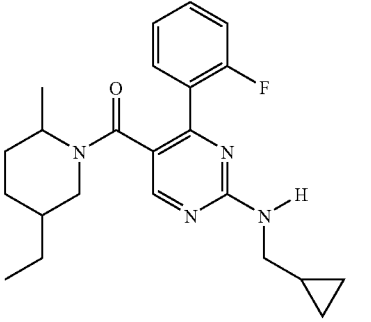 218
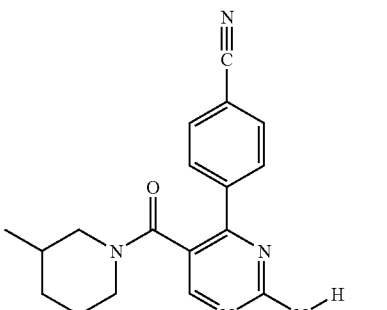 219
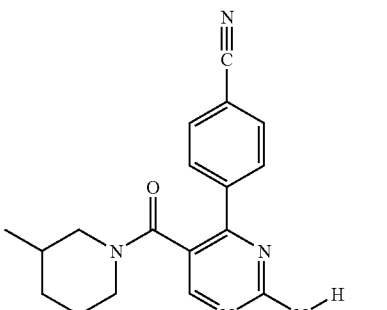 220

TABLE 1-continued
Examples of compounds of the present invention
221 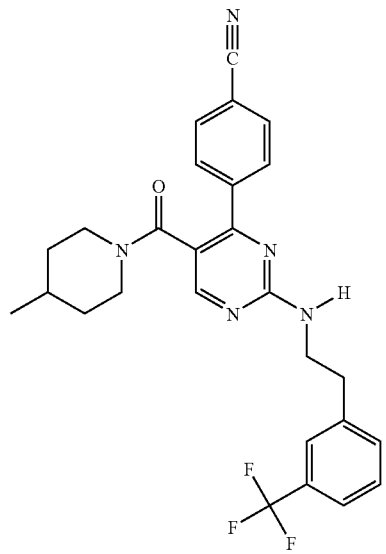
222 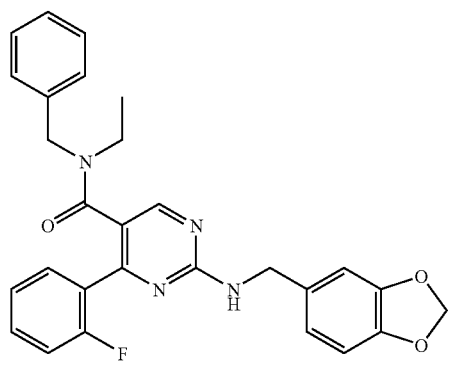
223 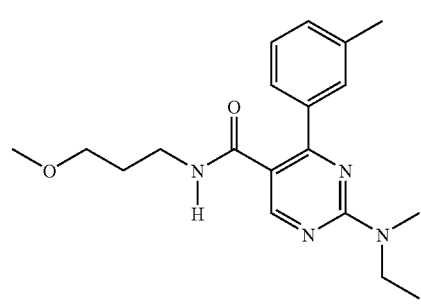
TABLE 1-continued
Examples of compounds of the present invention
224 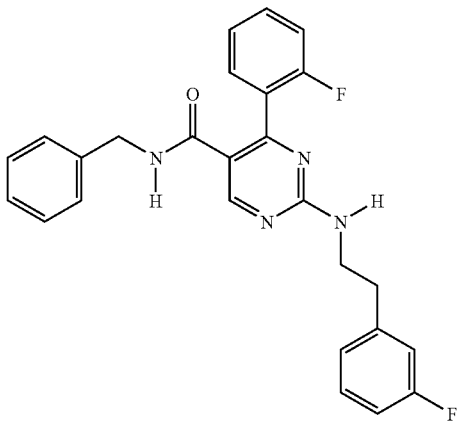
225 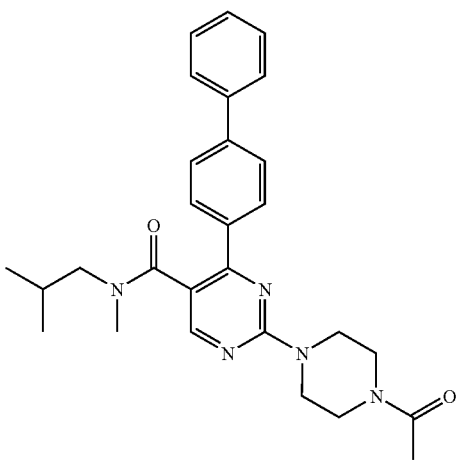
226 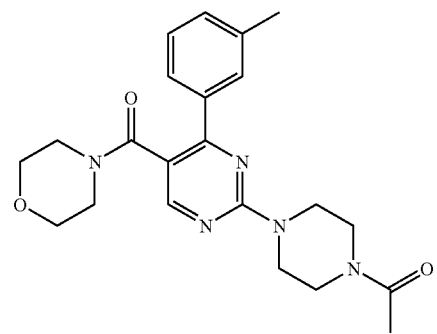

TABLE 1-continued
Examples of compounds of the present invention
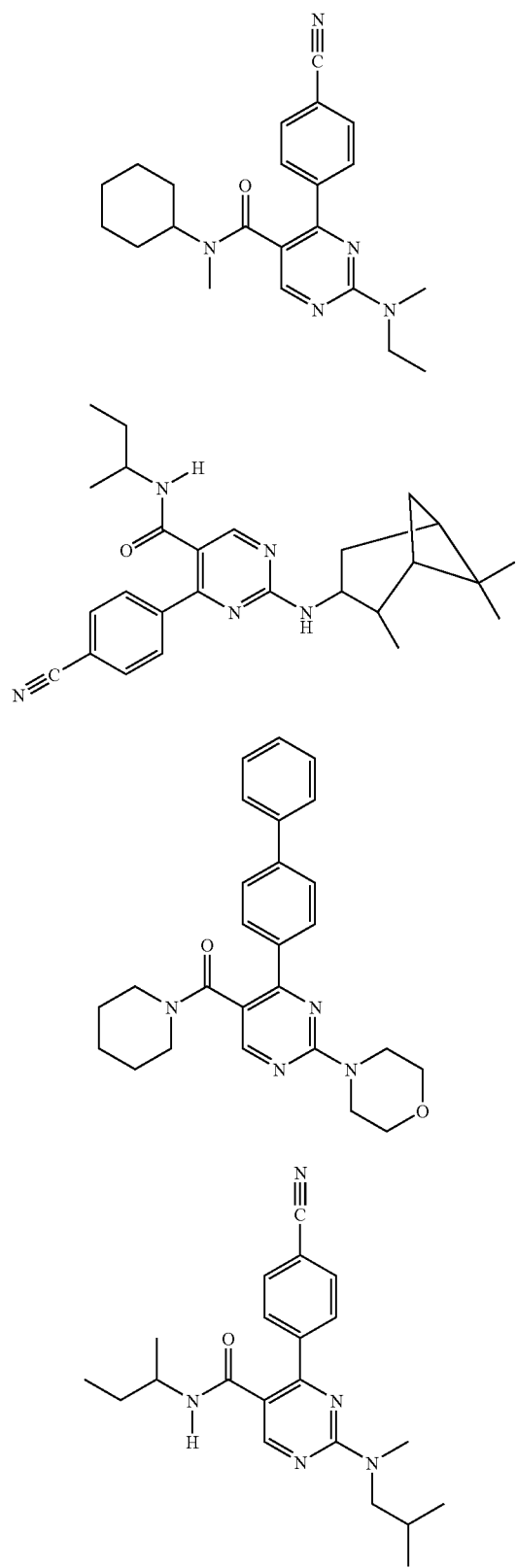
227
228
229
230
TABLE 1-continued
Examples of compounds of the present invention
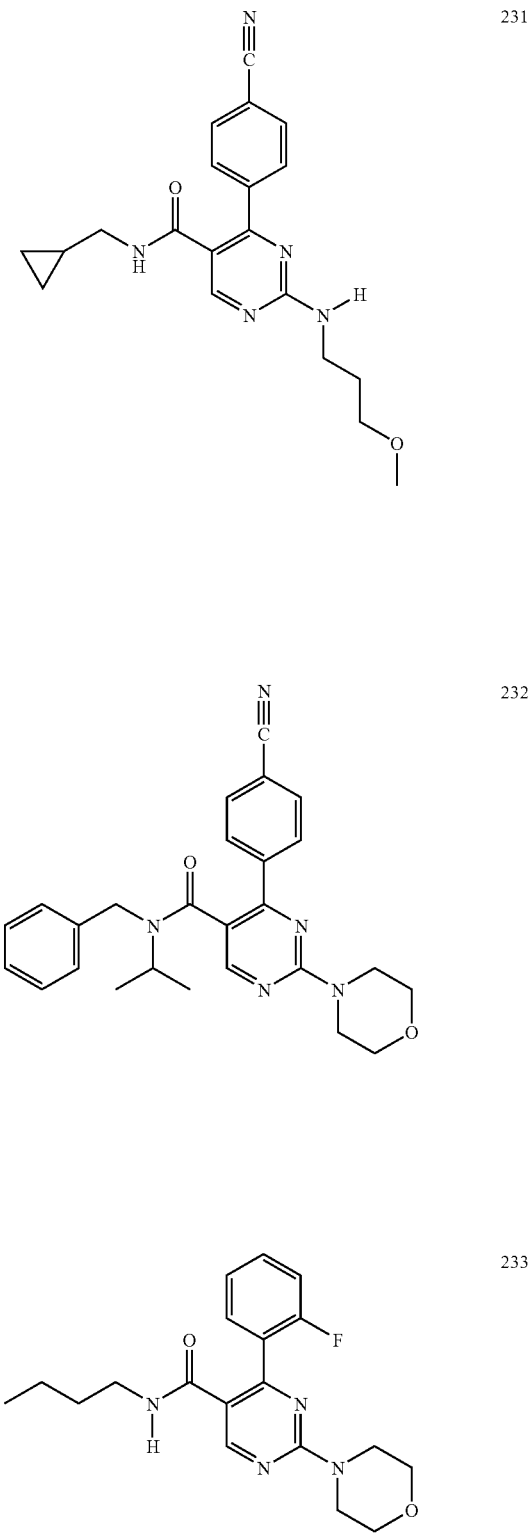
231
232
233

TABLE 1-continued

Examples of compounds of the present invention

| 234 | 235 | 236 | 237 | 238 | 239 | 240 | 241 |

TABLE 1-continued
Examples of compounds of the present invention
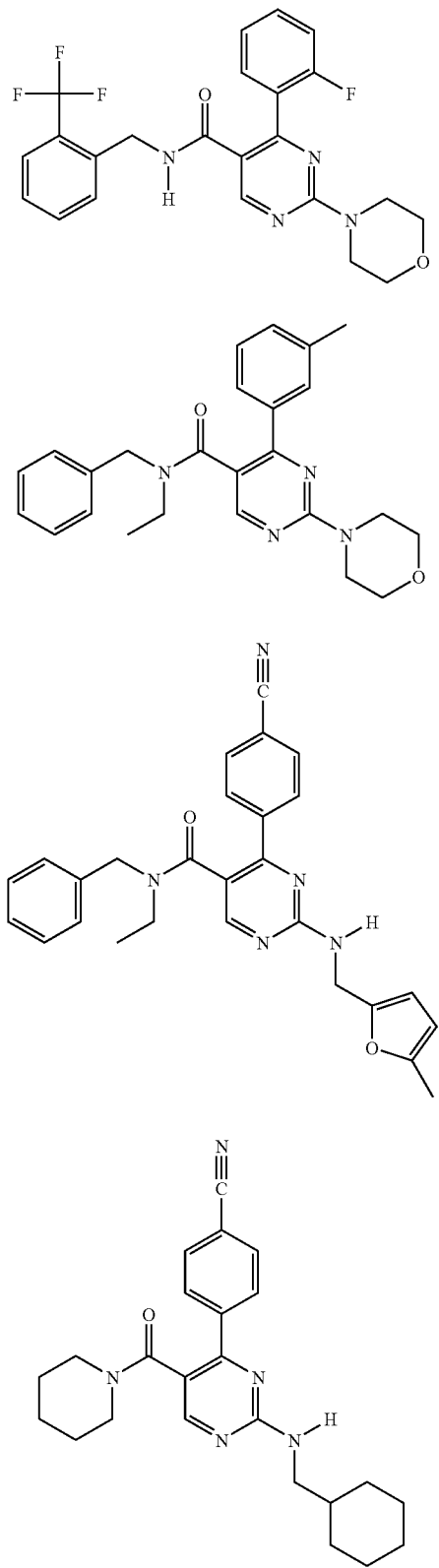
242
243
244
245
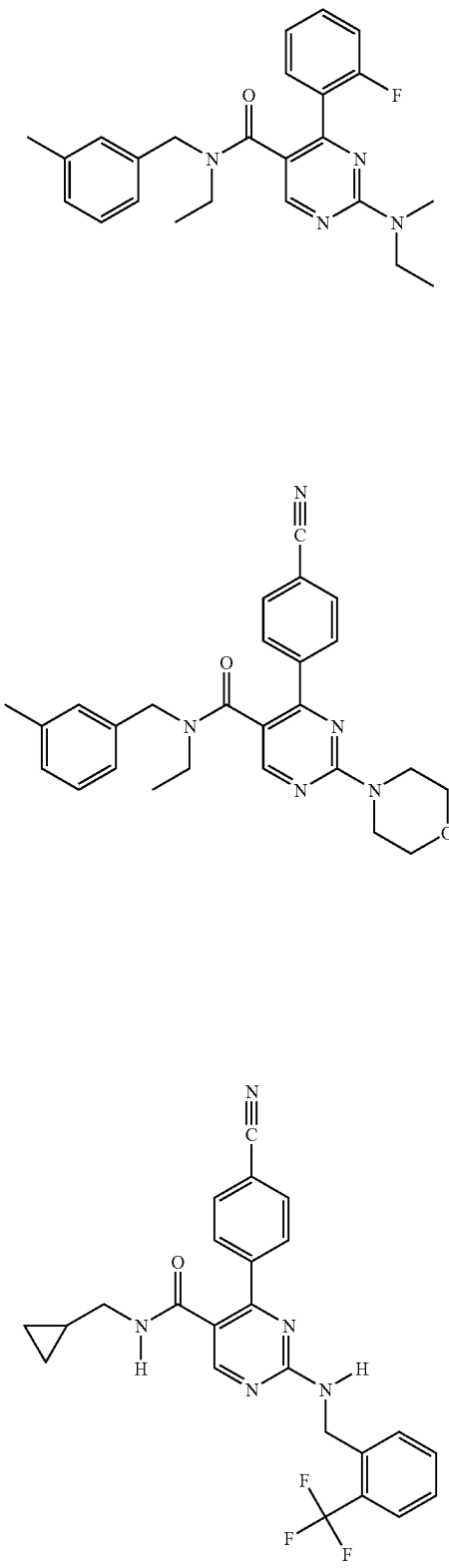
246
247
248

TABLE 1-continued
Examples of compounds of the present invention
249
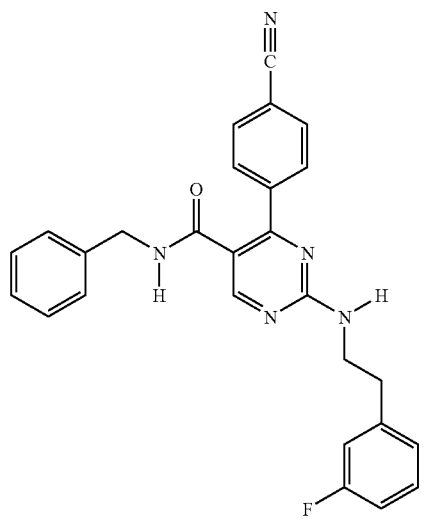
250
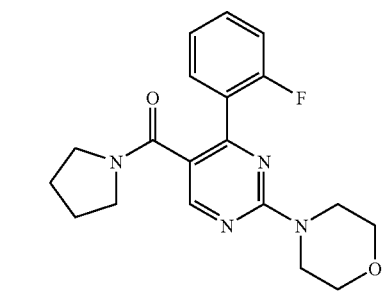
251
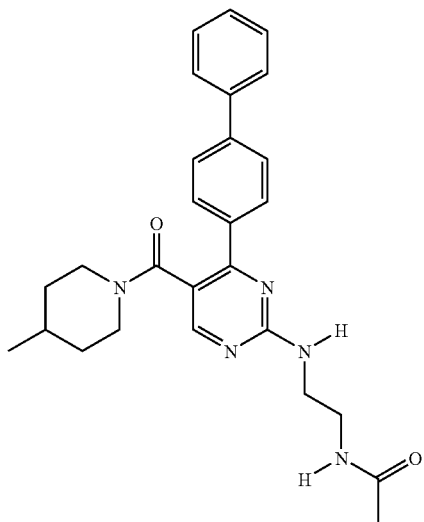
TABLE 1-continued
Examples of compounds of the present invention
252
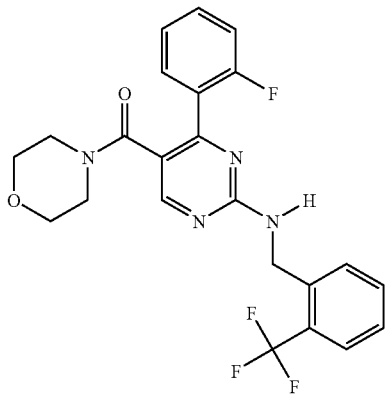
253
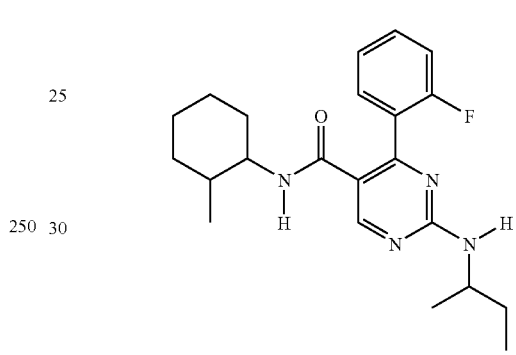
254
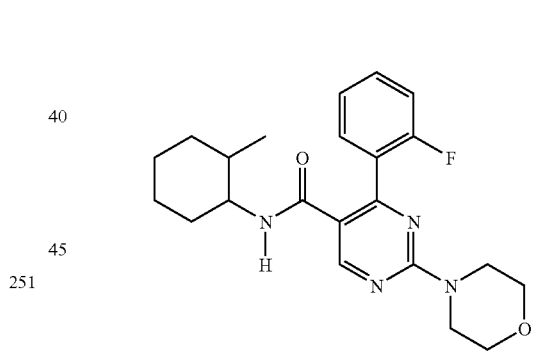
255
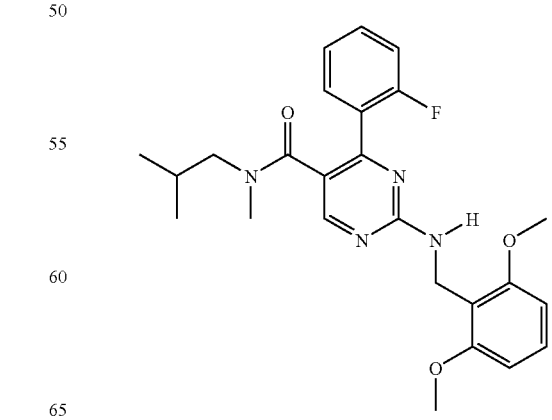

TABLE 1-continued
Examples of compounds of the present invention
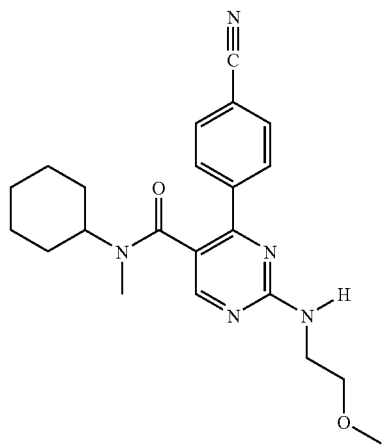
256
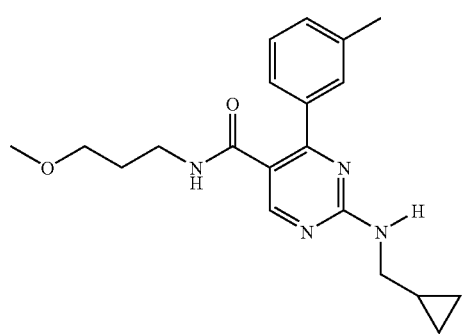
257
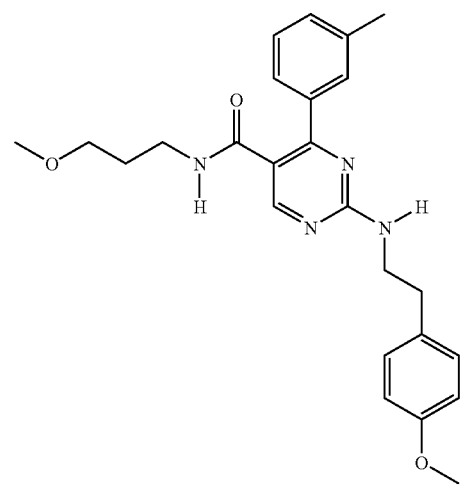
258
TABLE 1-continued
Examples of compounds of the present invention
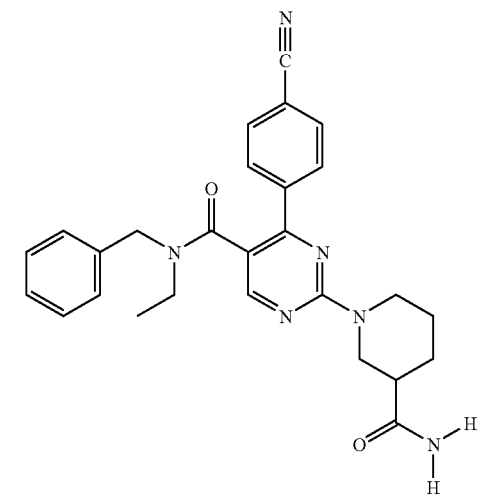
259
260
261
262

TABLE 1-continued
Examples of compounds of the present invention
263
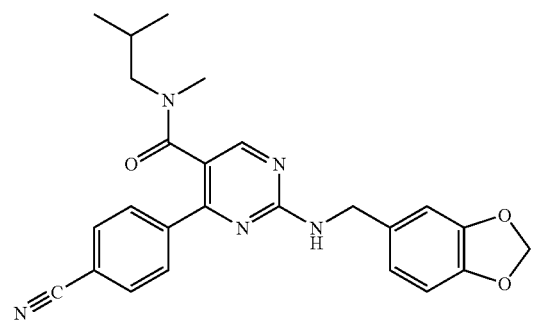
264
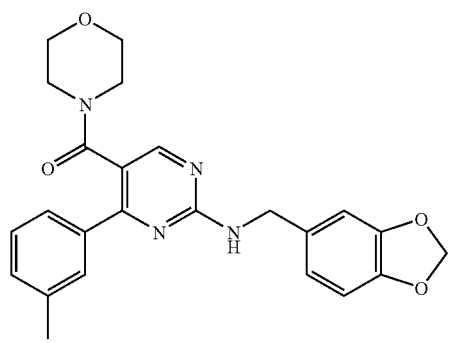
265
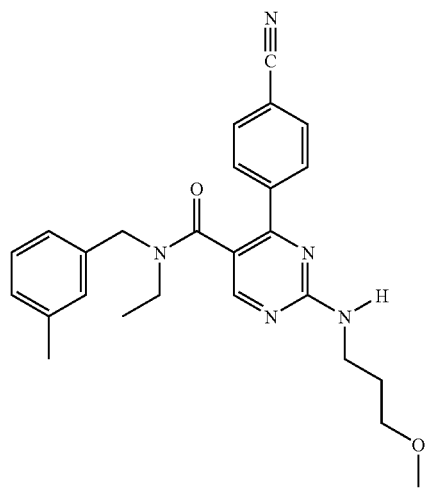
266
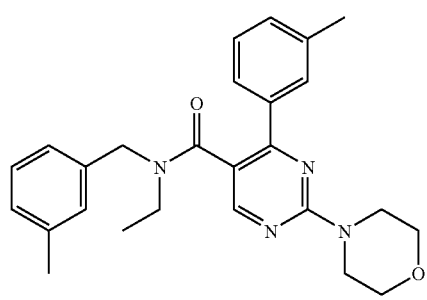
TABLE 1-continued
Examples of compounds of the present invention
267
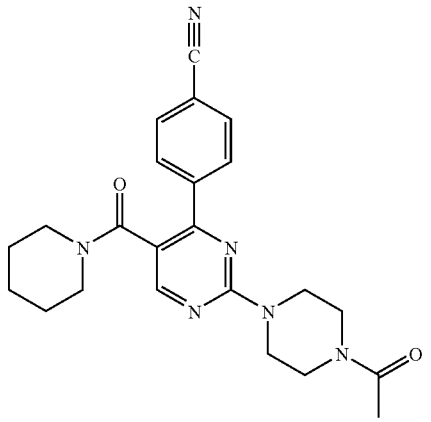
268
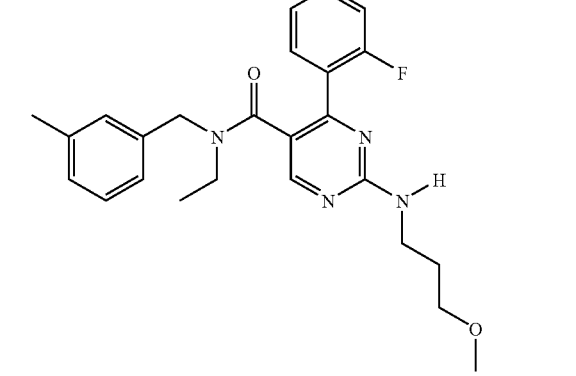
269
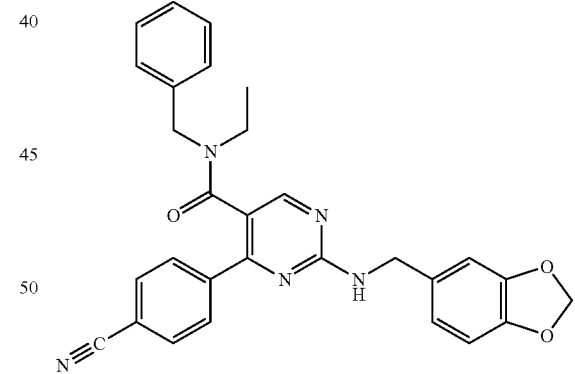
270
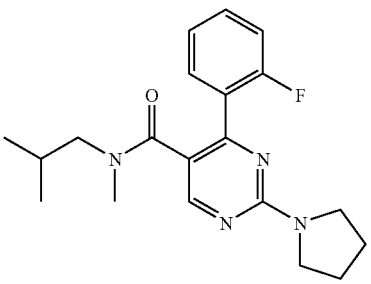

TABLE 1-continued
Examples of compounds of the present invention
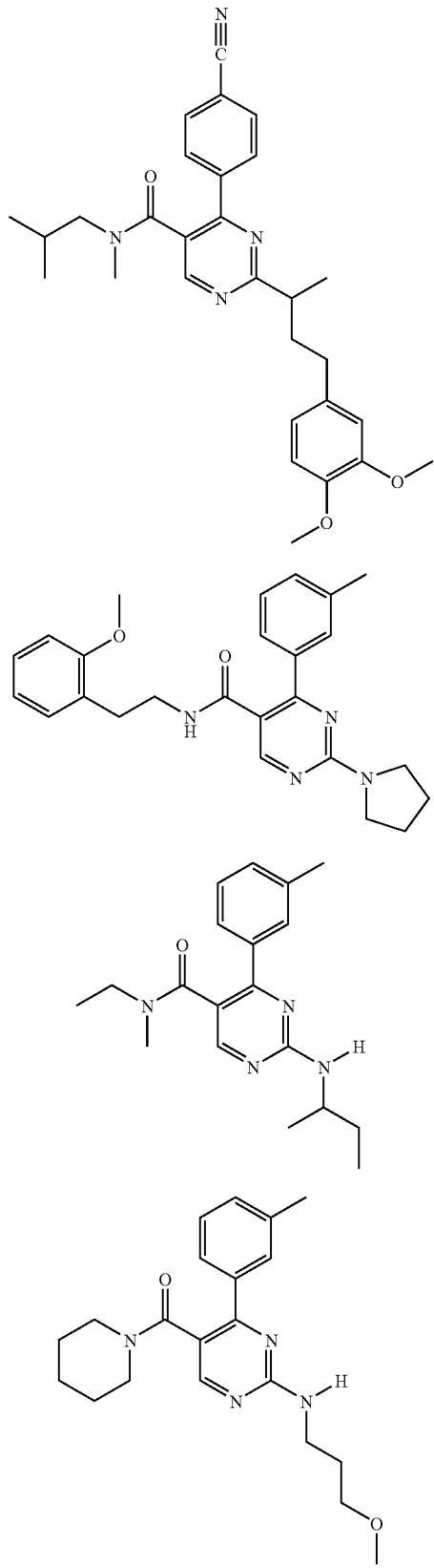
271
272
273
274
TABLE 1-continued
Examples of compounds of the present invention
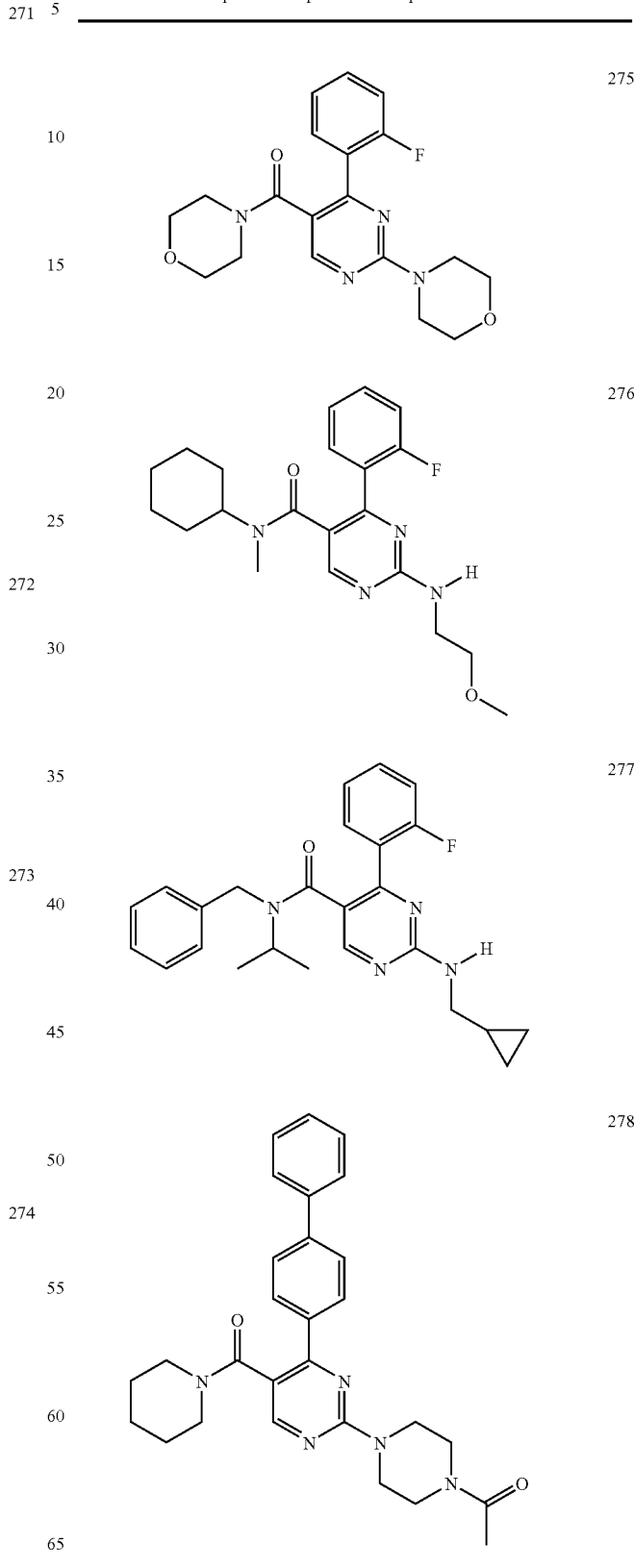
275
276
277
278

TABLE 1-continued
Examples of compounds of the present invention
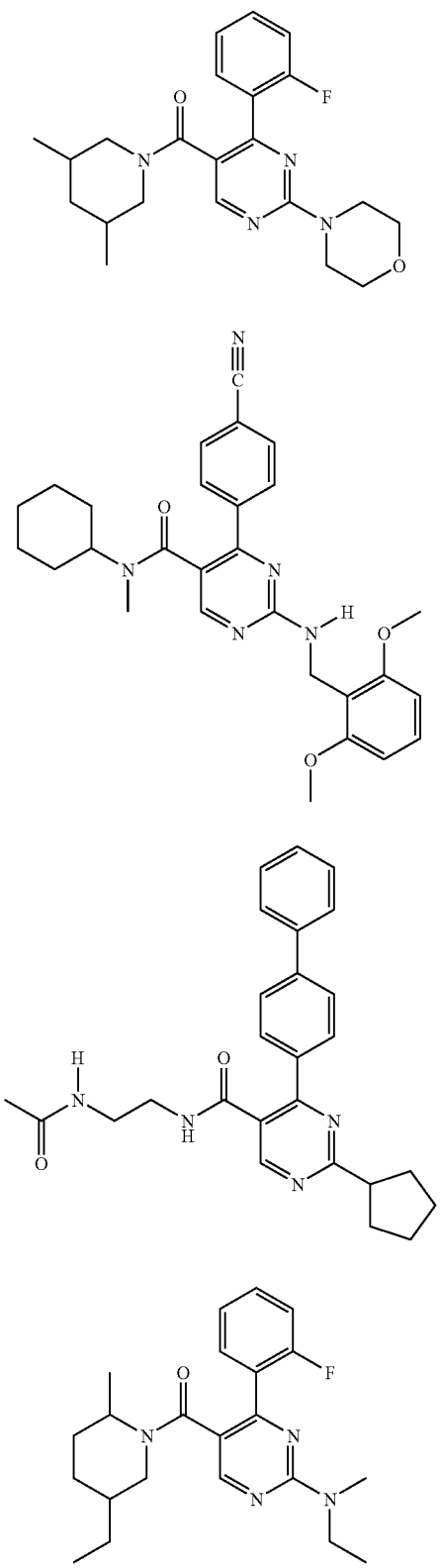
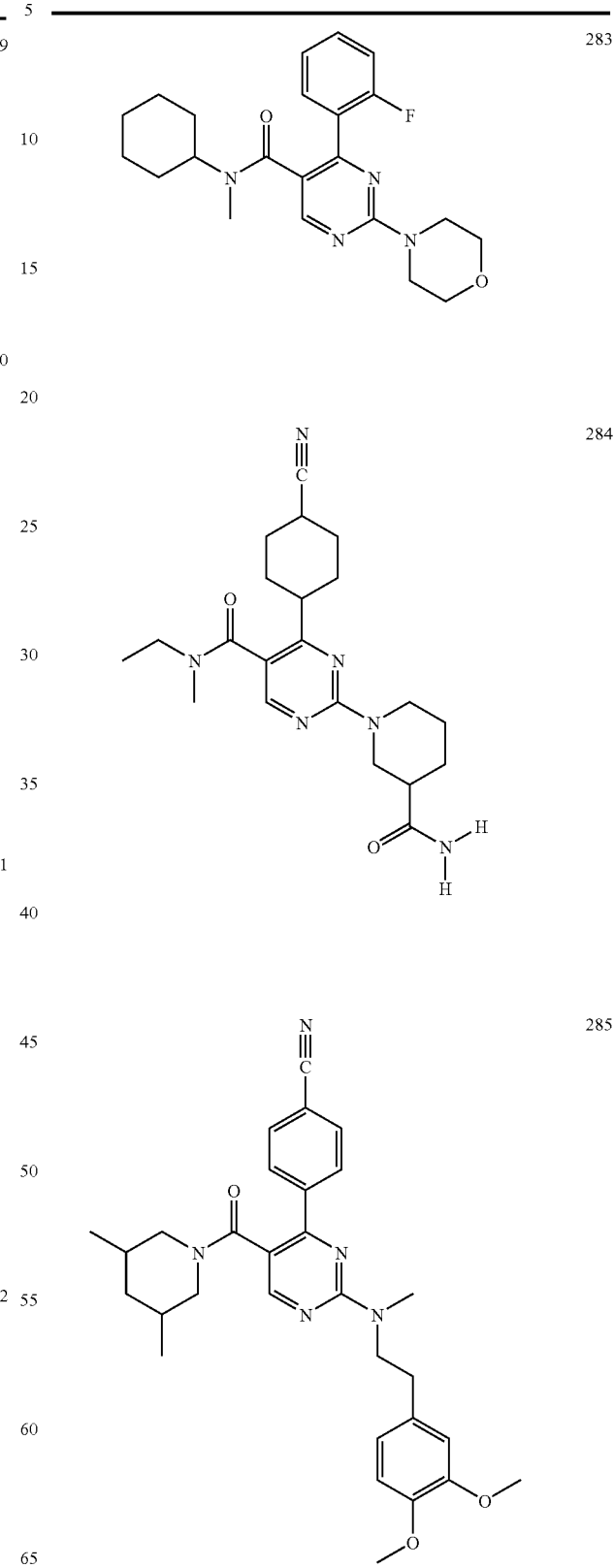

TABLE 1-continued
Examples of compounds of the present invention
286
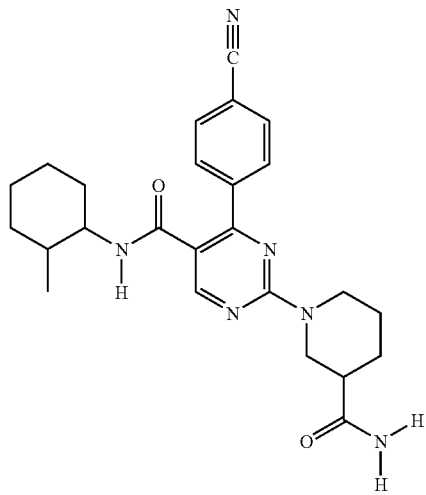
287
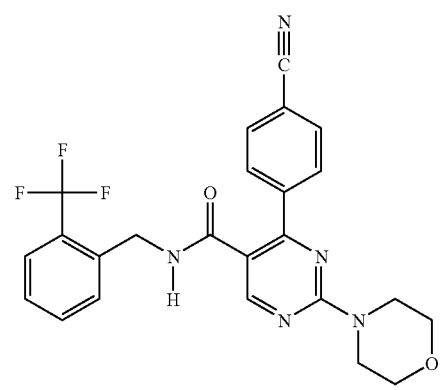
288
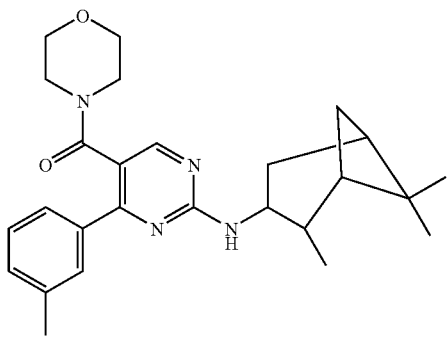
TABLE 1-continued
Examples of compounds of the present invention
289
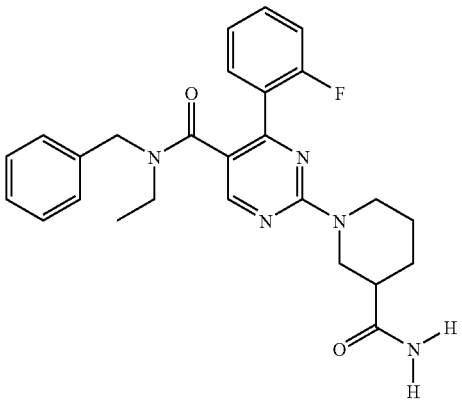
290
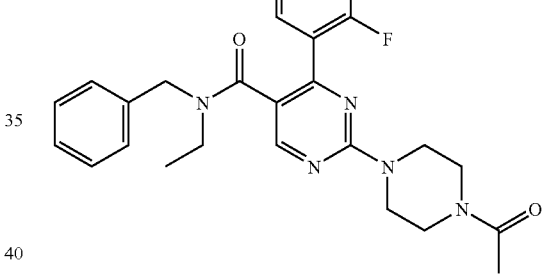
291
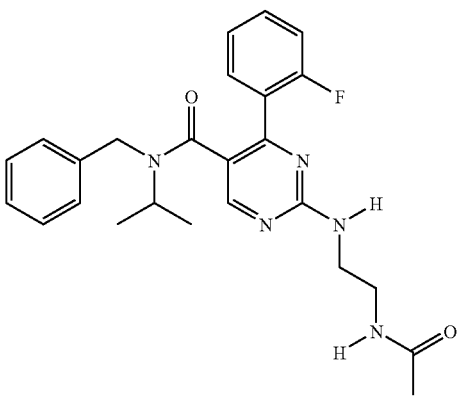

TABLE 1-continued
Examples of compounds of the present invention
292
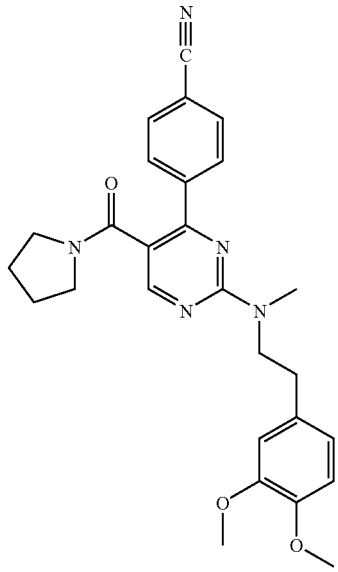
293
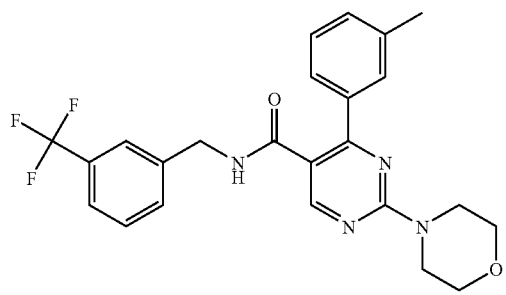
294
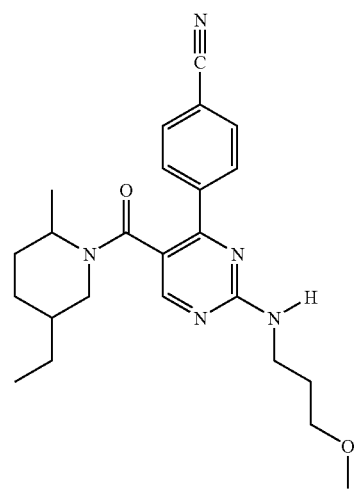
TABLE 1-continued
Examples of compounds of the present invention
295
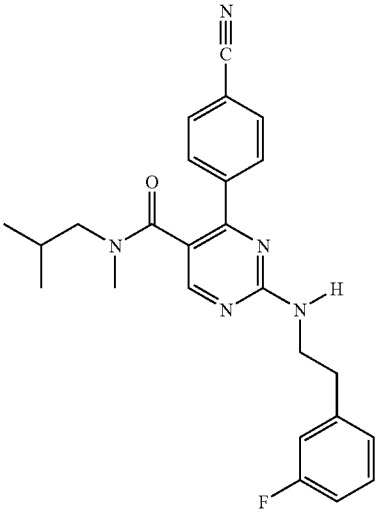
296
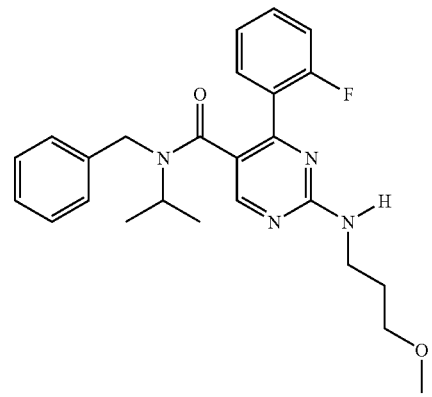
297
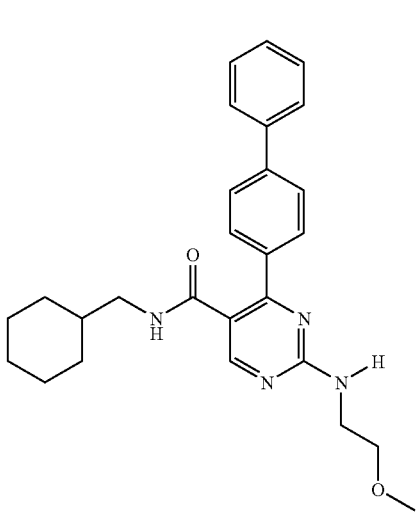

TABLE 1-continued
Examples of compounds of the present invention
298
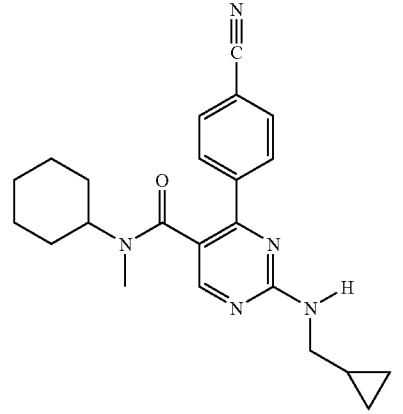
299
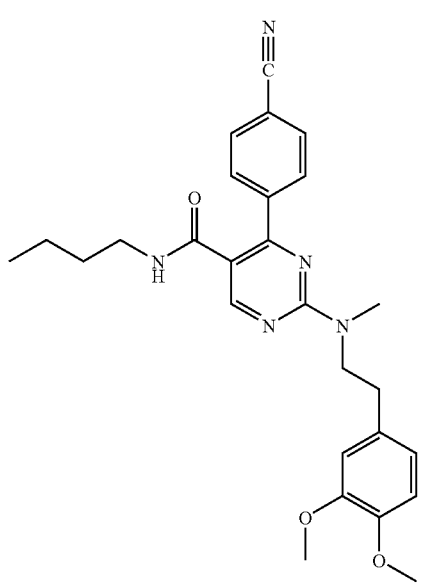
300
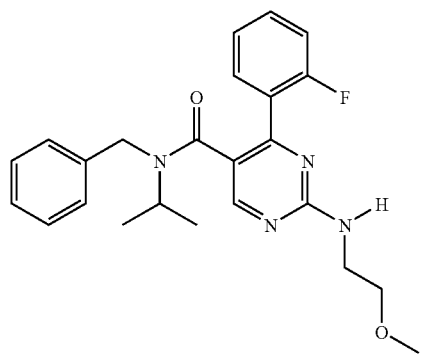
TABLE 1-continued
Examples of compounds of the present invention
301
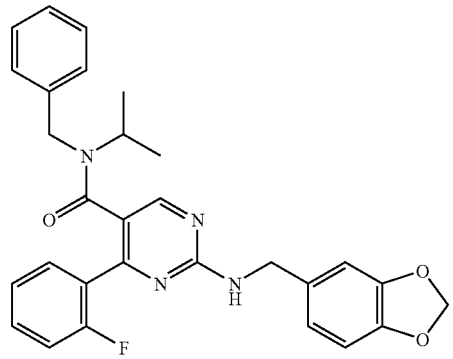
302
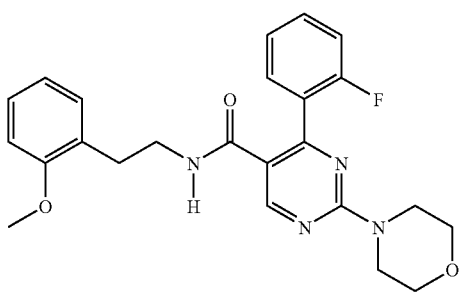
303
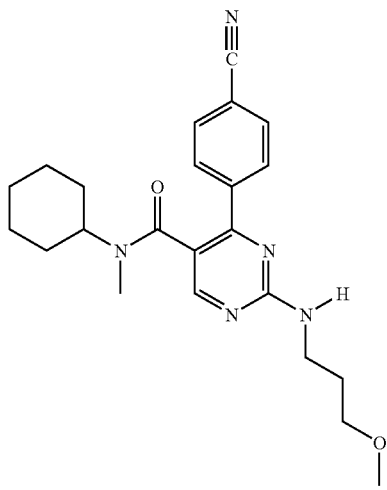
304
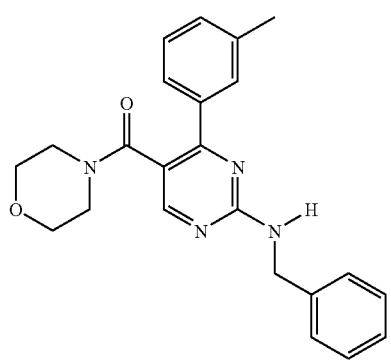

TABLE 1-continued

Examples of compounds of the present invention

TABLE 1-continued
Examples of compounds of the present invention
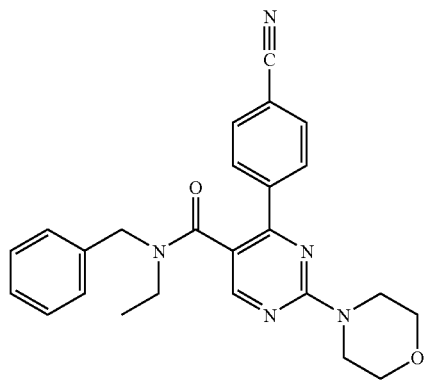 313
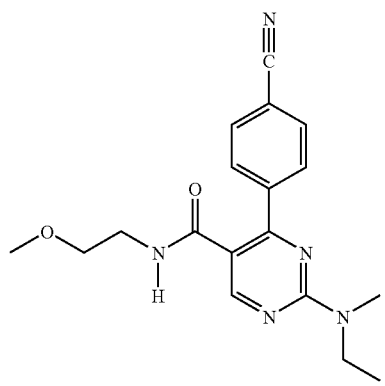 314
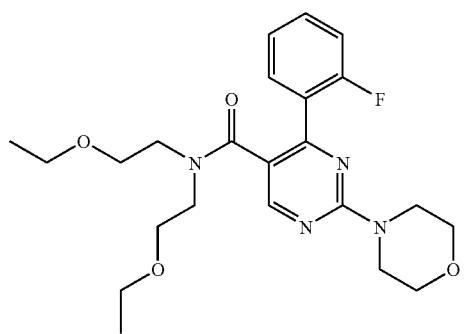 315
TABLE 1-continued
Examples of compounds of the present invention
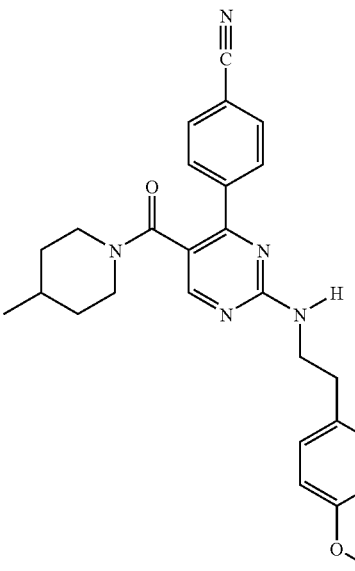 316
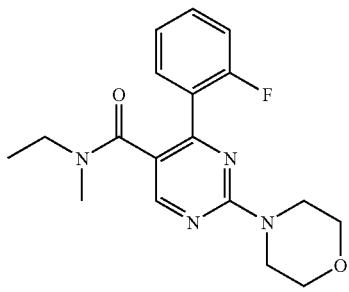 317
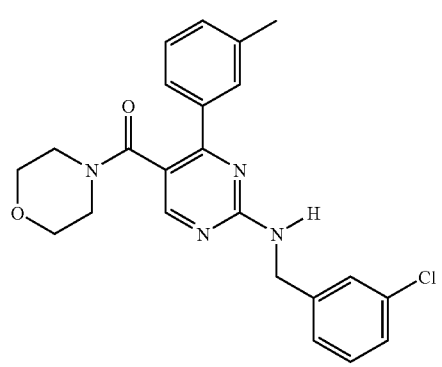 318

TABLE 1-continued
Examples of compounds of the present invention
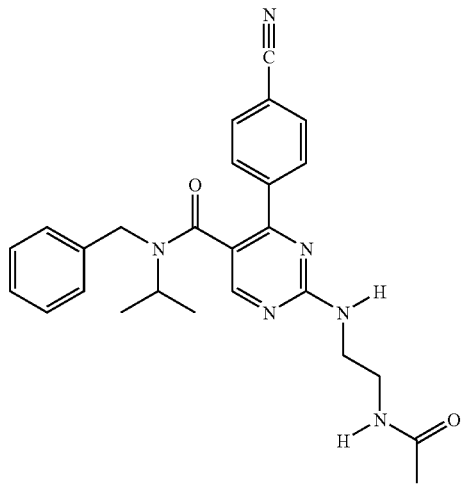
319
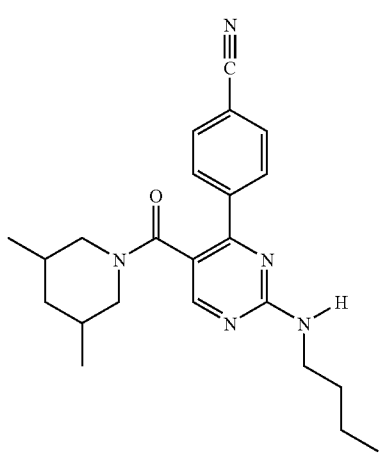
320
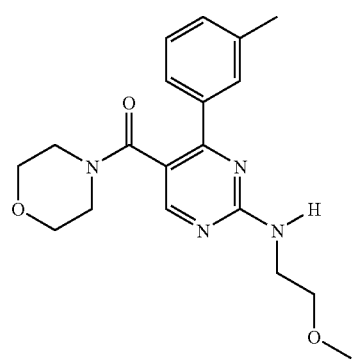
321
TABLE 1-continued
Examples of compounds of the present invention
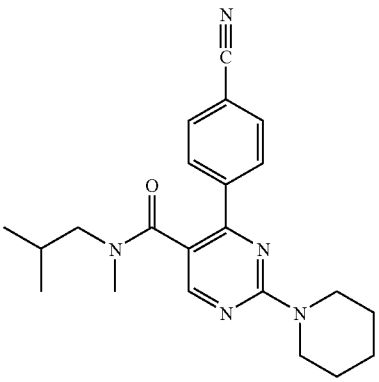
322
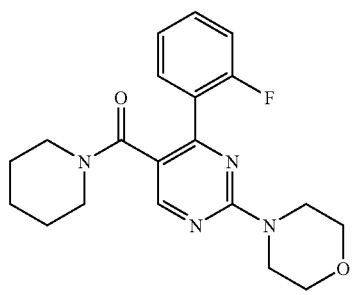
323
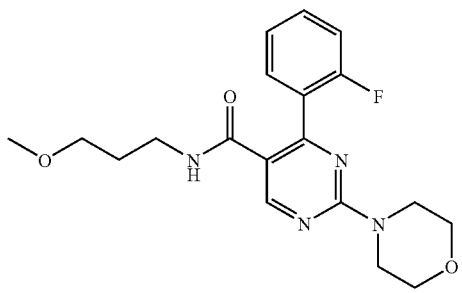
324
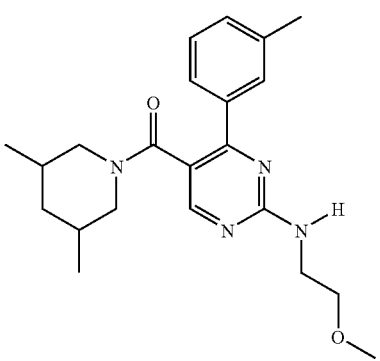
325

TABLE 1-continued
Examples of compounds of the present invention
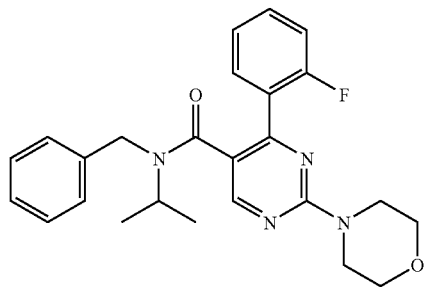 326
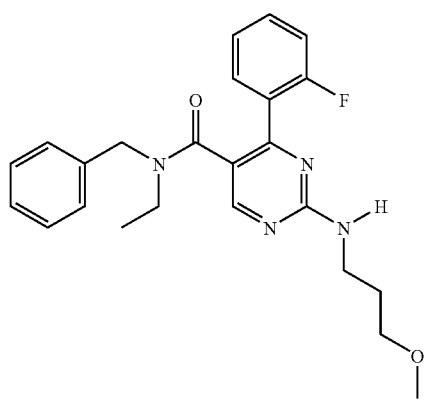 327
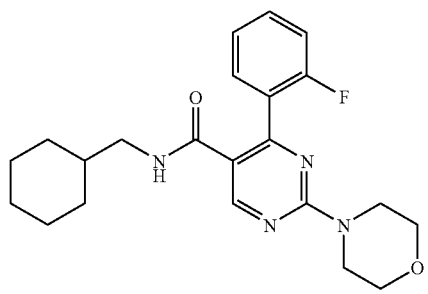 328
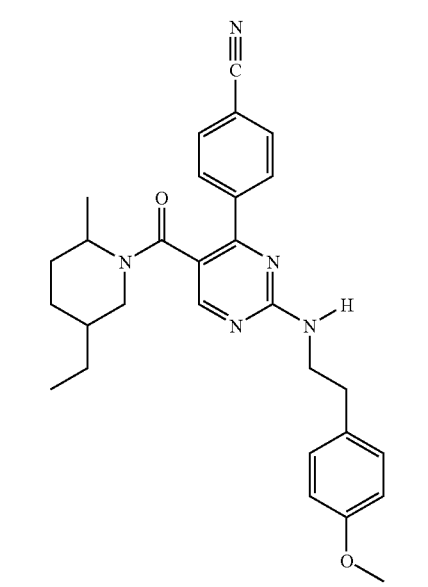 329
TABLE 1-continued
Examples of compounds of the present invention
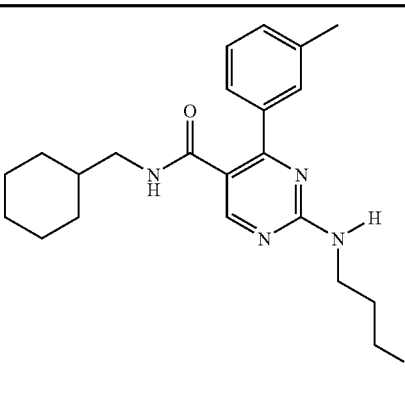 330
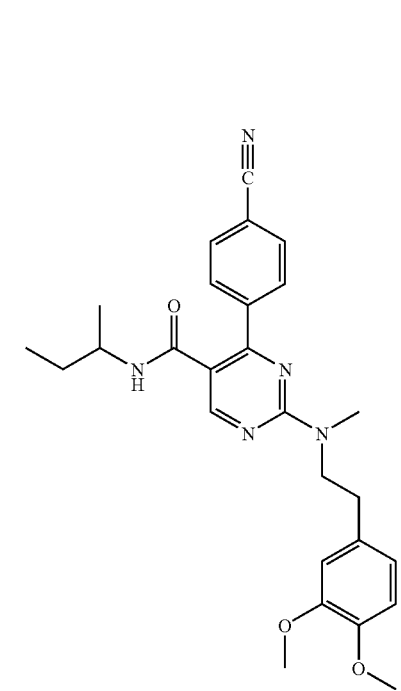 331
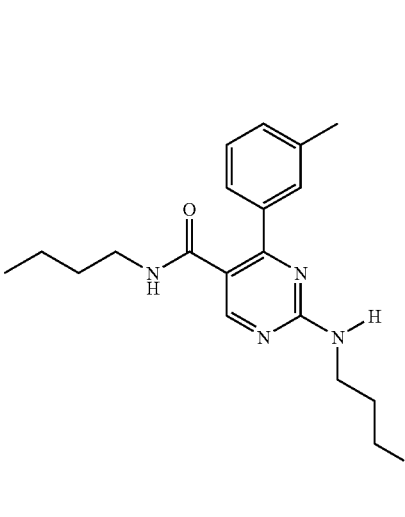 332

TABLE 1-continued
Examples of compounds of the present invention
| 333 | 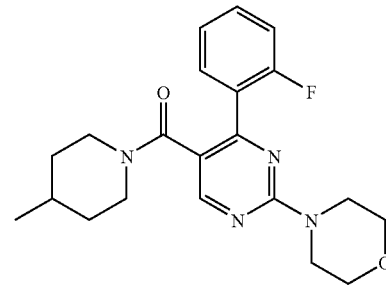 |
| 334 | |
| 335 | |
| 336 | |
TABLE 1-continued
Examples of compounds of the present invention
| 337 | 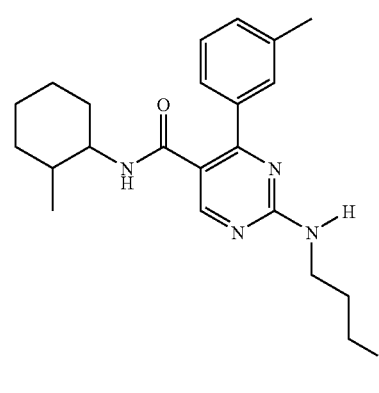 |
| 338 | |
| 339 | |
| 340 | |

TABLE 1-continued
Examples of compounds of the present invention
341
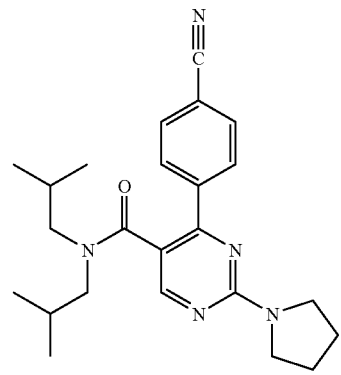
342
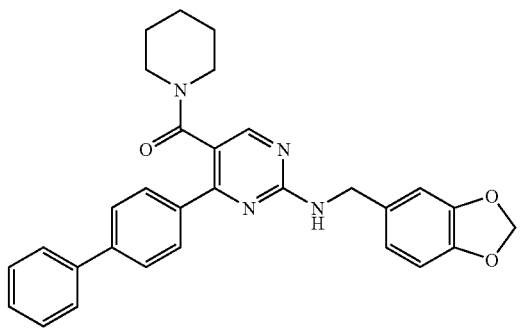
343
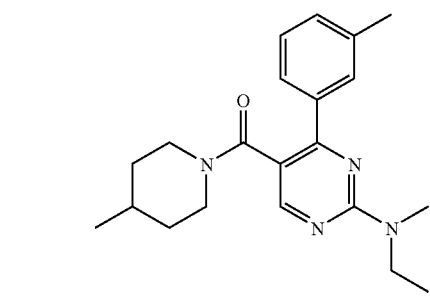
344
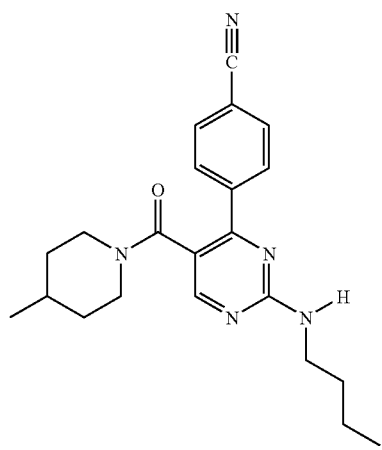
TABLE 1-continued
Examples of compounds of the present invention
345
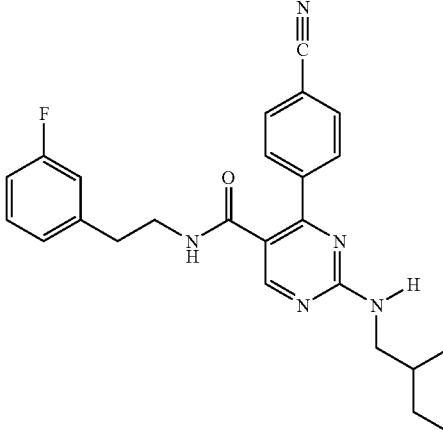
346
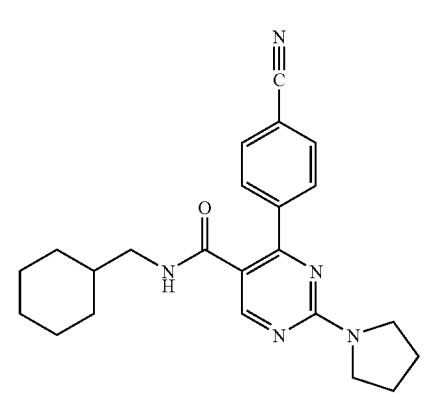
347
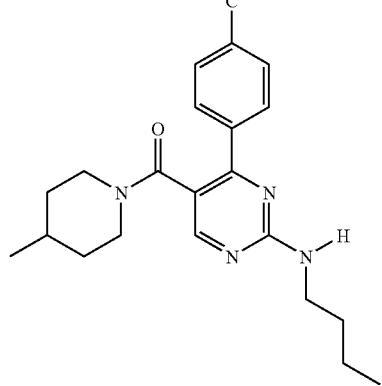
348
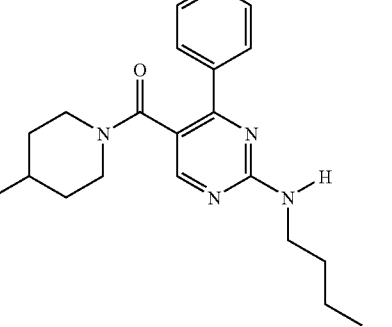

TABLE 1-continued
Examples of compounds of the present invention
349
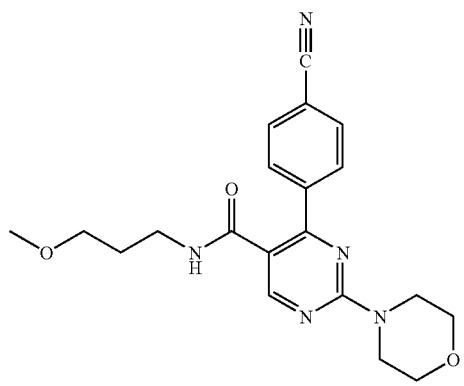
350
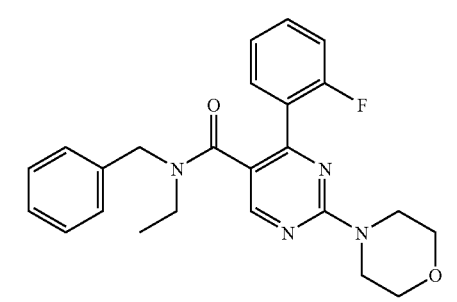
351
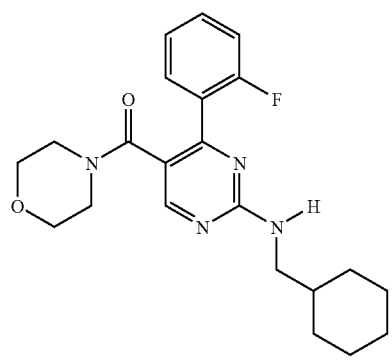
III. Synthetic Scheme
Compounds of the invention can be synthesized by any conventional reactions known in the art. One method of syntheses is illustrated in Scheme 1 without limitation.
Scheme 1
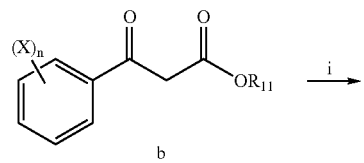
b
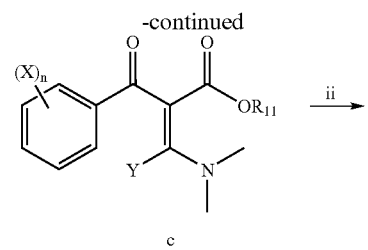
c
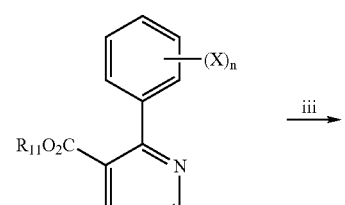
d
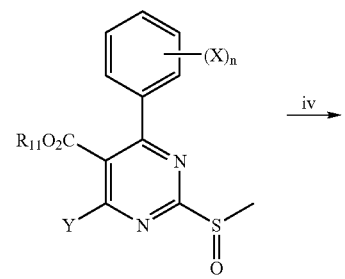
e
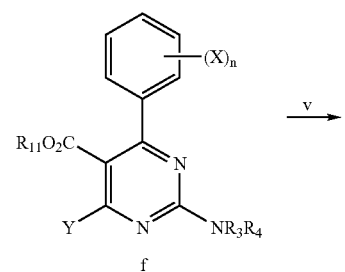
f
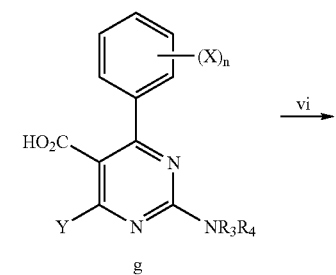
g

131

-continued

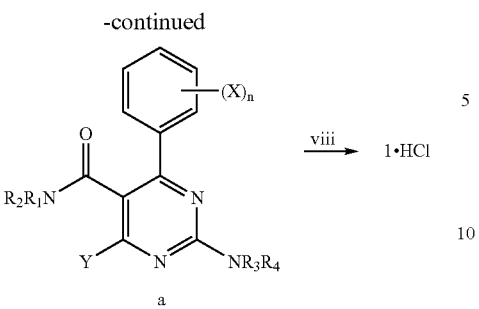

Synthesis of a. $R_{11}$ is an alkyl group.
i. DMF-DMA, toluene;
ii. 2-methylisothiourea sulfate, NaOAc, DMF, 80-90° C.;
iii. m-CPBA, $CH_2Cl_2$, -78 to 0° C.;
iv. $NHR_3R_4$, THF, reflux;
v. 10 N aq. NaOH, MeOH, reflux;
vi. 1) $(COCl)_2$, $CH_2Cl_2$; 2) $NHR_1R_2$, toluene;
vii. HCl, $Et_2O$.

Referring to Scheme 1, $R_5$ is a $C_{1-5}$ alkyl. Reaction of the keto-ester b with a formamide dialkylacetal such as, for example, dimethylformamide dimethylacetal, provides the aminomethylene compound c. Reaction of d with 2-methyl-isothiourea sulfate in the presence of sodium acetate provides the thiopyrimidine e. Oxidation of f with a suitable oxidizing reagent provides the sulfoxo-pyrimidine f. Suitable oxidizing reagents include, for example, m-chloroperbenzoic acid. Reaction of f with the amine $R_3R_4NH$ provides the 2-aminopyrimidine g. Hydrolysis of g with, for example, an alkaline earth hydroxide such as pottasium hydroxide or sodium hydroxide, provides the acid g. Conversion of g to the amide a, compounds of the invention, can be achieved by converting the acid g first to an active acid derivative such as, for example, an acid chloride followed by reaction of the active derivative with the amine $R_1R_2NH$. Alternatively, the amide formation may be achieved by reaction of g with the amine $R_1R_2NH$ in the presence of a suitable coupling reagent such as, for example, EDC or HATU. Acid addition salts such as, for example, a hydrochloride, may be prepared by reaction of the basic compound 1 with an acid in a solvent from which the salt will precipitate such as, for example, diethylether.

A variation of Scheme 1 is illustrated in Scheme 2 without limitation.

Scheme 2

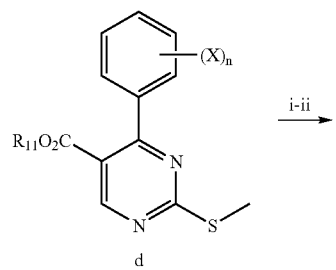

132

-continued

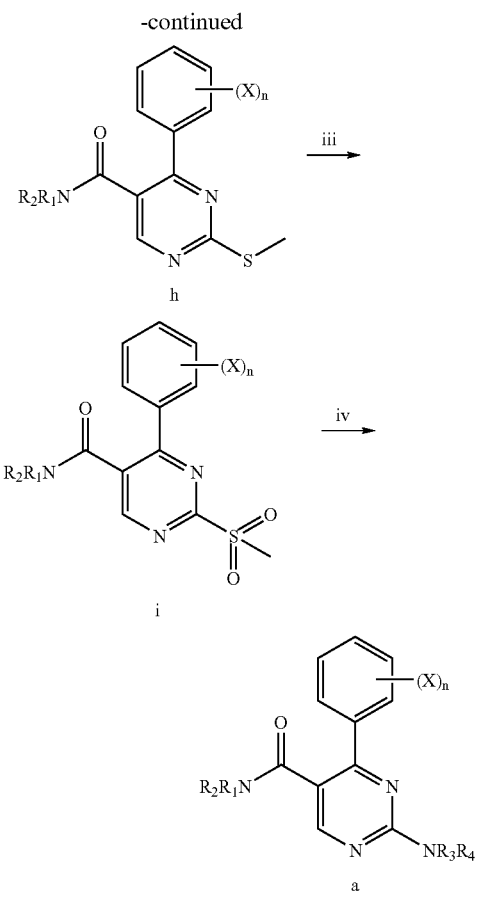

i. NaOH, water, MeOH, reflux, 1 h.
ii. a. $(COCl)_2$, DMF, $CH_2Cl_2$,
   b. $NHR_1R_2$, DIPEA
iii MCPBA, $CH_2Cl_2$
iv $NHR_3R_4$, THF, heat In reference to Scheme 2, the esterpyrimidine (Scheme 1) is converted to the corresponding amidepyrimidine h following procedures as described above for preparing the amides a. Oxidation of h and displacement of the sulfonyl group with $HNR_3R_4$ as previously described in scheme 1 provides the compounds of the invention a.

An alternative method for preparation of the compounds is illustrated in Scheme 3 without limitation.

Scheme 3

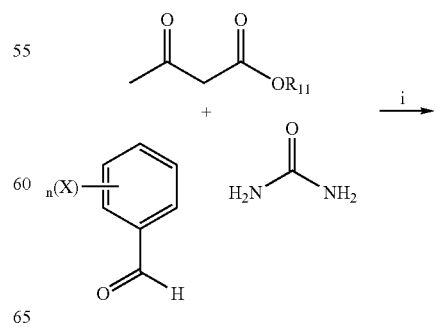

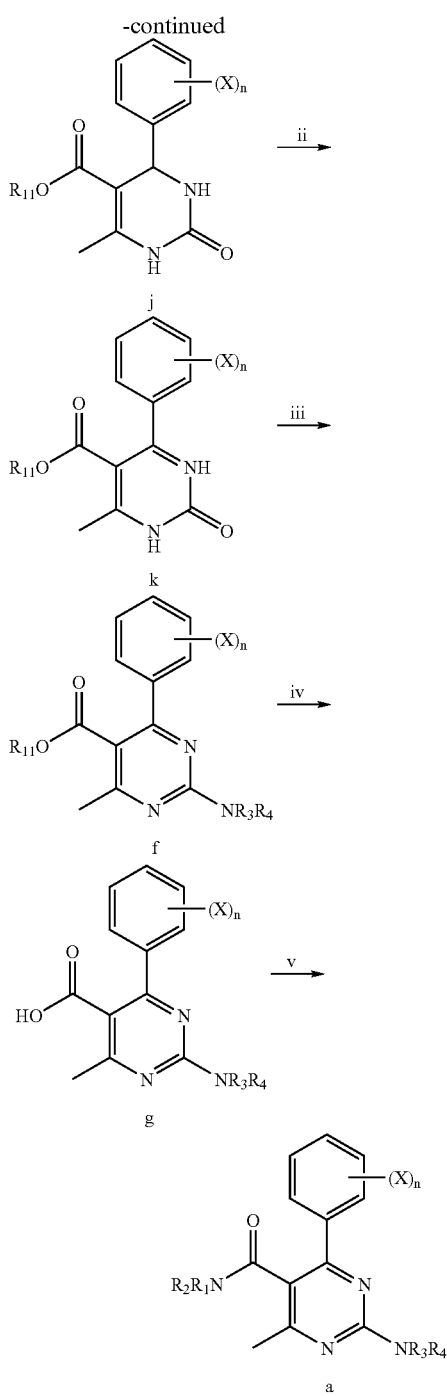

i. CuCl, BF₃OEt₂, THF, reflux, 18 h
ii. 60% HNO₃, rt, 30 min
iii. PyBrop, HNR₃R₄, Et₃N, THF, RT, 2 h
iv. NaOH, water, EtOH
v. a. (COCl)₂, DMF, CH₂Cl₂,
    b. DIPEA, NHR₁R₂, RT 16 h Referring to Scheme 3, condensation of an aryl aldehyde with an acetoacetate ester and urea in the presence of a catalyst such as, for example, cuprous chloride and a Lewis acid such as, for example, borontrifluoride ethereate provides the dihydropyrimidinone j. Oxidation of h with, for example, 60% nitric acid gives the pyrimidinone k. Condensation of i with an amine HNR₃R₄ in the presence of a condensation reagent such as, for example, PyBrop (Bromo-tris-pyrrolidino phosphoniumhexafluorophosphate) provides the aminopyridine f. Conversion of f to the compounds of the invention can be achieved as described above in Scheme 1.

The amine intermediates HNR₁R₂ are commercially available, known in the art, or may be prepared by known reductive amination methods or condensation of the amine with an aryl halide using known methodology and as illustrated in the Examples herein.

An alternative method for preparation of the compounds is illustrated in Scheme 4 without limitation.

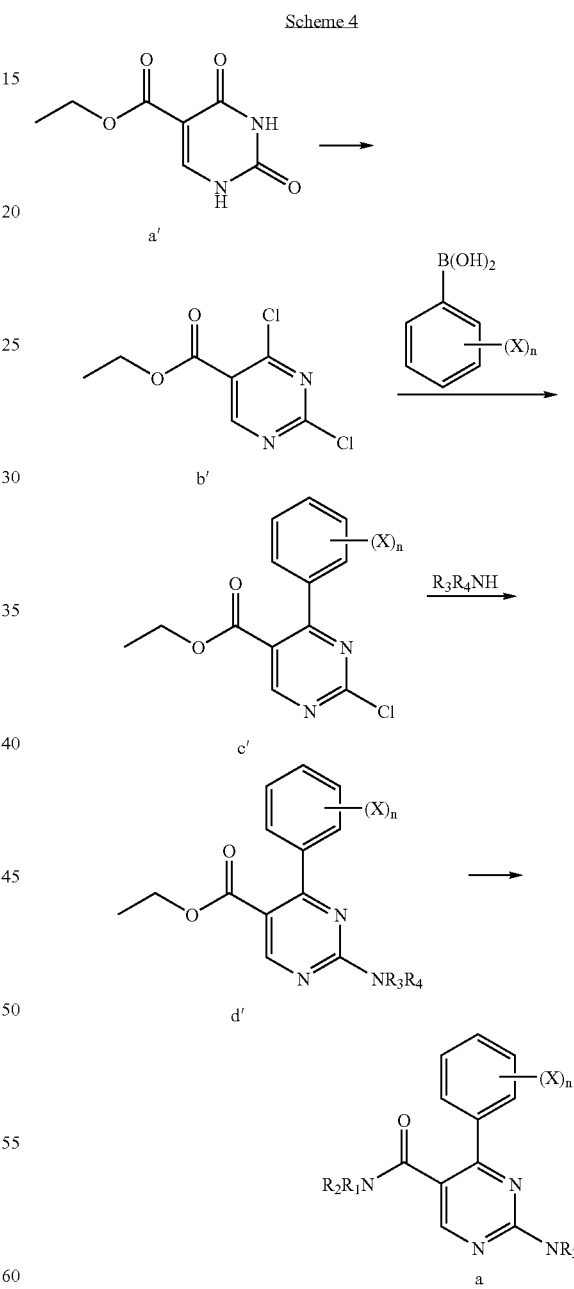

Referring to Scheme 4, the pyrimidinedione a' is converted to the dichloropyrimidine b' by reaction with phosphorous oxychloride in the presence of dimethylformamide. Coupling of b' with an arylboronic acid in the presence of a palladium catalyst such as, for example, Pd₂(dba)₃ and a trialkylphosphine such as, for example, tri-t-butyl phosphine provides the aryl substituted pyrimidine c'. Displacement of the chloro group in c' with the amine $HNR_3R_4$ provides the aminopyrimidine d'. Hydrolysis of the ester in d' with, for example, sodium hydroxide in ethanol provides the corresponding acid which is converted to the compounds of the invention a using known amide forming conditions.

IV. Formulations, Administrations, and Uses

A. Pharmaceutically Acceptable Compositions

As discussed above, the present invention provides compounds that are inhibitors of voltage-gated sodium ion channels and/or calcium channels, and thus the present compounds are useful for the treatment of diseases, disorders, and conditions including, but not limited to acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel or calcium channel.

Pharmaceutically acceptable salts are well known in the art. For example, S. M. Berge, et al. describes pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

B. Uses Of Compounds and Pharmaceutically Acceptable Compositions

In yet another aspect, a method for the treatment or lessening the severity of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitis or cancer pain is provided comprising administering an effective amount of a compound or a pharmaceutically acceptable composition to a subject in need thereof.

In certain embodiments of the present invention an "effective amount" of the compound or pharmaceutically acceptable composition is that amount effective for treating or lessening the severity of one or more of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the present invention, may be administered using any amount and any route of administration effective for treating or lessening the severity of one or more of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form", as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels or calcium channels, preferably N-type calcium channels. In one embodiment, the compounds and compositions of the invention are inhibitors of one or more of NaV1.1, NaV1.2, NaV1.3, NaV1.4, NaV1.5, NaV1.6, NaV1.7, NaV1.8, NaV1.9, or CaV2.2, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease, condition, or disorder. When activation or hyperactivity of NaV1.1, NaV1.2, NaV1.3, NaV1.4, NaV1.5, NaV1.6, NaV1.7, NaV1.8, NaV1.9, or CaV2.2, is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder" or a "CaV2.2-mediated condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, NaV1.9, or CaV2.2 maybe assayed according to methods described generally in the Examples herein, or according to methods available to one of ordinary skill in the art.

In certain exemplary embodiments, compounds of the invention are useful as inhibitors of NaV1.3. In other embodiments, compounds of the invention are useful as inhibitors of NaV1.3 and CaV2.2. In still other embodiments, compounds of the invention are useful as inhibitors of CaV2.2.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.,gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, NaV1.9, or CaV2.2 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, NaV1.9, or CaV2.2 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

V. Preparations and Examples

Preparation 1: N-Benzylcyclobutylamine.

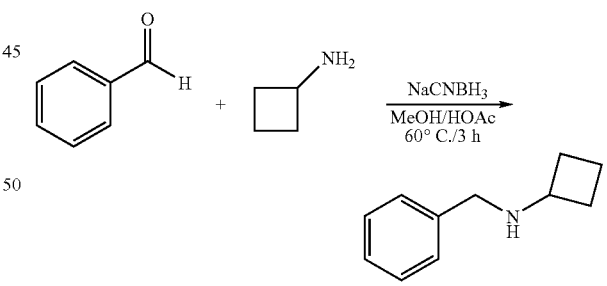

A sodium cyanoborohydride (0.88 g, 14 mmol) was added slowly to a stirred solution of benzaldehyde (0.71 g, 7.00 mmol) in methanol (9 mL) and glacial acetic acid (1 mL) at room temperature and the mixture was heated at 60° C. for 3 hr and cooled to room temperature. The solvent was evaporated under reduced pressure, and the crude material was dissolved in water and basified with a 2N NaOH solution (10 mL). The aqueous layer was extracted with EtOAc (3×50 mL), dried and concentrated. The residue was purified by Biotage SP1 on packed silica gel column (10%-80% EtOAc/Hexanes gradient) to give N-benzylcyclobutylamine (0.65 g,58%). Mass Spec. FIA MS 312 (M+1), $^1$H NMR (DMSO-d6, 500 MHz) δ7.26-7.31(m, 4H), 7.17-7.21(d,1H), 3.58(s, 2H), 3.13 (m,1H), 2.11 (brs, 1H), 2.04(m,2H), 1.50-1.69(m, 4H).

Preparation 2: N-Isopropyl-3-methoxybenzenamine

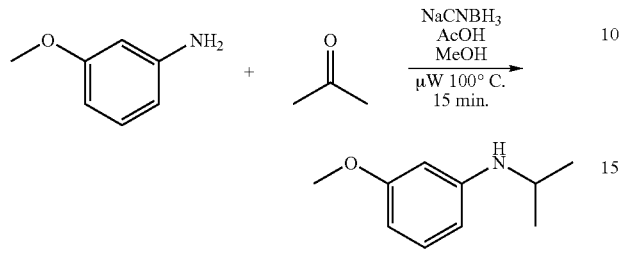

To a microwave tube charged with a stirring bar was added sodium cyanoborohydride (0.10 g, 1.6 mmol) and m-anisidine (0.075 mL, 0.8 mmol) in methanol (1 mL). To this solution was the added acetone (0.5 mL) and glacial acetic acid (0.5 mL). Once the gas evolution had subsided, the tube was crimped and subjected to microwave irradiation at 130° C. for 15 minutes. The solution was diluted with $CH_2Cl_2$, washed once with 1N NaOH, and the organic layer was dried ($Na_2SO_4$), filtered and concentrated to a yellow liquid. This was purified via silica gel chromatography with an ethyl acetate/hexanes gradient ($R_f$=0.60 in 4:1 Hex/EtOAc) to give N-isopropyl-3-methoxybenzenamine as a colorless oil. FIA MS 166 (M+1).

Preparation 3: N-Cyclopropyl-3-methoxybenzenamine

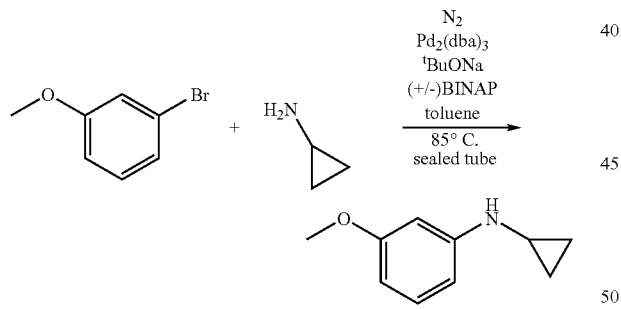

To a high-pressure tube was added 3-bromoanisole(0.250 mL, 2 mmol), cyclopropylamine (0.225 mL, 3.2 mmol), sodium t-butoxide (0.29 g, 3.0 mmol), (+/−) BINAP (0.04 g, 0.06 mmol), and $Pd_2(dba)_3$ (0.010 g, 0.01 mmol). This mixture was suspended in 4 mL anhydrous toluene. The tube was flushed with dry nitrogen gas, then capped and wrapped in aluminum foil. The reaction mixture was stirred and heated to 80° C. overnight, then allowed to cool, and the reaction vessel was opened. The mixture was diluted with diethyl ether, filtered through Celite, and the filtrate was concentrated to a yellow oil. LC/MS analysis showed one peak with the correct mass, and due to the limited stability of the material, it was carried through without further purification. FIA MS 164 (M+1).

Example 1

4-(2-Fluoro-phenyl)-2-morpholin-4-yl-pyrimidine-5-carboxylic acid benzyl-isopropyl-amide (Compound No. 326)

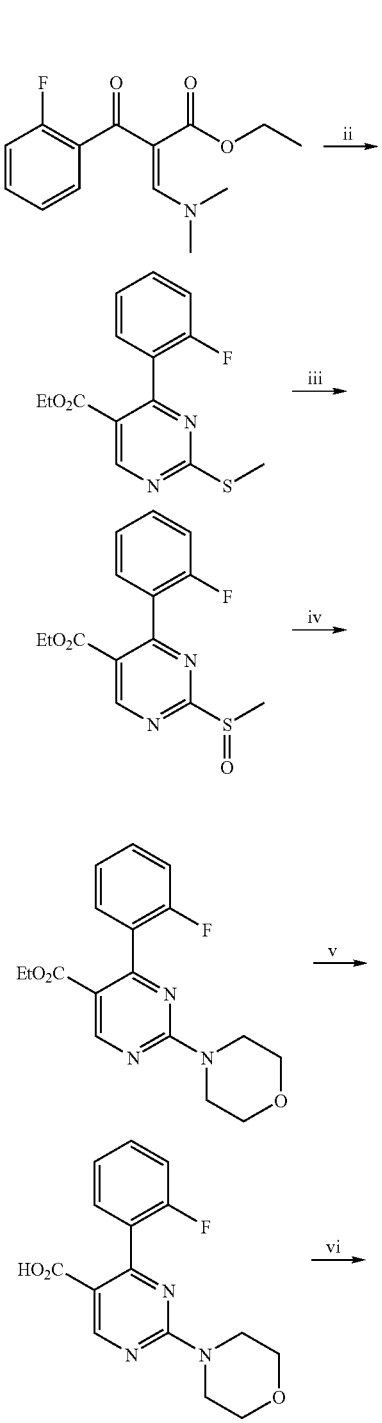

-continued

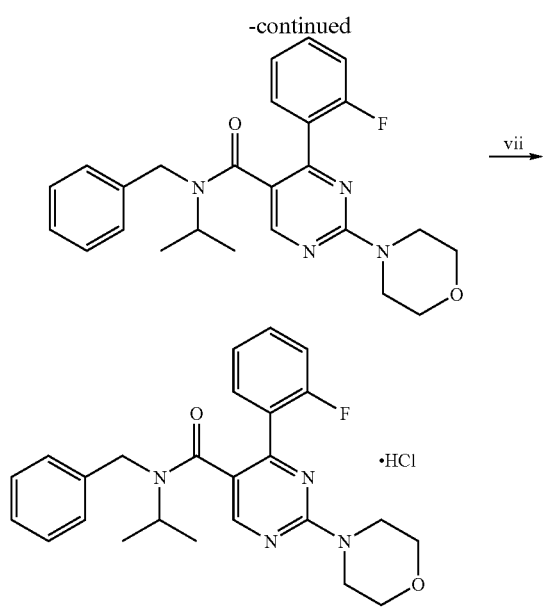

Synthesis of 4-(2-Fluoro-phenyl)-2-morpholin-4-yl-pyrimidine-5-carboxylic acid benzyl-isopropyl-amide (Compound No. 326):
i. DMF-DMA, toluene;
ii. 2-methylisothiourea sulfate, NaOAc, DMF, 80-90° C., 60% over 2 steps;
iii. m-CPBA, CH$_2$Cl$_2$, -78 to 0° C.;
iv. morpholine, THF, reflux;
v. 10 N aq. NaOH, MeOH, reflux, 74% over 3 steps;
vi. 1) (COCl)$_2$, CH$_2$Cl$_2$;
   2) Bn(i-Pr)NH, toluene, 92%;
vii. HCl, Et$_2$O.

Step i: 3-Dimethylamino-2-(2-fluoro-benzoyl)-acrylic acid ethyl ester

A mixture of ethyl 3-(2-fluorophenyl)-3-oxopropanoate (14.29 g, 68.0 mmol) and DMF-DMA (12.15 g, 0.102 mol, 1.5 eq.) in toluene (50 mL) was refluxed for 2 hours and concentrated to give 3-dimethylamino-2-(2-fluoro-benzoyl)-acrylic acid ethyl ester as a red oil in quantitative yield.

Step ii: 4-(2-Fluoro-phenyl)-2-methylsulfanyl-pyrimidine-5-carboxylic acid ethyl ester 3-Dimethylamino-2-(2-fluoro-benzoyl)-acrylic acid ethyl ester was dissolved in DMF (100 mL). To the solution was added isothiourea sulfate (18.92 g, 68.0 mmol) and NaOAc (23.24 g, 0.28 mol). The reaction mixture was heated at 80-90° C. overnight. Water was added to the cooled solution. The product was extracted with EtOAc (3×100 mL). The combined organic layers were washed with a saturated aqueous NaHCO$_3$ solution and water, dried over Na$_2$SO$_4$, and concentrated. The crude product was purified by column chromatography (1 L silica, EtOAc) to give 4-(2-fluoro-phenyl)-2-methylsulfanyl-pyrimidine-5-carboxylic acid ethyl ester as a yellow oil (11.86 g, 40.6 mmol, 60% over 2 steps).

Step iii: 4-(2-Fluoro-phenyl)-2-methanesulfinyl-pyrimidine-5-carboxylic acid ethyl ester A Na$_2$SO$_4$-dried solution of m-CPBA (10.64 g, ca. 45 mmol) in CH$_2$Cl$_2$ (100 mL) was added drop wise to a cold (−65° C.) solution of 4-(2-fluoro-phenyl)-2-methylsulfanyl-pyrimidine-5-carboxylic acid ethyl ester in CH$_2$Cl$_2$ (200 mL) keeping the temperature below −65° C. The yellow suspension was allowed to warm to 0° C. over 1 hour. After 3 hours at 0° C., a saturated aqueous NaHCO$_3$ solution (100 mL) was added to quench the reaction. The organic layer was separated, washed with saturated aqueous NaCl solution, dried over Na$_2$SO$_4$, and concentrated. The product was taken up in CH$_2$Cl$_2$ and washed again with a saturated aqueous NaHCO$_3$ solution to remove traces of m-C(P)BA giving 4-(2-fluoro-phenyl)-2-methanesulfinyl-pyrimidine-5-carboxylic acid ethyl ester (12.86 g, >100%).

Step iv: 4-(2-Fluoro-phenyl)-2-morpholin-4-yl-pyrimidine-5-carboxylic acid ethyl ester Morpholine (7.0 mL, 6.9 g, 80 mmol) was added to a solution of 4-(2-fluoro-phenyl)-2-methanesulfinyl-pyrimidine-5-carboxylic acid ethyl ester in THF (80 mL). The resulting mixture was heated at reflux for 3 hours. Concentration of the solution afforded the product as a yellow oil. Traces of morpholine were removed at oil pump vacuum in a Kugelrohr apparatus to yield 4-(2-fluoro-phenyl)-2-morpholin-4-yl-pyrimidine-5-carboxylic acid ethyl ester (16.00 g, >100%).

Step v: 4-(2-Fluoro-phenyl)-2-morpholin-4-yl-pyrimidine-5-carboxylic acid 4-(2-Fluoro-phenyl)-2-morpholin-4-yl-pyrimidine-5-carboxylic acid ethyl ester was dissolved in a mixture of methanol (150 mL) and a 33% aqueous NaOH solution (150 mL). The mixture was heated at reflux for 3 hours, and allowed to cool to room temperature overnight. The solution was concentrated to ca. half the volume under reduced pressure. The resulting suspension was adjusted to pH 7 with a 1-5N aqueous HCl solution. The formed precipitate was filtered off, washed with water (3×), and air-dried at 45° C. overnight to give 4-(2-fluoro-phenyl)-2-morpholin-4-yl-pyrimidine-5-carboxylic acid as a tan solid (9.051 g, 29.8 mmol, 74% over 3 steps).

Step vi: 4-(2-Fluoro-phenyl)-2-morpholin-4-yl-pyrimidine-5-carboxylic acid benzyl-isopropyl-amide To an ice-cooled solution of 4-(2-fluoro-phenyl)-2-morpholin-4-yl-pyrimidine-5-carboxylic acid (4.321 g, 14.25 mmol) in CH$_2$Cl$_2$ (100 mL) and DMF (2 drops) was added oxalyl chloride (1.5 mL, 2.21 g, 17.5 mmol) dropwise. Most solids dissolved at first, later a precipitate formed. The suspension was stirred for 1 hour at 0° C., and then allowed to warm to room temperature (all solids dissolved). The solution was concentrated to a dark oil, which crystallized upon standing. The crude acid chloride was taken up in toluene (50 mL, distilled, dried over Na$_2$SO$_4$) and cooled in ice. N-Isopropylbenzylamine (9.5 mL, 8.5 g, 56.8 mmol) was added. The resulting suspension was stirred at room temperature for 90 minutes, washed with water and a saturated aqueous NaCl solution, dried over Na$_2$SO$_4$, and concentrated. The crude product was purified by column chromatography (400 mL silica, EtOAc/heptanes 1:1). All fractions containing the product were combined and concentrated. Some of the excess amine eluted with the product. A solution of the mixture in CH$_2$Cl$_2$ (50 mL) was washed with a 10% aqueous citric acid solution (2×25 mL), water (25.mL), and saturated aqueous NaCl solution (25 mL), dried over Na$_2$SO$_4$, and concentrated to give pure 4-(2-fluoro-phenyl)-2-morpholin-4-yl-pyrimidine-5-carboxylic acid benzyl-isopropyl-amide as a yellowish foam (5.685 g, 13.08 mmol, 92%).

Step vii: 4-(2-Fluoro-phenyl)-2-morpholin-4-yl-pyrimidine-5-carboxylic acid benzyl-isopropyl-amide HCl salt To a solution of 4-(2-fluoro-phenyl)-2-morpholin-4-yl-pyrimidine-5-carboxylic acid benzyl-isopropyl-amide in Et$_2$O (20 mL) was added IN HCl in Et$_2$O (15 mL, 15 mmol). The resulting slurry was stirred vigorously for 1 hour. The solids were filtered off, washed with Et$_2$O (2×20 mL), and dried in vacuo (0.01 mbar) overnight to yield 4-(2-fluoro-phenyl)-2-morpholin-4-yl-pyrimidine-5-carboxylic acid benzyl-isopropyl-amide HCl salt (5.70 g, 12.10 mmol, 93%).

Example 2

N-benzyl-N-cyclobutyl-4-(2-fluorophenyl)-2-morpholinopyrimidine-5-carboxamide (Compound No. 86)

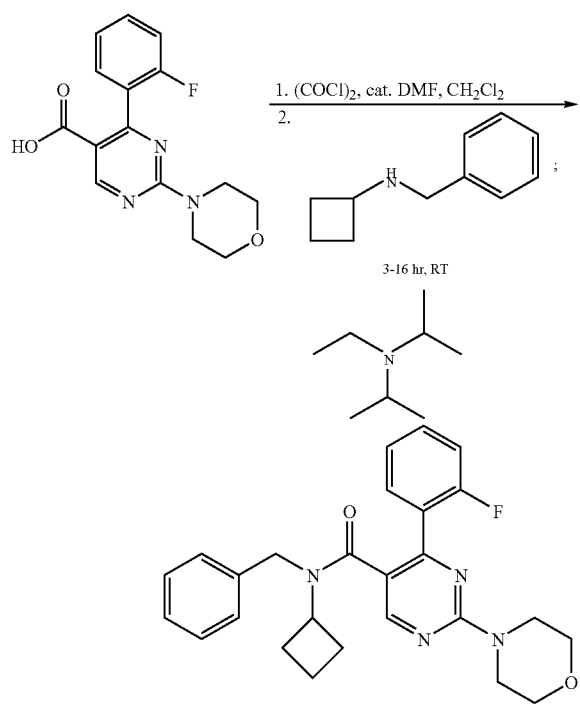

A solution of 2M oxalyl chloride in CH$_2$Cl$_2$ (0.062 mL, 0.125 mmol) was added to a stirred solution of 4-(2-fluorophenyl)-2-morpholinopyrimidine-5-carboxylic acid (Example 1; 0.03 g, 0.1 mmol) in CH$_2$Cl$_2$(2 mL) and DMF (0.030 mL) at room temperature, and stirring continued for 15 min. A solution of N-benzylcyclobutanamine (0.016 g, 0.1 mmol) in CH$_2$Cl$_2$ (1 mL) and diisopropylethylamine (0.044 mL, 0.25 mmol) were added and stirred for 3 h. The solvent was removed under reduced pressure, and the residue was purified by Biotage SP1 on packed silica gel column (10%-80% EtOAc/Hexanes gradient) to give N-benzyl-N-cyclobutyl-4-(2-fluorophenyl)-2-morpholinopyrimidine-5-carboxamide (0.032 g, 72%). Mass Spec. FIA MS 447 (M+1), $^1$H NMR (DMSO-d6, 500 MHz) δ 8.43(brs,1H), 7.52-7.55(m,2H), 6.99-7.31(m,7H), 4.62(brm,2H), 3.78(brm,4H0, 3.68(brn, 4H), 2.15(brm,2H), 1.85(brm,2H), 1.17(brm,2H).

Example 3

Following the procedures of Examples 1 and 2 making non-critical variations and using amines HNR$_1$R$_2$ prepared by the procedure of preparation 1 the following compounds were prepared.

TABLE 2

| Exemplary compounds using amines prepared by the procedure of preparation 1. Compound No. |
| --- |
| 5 |
| 12 |
| 38 |
| 65 |
| 111 |
| 129 |
| 133 |
| 144 |
| 149 |
| 155 |
| 156 |
| 157 |
| 188 |
| 208 |
| 215 |
| 228 |
| 242 |
| 268 |
| 292 |
| 328 |
| 339 |
| 342 |

Example 4

Following the procedures of Examples 1 and 2 making non-critical variations and using amines HNR$_1$R$_2$ prepared by the procedure of preparation 2 the following compounds were prepared.

TABLE 3

| Exemplary compounds using amines prepared by the procedure of preparation 2. Compound No. |
| --- |
| 4 |
| 8 |
| 14 |
| 19 |
| 20 |
| 29 |
| 41 |
| 47 |
| 53 |
| 62 |
| 63 |
| 74 |
| 91 |
| 94 |
| 95 |
| 101 |
| 102 |
| 116 |
| 119 |
| 127 |
| 128 |
| 131 |
| 135 |
| 142 |
| 152 |
| 153 |
| 159 |
| 161 |
| 162 |
| 170 |
| 172 |
| 177 |
| 190 |
| 196 |
| 200 |
| 210 |
| 212 |

TABLE 3-continued

Exemplary compounds using amines prepared
by the procedure of preparation 2.
Compound No.

213
219
222
224
230
244
247
249
252
256
258
263
265
267
294
297
300
320
322
325
327

Example 5

Following the procedures of Examples 1 and 2 making non-critical variations commonly known in the art and using amines $HNR_1R_2$ prepared by the procedure of preparation 3, Compound No. 31 was prepared.

Example 6

Additional compounds prepared following the above general procedures include those in Table 4.

TABLE 4

Exemplary compounds prepared using
general procedures of Examples 1-5.
Compound No.

6
7
11
13
23
25
34
36
45
46
57
59
64
75
76
80
85
85
103
107
112
115
117
120
122
137
158
174
187
192

TABLE 4-continued

Exemplary compounds prepared using
general procedures of Examples 1-5.
Compound No.

194
195
203
207
260
266
275
277
287
295
296
304
306
310
314
316
326
331
340
346

Example 7

4-(2-fluorophenyl)-N-isopropyl-N-(3-methoxybenzyl)-2-(piperidin-1-yl)pyrimidine-5-carboxamide
(Compound No. 20)

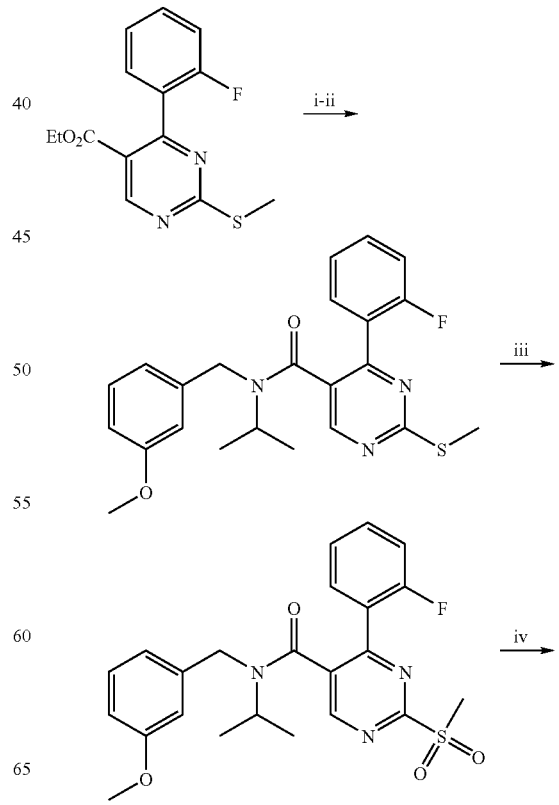

-continued

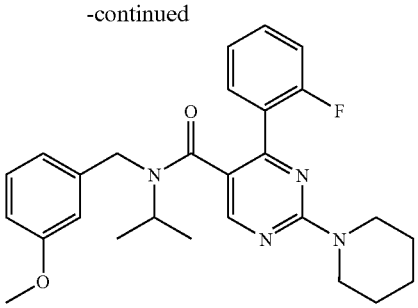

Synthesis of 4-(2-fluorophenyl)-N-isopropy-N-(3-methoxybenzyl)-2-(piperidin-1-yl)pyrimidine-5-carboxamide (Compound No.20).
i. NaOH, water, MeOH, reflux, 1h.
ii. a. (COCl)2, DMF, CH2Cl2,
   b. N-(3-methoxybenzyl)propan-2-amine, DIPEA.
iii MCPBA, CH2Cl2
iv piperidine, THF, heat Steps i and ii: N-3-Methoxybenzyl4-(2-fluorophenyl)-N-isopropyl-2(methylthio)pyrimidine-5-carboxamide A mixture of ethyl 4-(2-fluorophenyl)-2-(methylthio)pyrimidine-5-carboxylate (3.3 g, 10.96 mmol), solid NaOH (3.2 g) in ethanol(30 mL) and water (6 mL) was refluxed for 1 h. and cooled to room temperature. The solvent was removed under reduced pressure, and the residue was acidified with 6N HCl. The product was extracted with EtOAC (3×50 mL), and the organic extracts were dried and concentrated to give crude acids (1.6 g). A solution of 2 M oxalyl chloride in $CH_2Cl_2$ (3.00 mL, 6 mmol) was added to a stirred solution of the crude acids (1.6 g) in $CH_2Cl_2$ (25 mL) and DMF (1 mL) at room temperature, and stirring continued for 15 min. A solution of N-(3-methoxybenzyl)propan-2-amine, (1.07 g, 6.00 mmol) in $CH_2Cl_2$(2 mL) and diisopropylethylamine(2 mL, 12 mmol) was added and stirred for 1 hr. The solvent was removed under reduced pressure and the residue was purified by Biotage SP1 on packed silica gel column (10%-80% EtOAc/Hexanes gradient) to give N-(3-methoxybenzyl)-4-(2-fluorophenyl)-N-isopropyl-2(methylthio)pyrimidine-5-carboxamide (0.6 g, 13%). Mass Spec. FIA MS 426 (M+1).

Step iii: N-(3-Methoxybenzyl)4-(2-fluorophenyl)-N-isopropyl-2-(methylsulfonyl)pyrimidine-5-carboxamide 70% of MCPBA (0.688 g, 2.80 mmol) was added to a stirred solution of N-(3-methoxybenzyl)-4-(2-fluorophenyl)-N-isopropyl-2(methylthio)pyrimidine-5-carboxamide (0.60 g, 1.41 mmol) in $CH_2Cl_2$(10 mL), and the mixture was stirred at room temperature for 2 h. The solution was washed with saturated $NaHCO_3$, dried and concentrated. The solvent was removed under reduced pressure, and the residue was purified by Biotage SP1 on packed silica gel column (5%-40% MeOH/$CH_2Cl_2$ gradient) to give N-(3-methoxybenzyl)-4-(2-fluorophenyl)-N-isopropyl-2-(methylsulfonyl)pyrimidine-5-carboxamide (0.32 g, 49%). Mass Spec. FIA MS 463 (M+1).

Step iv: N-(3-Methoxybenzyl)-4-(2-fluorophenyl)-N-isopropyl-2-(piperdin-1-yl)pyrimidine-5-carboxamide (Compound No. 20)

Piperidine (0.0054 g, 0.064 mmol) was added to a stirred solution of N-(3-methoxybenzyl)-4-(2-fluorophenyl)-N-isopropyl-2-(methylsulfonyl)pyrimidine-5-carboxamide (0.015 g, 0.032 mmol) in THF (1 mL) and the mixture was heated at 80° C. for 1 h. The solvent was removed under reduced pressure, and the product was purified by preparative HPLC (5-80% $CH_3CN$/0.05% TFA gradient over 15 min) to give N-(3-methoxybenzyl)-4-(2-fluorophenyl)-N-isopropyl-2-(piperdin-1-yl)pyrimidine-5-carboxamide Compound No. 20 (0.012 g, 81%).

Example 8

Following the procedures of Example 7, and making non-critical variations, the following compounds in Table 5 were prepared.

TABLE 5

Exemplary compounds prepared by procedures of Example 7.
Compound No.

| |
|---|
| 2 |
| 3 |
| 9 |
| 17 |
| 21 |
| 24 |
| 35 |
| 44 |
| 50 |
| 67 |
| 69 |
| 84 |
| 89 |
| 92 |
| 113 |
| 114 |
| 134 |
| 139 |
| 151 |
| 164 |
| 165 |
| 189 |
| 204 |
| 218 |
| 226 |
| 229 |
| 235 |
| 238 |
| 246 |
| 250 |
| 255 |
| 270 |
| 274 |
| 279 |
| 284 |
| 288 |
| 308 |
| 311 |
| 312 |
| 313 |
| 321 |
| 323 |
| 332 |
| 335 |
| 336 |
| 351 |

Example 9

N-benzyl-4-(2-fluorophenyl)-N-isopropyl-6-methyl-2-morpholinopyrimidine-5-carboxamide (Compound No. 338)

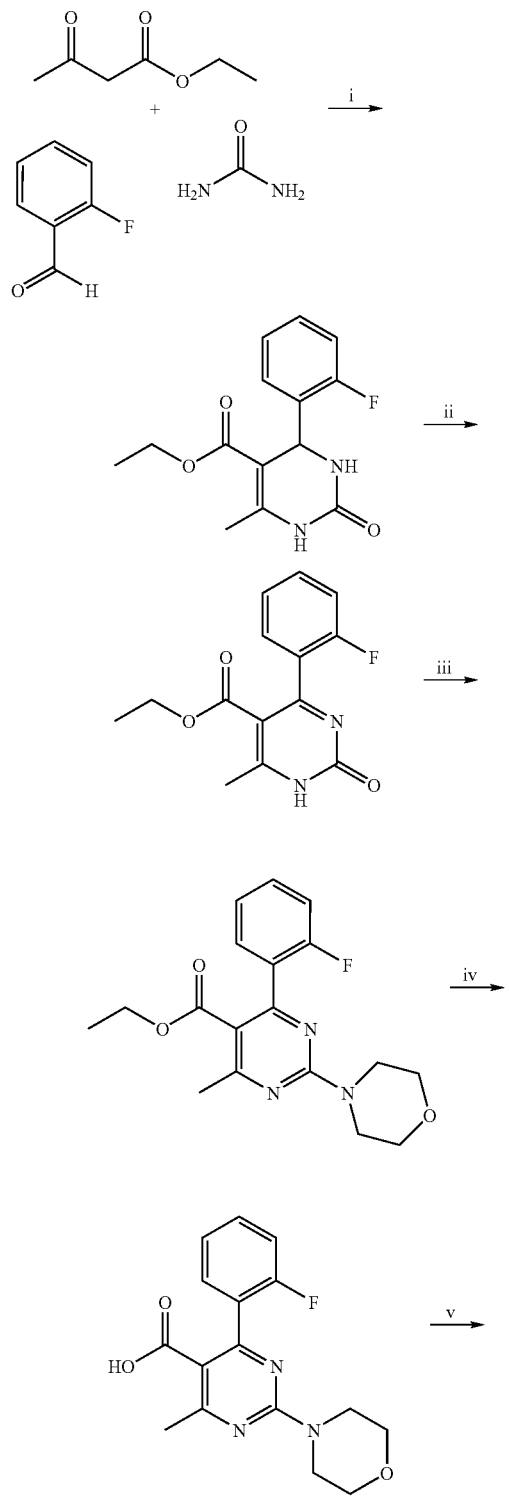

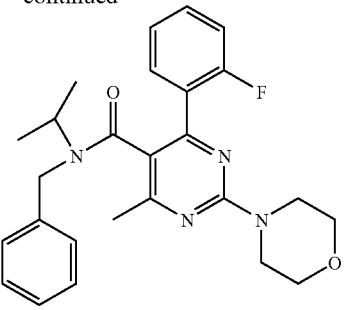

Synthesis of N-benyzl-4-(2-fluorophenyl)-N-isopropyl-6-methyl-2-morpholinopyrimidine-5-carboxamide Compound No. 338:
i. CuCl, BF$_3$OEt$_2$, THF, reflux, 18 h
ii 60% HNO3, rt, 30 min
iii PyBrop, morpholine, Et$_3$N, THF, RT, 2 h
iv NaOH, water, EtOH,
v. a. (COCl)$_2$, DMF, CH$_2$Cl$_2$
b. DIPEA, N-benzylpropan-2-amine, RT 16 h Step i: Ethyl 4-(2-fluorophenyl)-1,2,3,4-tetrahydro-6-methyl-2-oxopyrimidine-5-carboxylate A mixture of 2-fluorobenzaldehyde (5 g, 40.28 mmol), urea (3.8 g, 61 mmol), ethylacetoaceate(5.24 g, 40.28 mmol), CuCl (0.4 g,4 mmol), BF$_3$.OEt$_2$ (7 mL, 53 mmol), and glacial acetic acid(0.24g, 4 mmol) in THF (80 mL) was refluxed for 18 h and then cooled to room temperature. The mixture was quenched with saturated NaHCO$_3$ (50 mL), and EtOAc (100 mL) was added. The layers were separated and the organic layer with a white suspension was evaporated to give a white solid. The solid was suspended in toluene (100 mL) and stirred for 2 days at room temperature. The solid was filtered, washed with ether, and dried to give ethyl 4-(2-fluorophenyl)-1,2,3,4-tetrahydro-6-methyl-2-oxopyrimidine-5-carboxylate (9.9 g, 88%). Mass Spec. FIA MS 279 (M+1).

Step ii: Ethyl 4-(2-fluorophenyl)-1,2-dihydro-6-methyl-2-oxopyrimidine-5-carboxylate Ethyl 4-(2-fluorophenyl)-1,2,3,4-tetrahydro-6-methyl-2-oxopyrimidine-5-carboxylate (2.00 g, 7.2 mmol) was added in small portions to a stirred solution of a 60% nitric acid solution (12 mL) at 0° C. over 5 min. The resulting solution was warmed to room temperature (30 min) and then poured into ice and basified slowly with 6N NaOH. The product was extracted with CHCl$_3$ (3×50 mL), dried, and concentrated. The residue was purified by Biotage SP1 on packed silica gel column (7%-20% MeOH/CH$_2$Cl$_2$ gradient) to give ethyl 4-(2-fluorophenyl)-1,2-dihydro-6-methyl-2-oxopyrimidine-5-carboxylate as a green foam (1.5 g, 76%). Mass Spec. LCMS 277 (M+1).

Step iii: 4-(2-Fluorophenyl)-6-methyl-2-morpholin-4-yl-pyrimidine-5-carboxylic acid ethyl ester Morpholine (0.5 mL) was added to a stirred solution of ethyl 4-(2-fluorophenyl)-1,2-dihydro-6-methyl-2-oxopyrimidine-5-carboxylate (0.75 g, 2.72 mmol), PyBroP (1.4 g, 3 mmol), and triethylamine (1 mL) in 1,4-dioxane (20 mL) at room temperature. The solution was stirred at room temperature for 3 h and diluted with EtOAc. The solution was washed with saturated NH$_4$Cl and saturated aqueous NaCl solution, and dried. The solvent was removed under reduced pressure, and the residue was purified by Biotage SP1 on packed silica gel column (5%-80% EtOAC/hexanes gradient) to give 4-(2-fluorophenyl)-6-methyl-2-morpholin-4-yl-pyrimidine-5-carboxylic acid ethyl ester as an oil (0.937 g, 64%). Mass Spec. LCMS 346 (M+1).

Step iv: 4-(2-Fluorophenyl)-6-methyl-2-morpholin-4-yl-pyrimidine-5-carboxylic acid A mixture of 4-(2-fluorophenyl)-6-methyl-2-morpholin-4-yl-pyrimidine-5-carboxylic acid ethyl ester (0.6 g, 10.96 mmol), and solid NaOH (2 g, 50 mmol) in ethanol (5 mL) and water (1 mL) was refluxed for 1 h, then cooled to room temperature. The solvent was removed under reduced pressure, and the residue was acidified with a 6N HCl solution. Then, the product was extracted with EtOAC (3×25 mL) and the organic extracts were dried and concentrated to give 4-(2-fluorophenyl)-6-methyl-2-morpholin-4-yl-pyrimidine-5-carboxylic acid (0.43 g, 78%) as white solid. Mass Spec. LCMS 318 (M+1).

Step v: 4(2-Fluorophenyl)-6-methyl-2-morpholin-4-yl-pyrimidine-5-carboxylic acid benzyl-isopropyl-amide (Compound No. 338)

A solution of 2 M oxalyl chloride in $CH_2Cl_2$ (0.070 mL, 0.14 mmol) was added to a stirred solution of 4-(2-fluorophenyl)-6-methyl-2-morpholin-4-yl-pyrimidine-5-carboxylic acid (0.03 g, 0.09 mmol) in $CH_2Cl_2$ (2 mL) and DMF (0.030 mL) at room temperature, and stirring continued for 15 min. A solution of N-benzylisopropylamine (0.013 g, 0.1 mmol) in $CH_2Cl_2$ (1 mL) and diisopropylethylamine (0.044 mL, 0.25 mmol) were added and stirred for 24 hr. The solvent was removed under reduced pressure, and the residue was purified by Biotage SP1 on packed silica gel column (10%-80% EtOAc/Hexanes gradient) to give 4-(2-fluorophenyl)-6-methyl-2-morpholin-4-yl-pyrimidine-5-carboxylic acid benzyl-isopropyl-amide (0.016 g, 40%).

Mass Spec. LCMS 449(M+1).

Following the procedures of Example 9, and making non-critical variations, the following compounds were prepared.

TABLE 6

| Exemplary compounds prepared by the procedures of Example 9. Compound No. |
| --- |
| 49 |
| 83 |
| 173 |
| 186 |
| 245 |
| 251 |
| 253 |
| 259 |

Example 10

N-benzyl-4-(2-chlorophenyl)-N-isopropyl-2-morpholinopyrimidine-5-carboxamide (Compound No. 194)

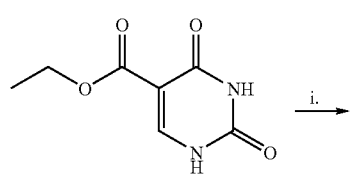

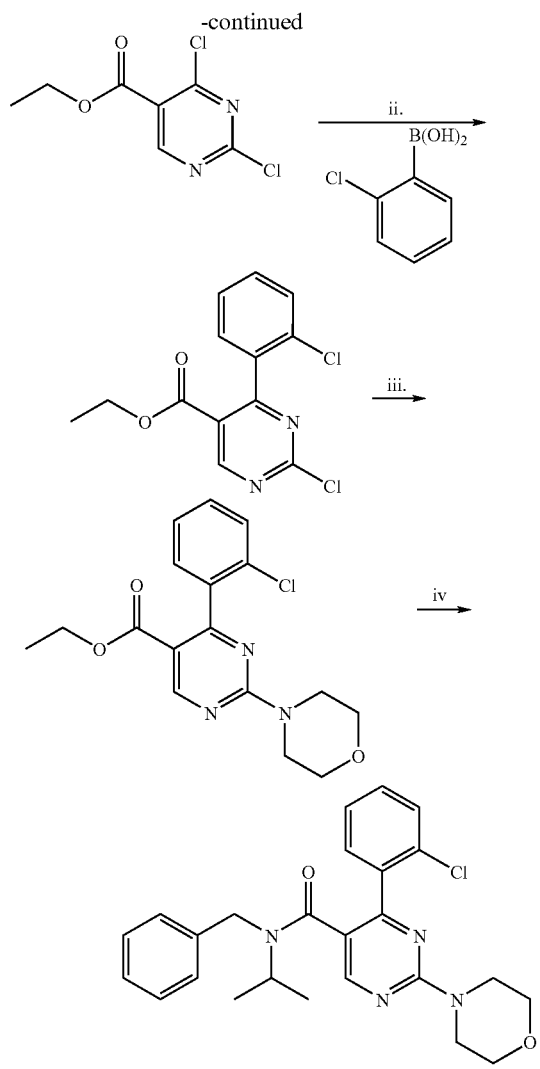

Synthesis of N-benzyl-4-(2-chlorophenyl)-N-isopropyl-2-morpholinopyrimidine-5-carboxamide:
i. $POCl_3$, DMA
ii. $Pd_2(dba)_3$, P(t-Bu)3, $K_3PO_4$, THF, 160° C. mW
iii. Morpholine, 100° C.
iv. A. NaOH, EtOH, 80° C.,
   B. amine, $BtSO_2Me$, $NEt_3$, Dioxane, 160° C., mW Step i. Ethyl 2,4-dichloropyrimidine-5-carboxylate Under an $N_2$ atmosphere, a mixture of 5-carbethoxyuracil (1.0 g, 5.4 mmol) and $POCl_3$ (10 mL) was heated at reflux for 30 minutes. The solution was concentrated under reduced pressure to remove the excess of $POCl_3$, and the residue was poured into ice (20 g). $CH_2Cl_2$ (100 mL) was added, and the mixture was basified to pH 9 using saturated aqueous $NaHCO_3$ solution. The organic portion was dried over $MgSO_4$ and concentrated to obtain ethyl 2,4-dichloropyrimidine-5-carboxylate as a yellow oil (900 mg, 75%).

Step ii. Ethyl 2-chloro-4-(2-chlorophenyl)pyrimidine-5-carboxylate

In a microwave tube was added 1 eq. of ethyl 2,4-dichloropyrimidine-5-carboxylate (200mg, 0.91 mmol), 0.5 eq. of 3-chlorophenyl boronic acid (67 mg), 0.1 eq. of $Pd_2(dba)_3$ (83 mg), 3 eq. of $K_3PO_4$ in 4 mL of Dioxane. To this solution was added 1 eq. of tri-(t-butyl) phospine. The reaction was heated in the microwave to 160° C./300 W/for 1200 sec. The crude product was purified by prep HPLC. ES+=296.8.

Step iii. Ethyl 4-(2-cyanophenyl)-2-morpholinopyrimidine-5-carboxylate

A flask containing ethyl 2-chloro-4-(2-chlorophenyl)pyrimidine-5-carboxylate (50 mg) in 1 mL morpholine was heated to 100° C. for 12 h. The crude mixture was purified by prep HPLC. The ester was then hydrolyzed with NaOH in ethanol at reflux for 5 hrs. ES+=319.9, ES−=318.0.

Step iv. N-Benzyl4-(2-chlorophenyl)-N-isopropyl-2-morpholinopyrimidine-5-carboxamide In a microwave tube was added 1 eq. of 4-(2-chlorophenyl)-2-morpholino pyrimidine-5-carboxylic acid (80 mg), 1.1 eq. of isopropyl benzylamine (43 mL), 2.5 eq. of triethylamine (80 mL) and 1.2 eq. of BtSO$_2$Me in 4 mL of dioxane. The reaction mixture was heated to 160° C./300 W for 1200 sec. The crude product was purified by prep HPLC. ES+=451.0. NMR confirmed the structure.

Example 11

Following the procedures of Example 11, and making non-critical variations known in the art, the following compounds were prepared.

TABLE 7

Exemplary compounds prepared by the procedures of Example 11.
Compound No.

| |
|---|
| 16 |
| 17 |
| 46 |
| 89 |
| 121 |
| 123 |
| 139 |
| 168 |

A person skilled in the chemical arts can use the examples and schemes along with known synthetic methodologies to synthesize compounds of the present invention, including the compounds in Table 8 below.

TABLE 8

Physical data for exemplary compounds.

| Compound No. | LC/MS M + 1 | LC/RT min | NMR |
|---|---|---|---|
| 1 | 449.4 | 4 | DMSO-d6: 8.49(s, 1H), 7.59(m, 1H), 7.52(m, 1H), 7.35-7.42(m, 2H), 7.11(brm, 3H), 6.77(brs, 2H), 3.78(brm, 7H), 1.63(brm, 2H), 1.53(brm, 4H), 0.83(brm, 6H) |
| 2 | 505 | 4.1 | DMSO-d6: 8.55(s, 1H), 7.44(m, 2H), 7.27(d, 2H), 7.15(m, 2H), 7.00(d, 2H), 4.46(brs, 2H), 4.12(m, 4H), 2.64(m, 4H), 1.95(brm, 1H), 0.49(brm, 4H). |
| 3 | 491.5 | 4.5 | DMSO-d6: 8.42(s, 1H), 7.49(br s, 2H), 7.41(m, 1H), 7.28(m, 1H), 7.22(m, 1H), 7.12(m, 1H), 6.74(s, 1H), 6.38(br s, 1H), 4.68(br s, 1H), 3.67(br s, 4H), 1.59(br s, 2H), 1.43(br s, 4H), 1.16(s, 9H), 0.92(br s, 6H). |
| 4 | 490.3 | 4 | DMSO-d6: 8.44(s, 1H), 7.52(m, 2H), 7.27(m, 2H), 7.08(m, 1H), 6.74(m, 2H), 6.50(m, 1H), 3.43-4.40(m, 8H), 1.64(m, 2H), 1.13(m, 1H), 0.88(m, 9H), 0.44(m, 2H), 0.30(m, 2H), |
| 5 | 451 | 3.09 | DMSO-d6: 8.51(s, 1H), 7.49(m, 2H), 7.30(m, 2H), 6.94(m, 1H), 6.34-6.62(m, 3H), 4.30(brs, 2H), 3.63-4.10(m, 9H), 0.82(brm, 6H). |
| 6 | 534.3 | 3.7 | DMSO-d6: 8.47(s, 1H), 7.52(m, 2H), 7.26(m, 2H), 7.07(m, 1H), 6.74(m, 2H), 6.49(m, 1H), 4.57(m, 2H), 4.30(m, 2H), 4.08(q, 2H), 3.95(m, 1H), 3.71(s, 3H), 3.13(m, 2H), 2.63(m, 1H), 1.92(m, 2H), 1.55(2H), 1.18(t, 3H), 0.92(m, 6H) |
| 7 | 489.5 | 3.8 | DMSO-d6: 8.49(s, 1H), 7.49(m, 2H), 7.30(m, 2H), 6.50-6.80(brm, 3H), 4.49(t, 2H), 4.35(brs, 2H), 3.78(t, 4H), 3.09(t, 2H), 1.95(brm, 1H), 1.63(m, 2H), 1.53(m, 4H), 0.49(4H) |
| 8 | 491.4 | 4.1 | DMSO-d6: 8.41(s, 1H), 7.53(d, 1H, J=8Hz), 7.49(t, 1H, J=8Hz), 7.43(t, 1H, J=8Hz), 7.34(d, 1H, J=8Hz), 7.14(t, 1H, J=8Hz), 6.81(d, 1H, J=8Hz), 6.32(d, 1H, J=7Hz), 6.17(s, 1H), 4.53(br s, 1H), 3.69(m, 4H), 3.63(s, 3H), 1.62(m, 4H), 1.46(m, 4H), 1.39(m, 4H), 1.22(m, 2H). |
| 9 | 465.2 | 3.4 | DMSO-d6: 7.15-7.50(m, 4H), 6.97(t, 2H), 6.86(m, 2H), 4.85(d, 1H), 3.99(d, 1H), 3.72(m, 4H), 3.65(m, 4H), 2.30(s, 3H), 2.29(s, 3H), 1.85(m, 1H), 0.20-0.50(m, 4H), |
| 10 | 460.2 | 3.5 | DMSO-d6: 7.15-7.47(m, 4H), 7.01(m, 2H), 6.78(s, 1H), 6.54(d, 1H) 4.79(d, 1H), 4.02(d, 1H), 3.73(m, 4H), 3.65(m, 4H), 2.30(s, 3H), 2.22(s, 3H), 1.90(m, 1H), 0.20-0.46(m, 4H), |
| 11 | 392.2 | 3 | |
| 12 | 503.5 | 4.2 | DMSO-d6: 8.25(s, 1H), 7.54(m, 1H), 7.36(m, 1H), 7.30(m, 2H), 6.72(d, 2H, J=8Hz), 6.61(d, 2H, J=6Hz), 4.76(m, 1H), 4.10(m, 1H), 4.00(m, 1H), 3.70(s, 3H), 3.21(m, 2H), 1.85(m, 1H), 1.75(m, 2H), 1.55-1.65(m, 3H), 1.15-1.40(m, 6H), 0.92(s, 6H). |
| 13 | 449.1 | 3.93 | CD3OD: 7.45(m, 2H), 7.13-7.25(m, 5H), 6.90(d, 1H), 4.75(d, 1H), 4.25(d, 1H), 3.85(m, 4H), 3.73(m, 4H), 2.41(s, 3H), 3.0(m, 1H), 1.05(d, 3H), 0.61(d, 3H) |
| 14 | 508.5 | 2.4 | DMSO-d6: 8.83(d, 2H), 8.56(s, 1H), 8.04(d, 2H), 7.79(d, 1H), 7.69(brs, 1H), 7.25-7.50(m, 6H), 4.61(brs, 2H), 3.80(m, 4H), 2.20(brm, 1H), 1.64(brm, 2H), 1.54(brm, 4H), 0.54(brm, 6H) |

TABLE 8-continued

Physical data for exemplary compounds.

| Compound No. | LC/MS M + 1 | LC/RT min | NMR |
|---|---|---|---|
| 15 | 471.5 | 3.47 | |
| 16 | 453.1 | 3.6 | |
| 17 | 487.1 | 3 | |
| 18 | 447 | 0.92 | CD3OD: 8.73(d, 2H), 8.71(brs, 1H), 7.79(m, 2H) 7.58(m, 1H), 7.52(m, 1H), 7.28(m, 1H), 7.19(m, 1H), 5.10(brs, 2H), 4.85(m, 2H), 3.40-3.65(brm, 4H), 3.15(brm, 2H), 2.98(s, 3H), 2.41(brm, 1H), 0.67(m, 2H), 0.61(m, 2H) |
| 19 | 371 | 2.91 | DMSO-d6: 1.33-1.46(m, 6H), 1.70(m, 2H), 3.66(m, 4H), 3.77(m, 4H), 4.03(m, 1H) 7.17(m, 1H), 7.26(t, 1H), 7.46(m, 1H), 7.53(m, 1H), 7.90(d, 1H), 8.50(s, 1H) |
| 20 | 462.2 | 3.8 | DMSO-d6: 8.48(s, 1H), 7.52(m, 2H), 7.30(m, 2H), 7.07(m, 1H), 6.74(m, 2H), 6.48(m, 1H), 4.27(m, 2H), 3.90(m, 1H), 3.79(m, 2H), 3.71(s, 3H)), 1.50-165(m, 6H), 0.91(m, 6H). |
| 21 | 465.5 | 3.3 | CD3OD: 7.53(m, 2H), 7.41(m, 1H), 7.23(m, 3H), 7.03(m, 1H), 6.79(m, 1H), 4.83(m, 1H), 3.75(m, 4H), 3.67(s, 3H), 3.65(m, 4H), 2.49(s, 3H), 0.98(d, 6H, J=7Hz). |
| 22 | 511.2 | 4 | DMSO-d6: 8.53(s, 1H), 7.50(m, 2H), 7.07-7.30(m, 8H), 6.74(m, 2H), 3.91-4.15(m, 5H), 2.91(m, 2H), 0.91(m, 6H) |
| 23 | 434.5 | 2.2 | CD3OD: 8.44(s, 1H), 7.58(q, 1H, J=8Hz, 12Hz), 7.37(t, 1H, J=7Hz), 7.27(t, 1H, J=7Hz), 7.21(q, 2H, J=11Hz, 20Hz), 7.15(t, 2H, J=8Hz), 6.59(d, 2H, J=8Hz), 4.87(m, 1H), 3.52(br s, 4H), 3.09(br s, 4H), 2.92(s, 3H), 1.05(d, 6H, J=7Hz). |
| 24 | 491 | 3.9 | DMSO-d6: 8.51(s, 1H), 7.53(m, 1H), 7.55(m, 1H)<7.17-7.29(m, 3H), 6.89(m, 2H), 4.07(m, 2H), 3.60-3.96(9H), 1.25(s, 9H), 0.90(brm 6H) |
| 25 | 435.4 | 3.3 | CD3OD: 7.55(q, 1H, J=7Hz, 14Hz), 7.18-7.46(m, 6H), 7.13(t, 2H, J=7Hz), 4.87(m, 1H), 3.70(m, 4H), 3.64(m, 4H), 2.49(s, 3H), 0.96(d, 6H, J=6Hz). |
| 26 | 447 | 3.68 | DMSO-d6: 1.67(brm, 2H), 1.70-2.10(brm, 6H), 3.68(brm, 4H), 3.78(brm, 4H), 4.27(m, 1H), 4.62(brs, 2H), 6.99(brm, 2H), 7.17-7.31(m, 5H), 7.54(m, 2H), 8.41(s, 1H) |
| 27 | 477.4 | 4 | DMSO-d6: 8.39(s, 1H), 7.52(d, 1H, J=7Hz), 7.50(t, 1H, J=7Hz), 7.42(t, 1H, J=11Hz), 7.31(d, 1H, J=8Hz), 7.19(t, 1H, J=8Hz), 6.84(d, 1H, J=8Hz), 6.34(d, 1H, J=8Hz), 6.20(s, 1H), 4.57(m, 1H), 3.70(t, 4H, J=5Hz), 3.68(s, 3H), 1.92(m, 2H), 1.66(m, 2H), 1.59(m, 2H), 1.48(m, 5H), 1.39(m, 1H). |
| 28 | 463 | 1.82 | CD3OD: 8.41(s, 1H), 7.65(t, 1H), 7.56(m, 1H), 7.34(m., 4H), 7.25(t, 1H), 7.15(d, 2H), 4.44(s, 2H), 3.88(m, 4H), 3.73(m, 4H), 3.65(m, 2H), 3.07(m, 2H), 2.83(s, 6H) |
| 29 | 459.1 | 3.7 | CD3OD: 8.38(s, 1H), 7.51(m, 2H), 7.18-7.30(m, 5H), 7.04(m, 2H),, 4.15(s, 2H), 3.97(m, 1H), 3.79(m, 1H), 2.29(m, 2H), 1.80(m, 1H), 1.15-1.60(8H), 1.01(brm, 6H). |
| 30 | 490.2 | 3.6 | DMSO-d6: 8.44(s, 1H), 7.50(m, 2H), 6.90-7.15(m, 4H), 6.60(d, 1H), 4.53(m, 4H), 4.22(m, 4H), 3.15(m, 2H), 2.65(m, 4H), 1.80(, 1H), 0.48(m, 4H) |
| 31 | 505.2 | 4 | DMSO-d6: 7.23-7.55(m, 4H), 7.13(d, 2H), 6.76(d, 2H), 4.56(d, 1H), 4.16(d, 1H), 3.63-3.73(m, 8H), 2.34(s, 3H), 1.25(9H, m), 0.98(d, 3H), 0.53(d, 3H) |
| 32 | 503.5 | 4.3 | CD3OD: 7.17-7.52(m, 6H), 6.86(m, 2H), 6.81(d, 1H), 4.68(d, 1H), 4.23(d, 1H), 3.81-3.87(m, 5H), 2.39(s, 1H)1.71(m, 2H), 1.60(m, 4H), 1.29(9H), 1.03(d, 3H), 0.63(d, 3H) |
| 33 | 419.1 | 3.1 | DMSO-d6: 8.58(s, 1H), 8.45(d, 1H), 7.57(m, 1H), 7.49(m, 1H), 7.09-7.30(m, 6H), 5.30(m, 1H), 3.77(m, 4H), 3.66(m, 4H), 2.86(m, 1H), 2.78(m, 1H), 2.35(M, 1H), 1.76(m, 1H) |
| 34 | 503.5 | 4.2 | DMSO-d6: 8.3(s, 1H), 7.55(m, 1H), 7.05,(m, 1H), 6.77(d, 1H, J=8Hz), (m, 3H), 6.18(m, 1H), 6.13(br s, 1H), 4.76(m, 1H), 4.08(m, 3H), 3.63(s, 3H), 3.20(br d, 2H), 1.69(m, 1H), 1.5-1.63(m, 4H), 1.24-1.45(M, 6H), 0.96(br s, 6H). |
| 35 | 491.5 | 3.5 | DMSO-d6: 8.63(s, 1H), 7.54(m, 1H), 7.31(m, 1H), 7.26(m, 2H), 7.15(m, 1H), 6.82(d, 1H, J=7Hz), 6.34(d, 1H, J=8Hz), 6.25(s, 1H), 4.56(br s, 1H), 3.86(m, 4H), 3.79(m, 2H), 3.62(s, 3H), 3.32(t, 2H, J=11Hz), 1.67(m, 2H), 1.58(m, 2H), 1.46(m, 4H), 1.29(m, 2H). |
| 36 | 477.4 | 3.8 | DMSO-d6: 8.49(s, 1H), 7.49(d, 1H), 7.44(m, 1H), 7.31(m, 2H), 6.84(m, 2H), 6.76(m, 2H), 4.35(brs, 2H), 3.78(m, 4H), 3.72(s, 3H), 1.95(m, 1H), 1.63(m, 2H), 1.53(m, 4H), 0.49(m, 4H) |
| 37 | 476.2 | 2.2 | DMSO-d6 8.78(s, 1H), 8.72(d, 1H), 7.31-7.49(m, 8H), 7.19(t, 1H), 7.02(t, 1H), 5.33(m, 1H), 3.79(t, 4H), 3.65(t, 4H), 3.52(m, 2H), 3.21(m, 1H), 3.13(m, 1H), 2.02(m, 1H), 1.88(m, 1H) |
| 38 | 553.2 | 4.2 | DMSO-d6: 8.44(s, 1H), 7.51(m, 2H), 7.07-7.30(m, 8H),, 6.73(m, 2H), 6.48(m, 1H), 4.07-4.70(m, 7H), 3.71(s, 3H), 2.87(m, 2H), 1.64-1.82(m, 3H), 1.16(m, 2H), 0.91(m, 6H) |
| 39 | 464 | 2.3 | DMSO-d6 8.64(s, 1H), 7.48(m, 2H), 7.23(m, 2H), 7.09(m, 4H), 6.99(m, 2H), 4.67(d, 2H), 4.50(brm, 2H), 3.50(m, 2H), |

TABLE 8-continued

Physical data for exemplary compounds.

| Compound No. | LC/MS M + 1 | LC/RT min | NMR |
|---|---|---|---|
| | | | 3.31(m, 2H), 3.10(m, 2H), 2.84(s, 3H), 2.00(m, 1H), 0.48(brm, 4H). |
| 40 | 483 | 3.87 | CD3OD: 8.45(s, 1H), 8.17(brs, 1H), 7.90(m, 1H), 7.82(m, 1H), 7.52(m, 2H), 7.37(m, m, 3H), 7.10(brs, 1H), 6.80(m, 2H), 5.09(brs, 2H), 3.85(m, 4H), 3.73(m, 4H), 1.80(brs, 1H), 0.60(brm, 4H) |
| 41 | 475.5 | 4.3 | DMSO-d6: 8.34(s, 1H), 7.45(m, 1H), 7.25(d, 3H, J=5Hz), 7.18(d, 1H, J=6Hz), 7.06(br s, 1H), 6.71(s, 1H), 6.37(br s, 1H), 4.75(br s, 1H), 3.66(br s, 4H), 1.59(br s, 2H), 1.43(br s, 4H), 1.12(s, 9H), 0.98(br s, 6H). |
| 42 | 475.5 | 3.9 | DMSO-d6: 8.34(s, 1H), 7.54(m, 1H), 7.34(m, 1H), 7.27(m, 2H), 7.12(t, 1H, J=8Hz), 6.79(d, 1H, J=6Hz), 6.34(d, 1H, J=7Hz), 6.24(s, 1H), 4.61(m, 1H), 3.69(m, 6H), 3.64(s, 3H), 1.17,(br s, 2H), 1.59(m, 2H), 1.44(d, 6H, J=18Hz), 1.29(m, 2H). |
| 43 | 465.4 | 3.8 | DMSO-d6: 8.33(s, 1H), 7.55(m, 1H), 7.49(t, 1H, J=7Hz), 7.43(t, 1H, J=7Hz), 7.35(d, 1H, J=7Hz), 6.76(m, 2H), 6.62(d, 2H, J=8Hz), 4.72(m, 1H), 3.71(s, 3H), 3.66(br s, 4H), 1.59(br s, 2H), 1.45(br s, 4H), 0.86(d, 6H, J=6Hz). |
| 44 | 477.2 | 3.4 | DMSO-d6: 8.48(s, 1H), 7.57(m, 2H), 7.34(m, 2H), 7.15(m, 1H), 6.91(m, 3H), 4.45(brs, 2H), 3.78(m, 4H), 3.75(s, 1H), 3.67(m, 4H), 3.60(brm, 2H), 3.00(brm, 2H), 1.30-1.80(m, 4H) |
| 45 | 434.2 | 2.8 | CD3OD: 8.43(s, 1H), 7.53(m, 2H), 7.03-7.30(m, 7H), 7.05(m, 2H), 4.50(m, 2H), 4.15(d, 2H), 3.97(m, 1H), 3.70(m, 3H), 2.05(m, 2H), 1.01(brm, 6H). |
| 46 | 495.1 | 3.5 | NMR 1H(DMSO-d6): 8.4(s, 1H), 8.3(s, 1H), 7.7(m, 2H), 7.4(m, 2H), 7.0-7.3(m, 10H), 3.8(s, 4H), 3.7(s, 4H), 3.1(m, 2H), 2.5(m, 2H), 1.7(m, 2H). |
| 47 | 491 | 3.9 | DMSO-d6: 8.51(s, 1H), 7.10-7.60(m, 7H), 6.95(d, 2H), 3.95-4.25(6H), 3.35(m, 1H), 2.65(m, 4H), 0.90-1.60(m, 10H) |
| 48 | 467 | 3.6 | DMSO-d6: 8.56(s, 1H), 7.47(t, 2H), 7.19(m, 2H), 7.06-7.12(d, 4H), 4.48(brs, 2H), 4.12(m, 4H), 2.63(m, 4H), 2.02(brm, 1H), 0.49(brm, 4H). |
| 49 | 492.3 | 3.6 | DMSO-d6: 6.75-7.50(m, 9H), 4.47(d, 1H), 4.33(d, 1H), 3.63-3.69(m, 8H), 3.45(m, 1H), 3.02(s, 3H), 2.37(s, 3H), 1.05(m, 2H), 0.50(t, 3H) |
| 50 | 502.5 | 3.1 | DMSO-d6: 8.46(s, 1H), 7.53(brm, 2H), 7.28(brm, 2H)_, 6.84(brm, 2H), 6.38(brm, 2H), 4.14(brm, 9H), 3.18(brm, 4H), 1.93(brm, 4H), 1.64(brm, 2H), 1.53(m, 4H), 0.88(brm, 6H) |
| 51 | 484.2 | 3.4 | |
| 52 | 433.1 | 3.5 | CDCl3: 8.27(brs, 1H), 7.29(q, 1H), 7.11(brs, 1H), 7.01(t, 1H), 6.92(m, 3H), 6.82(d, 2H), 6.64(brs, 1H), 4.71(brm, 2H), 3.70-3.90(m, 8H), 2.33(m, 1H), 2.11(m, 1H), 1.27(m, 1H), 1.07(d, 3H) |
| 53 | 475 | 3.4 | CD3OD: 88.45(s, 1H), 7.46(m, 1H), 7.39(m, 1H), 7.10(m, 1H), 7.00(m, 2H), 6.89(m, 1H), 6.60(d, 1H), 4.53(m, 4H), 3.87(t, 4H)<3.74(t, 4H), 3.15(t, 2H), 1.84(brm, 1H), 0.47-0.55(brm, 4H) |
| 54 | 498.5 | 4 | DMSO-d6: 8.42(s, 1H), 7.66(m, 1H), 7.60(m, 1H), 7.35(m, 1H), 7.29(m, 2H), 7.23(m, 1H), 6.93(m, 1H), 6.83(br s, 1H), 4.74(br s, 1H), 4.24(m, 2H), 1.85(m, 1H), 1.54-1.69(m, 5H), 1.45(m, 1H), 1.33(m, 4H), 1.24(m, 3H), 0.95(dd, 6H, J=6Hz, 20Hz). |
| 55 | 479.4 | 3.9 | DMSO-d6: 8.47(m, 1H), 7.35-7.56(m, 4H), 7.00(m, 1H), 6.64-6.75(m, 2H), 6.25(m, 1H), 3.77(m, 7H), 3.69(s, 3H), 1.63(m, 2H), 1.64(m, 2H), 1.53(m, 4H), 0.84(brm, 6H) |
| 56 | 463 | 3.3 | DMSO-d6: 8.58(s, 1H), 7.46(m, 2H), 7.17(m, 3H), 6.79(dd, 1H), 6.75(m, 1H), 6.63(t, 1H), 4.48(brs, 2H), 3.78(m, 4H), 3.72(s, 3H), 3.67(m, 4H), 2.15(brm, 1H), 0.50(m, 4H) |
| 57 | 502.2 | 3.3 | DMSO-d6: 8.44(s, 1H), 7.55(t, 1H), 7.45(m, 1H), 7.37(t, 2H), 7.21-7.29(m, 5H), 3.78(t, 4H), 3.67(t, 4H), 3.00-3.35(brm, 8H), 2.19(m, 2H), 0.73(t, 3H) |
| 58 | 463.4 | 3.8 | DMSO-d6: 8.48(s, 1H), 7.95(d, 1H, J=8Hz), 7.67(m, 1H), 7.49(m, 1H), 7.36(m, 2H), 7.17(m, 1H), 6.58(m, 1H), 6.28(m, 1H), 3.66(s, 3H), 3.57(br s, 4H), 2.74(m, 1H), 1.60(m, 2H), 1.49(m, 4H), 0.85(m, 1H), 0.65(m, 1H), 0.51(m, 1H), 0.36(m, 1H). |
| 59 | 507.1 | 4.2 | DMSO-d6: 8.50(s, 1H), 7.53(m, 1H), 7.45(m, 1H), 7.18-7.26(m, 3H), 6.90(m, 2H), 4.10(m, 6H), 3.85(m, 1H), 2.63(m, 4H), 1.25(s, 9H), 0.91(brm, 6H) |
| 60 | 510 | 2.1 | CD3OD: 8.67(d, 2H), 8.52(s, 1H), 8.36(d, 2H), 7.90(m, 2H), 7.57(t, 1H), 7.46(m, 1H), 7.25(m, 1H), 7.10(m, 1H), 6.80(m, 1H), 4.73(m, 1H), 3.88(m, 4H), 3.74(m, 4H), 2.02(m, 1H), 0.62(m, 4H) |
| 61 | 535.2 | 3.7 | DMSO-d6: 8.41(s, 1H), 7.06-8.21(m, 11H), 6.73(m, 2H), 6.40(m, 1H), 5.01(m, 2H), 4.35(m, 2H), 3.95(m, 3H), 3.70(s, 3H), 0.91(m, 6H) |

TABLE 8-continued

Physical data for exemplary compounds.

| Compound No. | LC/MS M + 1 | LC/RT min | NMR |
|---|---|---|---|
| 62 | 467.4 | 3.6 | DMF-d7: 8.42(s, 1H), 7.55(m, 1H), 7.35(br s, 1H), 7.28(m, 2H), 7.10(m, 1H), 6.79(d, 1H, J=9Hz), 6.29(br s, 1H), 6.19(br s, 1H), 4.78(br s, 1H), 4.00(br s, 4H), 3.64(s, 3H), 2.54(br s, 4H), 0.96(br s, 6H). |
| 63 | 454.2 | 3.6 | |
| 64 | 475 | 3.88 | DMSO-d6: 0.9-1.65(brm, 10H), 1.51(brm, 4H), 3.28(m, 1H), 3.68(brm, 4H), 3.77(brm, 4H), 4.03(brm, 1H), 6.93(brd, 2H), 7.15(brm, 3H), 7.29(m, 2H), 7.45(m, 1H), 7.55(m, 1H), 8.52(s, 1H) |
| 65 | 515.5 | 4.4 | DMSO-d6: 8.28(s, 1H), 7.52(m, 1H), 7.36,(m, 1H), 7.26(m, 2H), 7.17(t, 1H, J=8Hz), 6.77(d, 1H, J=8Hz), 6.80(d, 1H, J=8Hz), 6.32(d, 1H, J=7Hz), 6.26(s, 1H), 4.66(m, 1H), 4.08(m, 3H), 3.66(s, 3H), 3.23(m, 2H), 1.86(m, 2H), 1.72(m, 1H), 1.69(m, 4H), 1.43(m, 4H), 1.34(m, 6H). |
| 66 | 435.5 | 3.2 | DMSO-d6: 9.44(s, 1H), 8.28(s, 1H), 7.54(m, 1H), 7.37(m, 1H), 7.26(m, 2H), 6.98(t, 1H, J=7Hz), 6.61(d, 1H, J=8Hz), 6.16(m, 2H), 4.70(br s, 1H), 3.69(br s, 4H), 1.58(m, 2H), 1.47(m, 4H), 0.95(d, 6H, J=6Hz). |
| 67 | 479.4 | 3.1 | DMSO-d6: 8.39(s, 1H), 7.54(m, 1H), 7.37(m, 1H), 7.27(m, 2H), 6.65(d, 1H, J=8Hz), 6.25(d, 1H, J=8Hz), 6.02(s, 1H), 4.73(m, 1H), 4.19(s, 4H), 3.66(br s, 4H), 3.61(br s, 4H), 0.92(d, 6H, J=6Hz). |
| 68 | 545.6 | 4.1 | DMSO-d6: 8.30(s, 1H), 7.55(m, 1H), 7.30(m, 1H), 7.26(m, 2H), 7.15(m, 1H), 7.10(m, 1H), 6.80(d, 1H, J=8Hz), 6.23(s, 1H), 4.70(br s, 1H), 4.13(m, 2H), 3.80(m, 2H), 3.65(m, 3H), 3.30(m, 2H), 1.85(m, 1H), 1.69(m, 2H), 1.50-1.63(m, 4H), 1.22-1.44(m, 11H). |
| 69 | 462.2 | 3.6 | |
| 70 | 463.4 | 3.6 | DMSO-d6: 8.34(s, 1H), 7.54(m, 1H), 7.36(br s, 1H), 7.28(m, 2H), 6.71(d, 1H, J=6Hz), 6.18(m, 2H), 6.00(s, 2H), 4.73(m, 1H), 3.69(br s, 4H), 1.60(br s, 2H), 1.47(br s, 4H), 0.93(d, 6H, J=6Hz). |
| 71 | 463.1 | 3.4 | DMSO-d6: 8.46(2xs, 1H), 7.01-7.67(m, 8H), 5.74 &6.02(2xs, 1H), 4.16(brs, 1H), 3.86-3.90(m, 7H), 3.75(m, 4H), 3.44(m, 1H), 2.44(m, 1H), |
| 72 | 436.2 | 2.6 | |
| 73 | 484 | 2.94 | |
| 74 | 465 | 3.48 | CDCl3: 8.37&8.18(2xs, 1H), 7.00-7.60(m, 4H), 6.51-6.72(m, 3H), 4.36(brs, 2H), 3.66-4.02(m, 9H), 3.69(s, 3H), 0.88(brm, 6H) |
| 75 | 446 | 3.17 | CD3OD: 8.37(s, 1H), 7.00-7.70(m, 9H),, 4.46(brs, 2H), 3.86(m, 4H), 3.73(m, 4H), 3.58(m, 2H), 2.56(t, 2H). |
| 76 | 471.4 | 3.5 | DMSO-d6: 8.35(s, 1H), 7.87(d, 1H, J=8Hz), 7.81(d, 1H, J=8Hz), 7.76(d, 1H, J=8Hz), 7.61(m, 1H), 7.55(t, 1H, J=8Hz), 7.49(t, 1H, J=8Hz), 7.35(m, 3H), 7.23(t, 1H, J=8Hz), 6.24(d, 1H, J=7Hz), 4.82(m, 1H), 3.49(s, 4H), 3.34(s, 4H), 1.13(d, 3H, J=6Hz), 0.77(d, 3H, J=6Hz). |
| 77 | 473.5 | 3.6 | DMSO-d6: 8.48(m, 1H), 7.45(m, 2H), 7.30(m, 2H), 6.89(s, 1H), 6.79(m, 1H), 6.61(d, 1H), 4.51(t, 2H), 4.40(brs, 2H), 3.80(t, 2H), 3.12(t, 2H), 1.95(brm, 1H), 1.63(m, 2H), 1.54(m, 4H), 0.47(brm, 4H) |
| 78 | 480.2 | 4 | CD3OD: 8.48(s, 1H), 7.53(m, 2H), 7.00-7.45(m, 1H), 4.96(brs, 4H), 4.10(s, 2H), 3.97(m, 1H), 2.94(m, 2H), 1.02(brm, 6H) |
| 79 | 343 | 2.4 | DMSO-d6: 0.34(m, 2H), 0.59(m, 2H), 2.61(m, 1H), 3.65(m, 4H), 3.78(m, 4H), 7.19(m, 1H), 7.29(t, 1H), 7.48(m, 1H), 7.53(m, 1H), 8.11(d, 1H), 8.49(s, 1H) |
| 80 | 463 | 3.8 | DMSO-d6: 8.40(s, 1H), 7.55(m, 2H), 7.15-7.31(m, 5H), 7.00(m, 2H), 4.63(brS, 2H), 4.27(m, 1H), 4.13(m, 4H), 2.66(m, 4H), 1.33-2.15(brm, 6H) |
| 81 | 495 | 4.06 | CD3OD: 8.50(s, 1H), 7.50(m, 2H), 7.05-7.25(m, 9H), 4.10-4.25(m, 8H), 4.60(m, 1H), 3.17(s, 3H), 2.60-2.67(m, 4H), 1.30-1.60(m, 2H), 0.64(m, 3H) |
| 82 | 435.4 | 3.9 | DMSO-d6: 8.37(s, 1H), 7.53(m, 2H), 7.43(t, 1H, J=7Hz), 7.33(d, 1H, J=7Hz), 7.24(s, 3H), 6.70(br s, 2H), 4.65(br s, 1H), 3.67(br s, 4H), 1.58(br s, 2H), 1.45(br s, 4H), 0.88(d, 6H, J=6Hz). |
| 83 | 450.2 | 3.6 | CD3OD: 8.41(s, 1H), 7.57(m, 2H), 7.22(m, 5H), 7.05(m, 2H), 4.09(m, 2H), 3.55-4.15(m, 7H), 3.57(s, 3H), 1.20(t, 2H), 1.01(brm, 6H). |
| 84 | 435.4 | 3.2 | DMSO-d6: 8.60(br s, 1H), 7.45(m, 2H), 7.18(m, 2H), 6.94(m, 2H), 6.69(m, 2H), 4.61(br s, 1H), 4.05(m, 2H), 3.67-3.92(br m, 8H), 1.00(br s, 3H). |
| 85 | 517 | 3.8 | DMSO-d6: 8.60(s, 1H), 7.62(d, 2H), 7.46(m, 2H), 7.30(d, 2H), 7.20(m, 2H), 4.59(brs, 2H), 4.12(m, 4H), 2.64(m, 4H), 2.15(brm, 1H), 0.51(brm, 4H). |

TABLE 8-continued

Physical data for exemplary compounds.

| Compound No. | LC/MS M + 1 | LC/RT min | NMR |
|---|---|---|---|
| 86 | 491.5 | 3.6 | DMSO-d6: 8.40(s, 1H), 7.55(m, 1H), 7.37(br s, 1H), 7.30(d, 2H, J=6Hz), 7.11(m, 1H), 6.79(d, 1H, J=7Hz), 6.32(m, 1H), 6.21(br s, 1H), 4.37(m, 1H), 3.65(s, 3H), 3.58(br d, 8H, J=16Hz), 1.67(m, 4H), 1.49(d, 1H, J=11Hz), 1.24(m, 2H), 0.97(m, 2H), 0.86(m, 1H). |
| 87 | 464.5 | 2.2 | CD3OD: 8.47(s, 1H), 7.55(m, 1H), 7.39(m, 1H), 7.27(m, 1H), 7.21(m, 1H), 7.05(m, 1H), 6.77(m, 1H), 6.22(m, 1H), 6.10(m, 1H), 4.85(m, 1H), 3.66(s, 3H), 3.50(br s, 4H), 3.09(br s, 4H), 2.92(s, 3H), 1.06(d, 6H, J=7Hz). |
| 88 | 421 | 3.52 | CD3OD: 8.34(s, 1H), 7.54(m, 1H), 7.10-7.40(m, 6H), 6.60(m, 2H), 4.90(brm, 1H), 3.74(m, 4H), 3.67(m, 4H), 1.06(brm, 4H) |
| 89 | 477.2 | 3.1 | |
| 90 | 431.5 | 3.7 | CD3OD:: 8.43(s, 1H), 7.49(m, 1H), 7.39(m, 1H), 7.00-7.30(m, 7H), 4.59(m, 2H), 3.88(m, 4H), 1.91(m, 1H), 1.72(m, 2H), 1.63(m, 4H), 0.52(m, 4H) |
| 91 | 445.2 | 3.3 | DMSO-d6: 8.50(s, 1H), 7.20-7.70(m, 9H), 5.90&6.15(2xs, 1H), 4.07(brs, 1H), 3.68-3.80(m, 11H), 2.35(m, 2H) |
| 92 | 487.5 | 4.4 | CD3OD: 8.38(s, 1H), 7.05-7.70(brm, 9H), 4.4(m, 4H), 3.97(m, 1H), 3.40(m, 2H), 1.35-1.95(m, 12H), 1.02(m, 6H) |
| 93 | 419.4 | 3.7 | DMSO-d6: 8.91(s, 1H), 8.39(d, 1H, J=2Hz), 7.71(m, 1H), 7.55(m, 2H), 7.42(m, 1H), 7.33(m, 3H), 7.21(br s, 1H), 4.06(m, 1H), 3.89(m, 2H), 3.67(m, 2H), 1.59(m, 4H), 1.45(m, 2H), 0.94(br s, 6H). |
| 94 | 477.5 | 3.7 | DMSO-d6: 8.44(s, 1H), 7.51(m, 1H), 7.26(m, 2H), 6.69(m, 1H), 6.61(s, 1H), 6.50(m, 1H), 5.96(s, 2H), 4.59(m, 2H), 3.79-4.00(m, 7H), 1.63(m, 2H), 1.54(m, 4H), 0.90(m, 6H) |
| 95 | 527.5 | 4.2 | CD3OD: 8.39(s, 1H), 7.46(m2H), 6.85-7.25(m, 4H), 6.60(d, 1H), 4.53(t, 2H), 4.47(m, 4H), 3.40(m, 2H), 3.15(t, 2H), 1.97(m, 1H), 1.30-1.85(m12H), 0.50(m, 4H) |
| 96 | 445.2 | 3.4 | CD3OD: 8.48(s, 1H), 7.51(m, 2H), 6.99-7.35(m, 7H), 4.50(m, 1H), 4.06(s, 2H), 3.60-3.95(m, 6H), 2.85(t, 2H), 1.25(t, 3H), 1.02(brm, 6H) |
| 97 | 419.1 | 3.1 | DMSO-d6: 8.54(s, 1H), 8.39(d, 1H), 7.55(m, 1H) 7.50(m, 1H), 7.06-7.30(m, 7H), 3.78(t, 4H), 3.66(m, 4H), 2.80(m, 1H), 1.88(m, 1H), 1.13(m, 2H), |
| 98 | 451 | 3.7 | DMSO-d6: 8.52(s, 1H), 6.95-7.65(m, 9H), 4.00-4.25(m, 6H), 3.90(m, 1H), 2.5(m, 4H), 0.91(brS, 6H) |
| 99 | 484 | 2.64 | CD3OD: 9.11(s, 1H), 8.87(m, 2H), 8.56(s, 1H), 8.25(m, 2H), 8.16(m, 1H), 7.98(m, 1H), 7.47(m, 1H), 7.20(m, 1H), 6.98(m, 1H), 6.65(m, 1H), 4.90(brs, 2H), 3.88(t, 4H), 3.74(t, 4H), 2.22(brm, 1H), 0.72(m, 2H), 0.64(m, 2H) |
| 100 | 433 | 3.41 | DMSO-d6: 0.48(brs, 4H), 2.08(brs, 1H), 3.67(m, 1H), 3.77(m, 4H), 4.51(brs, 2H), 7.06(d, 2H), 7.21-7.26(m, 5H), 7.48(m, 2H), 8.58(s, 1H) |
| 101 | 460.5 | 3.7 | DMSO-d6: 8.50(s, 1H), 7.70(d, 1H, J=8Hz), 7.54(d, 2H, J=4Hz), 7.45(m, 2H), 7.29(d, 1H, J=8Hz), 7.04(d, 1H, J=8Hz), 6.79(br s, 1H), 4.63(br s, 1H), 3.70(br s, 4H), 1.59(m, 2H), 1.46(m, 4H), 0.90(d, 6H, J=6Hz). |
| 102 | 454.2 | 2.17 | |
| 103 | 481.2 | 3.6 | CD3OD: 8.45(s, 1H), 7.50(m, 2H), 7.25(m, 3H), 7.09(m, 1H), 6.73(m, 2H), 6.50(m, 1H), 3.50-4.10(m, 9H), 3.75(s, 3H), 3.25(brm, 3H), 1.23(brm, 3H), 0.91(brm, 6H) |
| 104 | 463.5 | 3.7 | DMF-d7: 7.57(m, 1H), 7.35(m, 1H), 7.26(m, 2H), 7.05(t, 1H, J=8Hz), 6.79(m, 1H), 6.00(br s, 1H), 5.75(br s, 1H), 4.75(m, 1H), 3.83(br s, 2H), 3.62(s, 3H), 3.61(br s, 2H), 2.40(s, 3H), 1.56(m, 2H), 1.42(m, 4H), 0.87(dd, 6H, J=7Hz, 12Hz). |
| 105 | 473.5 | 4.3 | CDCl3: 8.27(s, 1H), 7.46(m, 2H), 7.17(m, 5H), 6.65(br s, 2H), 4.92(m, 1H), 4.28(br d, 1H, J=8Hz), 4.20(br d, 1H, J=8Hz), 3.31(m, 2H), 1.98(s, 1H), 1.87(m, 1H), 1.74(m, 2H), 1.56(m, 2H), 1.49(m, 1H), 1.28(m, 4H), 1.36(m, 4H), 1.04(br s, 6H). |
| 106 | 480.2 | 2.6 | |
| 107 | 419 | 3.3 | DMSO-d6: 8.50(s, 1H), 6.95-7.60(m, 8H), 4.57(brs, 1H), 4.42(brs, 1H), 3.80(m, 4H), 3.68(m, 5H), 3.42(brm, 1H), 2.50-2.71(brm, 2H) |
| 108 | 449.4 | 3.7 | DMSO-d6: 8.28(s, 1H), 7.55(m, 1H), 7.37(m, 1H), 7.30(m, 2H), 6.74(d, 2H, J=8Hz), 6.63(d, 2H, J=8Hz), 4.76(m, 1H), 3.70(s, 3H), 3.67(br s, 4H), 1.59(m, 2H), 1.46(m, 4H), 0.91(d, 6H, J=6Hz). |
| 109 | 449 | 3.6 | DMSO-d6: 8.56(s, 1H), 7.48(t, 2H), 7.21-7.26(m, 5H), 7.06(d, 2H), 4.50(brS, 2H), 4.12(m, 4H), 2.64(m, 4H), 2.00(m, 1H), 0.48(m, 4H) |

TABLE 8-continued

Physical data for exemplary compounds.

| Compound No. | LC/MS M + 1 | LC/RT min | NMR |
|---|---|---|---|
| 110 | 451 | 3.3 | DMSO-d6: 8.61(s, 1H), 7.47(m, 2H), 7.29(m, 1H), 7.20(m, 2H), 7.06(m, 1H), 6.91(t, 2H), 4.51(brs, 2H), 3.78(m, 4H), 3.67(m, 4H), 2.15(brm, 1H), 0.51(m, 4H) |
| 111 | 464.5 | 2.5 | DMSO-d6: 8.40(s, 1H), 7.54(m, 1H), 7.38(m, 1H), 7.26(m, 2H), 6.98(m, 1H), 6.55(d, 1H, J=7Hz), 6.04(s, 2H), 4.73(br s, 1H), 3.64(br s, 4H), 3.60(br s, 4H), 2.78(s, 6H), 0.97(d, 6H, J=6Hz). |
| 112 | 469.5 | 3.9 | DMSO-d6: 8.27(s, 1H), 7.86(d, 1H, J=8Hz), 7.80(d, 1H, J=8Hz), 7.74(d, 1H, J=8Hz), 7.62(m, 1H), 7.54(t, 1H, J=7Hz), 7.48(t, 1H, J=7Hz), 7.33(m, 3H), 7.21(t, 1H, J=7Hz), 6.24(d, 1H, J=8Hz), 4.80(m, 1H), 3.46(br s, 4H), 1.50(m, 2H), 1.32(br s, 4H), 1.13(d, 3H, J=6Hz), 0.77(d, 3H, J=6Hz). |
| 113 | 479 | 3.63 | CD3OD: 0.64(t, 3H), 1.55(m, 2H), 3.15(s, 3H), 3.07-3.80(m, 7H), 3.87(m, 4H), 4.20(m, 2H), 7.06-7.53(m, 9H), 8.48(s, 1H) |
| 114 | 562.5 | 2.9 | CD3OD: 8.86(d, 2H), 8.44(s, 1H), 8.37(d, 2H), 7.89(m, 2H), 7.57(t, 1H), 7.55(m, 2H), 7.30(m, 1H), 7.15(m, 1H), 6.80(m, 1H), 4.70(m, 2H),, 4.40(m, 4H), 3.40(m, 2H), 3.15(t, 2H), 1.95(m, 1H), 1.30-1.85(m12H), 0.63(m, 2H), 0.56(m, 2H) |
| 115 | 505.5 | 4.2 | DMSO-d6: 8.41(s, 1H), 7.52(m, 2H), 7.44(t, 1H, J=7Hz), 7.34(d, 1H, J=7Hz), 7.13(m, 1H), 6.81(d, 1H, J=7Hz), 6.31(d, 1H, J=7Hz), 6.15(s, 1H), 4.38(br s, 1H), 3.67(s, 3H), 3.34(br s, 4H), 1.55-1.63(m, 5H), 1.45(br s, 5H), 1.22(m, 3H), 0.84-0.93(m, 3H). |
| 116 | 461.4 | 3.8 | DMSO-d6: 8.31(s, 1H), 7.52(m, 1H), 7.39(t, 1H, J=7Hz), 7.27(m, 2H), 7.17,(t, 1H, J=6Hz), 6.82(d, 1H, J=8Hz), 6.36(d, 1H, J=8Hz), 6.28(s, 1H), 4.66(m, 1H), 3.71(t, 4H, J=6Hz), 3.67(s, 3H), 1.98(m, 2H), 1.68(m, 2H), 1.59(m, 2H), 1.49(m, 6H). |
| 117 | 433.5 | 3.8 | DMSO-d6: 8.46(s, 1H), 7.55(m, 1H), 7.54(m, 1H), 7.15-7.30(m, 5H), 6.95(m, 2H), 3.70-4.10(m, 7H), 1.64(brm, 2H), 1.54(brm, 6H), 0.9(brm, 6H) |
| 118 | 487 | 3.91 | CD3OD: 8.37(s, 1H), 7.47-7.53(m, 3H), 7.18-7.27(m, 6H), 7.04(m, 2H), 6.96(m, 2H), 4.12(s, 2H), 3.95(m, 1H), 3.68(m, 2H), 2.92(m, 2H), 1.02(m, 6H). |
| 119 | 505.5 | 4.5 | CD3OD:: 8.48(s, 1H), 7.57(d, 1H), 7.50(t, 1H), 7.49(m, 1H), 7.39(m, 1H), 7.00-7.30(m, 7H), 7.35(m, 2H), 7.11(m, 2H), 6.72(m, 2H), 3.95(m, 1H), 3.78(m, 6H), 1.91(m, 1H), 1.63(m, 2H), 1.53(m, 4H), 1.24(s, 9H), 0.83(m, 4H) |
| 120 | 531.5 | 4.2 | CD3OD: 8.36(s, 1H), 7.49(m, 2H), 7.24(m, 1H), 7.15(m, 1H), 6.56-6.70(m, 3H), 5.90(s, 2H), 4.4(m, 4H), 3.95(m, 1H), 3.40(m, 2H), 1.35-1.95(m, 12H), 1.02(m, 6H) |
| 121 | 497.1 | 3.4 | NMR 1H(DMSO-d6): 8.6(s, 1H), 8.4(s, 1H), 7.7(m, 2H), 7.4(m, 2H), 7.2(m, 3H), 7.0(m, 2H), 6.9(m, 5H), 4.0(t, 2H), 3.8(m, 4H), 3.7(m, 4H), 3.5(m, 2H). |
| 122 | 489.5 | 4.3 | DMSO-d6: 8.45(m, 1H), 7.60(m, 1H), 7.54(m, 1H), 7.54(m, 1H), 7.17-7.30(m, 4H), 6.90(m, 2H), 3.70-4.10(m, 7H), 1.63(brm, 2H), 1.54(brm, 6H), 0.91(brm, 6H) |
| 123 | 509 | 4.08 | NMR 1H(CDCl3): "Show rotameres" 8.3(s, 1H), 7.8(d, 2H), 6.9-7.4(m, 12H), 4.7(m, 2H), 4.4(m, 1H), 3.7-4.0(m, 8H), 1.0-1.1(2xs, 4H), 0.6(s, 2H). |
| 124 | 501 | 3.5 | DMSO-d6: 8.62(s, 1H), 7.62(m, 2H), 7.46(brm, 2H), 7.30(d, 2H), 7.20(m, 2H), 4.59(brs, 2H), 3.78(m, 4H),, 3.67(m, 4H), 2.06(brm, 1H), 0.52(brm, 4H) |
| 125 | 444.5 | 3.6 | DMSO-d6: 8.45(s, 1H), 7.67(d, 1H, J=7Hz), 7.58(m, 1H), 7.38(m, 1H), 7.29(m, 3H), 7.01(m, 1H), 6.82(br s, 1H), 4.70(br s, 1H), 3.70(br s, 4H), 1.60(m, 2H), 1.46(m, 4H), 0.95(d, 6H, J=6Hz). |
| 126 | 514 | 2.5 | DMSO-d6 8.69(s, 1H), 7.62(d, 2H), 7.48(m, 2H), 7.29(d, 2H), 7.23(m, 2H), 4.77(d, 2H), 4.60(brm, 2H), 3.53(m, 2H), 3.32(m, 2H), 3.30(m, 2H), 2.84(s, 3H), 2.10(m, 1H), 0.51(brm, 4H). |
| 127 | 489.5 | 4 | DMSO-d6: 8.34(s, 1H), 7.54(m, 1H), 7.36(br s, 1H), 7.28(m, 2H), 7.10(m, 1H), 6.79(d, 1H, J=8Hz), 6.31(m, 1H), 6.20(s, 1H), 4.31(br s, 1H), 3.68(br s, 4H), 3.65(s, 3H), 1.66(m, 2H), 1.59(m, 2H), 1.46(m, 6H), 1.24(m, 2H), 0.97(m, 2H), 0.85(m, 2H). |
| 128 | 451 | 3.3 | DMSO-d6: 8.57(s, 1H), 7.47(m, 2H), DMSO-d6: 7.21(m, 2H), 7.11(m, 4H), 4.48(brs, 2H), 3.77(m, 4H),, 3.67(m, 4H), 2.05(brm, 1H), 0.49(brm, 4H) |
| 129 | 446 | 2.2 | DMSO-d6 0.5(brm, 4H), 0.85(brm, 1H), 2.95(s, 3H), 3.15-3.65(brm, 6H), 4.60(brm, 2H), 5.02(brs, 2H), 6.95-7.45(m, 9H), 8.56(s, 1H) |

TABLE 8-continued

Physical data for exemplary compounds.

| Compound No. | LC/MS M + 1 | LC/RT min | NMR |
|---|---|---|---|
| 130 | 467 | 3.8 | CD3OD: 8.51(s, 1H), 7.58(m, 2H), 7.06-7.40(m, 9H), 7.06(m, 2H), 4.96(brs, 4H), 4.15(s, 2H), 4.00(m, 1H), 1.03(brm, 6H) |
| 131 | 481 | 3.94 | CD3OD: 8.45 & 8.00(2xs, 1H), 7.11-7.65(m, 5H), 6.52-6.80(m, 3H), 3.95-4.25(m, 7H), 3.75(s, 3H), 2.65(m, 4H), 1.02(brm, 6H). |
| 132 | 457 | 3.22 | |
| 133 | 449 | 3.94 | CDCl3: 8.26(s, 1H), 7.41(m, 2H), 7.17(t, 1H, J=8Hz), 7.07(m, 2H), 6.70(d, 1H, J=7Hz), 6.29(br s, 1H), 6.14(br s, 1H), 5.90(br m, 1H), 3.73(br S, 4H), 3.66(s, 3H), 1.62(br s, 2H), 0.85(d, 6H, J=7Hz). |
| 134 | 497.1 | 3.8 | DMSO-d6: 8.56(s, 1H), 7.20-7.60(8H), 7.08(m, 1H), 6.73(m, 2H), 6.50(m, 1H), 4.92(brm, 2H), 4.87(brm, 2H), 4.11(brs, 2H), 3.92m, 1H), (s, 3H), 0.92(brm, 6H) |
| 135 | 505.1 | 3.7 | CD3OD: 8.45(s, 1H), 8.15(d, 1H), 7.87(d, 1H), 7.79(d, 1H), 7.49(m, 5H), 7.43(t, 1H), 7.18(m, 5H), 7.03(m, 2H), 5.12(s, 2H), 4.10(s, 2H), 3.97(m, 1H), 1.02(brm, 6H). |
| 136 | 459.5 | 4 | DMSO-d6: 8.43(s, 1H), 7.57(m, 1H), 7.47(m, 1H), 7.30(t, 2H), 7.17(m, 2H), 6.93(m, 2H), 3.70-4.10(m, 7H), 1.35-1.64(brm, 14H) |
| 137 | 556.5 | 3.7 | CD3OD: 8.37(s, 1H), 6.70-7.60(m, 9H), 4.40(m, 4H), 4.00(m, 1H), 3.59(m, 4H), 3.37(m, 4H), 2.20(m, 4H), 3.40(m, 2H), 1.20-2.10(m, 12H), 1.05(m, 6H) |
| 138 | 434 | 1.93 | CD3OD: 8.75(m, 2H), 8.55(s, 1H), 8.39(m, 1H), 8.00(m, 1H), 7.54(m, 1H), 7.46(m, 1H), 7.19(m, 1H), 7.03(m, 1H), 4.77(brS, 2H), 3.89(t, 4H), 3.75(t, 4H), 2.21(brm, 1H), 0.68(m, 2H), 0.59(m, 2H) |
| 139 | 453.1 | 3.6 | |
| 140 | 464.5 | 3.7 | DMSO-d6: 8.49(s, 1H), 8.07(d, 1H, J=8Hz), 7.56(m, 1H), 7.50(t, 1H, J=8Hz), 7.27(m, 5H), 4.76(m, 1H), 3.69(br s, 4H), 1.59(m, 2H), 1.45(br s, 4H), 0.97(d, 6H, J=6Hz) |
| 141 | 483.5 | 4.4 | |
| 142 | 463 | 3.2 | DMSO-d6: 8.54(s, 1H), 7.48(t, 2H), 7.20(brm, 2H), 7.69(d, 2H), 4.40(brs, 2H), 3.78(m, 4H), 3.73(s, 3H), 3.67(m, 4H), 1.90(brm, 1H), 0.47(brm, 4H) |
| 143 | 475.2 | 3.7 | DMSO-d6: 7.60(m, 1H), 7.27-7.40(m, 3H), 7.08(m, 3H), 6.43(d, 2H), 4.74(d, 1H), 4.10(d, 1H), 3.94(m, 1H), 3.72(m, 4H), 3.66(m, 4H), 2.32(s, 3H), 1.00-1.60(m, 8H) |
| 144 | 479 | 2.94 | CD3OD: 8.45(s, 1H), 7.65 & 6.90(2xt, 1H), 7.49(m, 1H), 7.26(m, 1H), 7.10(m, 1H), 6.61(d, 1H), 6.72 & 6.45(2xs, 1H), 4.58(brs, 1H), 4.28(brs, 1H), 3.90(m, 4H), 3.74-3.78(m, 11H), 3.449brS, 1H), 2.67(t, 1H), 2.45(brs, 1H) |
| 145 | 447.1 | 3.89 | CD3OD: 7.35-7.50(m, 2H), 7.01-7.25(m, 5H), 6.94(d, 1H), 5.00(d, 1H), 4.05(d, 1H), 3.84(m, 4H), 3.72(m, 4H), 2.36(s, 3H), 1.90(m, 1H), 0.45(m, 3H), 0.30(m, 1H) |
| 146 | 493.4 | 3.9 | DMSO-d6: 8.47(s, 1H), 7.34-7.55(m, 4H), 6.62(m, 1H), 6.46(m, 1H), 6.29(s, 1H), 5.95(s, 2H), 3.77(m, 7H), 1.63(m, 2H), 1.53(m, 4H), 0.83(m, 6H) |
| 147 | 488 | 2.5 | DMSO-d6 7.53(s, 1H), 6.45-6.60(m, 2H), 6.16-6.30(m, 5H), 6.03(m, 2H), 3.75-4.10(m, 4H), 3.14(m, 1H), 2.10-2.65(m, 6H), 1.95(s, 3H), 0.35-0.70(m, 10H) |
| 148 | 474 | 2.4 | DMSO-d6 8.53(s, 1H), 7.54-7.58(m, 2H), 7.18-7.30(m, 5H), 6.98-7.04(m, 2H), 4.90-5.10(m, 2H), 4.05-4.40(m, 3H), 3.05-3.70(m, 6H), 2.95(s, 3H), 1.30-1.70(m, 8H) |
| 149 | 429.4 | 3.8 | |
| 150 | 419.4 | 3.2 | CD3OD: 8.65(br s, 1H), 6.82-7.60(br m, 8H), 4.81(m, 1H), 3.92(t, 4H), 3.77(t, 4H), 2.61(br s, 1H), 2.34(br s, 1H), 1.17(brs, 3H). |
| 151 | 531.5 | 4 | DMSO-d6: 8.30(s, 1H), 7.53(m, 1H), 7.35(m, 1H), 7.27(m, 2H), 6.63(m, 1H), 6.21(m, 1H), 6.00(br s, 1H), 4.72(m, 1H), 4.18(s, 4H), 3.25(m, 2H), 2.07(s, 1H), 1.85(m, 1H), 1.67(m, 2H), 1.60(m, 3H), 1.56(m, 1H), 1.45(m, 3H), 1.24(m, 3H), 0.92(br s, 6H). |
| 152 | 462.5 | 3 | DMSO-d6: 8.35(s, 1H), 7.49(m, 1H), 7.36(s, 1H), 7.27(m, 2H), 6.98(m, 1H), 6.55(d, 1H, J=7Hz), 6.03(s, 2H), 4.71(m, 1H), 3.84(m, 2H), 3.67(m, 2H), 2.77(s, 6H), 1.58(m, 2H), 1.46(m, 2H), 0.97(br s, 6H). |
| 153 | 422.2 | 2.6 | |
| 154 | 529.5 | 4.5 | DMSO-d6: 8.31(s, 1H), 7.55(m, 1H), 7.34(m, 1H), 7.28(m, 1H), 7.10(m, 1H), 6.78(m, 1H), 6.22(br d, 2H), 4.61(br s, 1H), 4.14(br s, 4H), 3.64(s, 3H), 3.25(br d, 2H), 1.69(m, 1H), 1.4-1.8(m, 6H), 1.3-1.35(br m, 6H), 1.24(br s, 8H). |
| 155 | 445.4 | 4 | |
| 156 | 445.1 | 3.9 | DMSO-d6: 8.43(s, 1H), 7.50(m, 2H), 7.15-7.26(m, 5H), 7.06(m, 2H), 5.88(m, 2H), 5.14(m, 4H), 4.08-4.40(m, 5H), 3.98(m, 1H), 1.03(m, 6H) |

TABLE 8-continued

Physical data for exemplary compounds.

| Compound No. | LC/MS M + 1 | LC/RT min | NMR |
|---|---|---|---|
| 157 | 477 | 3.9 | DMSO-d6: 8.48(s, 1H), 7.56(m, 2H), 7.17-7.33(m, 5H), 6.94(m, 2H), 4.11(brS, 7H), 2.65(m, 4H), 1.30-1.5(brm, 8H) |
| 158 | 447.5 | 3.6 | |
| 159 | 461 | 3.78 | DMSO-d6: 1.35(brm, 4H), 1.51(brm, 4H), 3.67(brm, 4H), 3.76(brm, 4H), 4.03(brm, 1H), 6.91(brm, 2H), 7.16(brm, 3H), 7.31(m, 2H), 7.48(m, 1H), 7.57(m, 1H), 8.49(s, 1H) |
| 160 | 451.4 | 3.2 | CD3OD: 8.36(s, 1H), 7.53(m 1H), 7.36(m, 1H), 7.25(m, 1H), 7.19(m, 1H), 7.07(m, 1H), 6.78(m, 1H), 6.24(m, 1H), 6.10(m, 1H), 4.81(m, 1H), 3.76(m, 4H), 3.68(m, 7H), 1.07(br m, 6H). |
| 161 | 489 | 3.9 | DMSO-d6: 8.56(s, 1H), 7.45(m, 2H), DMSO-d6: 7.27(d, 2H), 7.10(brm, 2H), 7.00(d, 2H), 4.46(brs, 2H), 3.77(m, 4H), 3.67(m, 4H), 1.95(brm, 1H), 0.48(brm, 4H) |
| 162 | 516.3 | 4.4 | DMSO-d6: 8.42(s, 1H), 7.52(m, 2H), 7.25(m, 2H), 7.08(m, 1H), 6.74(m, 2H), 6.50(m, 1H), 4.26-4.90(m, 6H), 4.19(m, 1H), 3.71(s, 3H), 1.20-1.90(m, 12H), 0.90(m, 6H) |
| 163 | 447.1 | 3.5 | DMSO-d6: 8.55(s, 1H), 7.48(m, 2H), 7.15(m, 3H), 7.04(d, 1H), 6.95(m, 1H), 6.84(d, 1H), 4.45(brs, 2H), 3.78(m, 4H), 3.67(m, 4H), 2.26(s, 3H), 2.15(brm, 1H), 0.48(m, 4H) |
| 164 | 479 | 3.6 | CD3OD: 8.45(s, 1H), 7.40(m, 2H), 6.95-7.15(m, 4H), 6.81(d, 2H), 4.53(brs, 2H), 4.21(m, 4H), 2.65(m, 4H), 1.85(brm, 1H), 0.51(brm, 4H). |
| 165 | 477.5 | 3.8 | DMSO-d6: 8.41(s, 1H), 7.55(m, 1H), 7.26(m, 3H), 7.18(m, 1H), 7.07(m, 1H), 6.71(s, 1H), 6.39(br s, 1H), 4.76(br s, 1H), 3.62(br s, 4H), 3.58(br s, 4H), 1.12(s, 9H), 0.97(d, 6H, J=5Hz). |
| 166 | 532.2 | 2.5 | DMSO-d6: 8.51(s, 1H), 7.65(m, 2H), 7.29(m, 2H), 7.07(m, 1H), 6.74(m, 2H), 6.47(m, 1H), 4.78(m, 2H), 4.09(m, 1H), 3.87(s, 3H), 3.56(brm, 5H), 3.12(m, 2H), 2.98(m, 2H), 1.53-2.25(m, 8H), 0.91(m, 6H) |
| 167 | 448 | 2.3 | DMSO-d6: 8.61(s, 1H), 7.45-7.60(m, 2H), 7.15-7.45(m, 5H), 6.94(m, 2H), 4.74-7.80(m, 4H), 3.85(m, 1H), 3.50(m, 2H), 3.30(m, 2H), 3.10(m, 2H), 2.85(s, 3H), 0.90(brS, 6H) |
| 168 | 474.1 | 2.8 | |
| 169 | 477.5 | 3.5 | DMSO-d6: 8.40(s, 1H), 7.54(m, 1H), 7.39(m, 1H), 7.28(m, 2H), 7.13(t, 1H, J=8Hz), 6.80(d, 1H, J=7Hz), 6.35(d, 1H, J=7Hz), 6.25(s, 1H), 4.61(m, 1H), 3.73(br s, 4H), 3.65(s, 3H), 3.60(d, 4H, J=4Hz), 1.72(br s, 2H), 1.43(br s, 4H), 1.29(br s, 2H). |
| 170 | 475 | 3.98 | NMR 1H(CDCl3): "show rotameres" 8.8(s, 1H), 8.3(d, 2H), 7.2-7.4(m, 5H), 6.7-7.0(m, 2H), 4.4-4.8(m, 2H), 3.7-4.0(M, 8H), 3.2(m, 2H), 1.0-1.5(m, 12H). |
| 171 | 477.5 | 3.5 | DMSO-d6: 8.32(s, 1H), 7.54(m, 1H), 7.35(m, 1H), 7.27(m, 2H), 6.64(d, 1H, J=8Hz), 6.23(m, 1H), 6.02(s, 1H), 4.73(m, 1H), 4.19(s, 4H), 3.69(br s, 4H), 1.60(br s, 2H), 1.47(br s, 4H), 0.92(d, 6H, J=6Hz). |
| 172 | 431.4 | 3.3 | DMSO-d6: 8.41(s, 1H), 7.52(m, 2H), 7.29(m, 2H), 3.76(m, 4H), 3.67(m, 5H), 2.81(br s, 1H), 2.72(br s, 1H), 1.48(br s, 1H), 1.24(s, 6H), 1.13(m, 2H), 0.86(m, 1H). |
| 173 | 536.2 | 3.7 | CD3OD: 8.38(s, 1H), 7.75(m, 1H), 7.10-7.65(10H), 7.15(m, 1H), 3.85(brs, 2H), 3.55(m, 3H), 2.98(m, 2H), 0.89(brm, 6H) |
| 174 | 357 | 2.77 | DMSO-d6: 1.60(m, 2H), 1.83(m, 2H), 2.10(m, 2H), 3.66(m, 4H), 3.78(m, 4H), 7.17(m, 1H), 7.27(t, 1H), 7.46(m, 1H), 7.53(m, 1H), 8.23(d, 1H), 8.53(s, 1H) |
| 175 | 465.4 | 3.8 | DMSO-d6: 8.42(s, 1H), 7.50(m, 2H), 7.42(t, 1H, J=7Hz), 7.34(d, 1H, J=7Hz), 7.13(t, 1H, J=8Hz), 6.80(d, 1H, J=7Hz), 6.30(d, 1H, J=7Hz), 6.14(s, 1H), 4.66(br s, 1H), 3.68(br s, 4H), 3.66(s, 3H), 1.59(m, 2H), 1.46(br s, 4H), 0.88(d, 6H, J=6Hz). |
| 176 | 501 | 2.6 | DMSO-d6: 8.63(s, 1H), 7.45(m, 2H), 7.26(d, 2H), 7.17(m, 2H), 6.99(d, 2H), 4.77(d, 2H), 4.48(brs, 2H), 3.51(m, 2H), 4.48(m, 2H), 3.51(m, 2H), 3.31(m, 2H), 3.15(m, 2H), 2.84(s, 3H), 2.00(m, 1H), 1.28(s, 9H), 0.48(m, 4H). |
| 177 | 475.5 | 3.72 | |
| 178 | 466.4 | 3.2 | DMSO-d6: 8.55(s, 1H), 8.08(d, 1H, J=8Hz) 7.58(m, 1H), 7.51(m, 1H), 7.28(m, 5H), 4.76(br s, 1H), 3.67(br s, 4H), 3.59(d, 4H, J=4Hz), 0.98(d, 6H, J=4Hz). |
| 179 | 433.4 | 3.7 | DMSO-d6: 7.57(m, 1H), 7.37(m, 2H), 7.29(m, 2H), 7.19(m, 1H), 7.14(t, 2H, J=8Hz), 6.35(br s, 1H), 4.78(m, 1H), 3.79(br s, 2H), 3.62(br s, 2H), 2.41(s, 3H), 1.56(m, 2H), 1.42(m, 4H), 0.85(dd, 6H, J=7Hz, 16Hz). |
| 180 | 459 | 2.4 | DMSO-d6 8.49(s, 1H), 7.57(m, 2H), 7.32(t, 2H), 7.21(m, 3H), 6.98(m, 2H), 4.77(m, 2H), 4.65(m, 1H), 4.20(m, 2H), 3.51(m, 2H), 3.33(m, 2H), 3.11(m, 2H), 2.85(s, 3H), 2.05(m, 2H), 1.25-1.50(4H) |

TABLE 8-continued

Physical data for exemplary compounds.

| Compound No. | LC/MS M + 1 | LC/RT min | NMR |
|---|---|---|---|
| 181 | 459.4 | 3.5 | |
| 182 | 465.4 | 3.1 | DMSO-d6: 8.40(s, 1H), 7.54(m, 1H), 7.39(m, 1H), 7.29(m, 2H), 6.71(d, 1H, J=7Hz), 6.18(m, 2H), 6.01(s, 2H), 4.73(m, 1H), 3.66(br s, 4H), 3.61(br s, 4H), 0.93(d, 6H, J=6Hz). |
| 183 | 449.4 | 3.1 | DMSO-d6: 8.48(s, 1H), 7.55(m, 1H), 7.42(t, 1H, J=7Hz), 7.29(m, 2H), 7.13(t, 1H, J=8Hz), 6.76(dd, 1H, J=2Hz, 8Hz), 6.40(d, 1H, J=8Hz), 6.37(s, 1H), 3.72(t, 4H, J=5Hz), 3.67(s, 3H), 3.64(t, 4H, J=5Hz), 2.85(m, 1H), 0.67(m, 2H), 0.39(m, 2H). |
| 184 | 515.5 | 4.2 | DMSO-d6: 8.45(s, 1H), 7.60(m, 2H), 7.20(m, 2H), 6.99(d, 2H), 6.81(d, 2H), 4.30(m, 4H), 3.73(s, 3H), 3.40(m, 2H), 2.06(m, 1H), 1.25-1.90(m, 12H), 0.46(brm, 4H) |
| 185 | 451.5 | 3.2 | DMSO-d6: 8.35(s, 1H), 7.55(m, 1H), 7.39(m, 1H), 7.29(m, 2H), 6.75(d, 2H, J=8Hz), 6.63(d, 2H, J=8Hz), 4.76(m, 1H), 3.70(s, 3H), 3.64(br s, 4H), 3.60(br s, 4H), 0.92(d, 6H, J=6Hz). |
| 186 | 479.2 | 3.4 | DMSO-d6: 7.04-7.60(m, 6H), 6.72(m, 2H), 6.31(d, 2H), 4.52(d, 1H), 4.22(d, 1H), 3.62-3.82(m, 11H), 2.34(s, 3H), 0.95(d, 3H), 0.51(d, 3H) |
| 187 | 405 | 3.21 | CDCl3: 8.43(s, 1H), 7.61(t, 1H), 7.28(m, 1H), 7.12-7.21(m, 4H), 7.05(d, 1H), 6.96(m, 1H), 4.79(s, 2H), 4.55(s, 2H), 3.85(t, 4H), 3.72(t, 4H), |
| 188 | 499.1 | 3.6 | DMSO-d6: 8.36(s, 1H), 7.05-7.60(m, 10H), 6.72(2H), 5.17(m, 1H), 4.36(m, 2H), 3.89(m, 1H), 3.69(s, 3H), 1.45(m, 3H), 0.79(m, 6H) |
| 189 | 501.5 | 4.2 | |
| 190 | 463.4 | 3.4 | DMSO-d6: 8.37(s, 1H), 7.54(m, 1H), 7.41(t, 1H, J=7Hz), 7.29(m, 2H), 7.18,(t, 1H, J=6Hz), 6.82(d, 1H, J=8Hz), 6.36(d, 1H, J=8Hz), 6.28(s, 1H), 4.66(m, 1H), 3.67(m, 7H), 3.61(m, 4H), 1.98(m, 2H), 1.69(m, 2H), 1.52(m, 1H), 1.42(m, 1H). |
| 191 | 465.1 | 3.4 | DMSO-d6: 8.46(brs, 1H), 7.55(brm, 2H), 7.30(brm, 3H), 7.12(brm, 3H), 4.35(m, 1H), 3.65-3.80(m, 12H), 1.50-1.80(brm, 4H) |
| 192 | 487.5 | 3.6 | CD3OD: 7.36(m, 2H), 7.06(m, 2H), 6.82(s, 1H), 6.73(d, 1H), 6.53(d, 1H), 4.95(d, 1H), 4.52(t, 2H), 3.94(d, 1H), 3.84(m, 4H), 3.12(m, 2H), 2.35(s, 3H), 1.87(m, 1H), 1.70(m, 2H), 1.61(m, 4H), 0.51(3H), 0.20(m, 1H) |
| 193 | 476 | 2.2 | DMSO-d6 8.62(s, 1H), 7.47(m, 2H), 7.22(m, 2H), 6.98(d, 2H), 6.80(d, 2H), 4.76(d, 2H), 4.45(brm, 2H), 3.74(d, 3H), 3.51(m, 2H), 3.30(m, 2H), 2.84(s, 3H), 1.95(m, 1H), 0.47(brm, 4H). |
| 194 | 451.1 | 3.5 | |
| 195 | 501 | 3.6 | DMSO-d6: 8.65(brs, 1H), 7.61(d, 1H), 7.50(m, 4H), 7.38(d, 1H), 7.05-7.15(m, 2H), 4.60(brs, 2H), 3.78(m, 4H), 3.67(m, 4H), 2.20(brm, 1H), 0.53(m, 4H) |
| 196 | 385 | 3.11 | DMSO-d6: 1.06-1.23(m, 5H), 1.51(m, 1H), 1.61-1.69(m, 4H), 1.70(m, 2H), 3.54(m, 1H), 3.66(m, 4H), 3.77(m, 4H), 7.17(m, 1H), 7.25(t, 1H), 7.46(m, 1H), 7.53(m, 1H), 7.85(d, 1H), 8.50(s, 1H) |
| 197 | 493.5 | 2.9 | DMSO-d6: 8.69(s, 1H), 7.56(m, 1H), 7.39(m, 1H), 7.29(m, 2H), 7.16(m, 1H), 6.83(d, 1H, J=7Hz), 6.35(d, 1H, J=7Hz), 6.27(s, 1H), 4.55(br s, 1H), 3.82(m, 2H), 3.66(s, 3H), 3.45(br s, 8H), 3.33(m, 2H), 1.59(m, 2H), 1.28(m, 2H). |
| 198 | 518.5 | 3.2 | DMSO-d6: 8.45(d, 2H), 7.34-7.55(m, 4H), 6.67(m, 2H), 6.63(m, 2H), 3.77-3.98(m, 11H), 3.17(t, 4H), 1.93(t, 4H), 2.20(brm, 1H), 1.63(brm, 2H), 1.53(brm, 4H), 0.82(brm, 6H) |
| 199 | 421.2 | 3.2 | DMSO-d6: 8.33(s, 1H), 7.03-7.53(m, 9H), 3.77(m, 4H), 3.67(m, 4H), 3.49(m, 1H), 2.73(s, 3H), 2.66(m, 2H) |
| 200 | 489.2 | 3.3 | DMSO-d6: 7.10-7.60(m, 3H), 6.51-6.66(m, 3H), 4.83(d, 1H), 4.48(t, 2H), 3.89(d, 1H), 3.64-3.73(m, 8H), 2.29(s, 3H), 1.84(m, 1H), 0.20-0.50(m, 4H) |
| 201 | 437.4 | 3.6 | CD3OD: 8.33(s, 1H), 7.54(q, 1H, J=6Hz, 13Hz), 7.35(br s, 1H), 7.09-7.30(m, 5H), 6.60(br s, 2H), 4.86(m, 1H), 4.09(br s, 4H), 2.56(br s, 4H), 1.06(d, 6H, J=6Hz). |
| 202 | 446.4 | 3.1 | DMSO-d6: 8.51(s, 1H), 7.69(d, 1H, J=7Hz), 7.63(m, 1H), 7.40(m, 1H), 7.32(t, 3H, J=9Hz), 7.05(m, 1H), 6.8(br s, 1H), 4.75(br s, 1H), 3.67(d, 4H, J=5Hz), 3.61(d, 4H, J=5Hz), 0.96(d, 6H, J=6Hz). |
| 203 | 507.5 | 3.6 | DMSO-d6: 8.41(s, 1H), 7.51(m, 1H), 7.43(m, 2H), 7.17(m, 1H), 6.83(d, 1H, J=7Hz), 6.62(d, 1H, J=2Hz), 6.33(d, 1H, J=7Hz), 6.19(s, 1H), 4.54(br s, 1H), 3.82(m, 2H), 3.75(m, 4H), 3.68(s, 3H), 3.26(m, 2H), 1.65(m, 1H), 1.54-1.59(m, 4H), 1.45(m, 4H), 1.22(m, 3H). |
| 204 | 526.1 | 2.37 | DMSO-d6: 8.87(d, 2H), 8.51(s, 1H), 8.34(m, 2H), 7.89(m, 2H), 7.58(t, 1H), 7.56(m, 2H), 7.48(m, 1H), 7.05(m, 1H), 7.85(m, 1H), |

TABLE 8-continued

Physical data for exemplary compounds.

| Compound No. | LC/MS M + 1 | LC/RT min | NMR |
|---|---|---|---|
| | | | 4.73(brs, 2H), 4.22(m, 4H), 2.65(brm, 4H), 2.05(m, 1H), 0.63(m, 2H), 0.56(m, 2H) |
| 205 | 434 | 2 | DMSO-d6: 8.75(brs, 1H), 8.62(d, 2H), 7.52(m, 2H), 7.41(m, 2H), 7.26(m, 2H), 4.64(brs, 2H), 3.78(m, 4H), 3.67(m, 4H), 2.45(brm, 1H), 0.57(m, 4H) |
| 206 | 421 | 3.65 | CDCl3: 8.41(s, 1H), 7.59(t, 1H), 7.29(m, 1H), 7.12-7.21(m, 4H), 7.05(d, 1H), 6.96(m, 1H), 4.79(s, 2H), 4.55(s, 2H), 4.17(t, 4H), 2.63(t, 4H), |
| 207 | 475.4 | 3.72 | |

VI. Assays for Detecting and Measuring Inhibition Properties of Compounds

A. Optical Methods for Assaying CaV Inhibition Properties of Compounds:

Compounds of the embodiments are useful as antagonists of voltage-gated calcium ion channels. Antagonist properties of test compounds were assessed as follows. Cells expressing the CaV of interest were placed into microtiter plates. After an incubation period, the cells were stained with fluorescent dyes sensitive to the transmembrane potential. The test compounds were added to the microtiter plate. The cells were stimulated with electrical means to evoke a CaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" Drug Discov Today 4(9): 431-439).

VIPR® Optical Membrane Potential Assay Method with Electrical Stimulation

The following is an example of how CaV2.2 inhibition activity is measured using the optical membrane potential method. Other subtypes are performed in an analogous mode in a cell line expressing the CaV of interest.

HEK293 cells stably expressing CaV2.2 are plated into 96-well microtiter plates. After an appropriate incubation period, the cells are stained with the voltage sensitive dyes CC2-DMPE/DiSBAC2(3) as follows.

Reagents:
100 mg/mL Pluronic F-127 (Sigma #P2443), in dry DMSO
10 mM DiSBAC$_6$(3) (Aurora #00-100-010) in dry DMSO
10 mM CC2-DMPE (Aurora #00-100-008) in dry DMSO
200 mM Acid Yellow 17 (Aurora #VABSC) in H$_2$O
370 mM Barium Chloride (Sigma Cat# B6394) in H$_2$O Bath X
160 mM NaCl (Sigma Cat# S-9888)
4.5 mM KCl (Sigma Cat# P-5405)
1 mM MgCl2 (Fluka Cat# 63064)
10 mM HEPES (Sigma Cat# H-4034)
pH 7.4 using NaOH Loading Protocol:
2×CC2-DMPE=20 μM CC2-DMPE: 10 mM CC2-DMPE is vortexed with an equivalent volume of 10% Pluronic, followed by vortexing in required amount of HBSS containing 10 mM HEPES. Each cell plate will require 5 mL of 2×CC2-DMPE. 50 μL of 2×CC2-DMPE is added to wells containing washed cells, resulting in a 10 μM final staining concentration. The cells are stained for 30 minutes in the dark at RT.

2×CC2DMPE & DISBAC$_6$(3)=8 μM CC2DMPE & 2.5 μM DISBAC$_6$(3): Vortex together both dyes with an equivalent volume of 10% Pluronic (in DMSO). Vortex in required amount of Bath X with beta-cyclodextrin. Each 96 well cell plate will require 5 ml of 2×CC2DMPE. Wash plate with EL×405 with Bath X, leaving a residual volume of 50 μL/well. Add 50 μL of 2×CC2DMPE & DISBAC$_6$(3) to each well. Stain for 30 minutes in the dark at RT.

1.5×AY17=750 μM AY17 with 15 mM BaCl$_2$: Add Acid Yellow 17 to vessel containing Bath X. Mix well. Allow solution to sit for 10 minutes. Slowly mix in 370 mM BaCl$_2$. This solution can be used to solvate compound plates. Note that compound plates are made at 1.5× drug concentration and not the usual 2×. Wash CC2 stained plate, again, leaving residual volume of 50 μL. Add 100 uL/well of the AY17 solution. Stain for 15 minutes in the dark at RT. Run plate on the optical reader.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Assay Protocol

Insert or use electrodes into each well to be assayed.

Use the current-controlled amplifier to deliver stimulation wave pulses for 3-5 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as mibefradil, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound.

Electrophoresiology Assays for CaV Activity and Inhibition of Test Compounds

Patch clamp electrophysiology was used to assess the efficacy of calcium channel blockers expressed in HEK293 cells. HEK293 cells expressing CaV2.2 have been visually identified and probed with fine tip glass electrodes connected to an amplifier (Axon Instruments). The "voltage clamp" mode has been used to assess the compound's IC50 holding the cells at −100 mV. The results of these experiments have contributed to the definition of the efficacy profile of the compounds.

Voltage-clamp Assay in HEK293 Cells Expressing CaV2.2

CaV2.2 calcium currents were recorded from HEK293 cells using the whole-cell variation of the patch clamp technique. Recordings were made at room temperature (~22° C.) with thick walled borosilicate glass electrodes (WPI; resistance 3-4 MΩ using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +20 mV for 50 ms at frequencies of 0.1, 1, 5, 10, 15, and 20 Hz. Blocking effects were allowed to plateau before proceeding to the next test concentration.

Solutions

Intracellular solution (in mM): Cs-F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $BaCl_2$ (10), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10).

(A) Following these procedures, representative compounds of the embodiments were found to possess desired N-type calcium channel modulation activity and selectivity.

B. Assays for Detecting and Measuring NaV Inhibition Properties of Compounds

Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

VIPR® Optical Membrane Potential Assay Method with Chemical Stimulation Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 μL of Bath Solution #2 (BS#2).
2) A 15 μM CC2-DMPE solution is prepared by mixing 5 mM coumarin stock solution with 10% Pluronic 127 1:1 and then dissolving the mix in the appropriate volume of BS#2.
3) After bath solution is removed from the 96-well plates, the cells are loaded with 80 μL of the CC2-DMPE solution. Plates are incubated in the dark for 30 minutes at room temperature.
4) While the cells are being stained with coumarin, a 15 μL oxonol solution in BS#2 is prepared. In addition to DiSBAC₂(3), this solution should contain 0.75 mM ABSC1 and 30 μL veratridine (prepared from 10 mM EtOH stock, Sigma #V-5754).
5) After 30 minutes, CC2-DMPE is removed and the cells are washed twice with 225 μL of BS#2. As before, the residual volume should be 40 μL.
6) Upon removing the bath, the cells are loaded with 80 μL of the DiSBAC₂(3) solution, after which test compound, dissolved in DMSO, is added to achieve the desired test concentration to each well from the drug addition plate and mixed thoroughly. The volume in the well should be roughly 121 μL. The cells are then incubated for 20-30 minutes.

7) Once the incubation is complete, the cells are ready to be assayed on VIPR® with a sodium addback protocol. 120 µL of Bath solution #1 is added to stimulate the NaV dependent depolarization. 200 µL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the Na$^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound

Solutions [mM]:
Bath Solution #1: NaCl 160, KCl 4.5, CaCl$_2$ 2, MgCl$_2$ 1, HEPES 10, pH 7.4 with NaOH
Bath Solution #2 TMA-Cl 160, CaCl$_2$ 0.1, MgCl$_2$ 1, HEPES 10, pH 7.4 with KOH (final K concentration~5 mM)
CC2-DMPE: prepared as a 5 mM stock solution in DMSO and stored at −20° C.
DiSBAC$_2$(3): prepared as a 12 mM stock in DMSO and stored at −20° C.
ABSC1: prepared as a 200 mM stock in distilled H$_2$O and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

VIPR 8 Optical Membrane Potential Assay Method with Electrical Stimulation

The following is an example of how NaV1.3 inhibition activity is measured using the optical membrane potential method#2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents:
100 mg/mL Pluronic F-1 27 (Sigma #P2443), in dry DMSO
10 mM DiSBAC$_2$(3) (Aurora #00-100-010) in dry DMSO
10 mM CC2-DMPE (Aurora #00-100-008) in dry DMSO
200 mM ABSC1 in H$_2$O
Hank's Balanced Salt Solution (Hyclone #SH30268.02) supplemented with 10 mM HEPES (Gibco #15630-080)

Loading protocol:
2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2×CC2-DMPE is added to wells containing washed cells, resulting in a 10 µM final staining concentration. The cells are stained for 30 minutes in the dark at RT.

2×DISBAC$_2$(3) with ABSC1=6 µM DISBAC$_2$(3) and 1 mM ABSC1: The required amount of 10 mM DISBAC$_2$(3) is added to a 50 ml conical tube and mixed with 1 µL 10% pluronic for each mL of solution to be made and vortexed together. Then HBSS/HEPES is added to make up 2× solution. Finally, the ABSC1 is added.

The 2×DiSBAC$_2$(3) solution can be used to solvate compound plates. Note that compound plates are made at 2× drug concentration. Wash stained plate again, leaving residual volume of 50 µL. Add 50 µL/well of the 2×DiSBAC$_2$(3)w/ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents
Assay buffer #1
140 mM NaCl, 4.5 mM KCl, 2 mM CaCl$_2$, 1 mM MgCl$_2$, 10 mM HEPES, 10 mM glucose, pH 7.40, 330 mOsm
Pluronic stock (1000×): 100 mg/mL pluronic 127 in dry DMSO
Oxonol stock (3333×): 10 mM DiSBAC$_2$(3) in dry DMSO
Coumarin stock (1000×): 10 mM CC2-DMPE in dry DMSO
ABSC1 stock (400×): 200 mM ABSC1 in water Assay Protocol
1. Insert or use electrodes into each well to be assayed.
2. Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound.

Electrophysiology Assays for NaV Activity and Inhbition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 µm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

Voltage-clamp Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs-F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $CaCl_2$ (1.26), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10), $CdCl_2$ (0.4), $NiCl_2$ (0.1), TTX ($0.25 \times 10^{-3}$).

Current-clamp Assay for NaV Channel Inhibition Activity of Compounds

Cells were current-clamped in whole-cell configuration with a Multiclamp 700A amplifier (Axon Inst). Borosilicate pipettes (4-5 MOhm) were filled with (in mM): 150 K-gluconate, 10 NaCl, 0.1 EGTA, 10 HEPES, 2 $MgCl_2$, (buffered to pH 7.34 with KOH). Cells were bathed in (in mM): 140 NaCl, 3 KCl, 1 MgCl, 1 CaCl, and 10 HEPES). Pipette potential was zeroed before seal formation; liquid junction potentials were not corrected during acquisition. Recordings were made at room temperature.

Examples of activities of the ion channel modulators of formulae (I and Ia) on modulating CaV 2.2, NaV 1.3, and NaV 1.8 receptors are shown below in Table 9. The compound activity for the CaV 2.2, NaV 1.3, and NaV 1.8 receptors is illustrated with "+++" if activity was measured to be less than 2.0 µM, "++" if activity was measured to be 2.0 µM to 10.0 µM, "+" if activity was measured to be greater than 10.0 µM, and "−" if no data was available.

TABLE 9

Activities of the ion channel modulators of formulae (I, Ia)

| Compound No. | CaV 2.2 | NaV 1.3 | NaV 1.8 |
| --- | --- | --- | --- |
| 1 | +++ | ++ | ++ |
| 2 | ++ | + | + |
| 3 | + | ++ | + |
| 4 | +++ | ++ | ++ |
| 5 | ++ | + | + |
| 6 | − | − | − |
| 7 | ++ | ++ | + |
| 8 | ++ | ++ | + |
| 9 | ++ | ++ | + |
| 10 | ++ | ++ | + |
| 11 | + | + | + |
| 12 | +++ | + | + |
| 13 | ++ | + | + |
| 14 | ++ | + | + |
| 15 | + | + | + |
| 16 | + | + | + |
| 17 | + | + | + |
| 18 | + | + | + |
| 19 | + | + | + |
| 20 | +++ | ++ | ++ |
| 21 | + | + | + |
| 22 | +++ | ++ | + |
| 23 | + | + | + |
| 24 | +++ | ++ | ++ |
| 25 | + | + | + |
| 26 | ++ | ++ | + |
| 27 | ++ | ++ | + |
| 28 | + | + | + |
| 29 | +++ | ++ | ++ |
| 30 | ++ | ++ | + |
| 31 | ++ | ++ | + |
| 32 | ++ | ++ | + |
| 33 | + | + | + |

TABLE 9-continued

Activities of the ion channel modulators of formulae (I, Ia)

| Compound No. | CaV 2.2 | NaV 1.3 | NaV 1.8 |
|---|---|---|---|
| 34 | ++ | ++ | + |
| 35 | + | + | + |
| 36 | ++ | ++ | + |
| 37 | + | + | + |
| 38 | − | − | − |
| 39 | + | + | + |
| 40 | + | ++ | + |
| 41 | + | ++ | + |
| 42 | ++ | ++ | + |
| 43 | ++ | ++ | + |
| 44 | + | ++ | ++ |
| 45 | + | + | + |
| 46 | + | + | + |
| 47 | ++ | ++ | + |
| 48 | ++ | ++ | + |
| 49 | + | ++ | + |
| 50 | ++ | + | + |
| 51 | ++ | ++ | + |
| 52 | ++ | ++ | + |
| 53 | ++ | ++ | + |
| 54 | ++ | ++ | + |
| 55 | ++ | ++ | ++ |
| 56 | ++ | + | + |
| 57 | + | + | + |
| 58 | + | + | + |
| 59 | +++ | ++ | ++ |
| 60 | ++ | + | + |
| 61 | − | − | − |
| 62 | ++ | ++ | + |
| 63 | + | + | + |
| 64 | ++ | ++ | + |
| 65 | ++ | + | + |
| 66 | ++ | + | + |
| 67 | + | + | + |
| 68 | ++ | + | + |
| 69 | ++ | + | + |
| 70 | +++ | ++ | + |
| 71 | + | + | + |
| 72 | + | + | + |
| 73 | + | + | + |
| 74 | ++ | ++ | + |
| 75 | + | + | + |
| 76 | + | + | + |
| 77 | ++ | ++ | + |
| 78 | +++ | ++ | ++ |
| 79 | + | + | + |
| 80 | ++ | ++ | + |
| 81 | ++ | ++ | + |
| 82 | ++ | + | + |
| 83 | +++ | ++ | ++ |
| 84 | + | + | + |
| 85 | + | ++ | ++ |
| 86 | ++ | + | + |
| 87 | + | + | + |
| 88 | ++ | + | + |
| 89 | + | + | + |
| 90 | ++ | ++ | ++ |
| 91 | + | + | + |
| 92 | +++ | + | + |
| 93 | ++ | ++ | + |
| 94 | +++ | +++ | ++ |
| 95 | ++ | + | + |
| 96 | +++ | ++ | + |
| 97 | + | + | + |
| 98 | +++ | ++ | ++ |
| 99 | + | + | + |
| 100 | ++ | ++ | + |
| 101 | ++ | ++ | + |
| 102 | + | + | + |
| 103 | +++ | +++ | + |
| 104 | + | ++ | + |
| 105 | ++ | ++ | + |
| 106 | + | + | + |
| 107 | + | + | + |
| 108 | +++ | ++ | + |
| 109 | ++ | ++ | + |
| 110 | ++ | + | + |
| 111 | + | + | + |
| 112 | + | ++ | + |
| 113 | + | ++ | + |
| 114 | +++ | + | + |
| 115 | ++ | + | + |
| 116 | ++ | ++ | + |
| 117 | +++ | ++ | ++ |
| 118 | +++ | ++ | + |
| 119 | ++ | + | + |
| 120 | +++ | ++ | + |
| 121 | ++ | ++ | + |
| 122 | ++ | + | + |
| 123 | ++ | + | + |
| 124 | ++ | ++ | + |
| 125 | ++ | + | + |
| 126 | ++ | + | + |
| 127 | ++ | ++ | + |
| 128 | ++ | ++ | + |
| 129 | + | + | + |
| 130 | ++ | ++ | + |
| 131 | +++ | ++ | ++ |
| 132 | + | + | + |
| 133 | ++ | ++ | + |
| 134 | +++ | ++ | + |
| 135 | ++ | + | + |
| 136 | ++ | ++ | + |
| 137 | +++ | + | + |
| 138 | + | + | + |
| 139 | ++ | ++ | ++ |
| 140 | ++ | ++ | + |
| 141 | ++ | + | + |
| 142 | +++ | +++ | +++ |
| 143 | ++ | ++ | ++ |
| 144 | + | + | + |
| 145 | ++ | ++ | + |
| 146 | ++ | ++ | ++ |
| 147 | ++ | + | + |
| 148 | ++ | + | + |
| 149 | + | + | + |
| 150 | + | + | + |
| 151 | ++ | ++ | + |
| 152 | ++ | ++ | + |
| 153 | + | + | + |
| 154 | ++ | + | + |
| 155 | ++ | + | + |
| 156 | +++ | ++ | ++ |
| 157 | ++ | ++ | + |
| 158 | + | + | + |
| 159 | ++ | ++ | ++ |
| 160 | + | + | + |
| 161 | ++ | ++ | ++ |
| 162 | +++ | +++ | + |
| 163 | ++ | + | + |
| 164 | ++ | ++ | ++ |
| 165 | + | ++ | + |
| 166 | − | − | − |
| 167 | + | + | + |
| 168 | + | + | + |
| 169 | + | ++ | + |
| 170 | + | + | + |
| 171 | ++ | ++ | + |
| 172 | + | + | + |
| 173 | +++ | ++ | + |
| 174 | + | + | + |
| 175 | ++ | ++ | + |
| 176 | ++ | + | + |
| 177 | + | + | + |
| 178 | + | + | + |
| 179 | + | + | + |
| 180 | ++ | ++ | + |
| 181 | + | + | + |
| 182 | ++ | + | + |
| 183 | + | + | + |

TABLE 9-continued

Activities of the ion channel modulators of formulae (I, Ia)

| Compound No. | CaV 2.2 | NaV 1.3 | NaV 1.8 |
| --- | --- | --- | --- |
| 184 | ++ | + | + |
| 185 | ++ | + | + |
| 186 | ++ | ++ | + |
| 187 | + | + | + |
| 188 | +++ | +++ | ++ |
| 189 | ++ | + | + |
| 190 | + | ++ | + |
| 191 | + | + | + |
| 192 | + | + | + |
| 193 | + | + | + |
| 194 | +++ | ++ | ++ |
| 195 | ++ | + | + |
| 196 | + | + | + |
| 197 | + | + | + |
| 198 | ++ | + | + |
| 199 | + | + | + |
| 200 | ++ | ++ | + |
| 201 | ++ | ++ | + |
| 202 | + | + | + |
| 203 | + | + | + |
| 204 | ++ | ++ | + |
| 205 | + | + | + |
| 206 | + | + | + |
| 207 | + | + | + |
| 208 | + | + | − |
| 209 | + | + | − |
| 210 | + | + | − |
| 211 | + | + | − |
| 212 | + | − | − |
| 213 | + | − | − |
| 214 | + | − | − |
| 215 | + | − | − |
| 216 | + | + | − |
| 217 | + | + | − |
| 218 | + | + | − |
| 219 | ++ | + | − |
| 220 | ++ | + | − |
| 221 | + | − | − |
| 222 | + | + | − |
| 223 | + | + | − |
| 224 | + | + | − |
| 225 | ++ | + | − |
| 226 | + | + | − |
| 227 | + | + | − |
| 228 | + | + | − |
| 229 | + | + | − |
| 230 | + | + | − |
| 231 | + | + | − |
| 232 | ++ | + | − |
| 233 | + | + | − |
| 234 | + | − | − |
| 235 | + | + | − |
| 236 | + | + | − |
| 237 | ++ | + | − |
| 238 | + | + | − |
| 239 | ++ | + | − |
| 240 | + | + | − |
| 241 | + | + | − |
| 242 | + | + | − |
| 243 | + | + | − |
| 244 | + | + | − |
| 245 | + | + | − |
| 246 | ++ | + | − |
| 247 | + | + | − |
| 248 | + | + | − |
| 249 | + | − | − |
| 250 | + | − | − |
| 251 | ++ | + | − |
| 252 | + | + | − |
| 253 | + | + | − |
| 254 | + | − | − |
| 255 | + | + | − |
| 256 | + | + | − |
| 257 | + | + | − |
| 258 | + | + | − |
| 259 | + | + | − |
| 260 | + | + | − |
| 261 | + | + | − |
| 262 | + | + | − |
| 263 | ++ | + | − |
| 264 | + | + | − |
| 265 | + | + | − |
| 266 | + | + | − |
| 267 | + | + | − |
| 268 | + | + | − |
| 269 | + | + | − |
| 270 | + | + | − |
| 271 | + | + | − |
| 272 | + | + | − |
| 273 | + | + | − |
| 274 | + | + | − |
| 275 | + | − | − |
| 276 | + | + | − |
| 277 | ++ | + | − |
| 278 | ++ | − | − |
| 279 | + | + | − |
| 280 | + | + | − |
| 281 | + | + | − |
| 282 | ++ | + | − |
| 283 | + | − | − |
| 284 | + | + | − |
| 285 | + | + | − |
| 286 | + | + | − |
| 287 | + | − | − |
| 288 | + | + | − |
| 289 | + | + | − |
| 290 | + | + | − |
| 291 | + | + | − |
| 292 | + | + | − |
| 293 | + | + | − |
| 294 | + | + | − |
| 295 | ++ | + | − |
| 296 | + | + | − |
| 297 | + | + | − |
| 298 | + | + | − |
| 299 | + | + | − |
| 300 | + | + | − |
| 301 | + | + | − |
| 302 | + | + | − |
| 303 | + | + | − |
| 304 | + | + | − |
| 305 | + | + | − |
| 306 | + | + | − |
| 307 | + | + | − |
| 308 | + | + | − |
| 309 | + | + | − |
| 310 | + | + | − |
| 311 | + | − | − |
| 312 | ++ | − | − |
| 313 | + | + | − |
| 314 | + | + | − |
| 315 | + | − | − |
| 316 | + | + | − |
| 317 | + | + | − |
| 318 | + | − | − |
| 319 | + | + | − |
| 320 | + | + | − |
| 321 | + | + | − |
| 322 | + | + | − |
| 323 | + | + | − |
| 324 | + | + | − |
| 325 | + | + | − |
| 326 | ++ | + | − |
| 327 | + | + | − |
| 328 | + | − | − |
| 329 | ++ | + | − |
| 330 | + | + | − |
| 331 | + | + | − |
| 332 | + | + | − |
| 333 | + | + | − |

TABLE 9-continued

Activities of the ion channel modulators of formulae (I, Ia)

| Compound No. | CaV 2.2 | NaV 1.3 | NaV 1.8 |
|---|---|---|---|
| 334 | ++ | + | − |
| 335 | ++ | − | − |
| 336 | + | + | − |
| 337 | + | + | − |
| 338 | + | + | − |
| 339 | + | + | − |
| 340 | + | + | − |
| 341 | + | + | − |
| 342 | + | + | − |
| 343 | + | + | − |
| 344 | + | + | − |
| 345 | + | + | − |
| 346 | + | + | − |
| 347 | + | + | − |
| 348 | + | + | − |
| 349 | + | + | − |
| 350 | + | + | − |
| 351 | + | + | − |

VIII. OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula Ia:

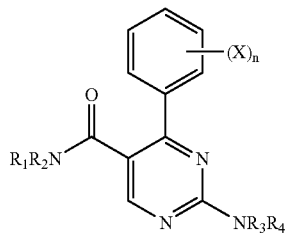

or a pharmaceutically acceptable salt thereof, wherein:
- Each X is defined by $-Z^A R_6$, wherein each $Z^A$ is independently a bond;
- Each $R_6$ is independently $R^A$, halo, —OH, —NH$_2$, —NO$_2$, —CN, —CF$_3$, or —OCF$_3$, —CH$_3$, —O-Phenyl, —OCH$_3$, —O-isopropyl, —N(H)C(O)—CH$_3$, —CH$_2$═CH$_2$—COOH, and phenyl;
- Each $R^A$ is independently hydrogen;
- Each n is 1-4;
- Each $R_1$ is an alkyl or cycloalkyl; and
- $R_2$ is defined by $-Z^B R_7$, wherein $Z^B$ is a bond;
- Each $R_7$ is $R^B$;
- Each $R^B$ is an optionally substituted phenyl;
- $R_3$ and $R_4$ form an optionally substituted six-membered monocyclic heterocycloalkyl ring with at least two heteroatoms, at least one being nitrogen.

2. The compound of claim 1, wherein $R_1$ is an cycloalkyl.
3. The compound of claim 2, wherein $R_1$ is an —$C_{1-3}$-alkyl.
4. The compound of claim 2, wherein $R_1$ is methyl, ethyl, propyl, butyl, or isopropyl.
5. The compound of claim 4, wherein $R_1$ is isopropyl.
6. The compound of claim 1, wherein $R_1$ is cyclopropyl, cyclobutyl, cyclopentyl, cyclohexyl, bicyclo[2.1.1]hexyl, bicyclo[3.1.1]heptyl, or bicyclo[2.2.1]heptyl.
7. The compound of claim 1, wherein $R_1$ is selected from methyl, ethyl,

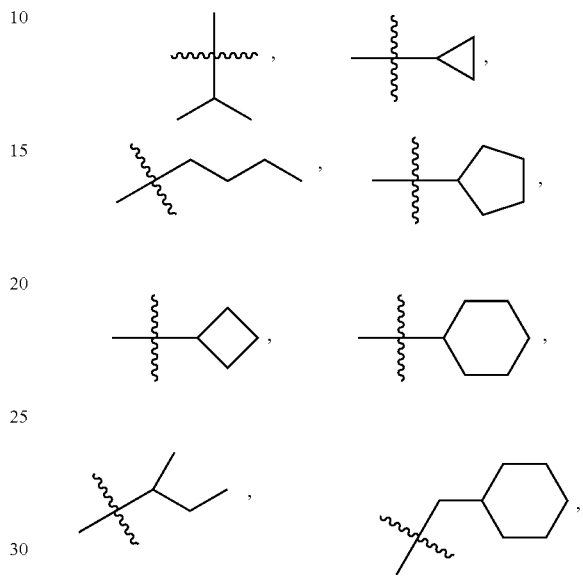

8. The compound of claim 1, wherein $R_3$, $R_4$ and the nitrogen atom to which they are attached form a morpholinyl, thiomorpholinyl, or piperazinyl.
9. The compound of claim 1, wherein X is o-halo.
10. The compound of claim 1, wherein $R_3$, $R_4$, and the nitrogen atom to which they are attached, form a heterocycloaliphatic selected from:

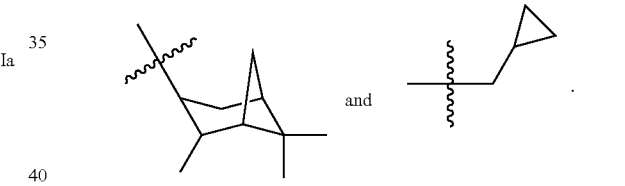

and

.

11. The compound of claim 1 selected from
23
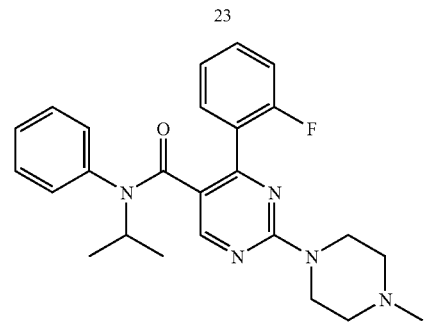
62
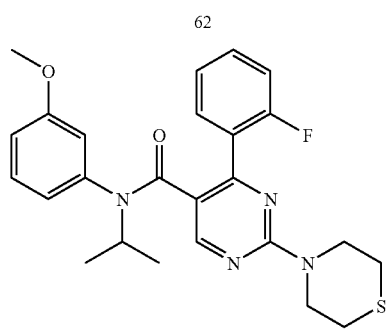
76
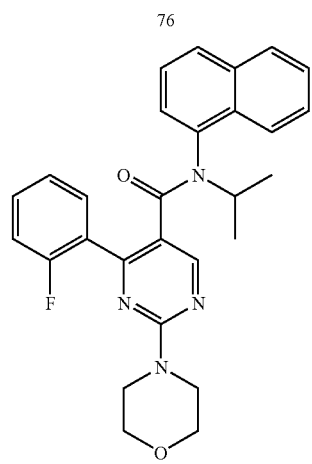
86
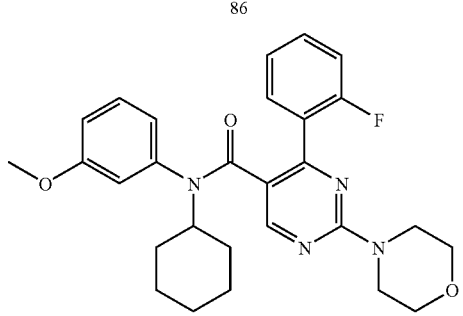
87
5
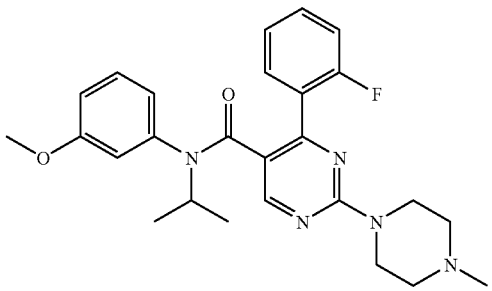
88
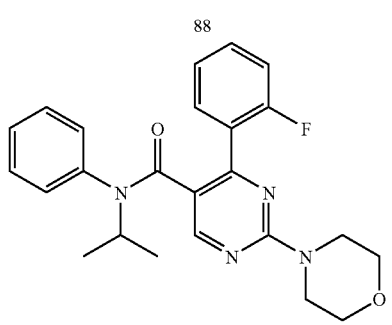
111
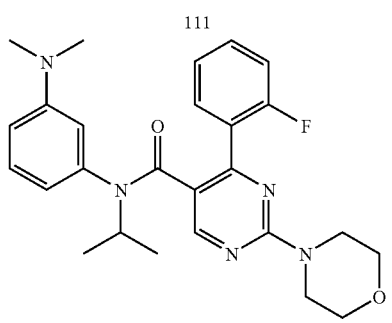
160
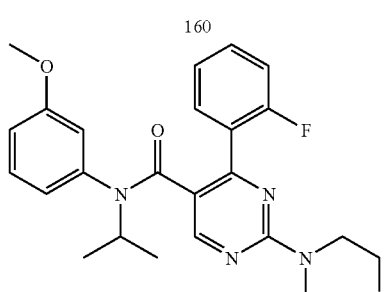
165
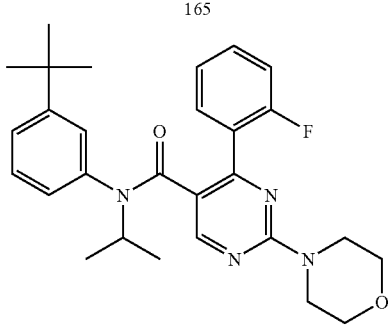
169

-continued

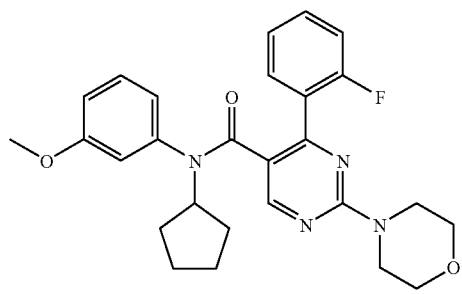

178

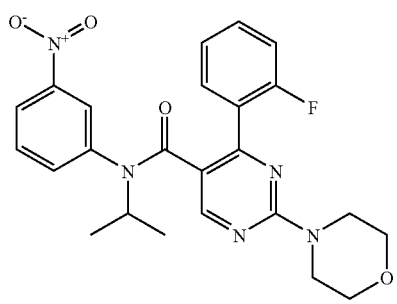

182

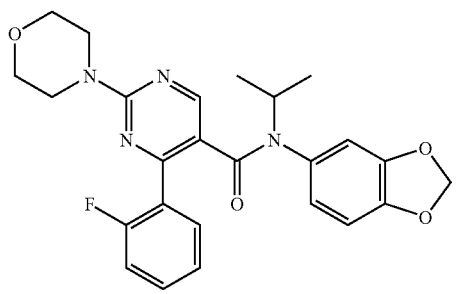

183

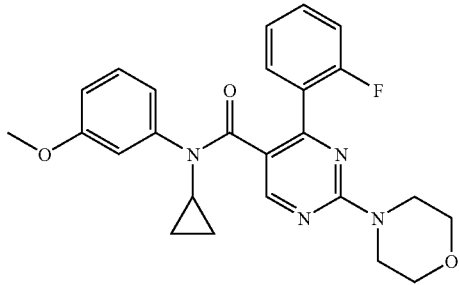

185

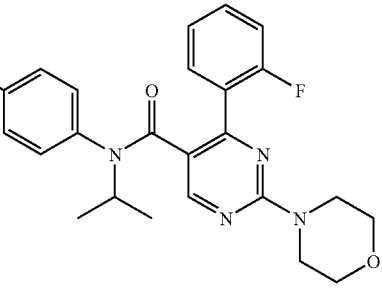

190

-continued

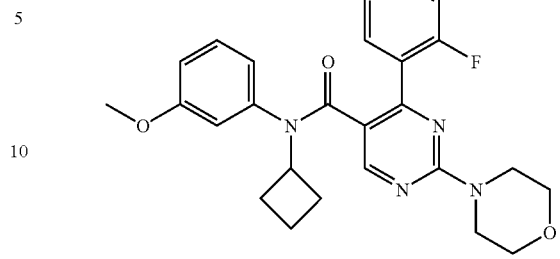

201

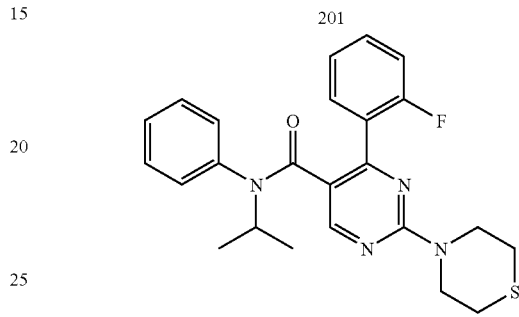

202

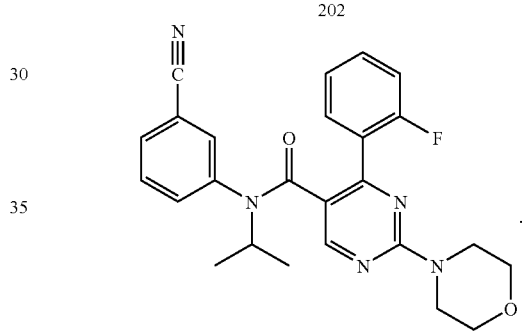

12. A pharmaceutical composition, comprising a compound as in claim 1 and a pharmaceutically acceptable carrier.

13. A compound of formula Ia:

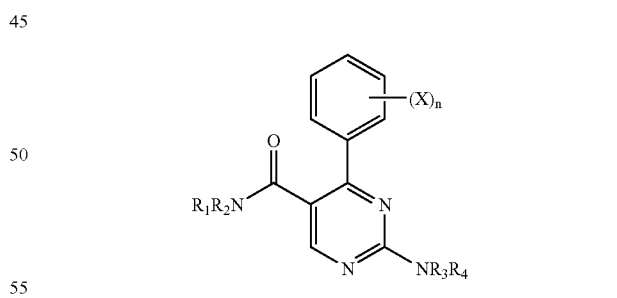

or a pharmaceutically acceptable salt thereof, wherein:

Each X is defined by -$Z^A R_6$, wherein each $Z^A$ is independently a bond;

Each $R_6$ is independently $R^A$, halo, —OH, —$NH_2$, —$NO_2$, —CN, —$CF_3$, or —$OCF_3$, —$CH_3$, —O-Phenyl, —$OCH_3$, —O-isopropyl, —N(H)C(O)—$CH_3$, —$CH_2$=$CH_2$—COOH, and phenyl;

Each $R^A$ is independently hydrogen;

Each n is 1-4;

Each $R_1$ is an alkyl or cycloalkyl; and $R_2$ is defined by -$Z^B R_7$, wherein $Z^B$ is a bond;

Each R_7 is $R^B$;
Each $R^B$ is

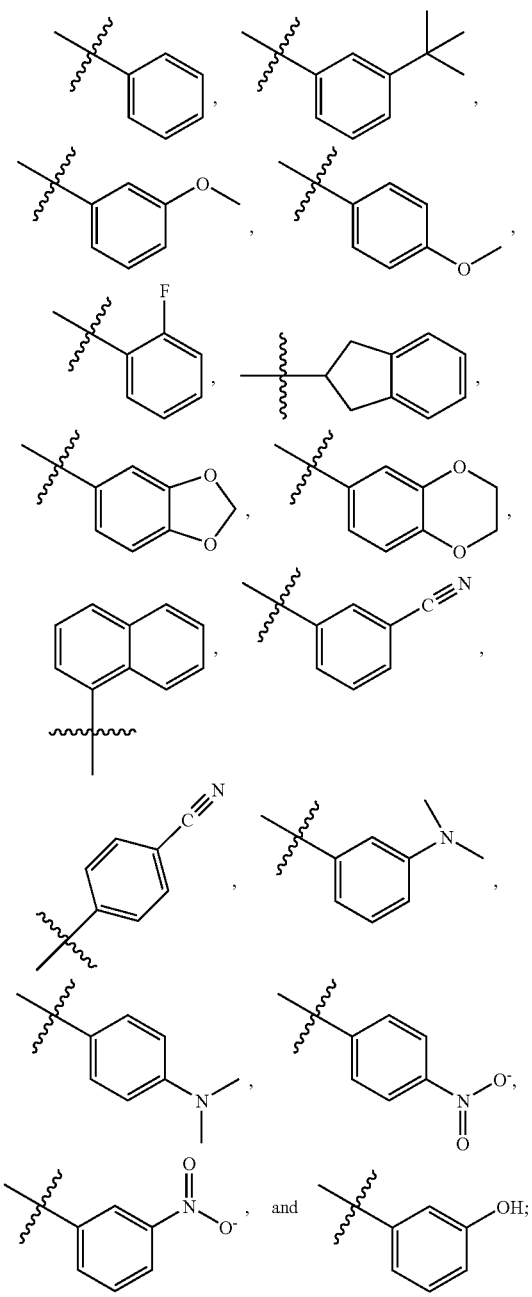

R_3 and R_4 form an optionally substituted six-membered monocyclic heterocycloalkyl ring with at least two heteroatoms, at least one being nitrogen.

14. The compound of claim 13, wherein $R_1$ is a $C_{1-8}$ alkyl a cycloalkyl.

15. The compound of claim 14, wherein $R_1$ is an optionally substituted —$C_{1-3}$ alkyl.

16. The compound of claim 14, wherein $R_1$ is methyl, ethyl, propyl, butyl, or isopropyl.

17. The compound of claim 16, wherein $R_1$ is isopropyl.

18. The compound of claim 14, wherein $R_1$ is cyclopropyl, cyclobutyl, cyclopentyl, cyclohexyl, bicyclo[2.1.1]hexyl, bicyclo[3.1.1]heptyl, or bicyclo[2.2.1]heptyl.

19. The compound of claim 14, wherein $R_1$ is selected from methyl, ethyl,

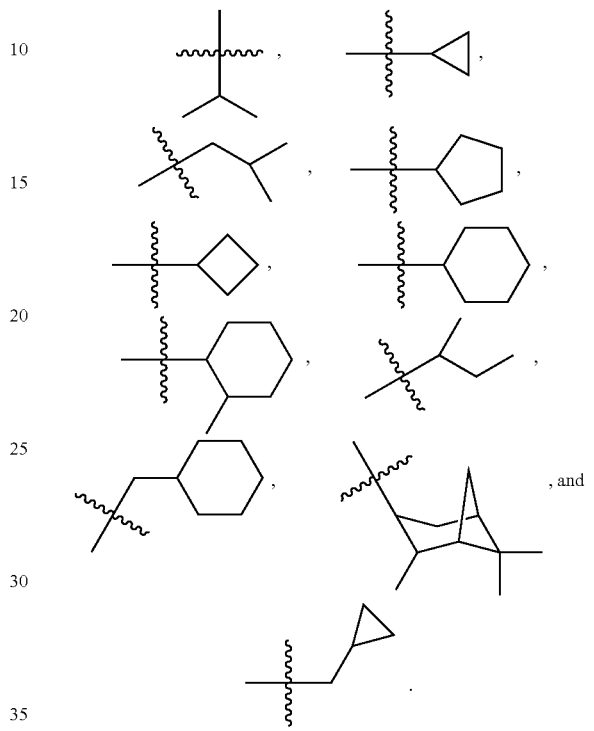

20. The compound of claim 13, wherein $R_3$, $R_4$ and the nitrogen atom to which they are attached form a morpholinyl, thiomorpholinyl, or piperazinyl.

21. The compound of claim 13, wherein X is o-halo.

22. The compound of claim 13, wherein $R_3$, $R_4$, and the nitrogen atom to which they are attached form a heterocycloaliphatic selected from:

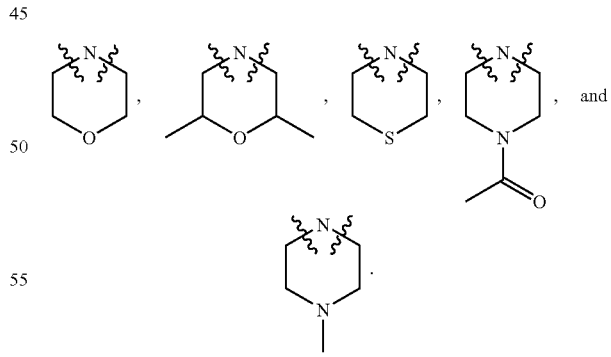

23. A pharmaceutical composition, comprising a compound as in claim 13 and a pharmaceutically acceptable carrier.

* * * * *